United States Patent
Tezcan et al.

(10) Patent No.: US 11,286,277 B2
(45) Date of Patent: Mar. 29, 2022

(54) METHOD FOR FABRICATING TWO-DIMENSIONAL PROTEIN CRYSTALS

(71) Applicant: The Regents of the University of California, Oakland, CA (US)

(72) Inventors: Faik Akif Tezcan, La Jolla, CA (US); Yuta Suzuki, Tsuruoka (JP)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/746,789

(22) PCT Filed: Jul. 14, 2016

(86) PCT No.: PCT/US2016/042361
§ 371 (c)(1),
(2) Date: Jan. 22, 2018

(87) PCT Pub. No.: WO2017/011705
PCT Pub. Date: Jan. 19, 2017

(65) Prior Publication Data
US 2018/0354988 A1    Dec. 13, 2018

Related U.S. Application Data

(60) Provisional application No. 62/193,459, filed on Jul. 16, 2015, provisional application No. 62/220,157, filed on Sep. 17, 2015.

(51) Int. Cl.
| | |
|---|---|
| *C07K 2/00* | (2006.01) |
| *C12N 9/88* | (2006.01) |
| *C12N 9/16* | (2006.01) |
| *C07K 1/30* | (2006.01) |
| *C12N 15/10* | (2006.01) |

(52) U.S. Cl.
CPC ............... *C07K 2/00* (2013.01); *C07K 1/306* (2013.01); *C12N 9/16* (2013.01); *C12N 9/88* (2013.01); *C12N 15/1031* (2013.01); *C07K 2319/00* (2013.01); *C07K 2319/21* (2013.01); *C07K 2319/60* (2013.01); *C07K 2319/735* (2013.01)

(58) Field of Classification Search
CPC .... A61K 38/00; C07K 2319/00; C12N 15/00; C12N 2310/344; G01N 33/6845; G01N 21/6428; G01N 2333/195
See application file for complete search history.

(56) References Cited

FOREIGN PATENT DOCUMENTS

CN           101381738 A    *    3/2009    ............. C12N 15/63

OTHER PUBLICATIONS

Ringler et al. Self-Assembly of Proteins into Designed Networks. Science 2003, 302: 106-109. (Year: 2003).*
Ringler et al. Self-assembly of proteins into designed networks. Science. Oct. 3, 2003;302(5642): 106-9. (Year: 2003).*
Karnik et al. Assembly of functional rhodopsin requires a disulfide bond between cysteine residues 110 and 187. J. Biol. Chem. 1990, 265:17520-17524. (Year: 1990).*
Mielke et al. X-ray diffraction of heavy-atom labelled two-dimensional crystals of rhodopsin identifies the position of cysteine 140 in helix 3 and cysteine 316 in helix 8. J. Mol. Biol. (2002) 316, 693-709. (Year: 2002).*
Banatao et al. An approach to crystallizing proteins by synthetic symmetrization. Proc Natl Acad Sci U S A. Oct. 31, 2006; 103(44): 16230-5. (Year: 2006).*
Kroemer et al. The structure of L-rhamnulose-1-phosphate aldolase (class II) solved by low-resolution SIR phasing and 20-fold NCS averaging. Acta Cryst. 2002; 058:824-832. * A crystal structure of RhuA protein is attached at the last page. (Year: 2002).*
Laganowsky et al. An approach to crystallizing proteins by metal-mediated synthetic symmetrization. Protein Science. 2011; 20: 1876-1890. (Year: 2011).*
Tang, G. et al., EMAN2: An extensible image processing suite for electron microscopy, J. Struct. Biol. 157, 38 (2007).
Uzgiris, E. et al., "Two-dimensional crystallization technique or imaging macromolecules with application to antigen-antibody-complement complexes", 1983, Nature, 301, pp. 125-129.
Yeats, T.O., "Nanobiotechnology: Protein arrays made to order", Nat. Nanotechnol. 2011, 6, pp. 541-542.
International Search Report and Written Opinion for PCT Application No. PCT/US2016/042361, dated Dec. 16, 2016, 12 pages.
Appx A, Materials Research Society Bulletin, vol. 41, Jul. 2016, pp. 509-511, https://www.cambridge.org/core.
Appx B, Novel Protein Crystal Thickens When Stretched, Materials Today, Jul. 31, 2020, pp. 1-3, https://www.materialstoday.com/mechanical-properties/news/novel-protein-crystal-thickens-when-stretched/.
Gunther, Matthew, Appx C, Protein crystals stretch knowledge of exotic materials, Chemistry World, May 9, 2016, pp. 1-3, https://www.chemistryworld.com/news/protein-crystals-stretch-knowledge-of-exotic-materials/1010251.article.
Appx D, Unprecedented two-way stretchiness achieved—CEN, pp. 1-4, https://pubs.acs.org/doi/full/10.1021/cen-09419-notw6.

* cited by examiner

Primary Examiner — Soren Harward
Assistant Examiner — Jia-Hai Lee
(74) Attorney, Agent, or Firm — Perkins Coie LLP

(57) ABSTRACT

Polypeptide assemblies and building blocks and methods for making them are provided.

15 Claims, 84 Drawing Sheets

Specification includes a Sequence Listing.

FIG. 1 A majority of biological machines and materials are self-assembled, dynamic/responsive multiprotein architectures

FIG. 3  Proteins as building blocks for functional nanomaterials
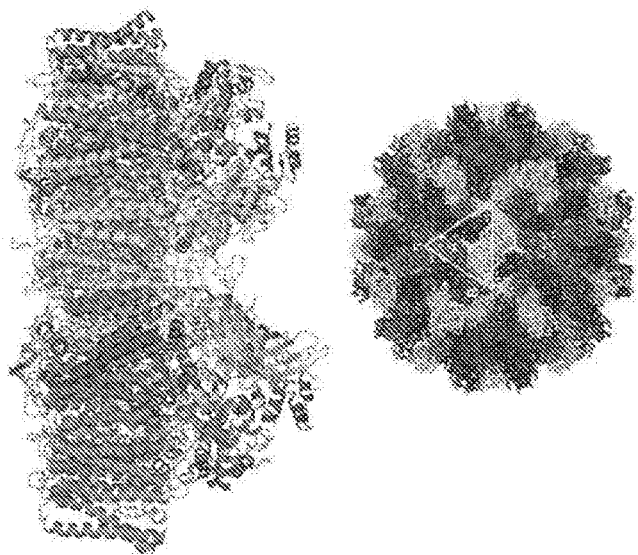
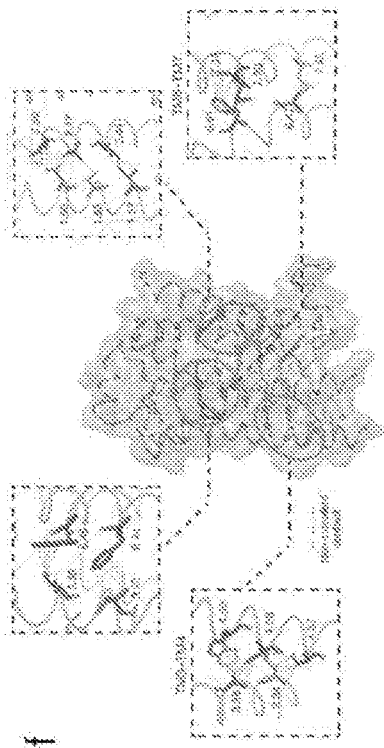
Advantages
— 20 distinct components (i.e., amino acids) → nearly infinite structural and functional diversity
— inherently nanoscale
— genetically encoded → producible and evolvable in living systems
Disadvantages
— 20 distinct components → structure, self assembly and function difficult to program FIG. 4 What would we gain by fabricating 2D supramolecular protein assemblies?

-high surface area/volume ratio
-dense display of a diverse set of chemical functionalities in a highly ordered, yet dynamic fashion
-innately functional building blocks (e.g., functional enzymes)
-potential for smart materials, lab-on-a-chip technologies, heterogeneous catalyst platforms

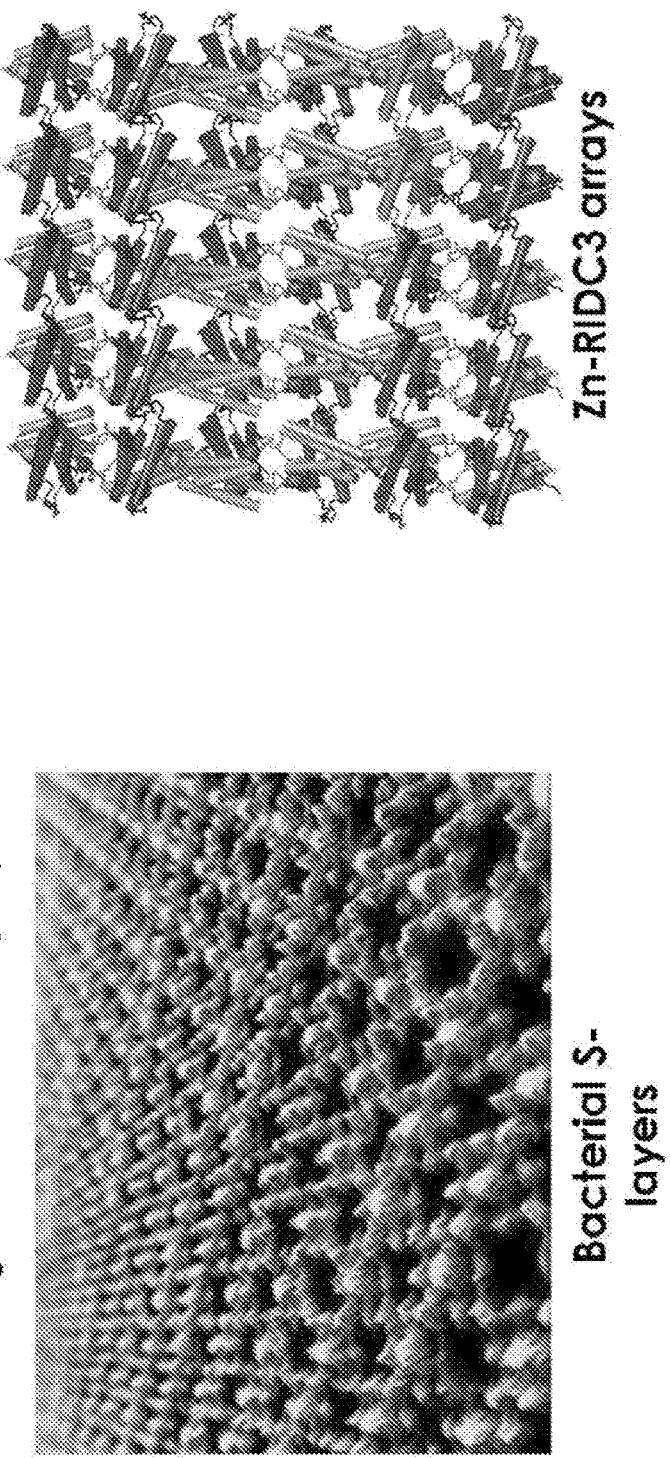

Zn-RIDC3 arrays

Bacterial S-layers

FIG. 7

Our approach: Disulfide-mediated assembly of 2D protein materials

- Bypasses the need for time-/cost-intensive computational design or protein-fusion: the only step is the engineering of cysteine residues at proper positions on a protein building block of choice.
- The requirement is a C3, C4 or C6-symmetric protein that is expressible in bacteria.
- Experimental flow/feasibility testing is highly streamlined: 1) protein expression/purification, 2) testing of different oxidative conditions for self-assembly (air oxidation or redox buffer systems). 3) characterization by electron microscopy)

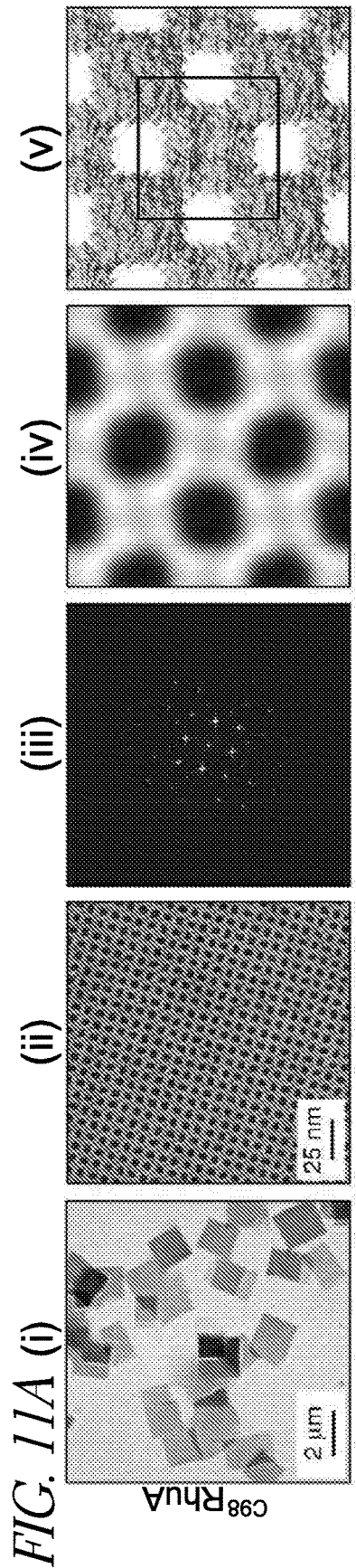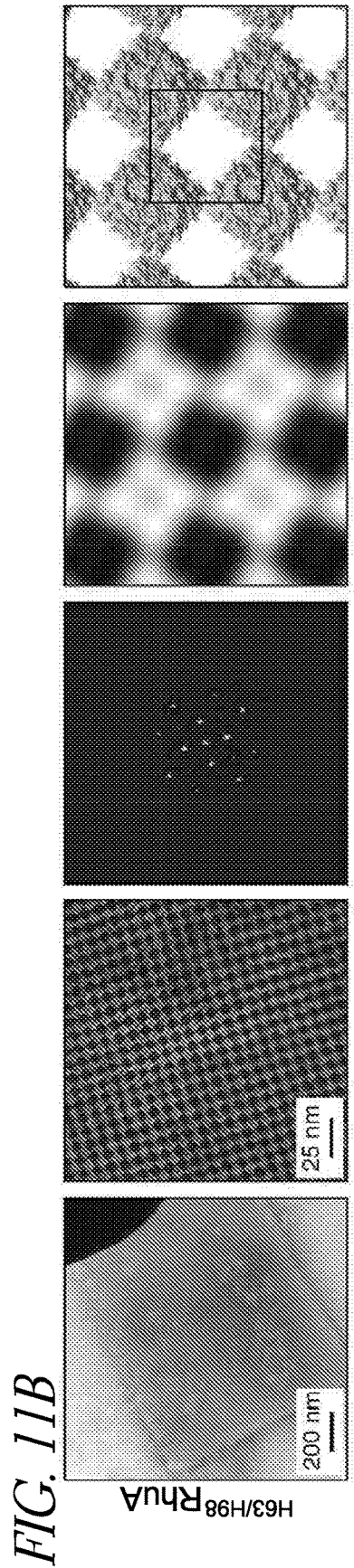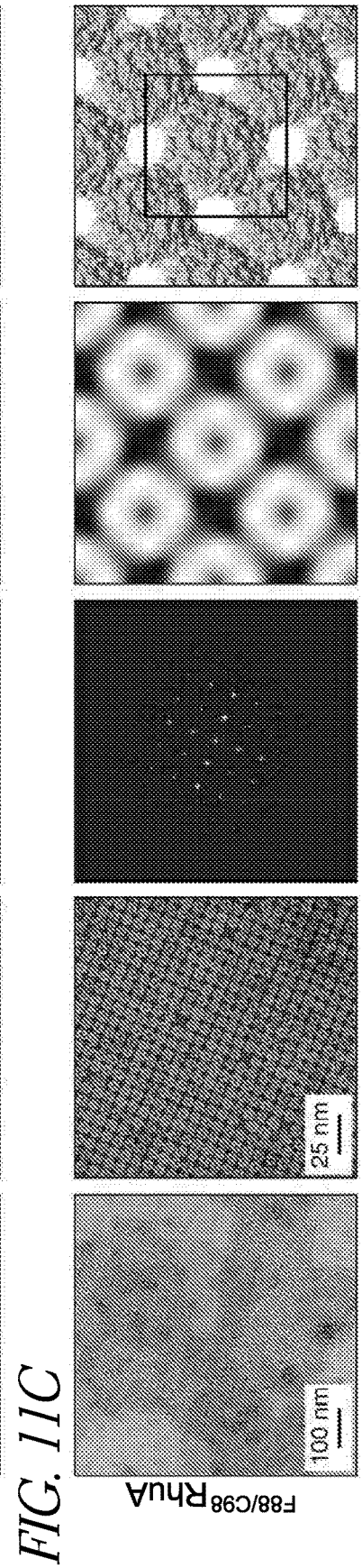
FIG. 11A C98RhuA
FIG. 11B H63/H98RhuA
FIG. 11C F88/C98RhuA

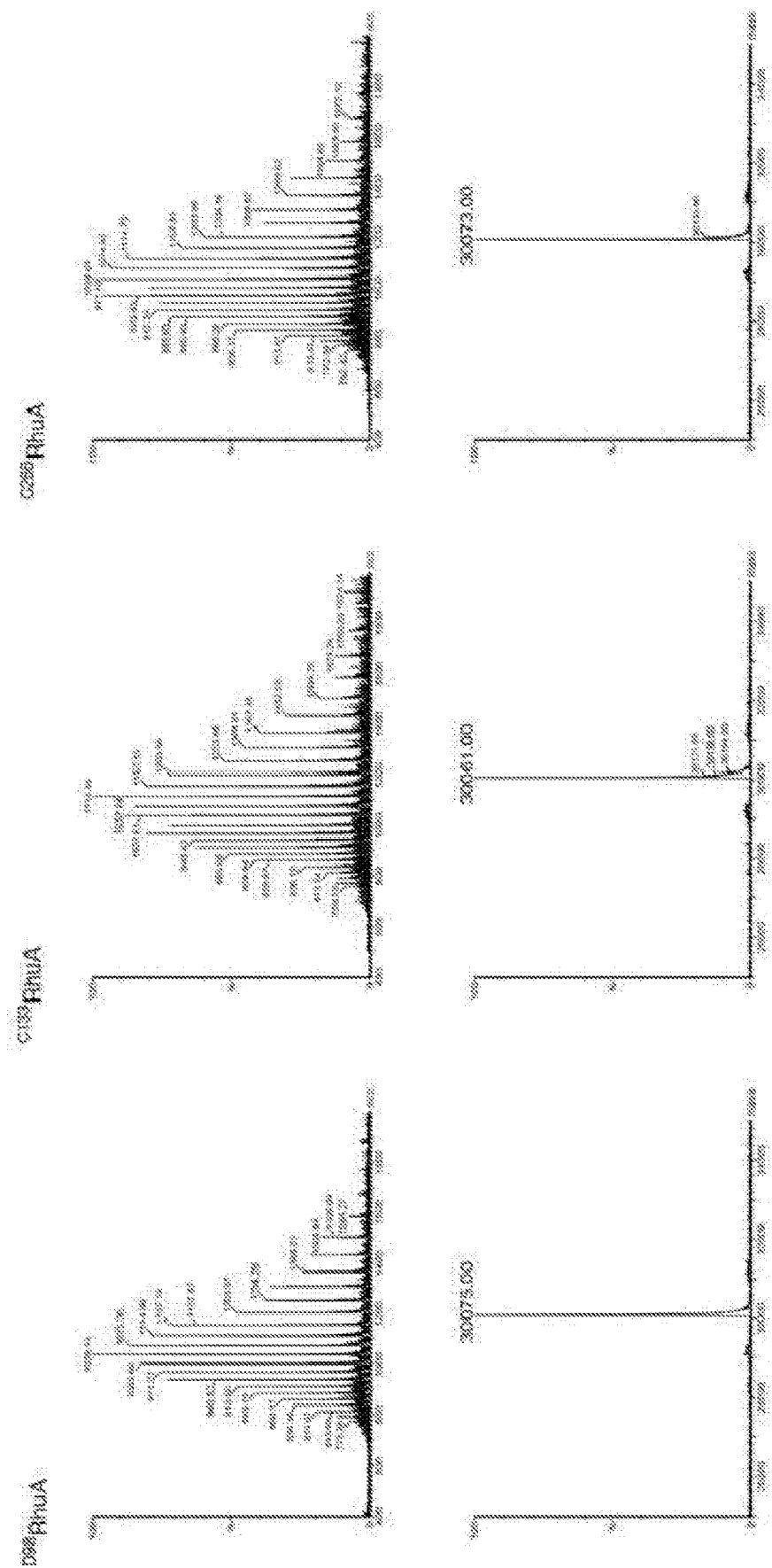
FIG. 14 (Con'd)

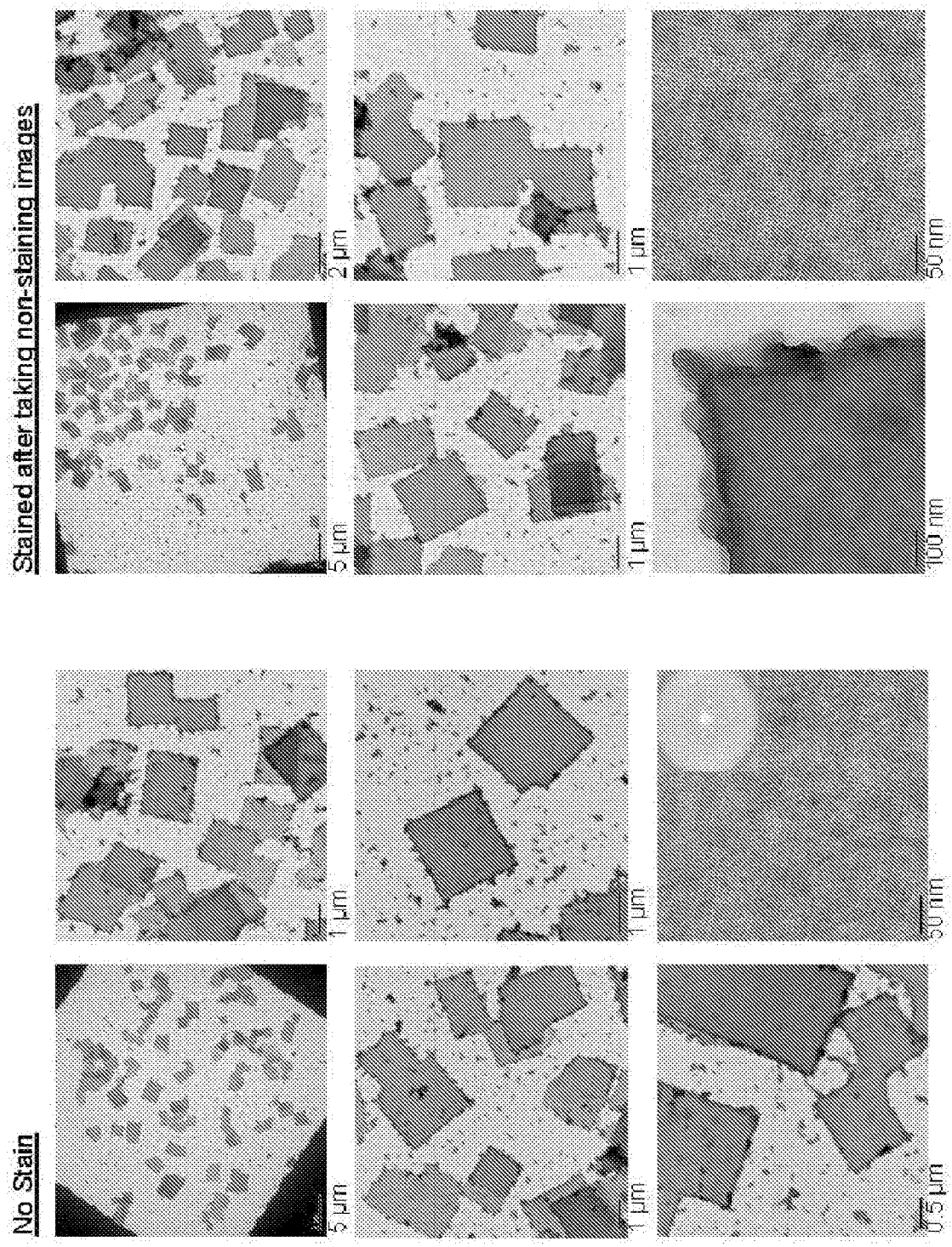
FIG. 24 RhuA-C98 Sheet on Grid Followed by Addition of Maleimido-Au for 2 Hours FIG. 25  RhuA-C98 Sheet on Grid Followed by Addition of Maleimido-Au for 2 Hours
*Different preparation from previous slide
- This sample was prepared on grid
- Sample showed in previous slide was prepared in crystal tray
No Stain
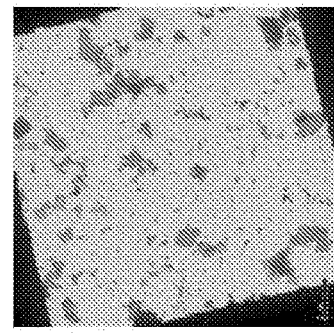
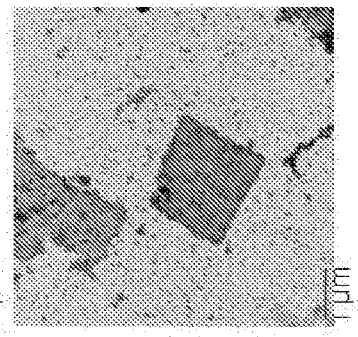
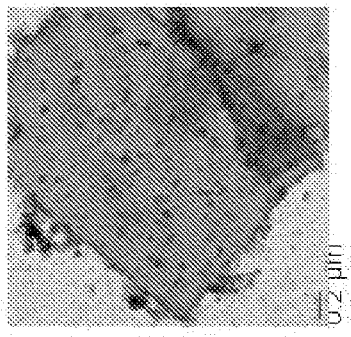
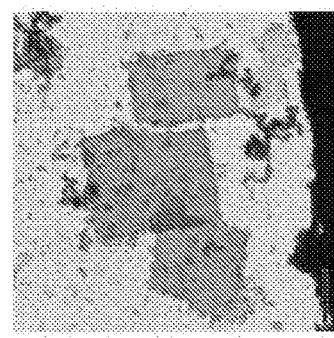
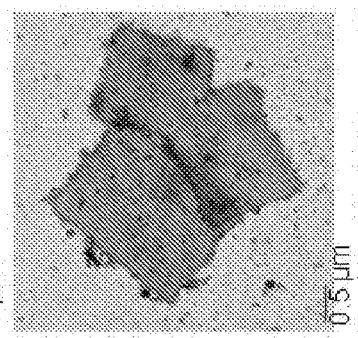
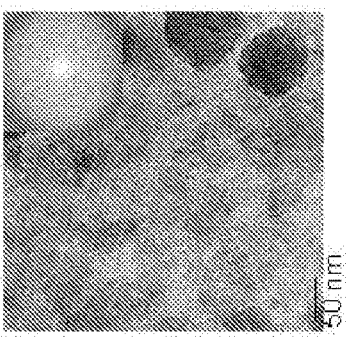

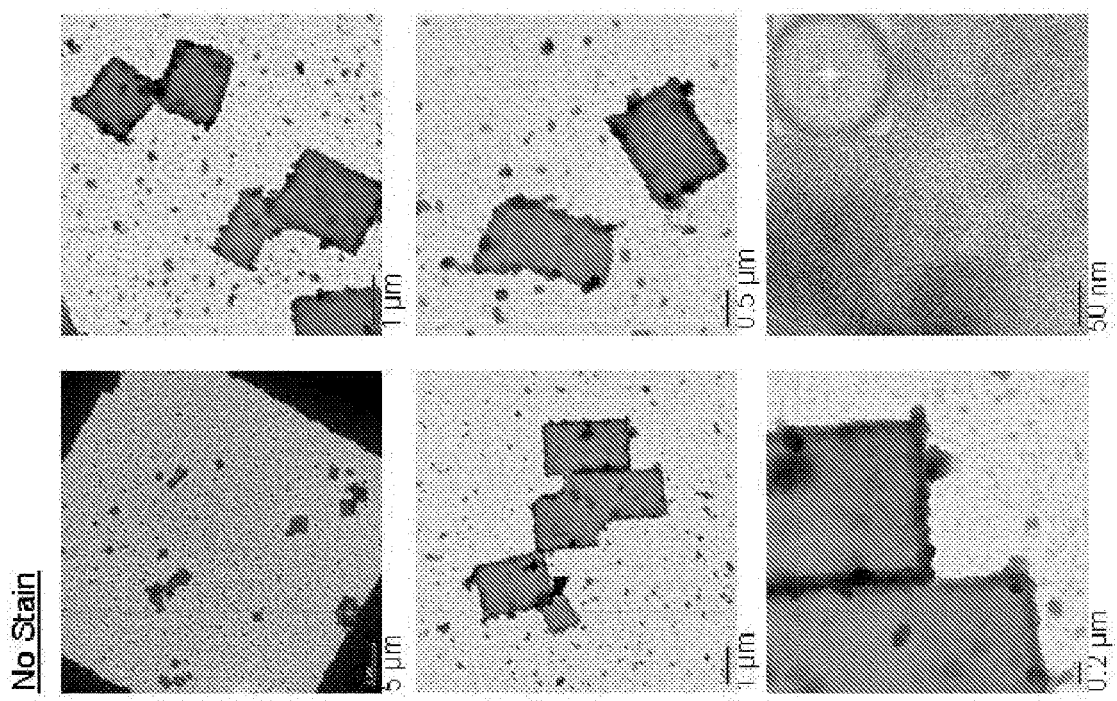
FIG. 26  RhuA-C98 Sheet on Grid Followed by Addition of Maleimido-Au for Overnight

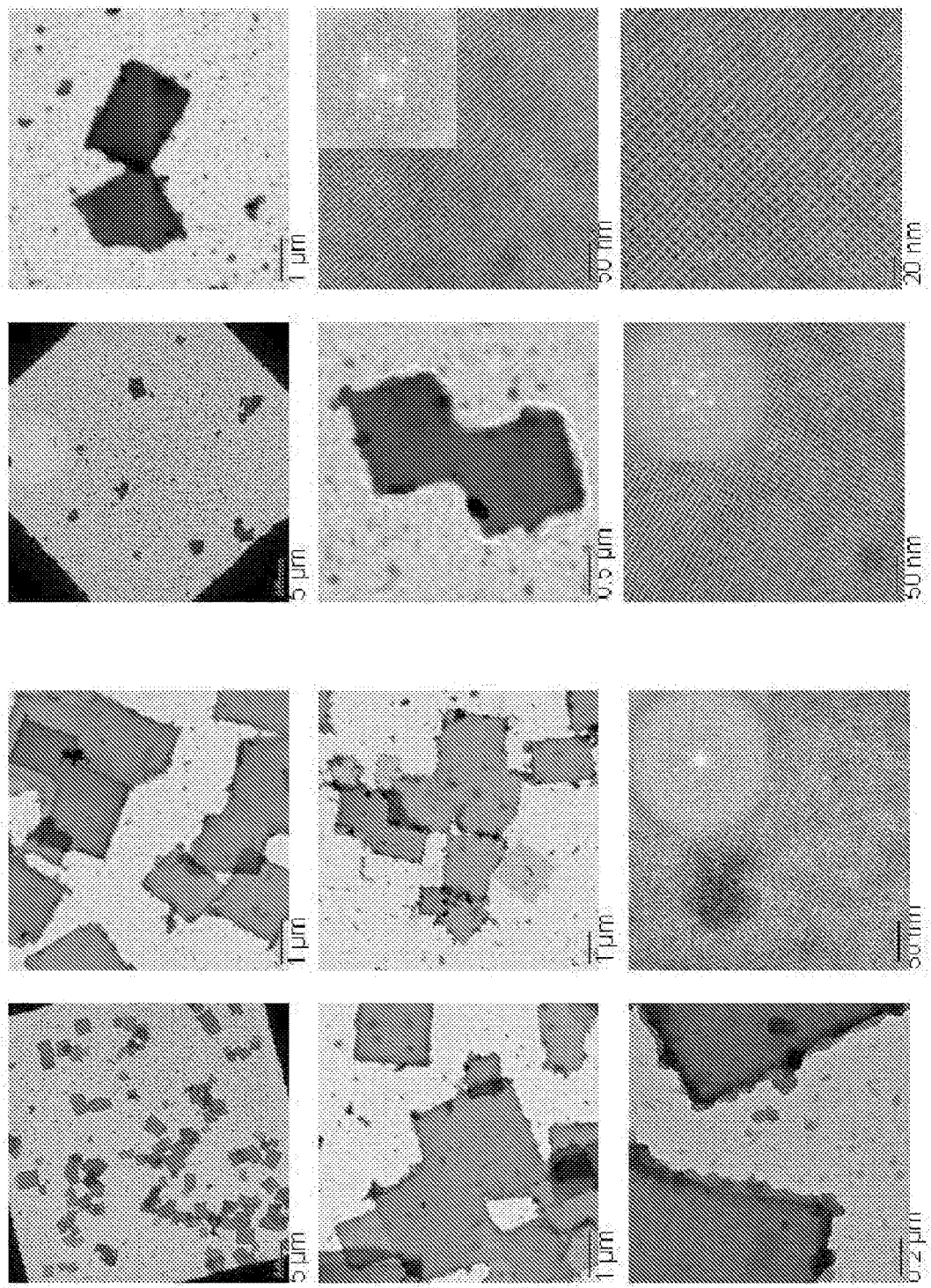
FIG. 27 RhuA-C98 Sheet on Grid Followed by Addition of Maleimido-Au for 3 Hours (Repeat)

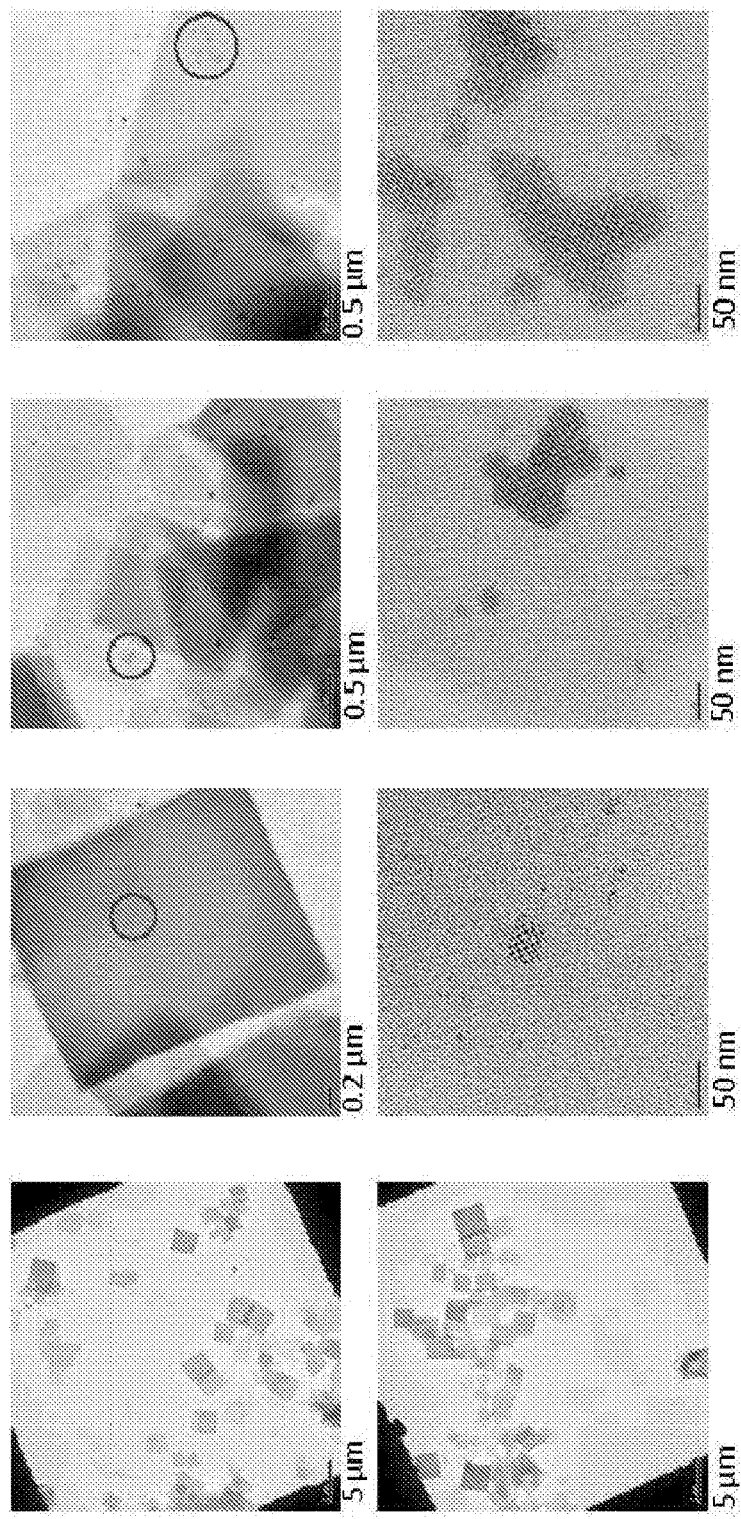
FIG. 28 RhuA-C98 Sheet: Stock Sample with HAuCl₄

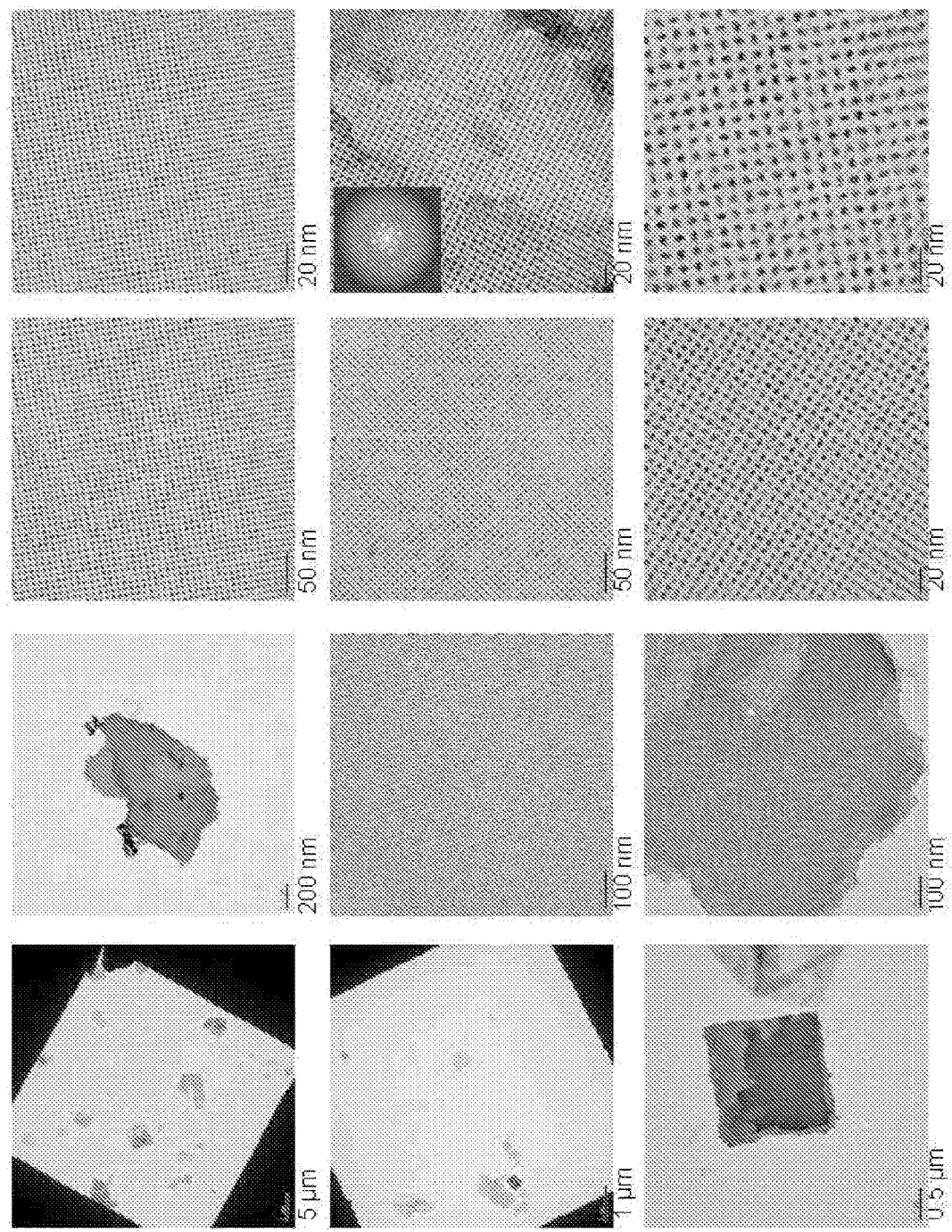
FIG. 29  RhuA-C98 (4uL) added into 0.5 mM HAuCl$_4$ in 5 mM NaPi pH 7.2 6 days then added 5 mM bME for 1 day

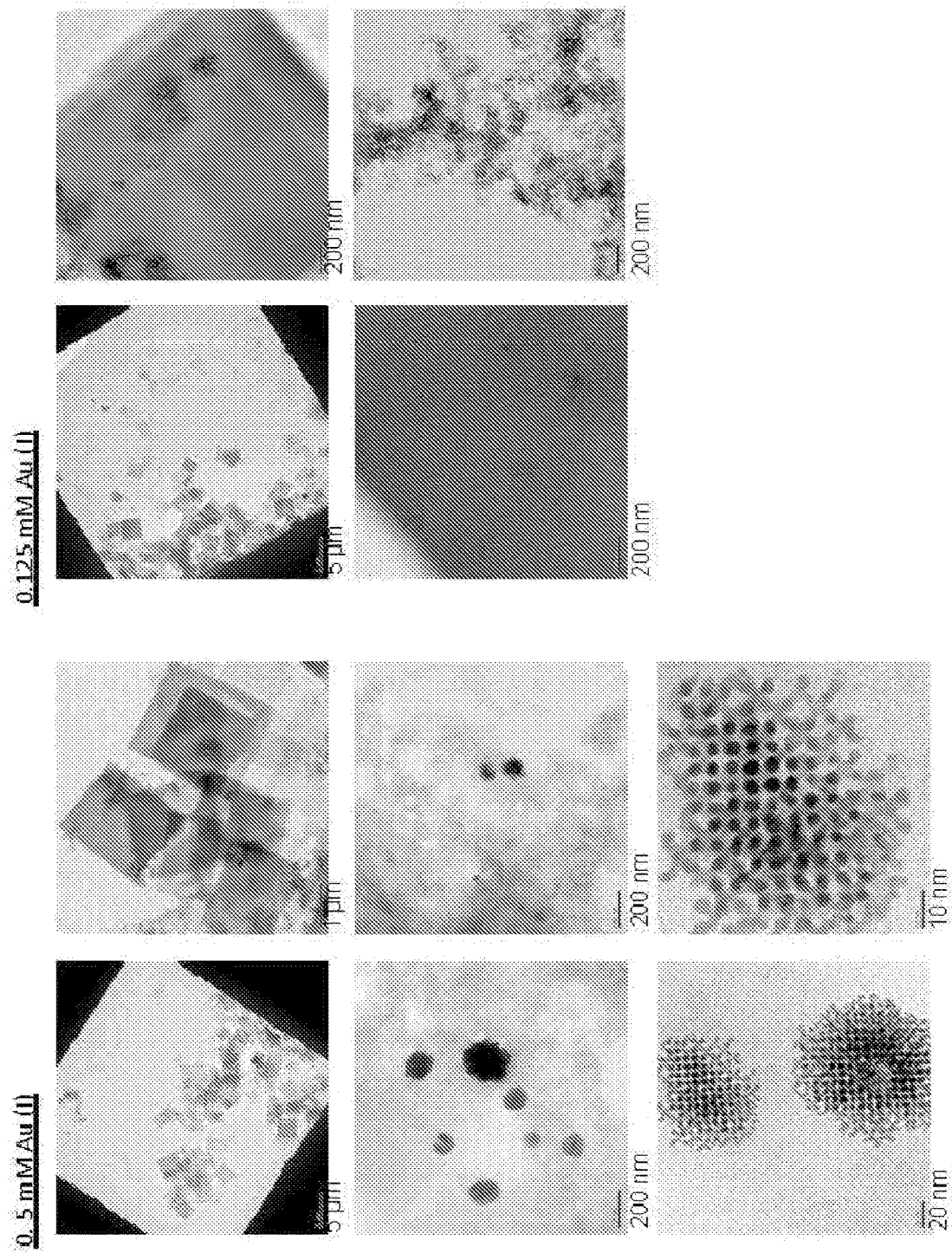
FIG. 30 RhuA-C98 (4uL) added into 100 μL of Au(I) (HAuCl₄ + 2 eq thiodiethanol) in 5 mM NaPi, pH 7.2 for 4 days

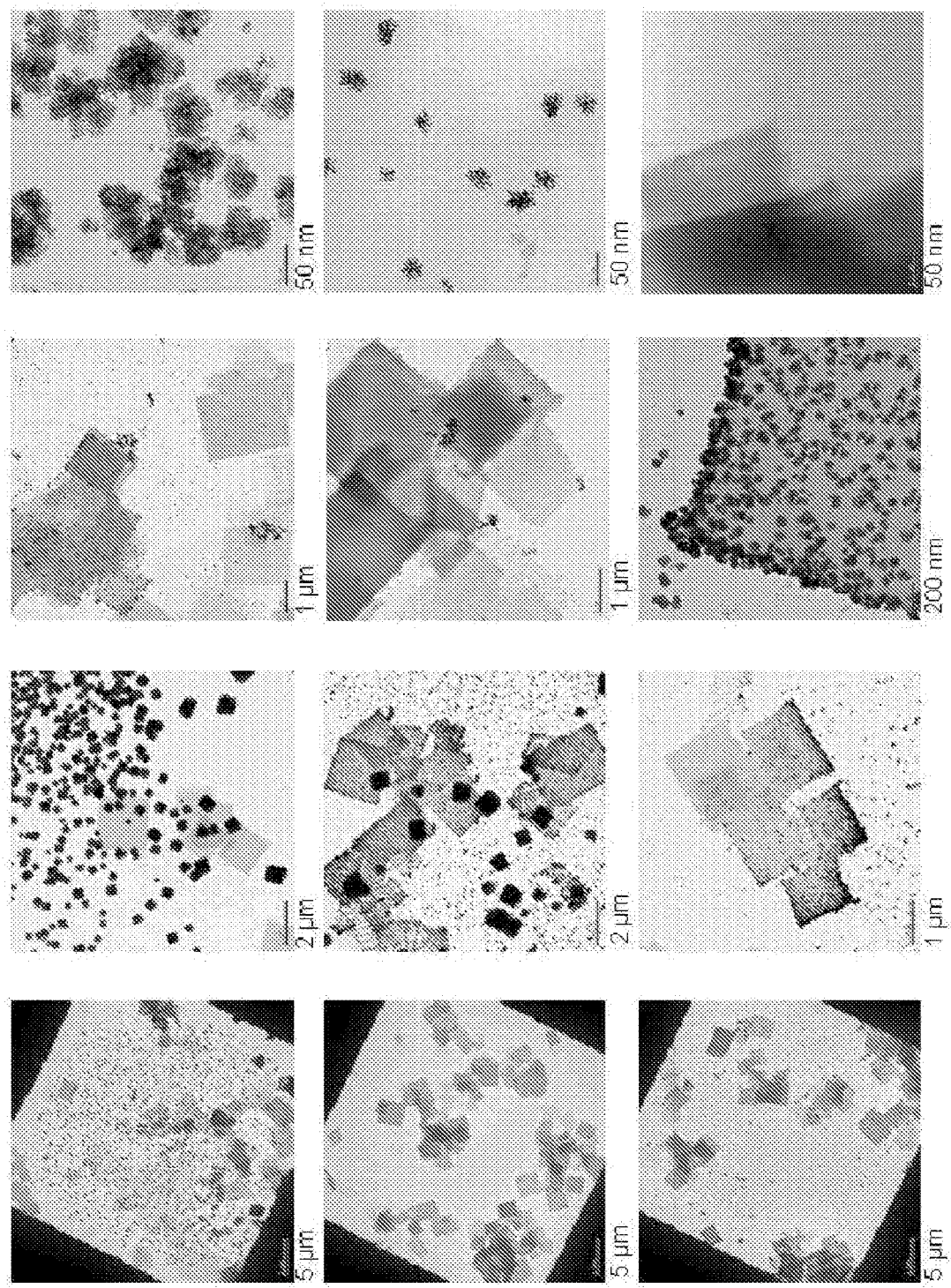
FIG. 32 RhuA-C98 sheet/HAuCl4 on grids followed by HAuCl4/K2CO3/NaBH4 in NaPi, pH 7.2 for 2 hours

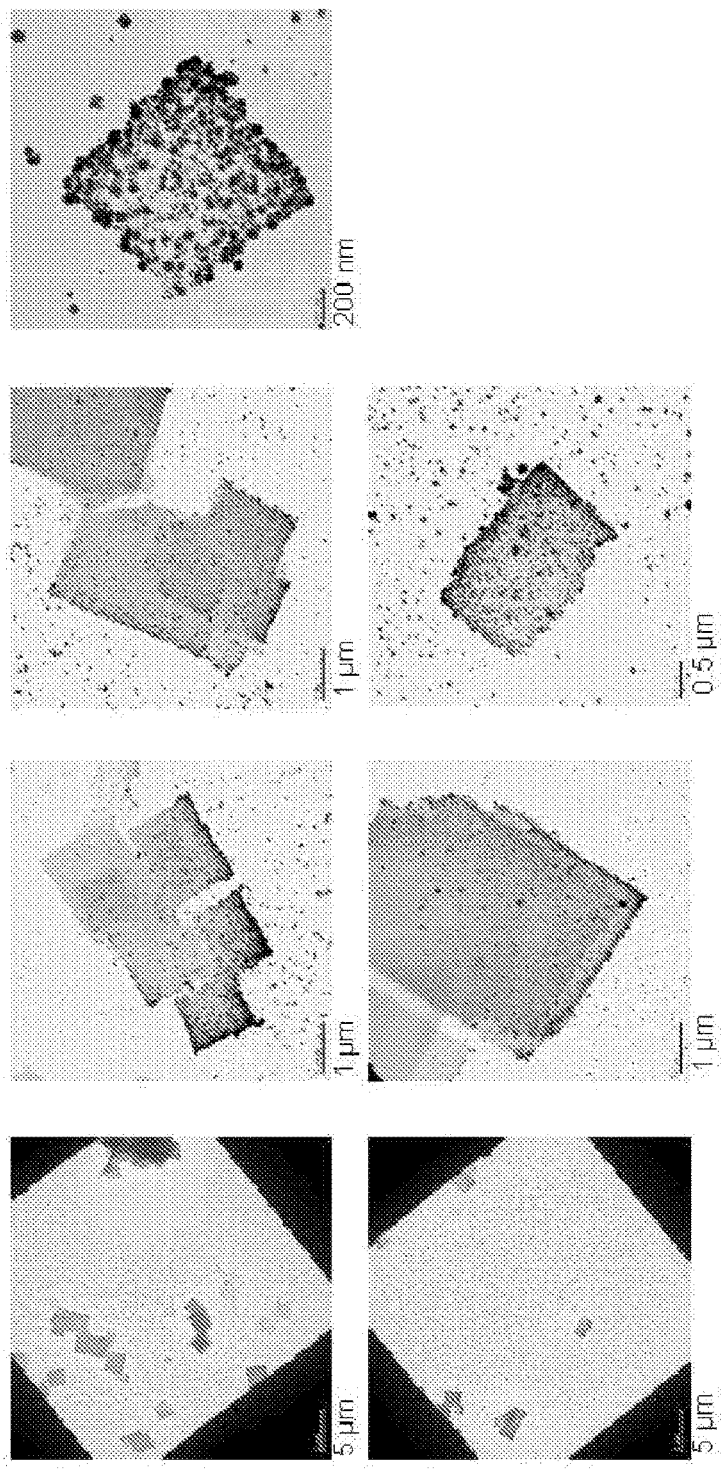

FIG. 33  RhuA-C98 sheet/HAuCl4 on grids followed by HAuCl4/K2CO3/Formaldehyde in NaPi pH 7.2 for 2 hours Other conditions:
Sheet/HAuCl4/K2CO3 for 1day on grid; then grids into HAuCl4/K2CO3/NaBH4 for 2hours
Sheet/HAuCl4/K2CO3 for 1day on grid; then grid into HAuCl4/K2CO3/formaldehyde for 2hours
Sheet/HAuCl4/K2CO3 for 1day then mixed formaldehyde for 2hours
Sheet/HAuCl4/K2CO3 for 1day then mixed NaBH4 for 2hours
Sheet/HAuCl4 mixed 10percent formaldehyde for 2hours
Mix HAuCl4/K2CO3 for 2hr then added sheet for 1day; then mixed NaBH4 for 2hours
Sheet/HAuCl4 mixed NaBH4 for 2hours

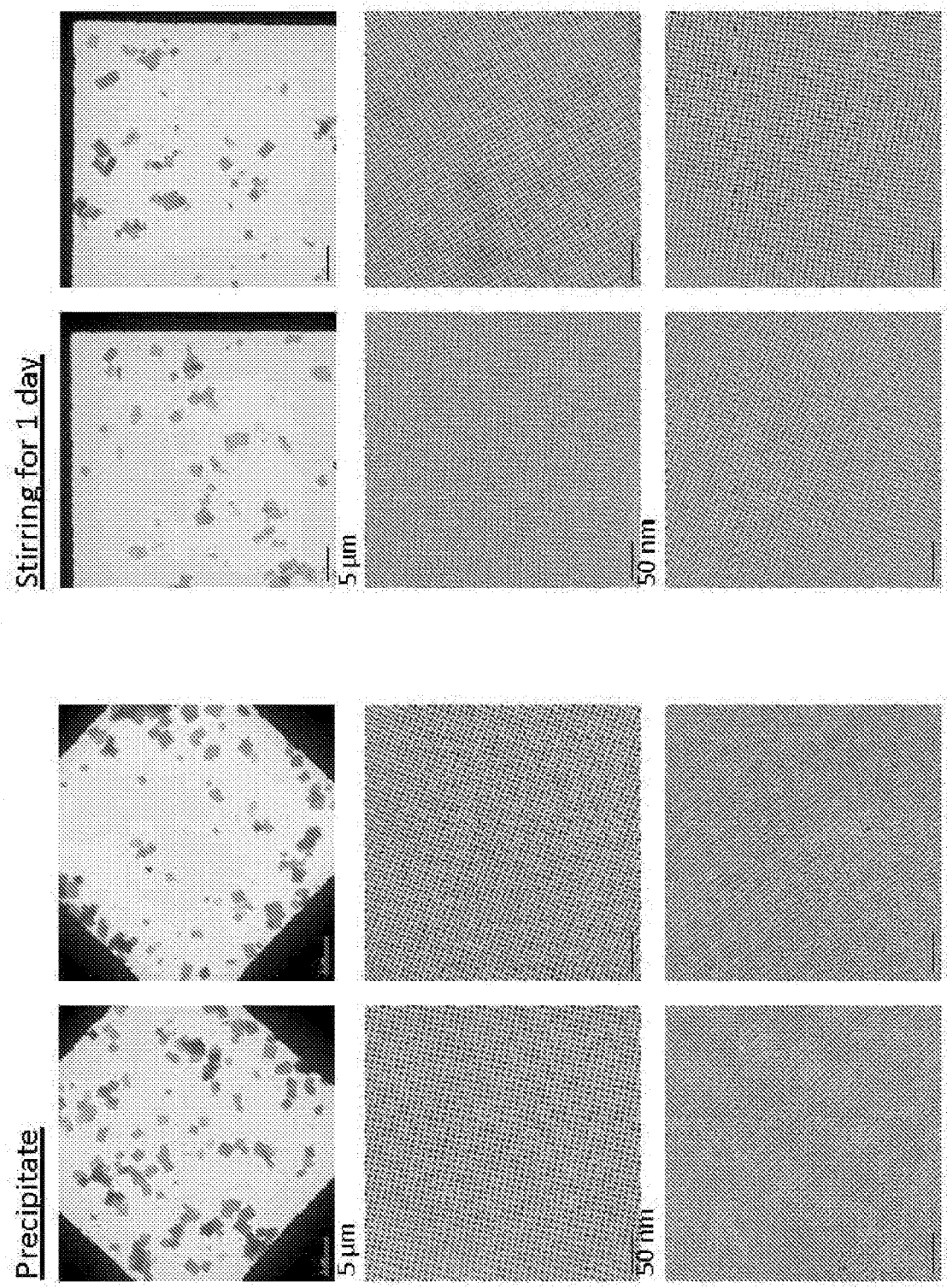
FIG. 34 RhuA-C98 Sheet: Addition of 200 µM Iodo-Fl

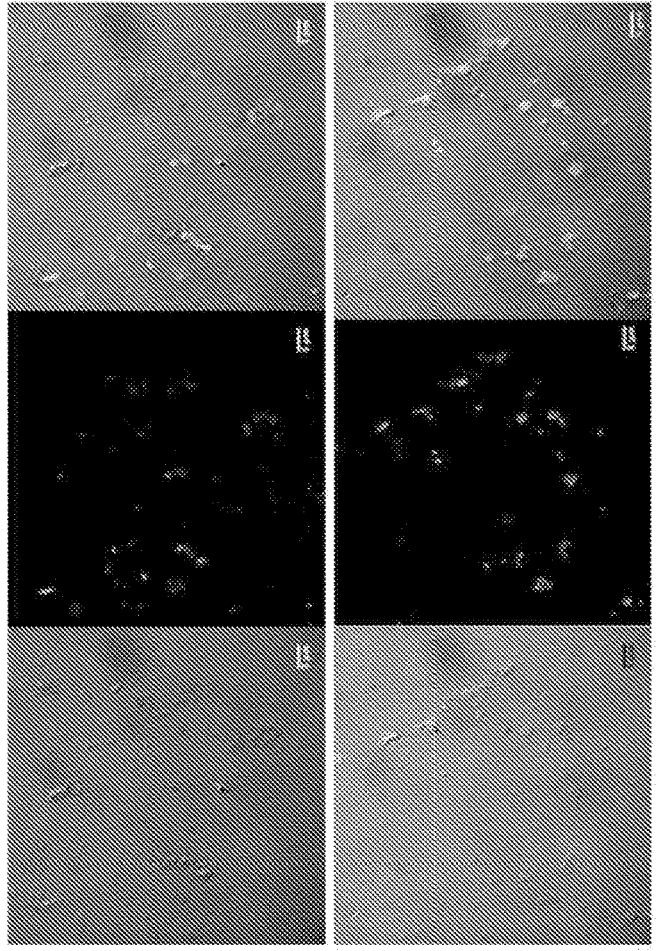
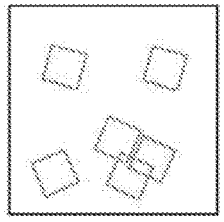
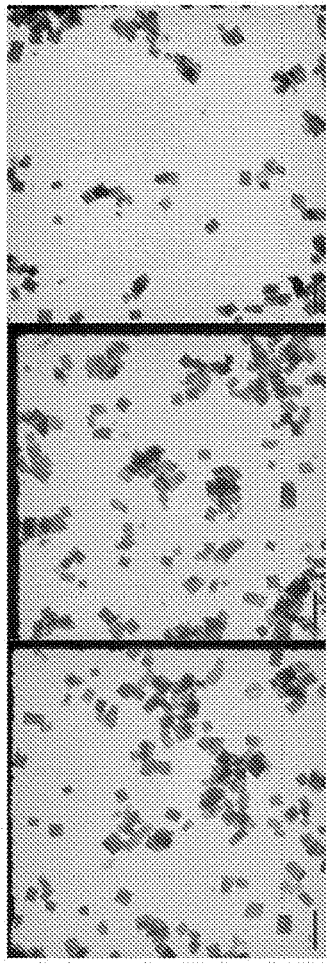
FIG. 35 RhuA-C98 Sheet: Addition of 200 μM Iodo-Fl
To see if outside of protein sheet thiols are able to protect by iodoFl in solution as of maleimido-Au (on grid).
Expectation:
Result: Inside of sheet was also fluorescent...
Next: Analysis of this sheet

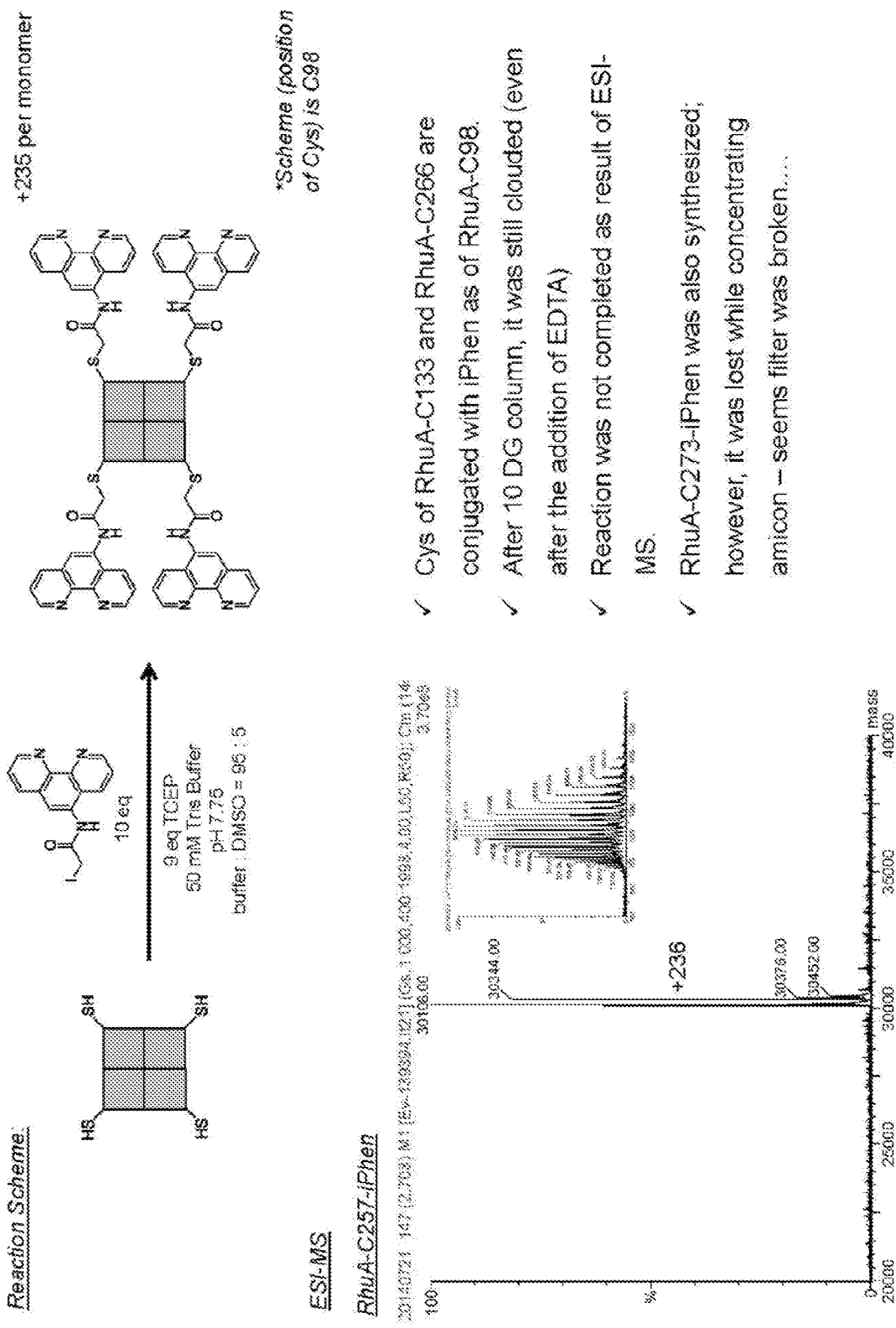
FIG. 36 Synthesis of RhuA-Cys-iPhen

RhuA-C98-iphen (100 μM) with 2eqNiCl$_2$ in 20 mM Mes at pH5.5 after 1day

FIG. 40 RhuA-C98-iphen (100 μM) with 2 eq NiCl$_2$ in 20 mM Mes at pH5.5 after 12 days
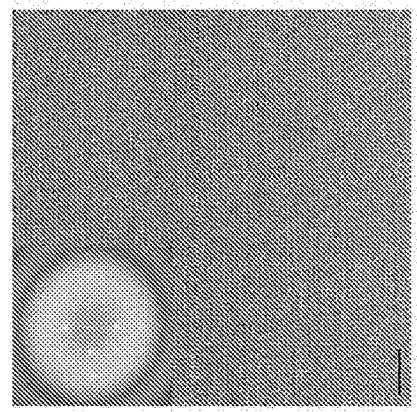
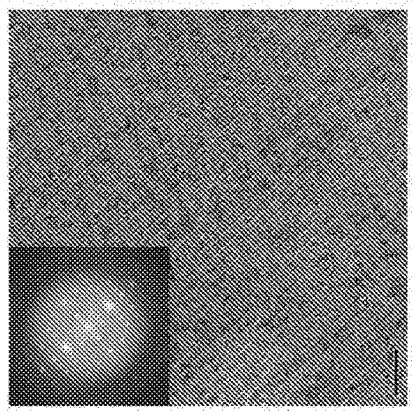
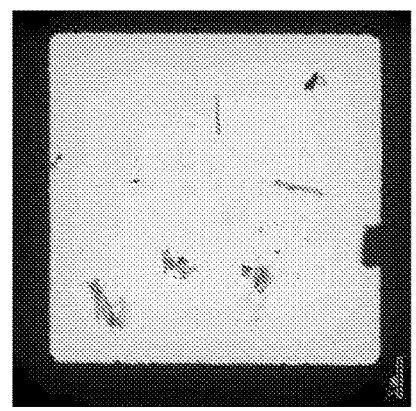
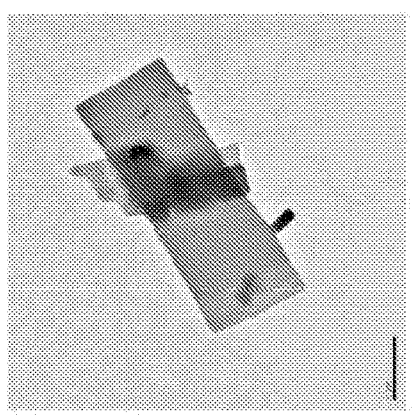
with additional of 4 eq Imidazole
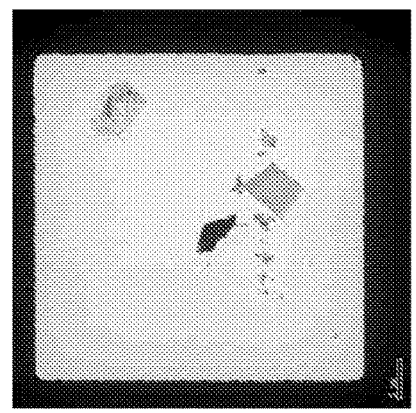
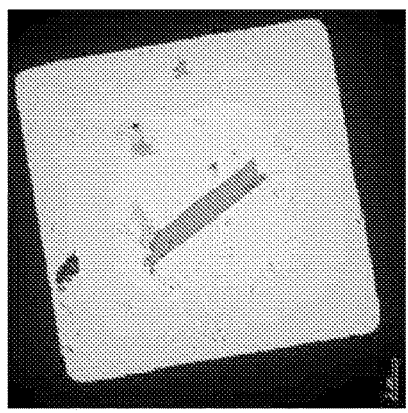
Samples were prepared on July 21
TEM samples were prepared on Aug 2nd

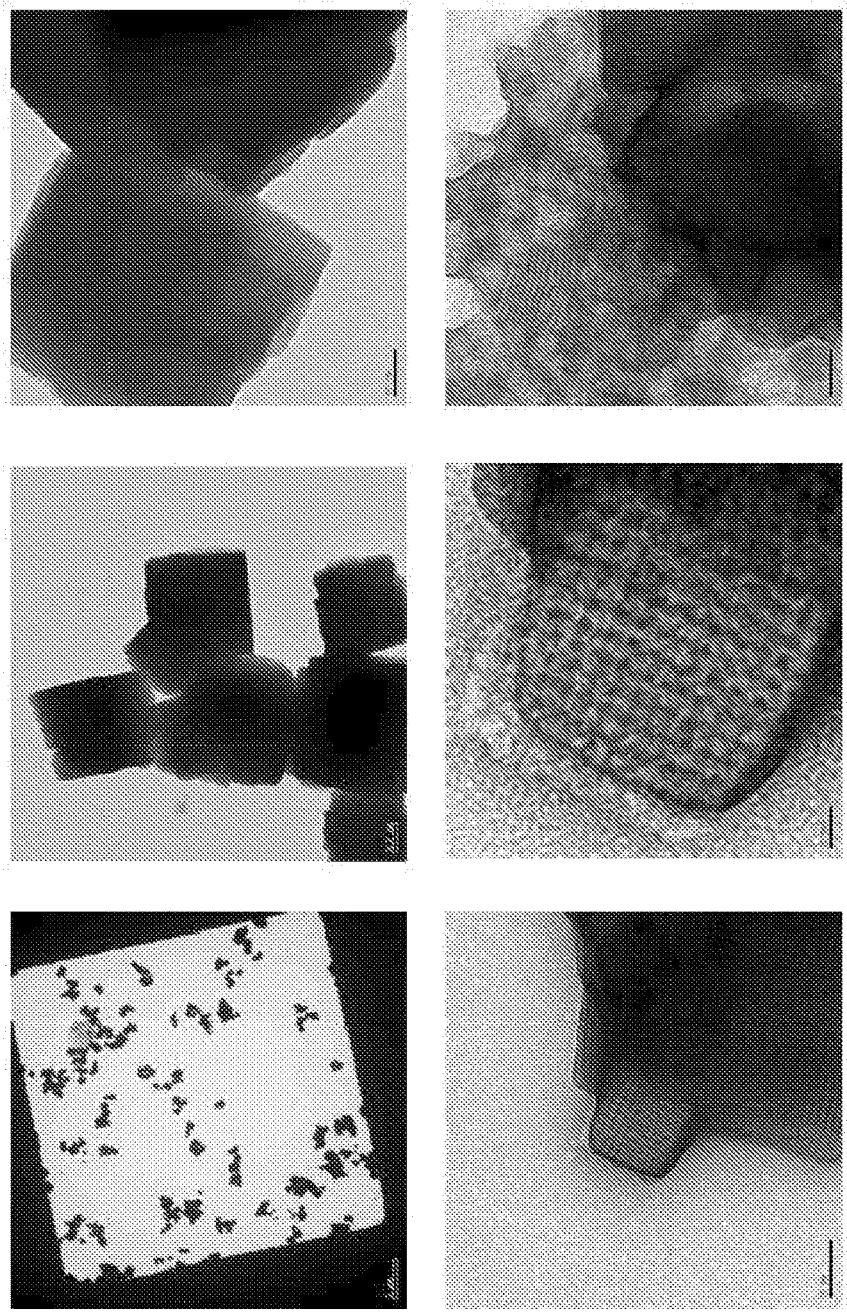
FIG. 41 RhuA-C133-iphen (100 uM) with 2 eq NiCl₂ in 20 mM Mes at pH5.5 after 12 days
w/ 2eq Zinc
Samples were prepared on July 21.
TEM samples were prepared on Aug 2nd

*FIG. 42* Photoswitchable Protein Assembly Via Azo-CD
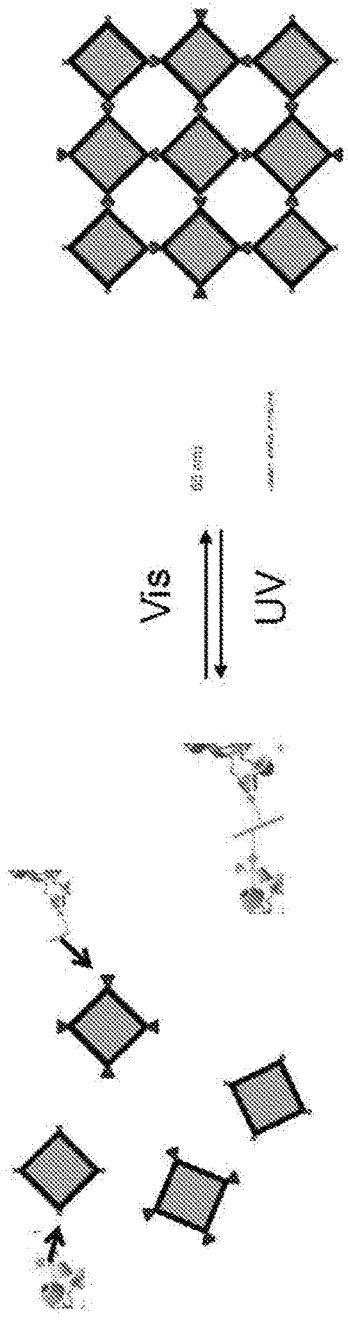
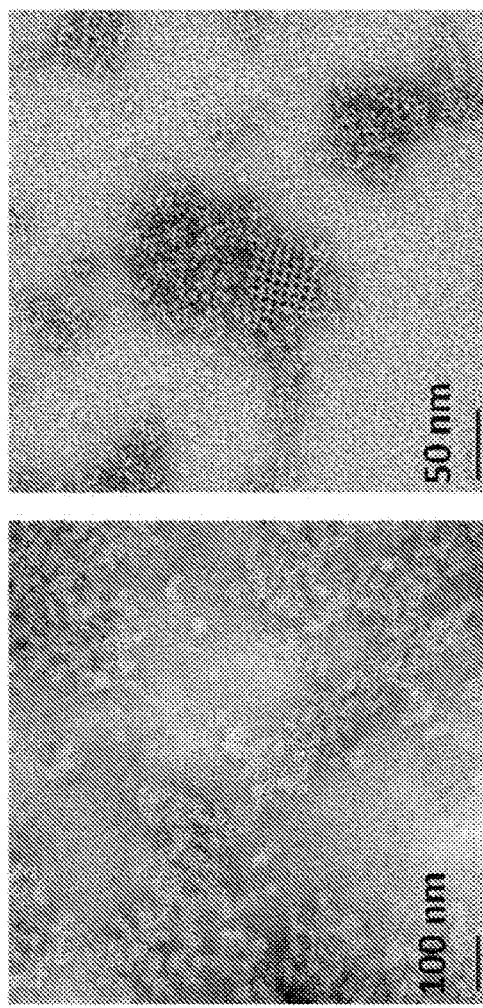
Scheme
- Still reaction was incomplete, I took partial solution and removed small molecules, then mixed C98-CD and C98-Azo
Found two partial sheet formation.
It is possible to be C98 sheet since reaction of RhuA-Azo was not complete.
~100 uM each

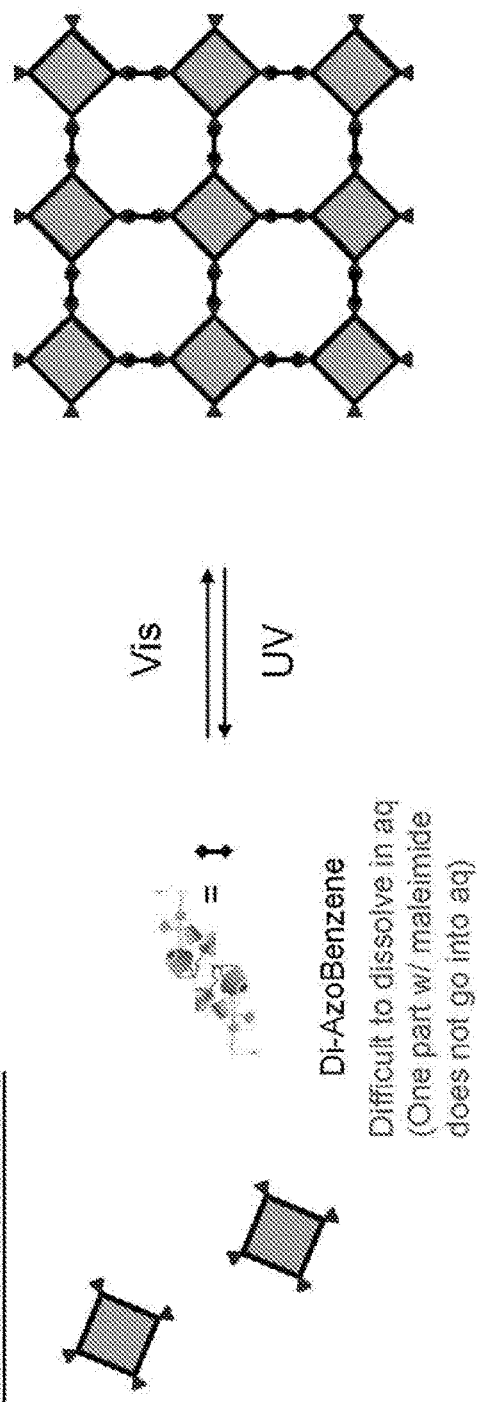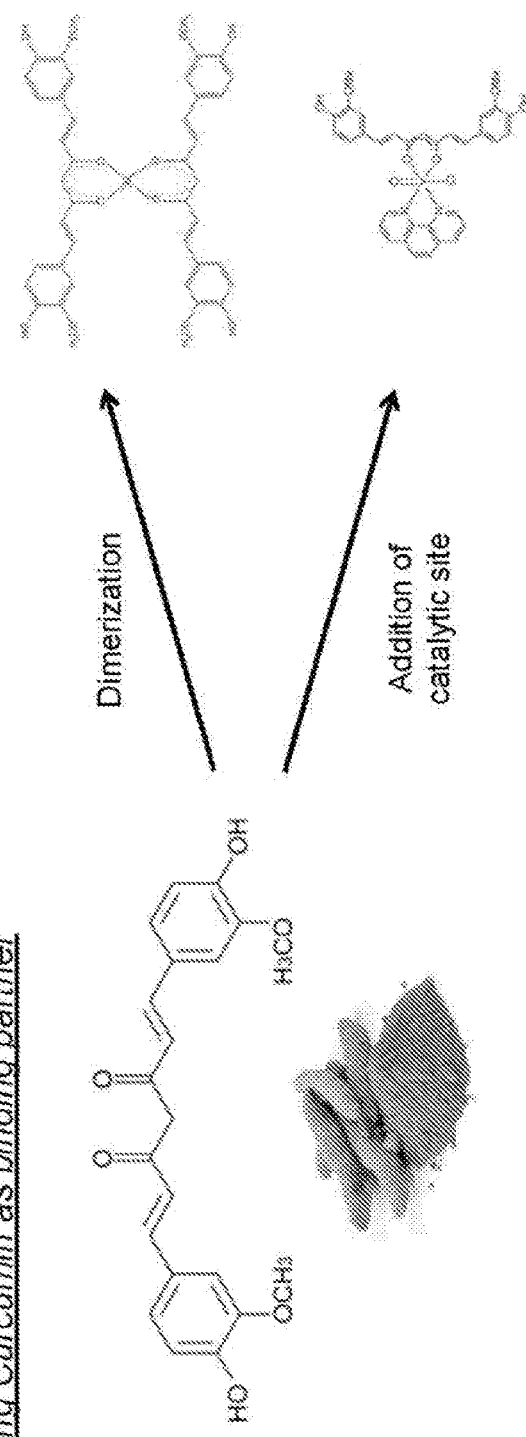
FIG. 43

FIG. 44  Protein Assembly Via Small Molecule - 1 mM Curcumin After 1 hr

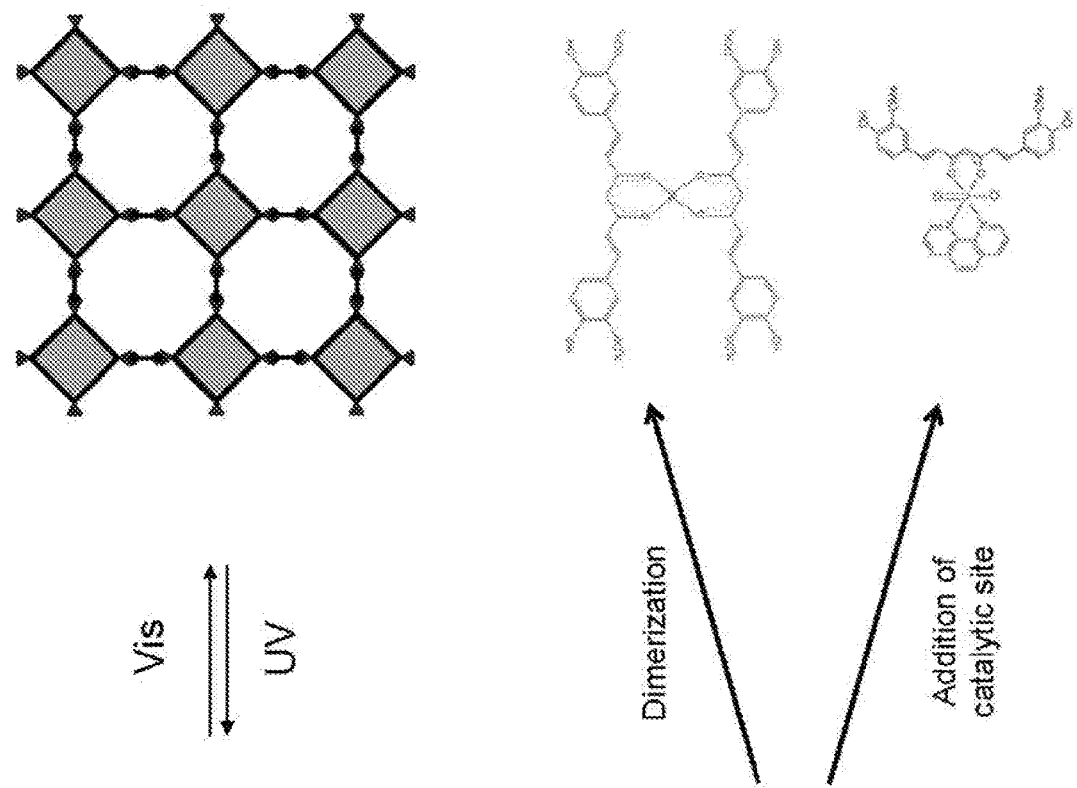
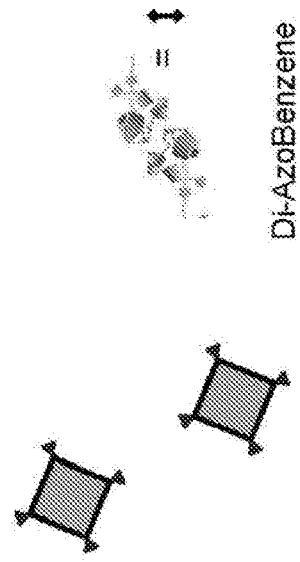
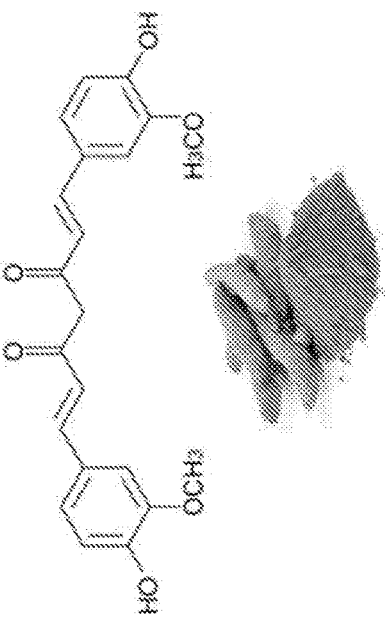
FIG. 46

FIG. 47 Protein Assembly Via Small Molecule - 100 μM Curcumin After 1 hr

FIG. 49  Protein Assembly Via Small Molecule – 1 mM Curcumin After 3 Days

FIG. 50  2nd Trial: Protein Assembly Via Small Molecule - 1 mM Curcumin After 1 hr FIG. 52  Protein Assembly Via Small Molecule – 5 mM Curcumin After 3 Days FIG. 53  2nd Trial: Protein Assembly Via Small Molecule – 5 mM Curcumin After 1 hr FIG. 55 RhuA-C98-HisTag (100 µM) in 20 mM MOPS at pH 7 in Reduced Condition After 5 Days

FIG. 57 Assembly of $^{C98}$RhuA-Pd4 (125 μM) under various conditions (after 1 day w/ shake)

RhuA

MQNITQSMFVQGMIKATTDAWLKGWDERNGGNITLRLDDADIAPYHDNFHQQPRYIPLSQPMPL
LANTPFIVTGSGKFFRNVQLDPAANLGIVKVDSCGAGYHILWGLTNEAVPTSELPAHFLSHSERIKATN
GKDRVIMHCHATNLIALTYVLENDTAVFTROLWEGSTECLVVFPDGVGILPMMVPGTDAIGQATAQ
EMQKHSLVLWPFHGVFGSGPTLDETFGLIDTAEKSAQVLVKVYSMGGMKQTISREELIALGKRFGVT
PLASALALGSGSGTSNAVHPTLRHL

← $^{C98}$RhuA

← Pd4 peptide

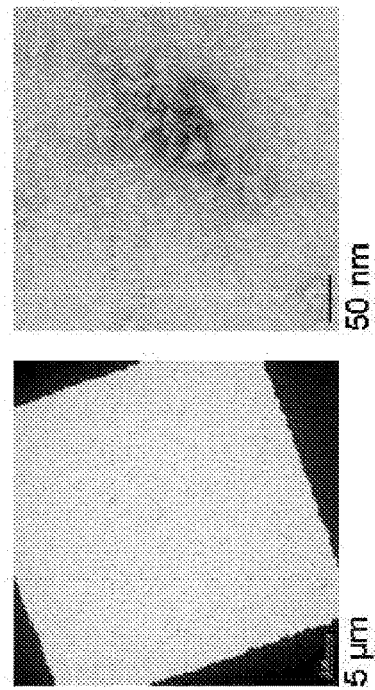

10 mM Tris pH 7.5, 10 mM βME, no ZnCl$_2$ 50 nm / 5 μm

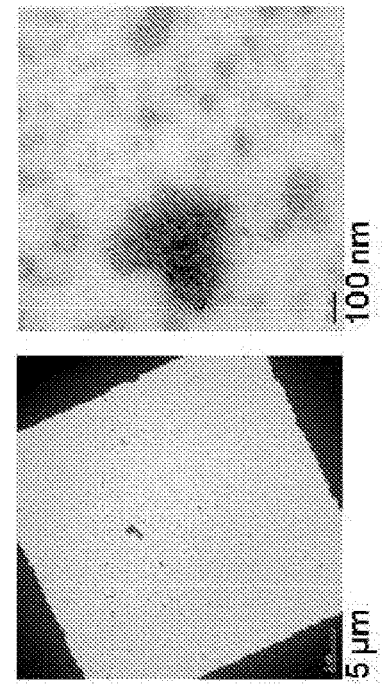

20 mM Mes pH 5.5, 10 mM βME, no ZnCl$_2$ 100 nm / 5 μm

Immediately became cloudy

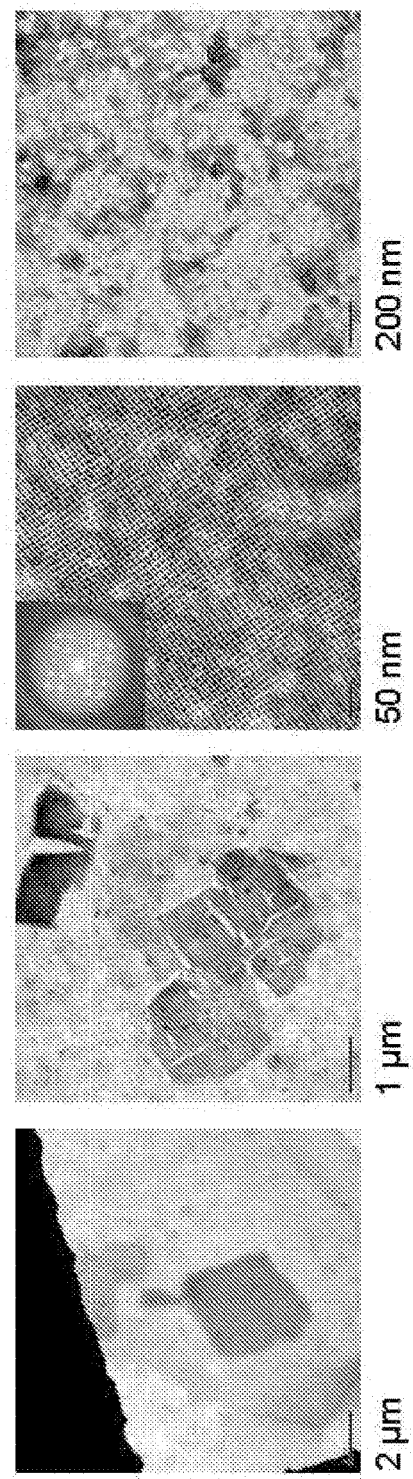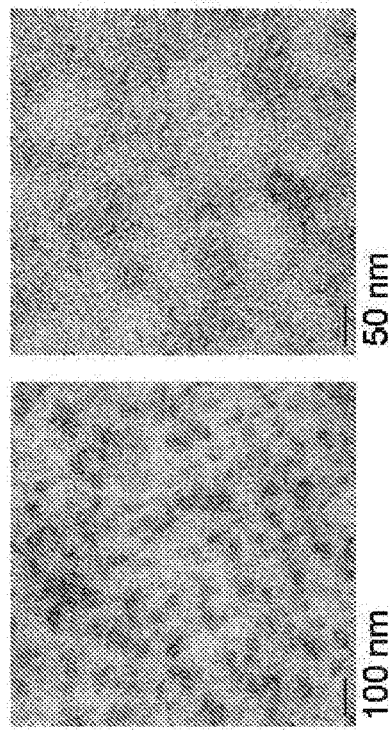
FIG. 58 Assembly of C98RhuA-Pd4 (125 μM) under various conditions (after 1 day w/ shake)

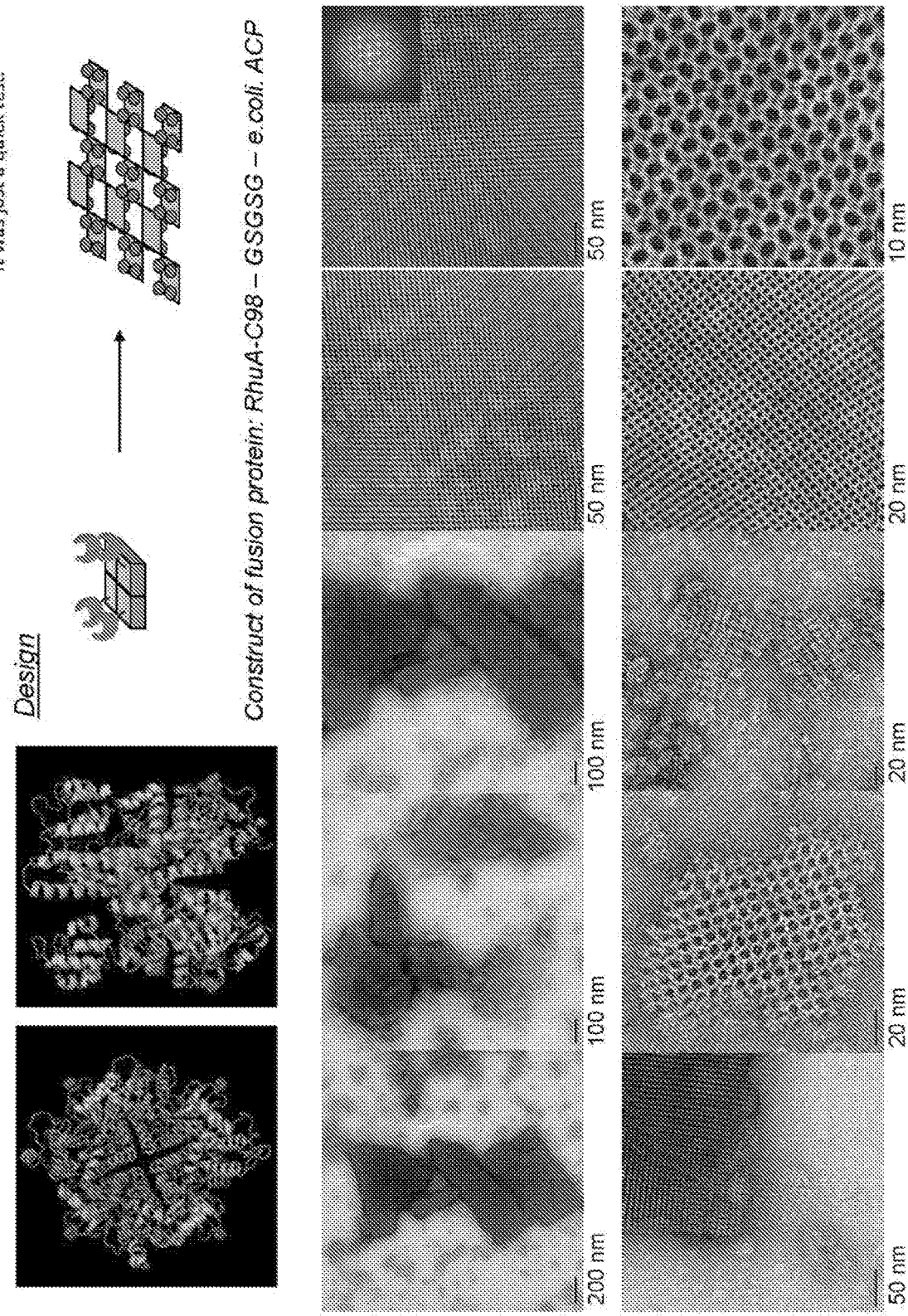
FIG. 59 Fusion Protein 2D Assemblies: RhuA-ACP – Most up-to-date Data

| | C98RhuA | H63/H98RhuA | F88/C98RhuA |
|---|---|---|---|
| No. of images used for analysis | 43 (12) | 50 (44) | 33 (13) |
| Unit cell dimensions a = b (Å) | 114 ± 3 | 91 ± 3 | 115 ± 1 |
| γ (°) | 90 | 90 | 90 |
| Plane-group symmetry | p4₂2 | p4 | p4₂2 |

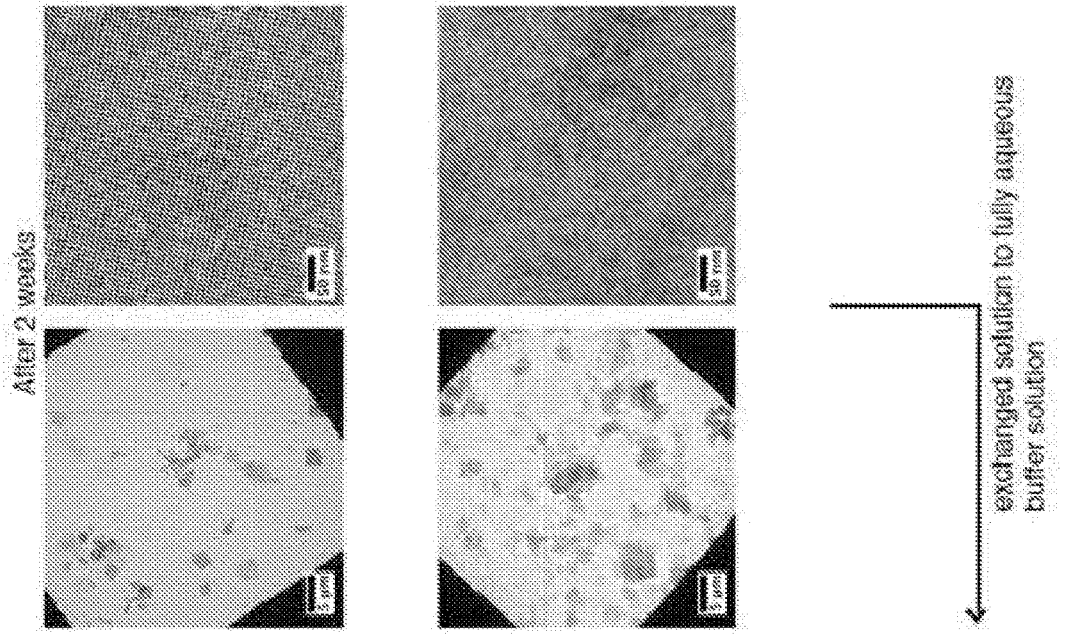
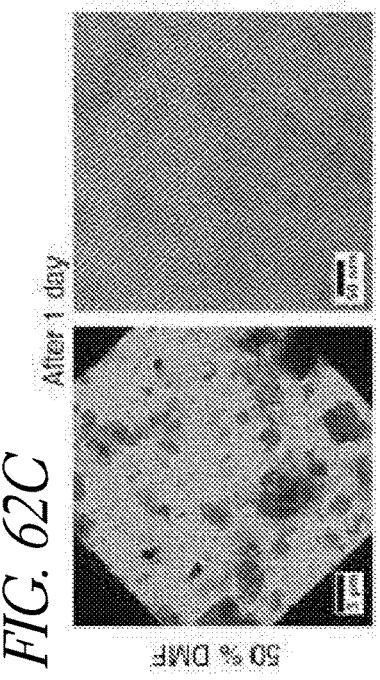
FIG. 62C
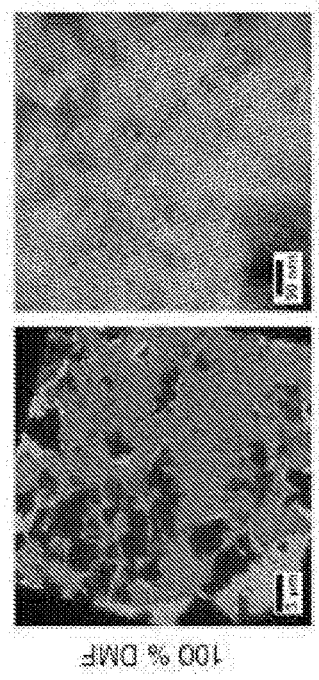
FIG. 62D
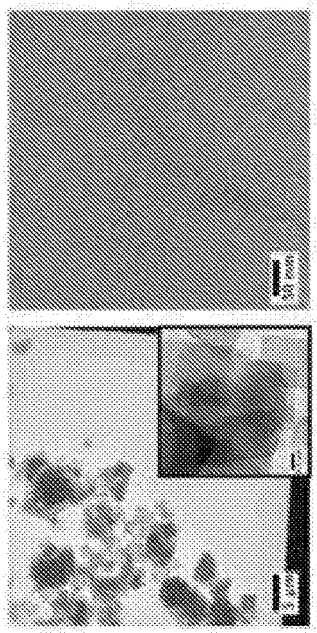
FIG. 62E

RhuA-C98-iphen (100 μM) with 2eq NiSO$_4$ in 20 mM Mes at pH5.5 after 1day
Sheet observed
2dx

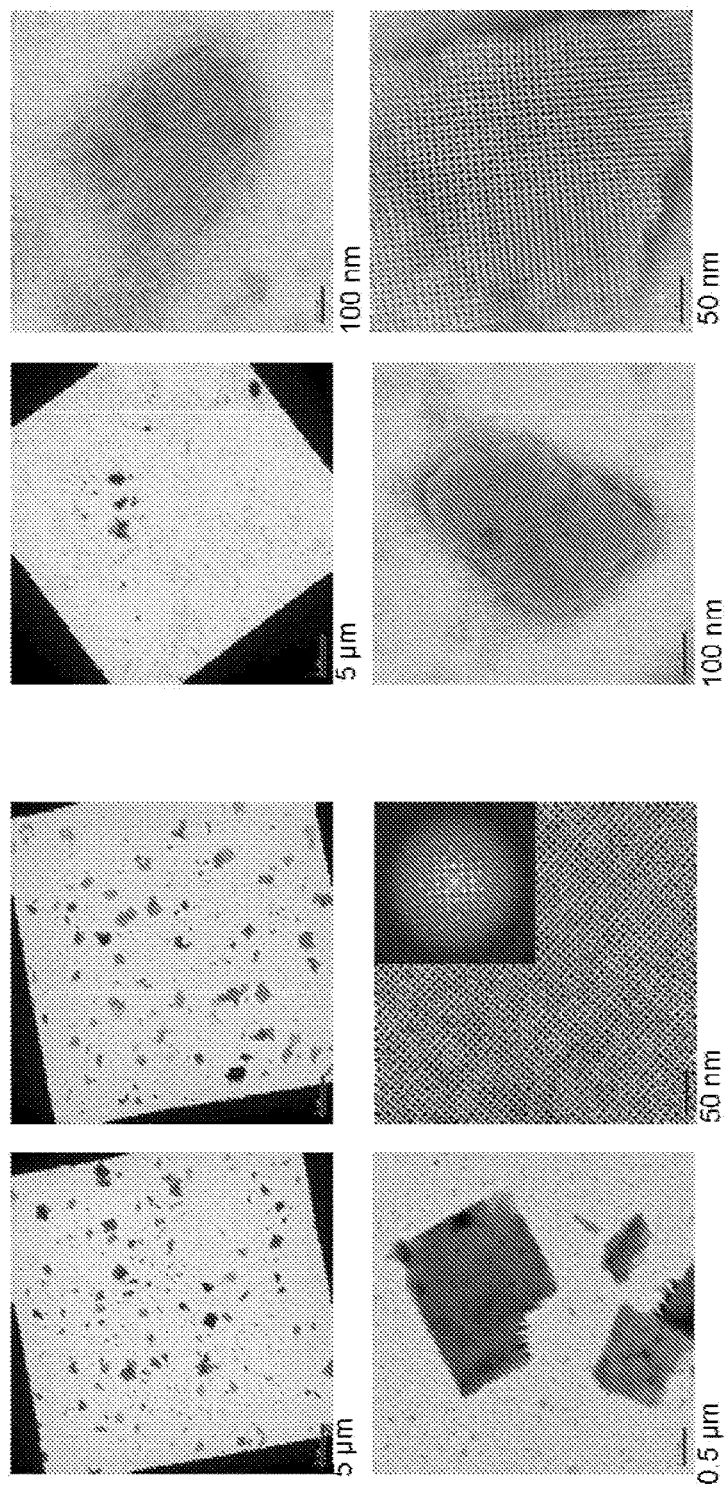
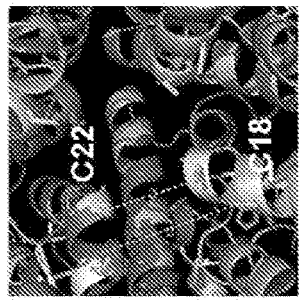
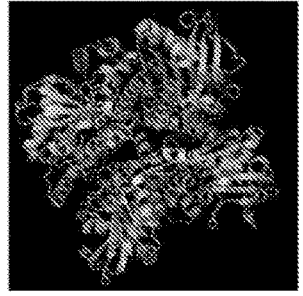
FIG. 64

SEQUENCE LISTING

```
<160> NUMBER OF SEQ ID NOS: 26

<210> SEQ ID NO 1
<211> LENGTH: 274
<212> TYPE: PRT
<213> ORGANISM: E. coli

<400> SEQUENCE: 1

Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
                20                  25                  30

Leu Thr Leu Arg Leu Asp Asp Ala Asp Ile Ala Pro Tyr His Asp Asn
            35                  40                  45

Phe His Gln Gln Pro Arg Tyr Ile Pro Leu Ser Gln Pro Met Pro Leu
        50                  55                  60

Leu Ala Asn Thr Pro Phe Ile Val Thr Gly Ser Gly Lys Phe Phe Arg
65                  70                  75                  80

Asn Val Gln Leu Asp Pro Ala Ala Asn Leu Gly Ile Val Lys Val Asp
                85                  90                  95

Ser Asp Gly Ala Gly Tyr His Ile Leu Trp Gly Leu Thr Asn Glu Ala
            100                 105                 110

Val Pro Thr Ser Glu Leu Pro Ala His Phe Leu Ser His Cys Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Glu
            180                 185                 190

Ile Gly Gln Ala Thr Ala Gln Glu Met Gln Lys His Ser Leu Val Leu
        195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240
```

```
Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
            260                 265                 270

Ala Leu

<210> SEQ ID NO 2
<211> LENGTH: 274
<212> TYPE: PRT
<213> ORGANISM: Artificial Sequence
<220> FEATURE:
<223> OTHER INFORMATION: Modified RhuA protein

<400> SEQUENCE: 2

Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45

Phe His Gln Gln Pro Arg Tyr Ile Pro Leu Ser Gln Pro Met Pro Leu
    50                  55                  60

Leu Ala Asn Thr Pro Phe Ile Val Thr Gly Ser Gly Lys Phe Phe Arg
65                  70                  75                  80

Asn Val Gln Leu Asp Pro Ala Ala Asn Leu Gly Ile Val Lys Val Asp
                85                  90                  95

Ser Cys Gly Ala Gly Tyr His Ile Leu Trp Gly Leu Thr Asn Glu Ala
            100                 105                 110

Val Pro Thr Ser Glu Leu Pro Ala His Phe Leu Ser His Ser Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Glu
            180                 185                 190

Ile Gly Gln Ala Thr Ala Gln Glu Met Gln Lys His Ser Leu Val Leu
        195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
            260                 265                 270

Ala Leu

<210> SEQ ID NO 3
<211> LENGTH: 274
<212> TYPE: PRT
<213> ORGANISM: Artificial Sequence
<220> FEATURE:
<223> OTHER INFORMATION: Modified RhuA protein
```

<400> SEQUENCE: 3

```
Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45

Phe His Gln Gln Pro Arg Tyr Ile Pro Leu Ser Gln Pro Met Pro Leu
    50                  55                  60

Leu Ala Asn Thr Pro Phe Ile Val Thr Gly Ser Gly Lys Phe Phe Arg
65                  70                  75                  80

Asn Val Gln Leu Asp Pro Ala Ala Asn Leu Gly Ile Val Lys Val Asp
                85                  90                  95

Ser Cys Gly Ala Gly Tyr His Ile Leu Trp Gly Leu Thr Asn Glu Ala
            100                 105                 110

Val Pro Thr Ser Glu Leu Pro Ala His Phe Leu Ser His Ser Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Ala
            180                 185                 190

Ile Gly Gln Ala Thr Ala Gln Glu Met Gln Lys His Ser Leu Val Leu
        195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
            260                 265                 270

Ala Leu
```

<210> SEQ ID NO 4
<211> LENGTH: 274
<212> TYPE: PRT
<213> ORGANISM: Artificial Sequence
<220> FEATURE:
<223> OTHER INFORMATION: Modified RhuA protein

<400> SEQUENCE: 4

```
Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45

Phe His Gln Gln Pro Arg Tyr Ile Pro Leu Ser Gln Pro Met His Leu
    50                  55                  60

Leu Ala Asn Thr Pro Phe Ile Val Thr Gly Ser Gly Lys Phe Phe Arg
65                  70                  75                  80
```

```
Asn Val Gln Leu Asp Pro Ala Ala Asn Leu Gly Ile Val Lys Val Asp
                85                  90                  95

Ser His Gly Ala Gly Tyr His Ile Leu Trp Gly Leu Thr Asn Glu Ala
            100                 105                 110

Val Pro Thr Ser Glu Leu Pro Ala His Phe Leu Ser His Ser Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Ala
            180                 185                 190

Ile Gly Gln Ala Thr Ala Gln Glu Met Gln Lys His Ser Leu Val Leu
        195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
            260                 265                 270

Ala Leu

<210> SEQ ID NO 5
<211> LENGTH: 274
<212> TYPE: PRT
<213> ORGANISM: Artificial Sequence
<220> FEATURE:
<223> OTHER INFORMATION: Modified RhuA protein

<400> SEQUENCE: 5

Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45

Phe His Gln Gln Pro Arg Tyr Ile Pro Leu Ser Gln Pro Met Pro Leu
    50                  55                  60

Leu Ala Asn Thr Pro Phe Ile Val Thr Gly Ser Gly Lys Phe Phe Arg
65                  70                  75                  80

Asn Val Gln Leu Asp Pro Ala Phe Asn Leu Gly Ile Val Lys Val Asp
                85                  90                  95

Ser Cys Gly Ala Gly Tyr His Ile Leu Trp Gly Leu Thr Asn Glu Ala
            100                 105                 110

Val Pro Thr Ser Glu Leu Pro Ala His Phe Leu Ser His Ser Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160
```

```
Phe Thr Arg Gln Leu Trp Glu Gly Ser Thr Glu Cys Leu Val Val Phe
                165                 170                 175
Pro Asp Gly Val Gly Ile Leu Pro Trp Met Val Pro Gly Thr Asp Ala
            180                 185                 190
Ile Gly Gln Ala Thr Ala Gln Glu Met Gln Lys His Ser Leu Val Leu
        195                 200                 205
Trp Pro Phe His Gly Val Phe Gly Ser Gly Pro Thr Leu Asp Glu Thr
    210                 215                 220
Phe Gly Leu Ile Asp Thr Ala Glu Lys Ser Ala Gln Val Leu Val Lys
225                 230                 235                 240
Val Tyr Ser Met Gly Gly Met Lys Gln Thr Ile Ser Arg Glu Glu Leu
                245                 250                 255
Ile Ala Leu Gly Lys Arg Phe Gly Val Thr Pro Leu Ala Ser Ala Leu
            260                 265                 270
Ala Leu

<210> SEQ ID NO 6
<211> LENGTH: 49
<212> TYPE: DNA
<213> ORGANISM: Artificial Sequence
<220> FEATURE:
<223> OTHER INFORMATION: Primer

<400> SEQUENCE: 6
cgcaatgtcc agttggaccc agcgtttaac ctgggcattg ttaaggtgg              49

<210> SEQ ID NO 7
<211> LENGTH: 49
<212> TYPE: DNA
<213> ORGANISM: Artificial Sequence
<220> FEATURE:
<223> OTHER INFORMATION: Primer

<400> SEQUENCE: 7
ccaccttaac aatgcccagg ttaaacgctg ggtccaactg gacattgcg              49

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
cgctgagcca gccgatgcat ctgttggcga ataccc                           36

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
gggtattcgc caacagatgc atcggctggc tcagcg                           36

<210> SEQ ID NO 10
<211> LENGTH: 44
<212> TYPE: DNA
<213> ORGANISM: Artificial Sequence
<220> FEATURE:
<223> OTHER INFORMATION: Primer
```

<400> SEQUENCE: 10
gggcattgtt aaggtggata gccatggtgc aggttaccac atcc        44

<210> SEQ ID NO 11
<211> LENGTH: 44
<212> TYPE: DNA
<213> ORGANISM: Artificial Sequence
<220> FEATURE:
<223> OTHER INFORMATION: Primer

<400> SEQUENCE: 11
ggatgtggta acctgcacca tggctatcca ccttaacaat gccc        44

<210> SEQ ID NO 12
<211> LENGTH: 291
<212> TYPE: PRT
<213> ORGANISM: Artificial Sequence
<220> FEATURE:
<223> OTHER INFORMATION: RhuA-Pd4

<400> SEQUENCE: 12

Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45

Phe His Gln Gln Pro Arg Tyr Ile Pro Leu Ser Gln Pro Met Pro Leu
    50                  55                  60

Leu Ala Asn Thr Pro Phe Ile Val Thr Gly Ser Gly Lys Phe Phe Arg
65                  70                  75                  80

Asn Val Gln Leu Asp Pro Ala Ala Asn Leu Gly Ile Val Lys Val Asp
                85                  90                  95

Ser Cys Gly Ala Gly Tyr His Ile Leu Trp Gly Leu Thr Asn Glu Ala
            100                 105                 110

Val Pro Thr Ser Glu Leu Pro Ala His Phe Leu Ser His Ser Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Ala
            180                 185                 190

Ile Gly Gln Ala Thr Ala Gln Glu Met Gln Lys His Ser Leu Val Leu
        195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
            260                 265                 270

Ala Leu Gly Ser Gly Ser Gly Thr Ser Asn Ala Val His Pro Thr Leu
        275                 280                 285

Arg His Leu
    290

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
gcattgttaa ggtggatagc gacggtgcag gttaccacat cc          42

<210> SEQ ID NO 14
<211> LENGTH: 42
<212> TYPE: DNA
<213> ORGANISM: Artificial Sequence
<220> FEATURE:
<223> OTHER INFORMATION: Primer

<400> SEQUENCE: 14
ggatgtggta acctgcaccg tcgctatcca ccttaacaat gc          42

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
gcgagcgtat caaggcgacc tgcggcaaag accgcg          36

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
cgcggtcttt gccgcaggtc gccttgatac gctcgc          36

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
ggtaagcgtt ttggtgtctg tccgctggcg tccgcgctgg          40

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
ccagcgcgga cgccagcgga cagacaccaa aacgcttacc          40

<210> SEQ ID NO 19
<211> LENGTH: 274

<212> TYPE: PRT
<213> ORGANISM: Artificial Sequence
<220> FEATURE:
<223> OTHER INFORMATION: Modified RhuA protein

<400> SEQUENCE: 19

```
Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45

Phe His Gln Gln Pro Arg Tyr Ile Pro Leu Ser Gln Pro Met Pro Leu
    50                  55                  60

Leu Ala Asn Thr Pro Phe Ile Val Thr Gly Ser Gly Lys Phe Phe Arg
65                  70                  75                  80

Asn Val Gln Leu Asp Pro Ala Ala Asn Leu Gly Ile Val Lys Val Asp
                85                  90                  95

Ser Asp Gly Ala Gly Tyr His Ile Leu Trp Gly Leu Thr Asn Glu Ala
            100                 105                 110

Val Pro Thr Ser Glu Leu Pro Ala His Phe Leu Ser His Ser Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Ala
            180                 185                 190

Ile Gly Gln Ala Thr Ala Gln Glu Met Gln Lys His Ser Leu Val Leu
        195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
            260                 265                 270

Ala Leu
```

<210> SEQ ID NO 20
<211> LENGTH: 274
<212> TYPE: PRT
<213> ORGANISM: Artificial Sequence
<220> FEATURE:
<223> OTHER INFORMATION: Modified RhuA protein

<400> SEQUENCE: 20

```
Met Gln Asn Ile Thr Gln Ser Trp Phe Val Gln Gly Met Ile Lys Ala
1               5                   10                  15

Thr Thr Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45
```

```
Phe His Gln Gln Pro Arg Tyr Ile Pro Leu Ser Gln Pro Met Pro Leu
 50                  55                  60

Leu Ala Asn Thr Pro Phe Ile Val Thr Gly Ser Gly Lys Phe Phe Arg
 65                  70                  75                  80

Asn Val Gln Leu Asp Pro Ala Ala Asn Leu Gly Ile Val Lys Val Asp
                 85                  90                  95

Ser Asp Gly Ala Gly Tyr His Ile Leu Trp Gly Leu Thr Asn Glu Ala
                100                 105                 110

Val Pro Thr Ser Glu Leu Pro Ala His Phe Leu Ser His Ser Glu Arg
                115                 120                 125

Ile Lys Ala Thr Cys Gly Lys Asp Arg Val Ile Met His Cys His Ala
130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Ala
                180                 185                 190

Ile Gly Gln Ala Thr Ala Gln Glu Met Gln Lys His Ser Leu Val Leu
                195                 200                 205

Trp Pro Phe His Gly Val Phe Gly Ser Gly Pro Thr Leu Asp Glu Thr
210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Thr Pro Leu Ala Ser Ala Leu
                260                 265                 270

Ala Leu

<210> SEQ ID NO 21
<211> LENGTH: 274
<212> TYPE: PRT
<213> ORGANISM: Artificial Sequence
<220> FEATURE:
<223> OTHER INFORMATION: Modified RhuA protein

<400> SEQUENCE: 21

Met Gln Asn Ile Thr Gln Ser Trp Phe Val Gln Gly Met Ile Lys Ala
 1                5                  10                  15

Thr Thr Asp Ala Trp Leu Lys Gly Trp Asp Glu Arg Asn Gly Gly Asn
                 20                  25                  30

Leu Thr Leu Arg Leu Asp Asp Ala Asp Ile Ala Pro Tyr His Asp Asn
                 35                  40                  45

Phe His Gln Gln Pro Arg Tyr Ile Pro Leu Ser Gln Pro Met Pro Leu
 50                  55                  60

Leu Ala Asn Thr Pro Phe Ile Val Thr Gly Ser Gly Lys Phe Phe Arg
 65                  70                  75                  80

Asn Val Gln Leu Asp Pro Ala Ala Asn Leu Gly Ile Val Lys Val Asp
                 85                  90                  95

Ser Asp Gly Ala Gly Tyr His Ile Leu Trp Gly Leu Thr Asn Glu Ala
                100                 105                 110

Val Pro Thr Ser Glu Leu Pro Ala His Phe Leu Ser His Ser Glu Arg
                115                 120                 125

Ile Lys Ala Thr Asn Gly Lys Asp Arg Val Ile Met His Cys His Ala
```

```
                130                 135                 140
Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Ala
            180                 185                 190

Ile Gly Gln Ala Thr Ala Gln Glu Met Gln Lys His Ser Leu Val Leu
            195                 200                 205

Trp Pro Phe His Gly Val Phe Gly Ser Gly Pro Thr Leu Asp Glu Thr
            210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
                245                 250                 255

Ile Ala Leu Gly Lys Arg Phe Gly Val Cys Pro Leu Ala Ser Ala Leu
                260                 265                 270

Ala Leu

<210> SEQ ID NO 22
<211> LENGTH: 11
<212> TYPE: PRT
<213> ORGANISM: Artificial Sequence
<220> FEATURE:
<223> OTHER INFORMATION: Linker-HisTag

<400> SEQUENCE: 22

Gly Ser Gly Ser Gly His His His His His His
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Linker-Pd4 peptide

<400> SEQUENCE: 23

Gly Ser Gly Ser Gly Thr Ser Asn Ala Val His Pro Thr Leu Arg His
1               5                   10                  15

Leu

<210> SEQ ID NO 24
<211> LENGTH: 82
<212> TYPE: PRT
<213> ORGANISM: Artificial Sequence
<220> FEATURE:
<223> OTHER INFORMATION: Linker-ACP protein

<400> SEQUENCE: 24

Gly Ser Gly Ser Gly Ser Thr Ile Glu Glu Arg Val Lys Lys Ile Ile
1               5                   10                  15

Gly Glu Gln Leu Gly Val Lys Gln Glu Glu Val Thr Asn Asn Ala Ser
                20                  25                  30

Phe Val Glu Asp Leu Gly Ala Asp Ser Leu Asp Thr Val Glu Leu Val
            35                  40                  45

Met Ala Leu Glu Glu Glu Phe Asp Thr Glu Ile Pro Asp Glu Glu Ala
        50                  55                  60

Glu Lys Ile Thr Thr Val Gln Ala Ala Ile Asp Tyr Ile Asn Gly His
```

65          70          75          80

Gln Ala

<210> SEQ ID NO 25
<211> LENGTH: 274
<212> TYPE: PRT
<213> ORGANISM: Artificial Sequence
<220> FEATURE:
<223> OTHER INFORMATION: Modified RhuA protein

<400> SEQUENCE: 25

Met Gln Asn Ile Thr Gln Ser Trp Phe Val Gln Gly Met Ile Lys Ala
1               5                   10                  15

Thr Cys Asp Ala Trp Leu Lys Gly Trp Asp Glu Arg Asn Gly Gly Asn
            20                  25                  30

Leu Thr Leu Arg Leu Asp Asp Ala Asp Ile Ala Pro Tyr His Asp Asn
        35                  40                  45

Phe His Gln Gln Pro Arg Tyr Ile Pro Leu Ser Gln Pro Met Pro Leu
    50                  55                  60

Leu Ala Asn Thr Pro Phe Ile Val Thr Gly Ser Gly Lys Phe Phe Arg
65                  70                  75                  80

Asn Val Gln Leu Asp Pro Ala Ala Asn Leu Gly Ile Val Lys Val Asp
            85                  90                  95

Ser Cys Gly Ala Gly Tyr His Ile Leu Trp Gly Leu Thr Asn Glu Ala
        100                 105                 110

Val Pro Thr Ser Glu Leu Pro Ala His Phe Leu Ser His Cys Glu Arg
    115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
            165                 170                 175

Pro Asp Gly Val Gly Ile Leu Pro Trp Met Val Pro Gly Thr Asp Glu
        180                 185                 190

Ile Gly Gln Ala Thr Ala Gln Glu Met Gln Lys His Ser Leu Val Leu
    195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
            245                 250                 255

Ile Ala Leu Gly Lys Arg Phe Gly Val Thr Pro Leu Ala Ser Ala Leu
        260                 265                 270

Ala Leu

<210> SEQ ID NO 26
<211> LENGTH: 274
<212> TYPE: PRT
<213> ORGANISM: Artificial Sequence
<220> FEATURE:
<223> OTHER INFORMATION: Modified RhuA protein

<400> SEQUENCE: 26

Met Gln Asn Ile Thr Gln Ser Trp Phe Val Gln Gly Met Ile Lys Ala
1               5                   10                  15

-continued

```
Thr Thr Asp Ala Trp Cys Lys Gly Trp Asp Glu Arg Asn Gly Gly Asn
            20              25              30
Leu Thr Leu Arg Leu Asp Asp Ala Asp Ile Ala Pro Tyr His Asp Asn
        35              40              45
Phe His Gln Gln Pro Arg Tyr Ile Pro Leu Ser Gln Pro Met Pro Leu
    50              55              60
Leu Ala Asn Thr Pro Phe Ile Val Thr Gly Ser Gly Lys Phe Phe Arg
65              70              75              80
Asn Val Gln Leu Asp Pro Ala Ala Asn Leu Gly Ile Val Lys Val Asp
            85              90              95
Ser Cys Gly Ala Gly Tyr His Ile Leu Trp Gly Leu Thr Asn Glu Ala
            100             105             110
Val Pro Thr Ser Glu Leu Pro Ala His Phe Leu Ser His Cys Glu Arg
            115             120             125
Ile Lys Ala Thr Asn Gly Lys Asp Arg Val Ile Met His Cys His Ala
        130             135             140
Thr Asn Leu Ile Ala Leu Thr Tyr Val Leu Glu Asn Asp Thr Ala Val
145             150             155             160
Phe Thr Arg Gln Leu Trp Glu Gly Ser Thr Glu Cys Leu Val Val Phe
            165             170             175
Pro Asp Gly Val Gly Ile Leu Pro Trp Met Val Pro Gly Thr Asp Glu
            180             185             190
Ile Gly Gln Ala Thr Ala Gln Glu Met Gln Lys His Ser Leu Val Leu
            195             200             205
Trp Pro Phe His Gly Val Phe Gly Ser Gly Pro Thr Leu Asp Glu Thr
        210             215             220
Phe Gly Leu Ile Asp Thr Ala Glu Lys Ser Ala Gln Val Leu Val Lys
225             230             235             240
Val Tyr Ser Met Gly Gly Met Lys Gln Thr Ile Ser Arg Glu Glu Leu
            245             250             255
Ile Ala Leu Gly Lys Arg Phe Gly Val Thr Pro Leu Ala Ser Ala Leu
            260             265             270
Ala Leu
```

METHOD FOR FABRICATING TWO-DIMENSIONAL PROTEIN CRYSTALS

INCORPORATION BY REFERENCE TO ANY PRIORITY APPLICATIONS

This patent document is a 371 National Phase Application of PCT Application No. PCT/US16/42361 entitled "METHOD FOR FABRICATING TWO-DIMENSIONAL PROTEIN CRYSTALS" filed on Jul. 14, 2016, which claims priorities to and benefits of U.S. Provisional Patent Application No. 62/193,459 entitled "METHOD FOR FABRICATING TWO-DIMENSIONAL PROTEIN CRYSTALS" filed on Jul. 16, 2015 and U.S. Provisional Patent Application No. 62/220,157 entitled "METHOD FOR FABRICATING TWO-DIMENSIONAL PROTEIN CRYSTALS" filed on Sep. 17, 2015. The entire contents of the aforementioned patent applications are incorporated by reference as part of the disclosure of this patent document.

This invention was made with government support under DE-SC0003844 awarded by the Department of Energy. The government has certain rights in the invention.

STATEMENT REGARDING FEDERALLY SPONSORED R&D

This invention was made with government support under U.S. Department of Energy Grant/Contract Number DE-FG02-10ER46677. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file entitled UCSD093-001WO_Sequence_Listing.TXT, created Jul. 11, 2016, which is 29 Kb in size. The information in the electronic format of the Sequence Listing is incorporated herein by reference in its entirety.

BACKGROUND OF THE INVENTION

Field of the Invention

Some embodiments described herein relate to 2D crystalline structures and to polypeptide building blocks for making such structures.

Description of the Related Art

Existing approaches for designed protein assembly may be too design-intensive and involve sophisticated, but not sure-fire computational methods or protein fusion strategies that do not always give the desired product, and the desired products are not scalable and do not always possess superior materials properties.

Accordingly, there is a need for improved polypeptide assemblies and building blocks and methods for making them.

SUMMARY OF THE INVENTION

In a first aspect, a non-naturally occurring symmetrical polypeptide building block is provided. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides.

In a second aspect, a 2D crystalline material comprising a polypeptide building block as described in the embodiments of the first aspect is provided. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a third aspect, a lab-on-a-chip comprising the 2D crystalline material as described in the embodiments of the second aspect is provided. The 2D crystalline material can comprise the polypeptide building block as described in the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a fourth aspect, a molecular membrane comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a fifth aspect, a molecular template comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a sixth aspect a stabilized polypeptide formulation comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a seventh aspect, a molecular scaffold comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In an eighth aspect, a protective armor comprising the 2D crystalline material as described in the embodiments of the second aspect is provided. The 2D crystalline material can comprise the polypeptide building block as described in the embodiments of first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a ninth aspect, a smart textile comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a tenth aspect, a piezo electronic component comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In an eleventh aspect, an adaptive membrane or sieve comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twelfth aspect a controlled drug release formulation comprising the 2D crystalline material as described in the embodiments of the second aspect is provided. The 2D crystalline material can comprise the polypeptide building block as described in embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a thirteenth aspect, a run-flat tire comprising the 2D crystalline material as described in the embodiments of the second aspect is provided. The 2D crystalline material can comprise the polypeptide building block as described in the embodiments of the first aspect. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a fourteenth aspect a method of making a crystalline material is provided. The method can comprise placing a plurality of polypeptide building blocks as described in the embodiments of the first aspect under oxidizing conditions and allowing said plurality of polypeptide building blocks to self-assemble into said crystalline material. The non-naturally occurring symmetrical polypeptide building block can comprise a plurality of cysteine residues positioned such that formation of disulfide bonds between some or all of said plurality of cysteine residues facilitates formation of 2D crystals. In some embodiments, said polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide comprises the RhuA protein. In some embodiments, said polypeptide further comprises an additional polypeptide modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, oxidizing conditions are controllable. In some embodiments, said plurality of polypeptide building blocks are incubated in solution under said oxidizing conditions.

In a fifteenth aspect, a non-naturally occurring symmetrical polypeptide building block is provided. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, the 2D crystalline material can be assembled by visible light and dissembled by UV light.

In a sixteenth aspect, a 2D crystalline material is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a seventeenth aspect, a lab-on-a-chip comprising the 2D crystalline material of the embodiments described in the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In an eighteenth aspect, a molecular membrane comprising the 2D crystalline material as described in the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a nineteenth aspect, a molecular template comprising the 2D crystalline material as described in the embodiments of the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twentieth aspect, a stabilized polypeptide formulation comprising the 2D crystalline material as described in the embodiments of the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light. In some embodiments, the stabilized polypeptide comprises an enzyme or protein.

In a twenty-second aspect, a molecular scaffold comprising the 2D crystalline material as described in the embodiments of the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twenty-third aspect, a protective armor comprising the 2D crystalline material as described in the embodiments of the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twenty-fourth aspect, a smart textile comprising the 2D crystalline material of any one of the embodiments as described in the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twenty-fifth aspect, a piezo electronic component comprising the 2D crystalline material as described in the embodiments of the sixteenth aspect are provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twenty-sixth aspect, an adaptive membrane or sieve comprising the 2D crystalline material as described in the embodiments of the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twenty-seventh aspect, a controlled drug release formulation comprising the 2D crystalline material as described in the embodiments of the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twenty-eighth aspect, a run-flat tire comprising the 2D crystalline material of any as described in the embodiments of the sixteenth aspect is provided. The 2D crystalline material can comprise the polypeptide building block as described in the embodiments of the fifteenth aspect. The polypeptide building block is a non-naturally occurring symmetrical polypeptide building block. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

In a twenty-ninth aspect, a method of making a crystalline material is provided. The method can comprise placing a plurality of the polypeptide building blocks as described in the embodiments of the fifteenth aspect under conditions in which said histidine residues form metal coordinates and allowing said plurality of polypeptide building blocks to self-assemble into said crystalline material. The non-naturally occurring symmetrical polypeptide building block can comprise a plurality of histidine residues positioned such that coordination of some or all of said plurality of histidine residues with one or more metal ions facilitates formation of 2D crystals. In some embodiments, said polypeptide building block comprises a symmetrical polypeptide comprising surface histidine residues in the corner positions. In some embodiments, said polypeptide has inherent C3, C4, C6, D3, D4 or D6 symmetry. In some embodiments, at least one of said histidine residues has been introduced into said polypeptide building block through genetic engineering. In some embodiments, said polypeptide is generated via solid phase synthesis. In some embodiments, said polypeptide is genetically engineered. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said symmetrical polypeptide comprises the RhuA protein. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, the 2D crystalline material can be assembled by visible light and dissembled by UV light. In some embodiments, said conditions in which said histidine residues form metal coordinates are controllable. In some embodiments, said metal coordinates comprise a metal selected from the group consisting of Zn2+ and Cu2+.

In a thirtieth aspect, a polypeptide comprising an amino acid sequence selected from the group consisting of SEQ ID NO: 3, SEQ ID NO: 4 and SEQ ID NO: 5 is provided. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides.

In a thirty first aspect, a 2D crystalline material comprising the polypeptide of the embodiments described in the thirtieth aspect is provided. The polypeptide can comprise an amino acid sequence selected from the group consisting of SEQ ID NO: 3, SEQ ID NO: 4 and SEQ ID NO: 5. a polypeptide comprising an amino acid sequence selected from the group consisting of SEQ ID NO: 3, SEQ ID NO: 4 and SEQ ID NO: 5 are provided. In some embodiments, the polypeptide further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide building block can be chemically modified. In some embodiments, the polypeptide is chemically modified with inorganic nanoparticles. In some embodiments, the polypeptide building block is modified with one or more organic functional groups. In some embodiments, the polypeptide building block is modified for different modes of controllable self-assembly. In some embodiments, the organic functional group is a fluorophore, metal chelating group or a host complex. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, the organic functional group is a fluorophore, metal chelating group or a host complex. In some embodiments, the 2D crystalline material can be genetically modified/fused with functional proteins and peptides.

In a thirty-second aspect, a polypeptide comprising the amino acid sequence of SEQ ID NO: 2, 19, 20, 21 or 24 is provided. In some embodiments, the further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide can be chemically modified. In some embodiments, the polypeptide is chemically modified with inorganic nanoparticles. In some embodiments, the polypeptide is modified with one or more organic functional groups. In some embodiments, the polypeptide is modified for different modes of controllable self-assembly. In some embodiments, the organic functional group is a fluorophore, metal chelating group or a host complex. In some embodiments, the polypeptide can be genetically modified/fused with functional proteins and peptides.

In a thirty-third aspect, 2D crystalline material comprising the polypeptide as described in the embodiments of the thirty-second aspect is provided. The polypeptide can comprise the amino acid sequence of SEQ ID NO: 2, 19, 20, 21 or 24. In some embodiments, the further comprises an additional modification. In some embodiments, said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, the peptide tag comprises a His tag. In some embodiments, the His tag comprises a sequence set forth in SEQ ID NO: 22. In some embodiments, the peptide tag comprises a Pd4 peptide. In some embodiments, the Pd4 peptide comprises a sequence set forth in SEQ ID NO: 23. In some embodiments, the peptide tag comprises an ACP protein. In some embodiments, the ACP protein comprises a sequence set forth in SEQ ID NO: 24. In some embodiments, the polypeptide can be chemically modified. In some embodiments, the polypeptide is chemically modified with inorganic nanoparticles. In some embodiments, the polypeptide is modified with one or more organic functional groups. In some embodiments, the polypeptide is modified for different modes of controllable self-assembly. In some embodiments, the organic functional group is a fluorophore, metal chelating group or a host complex. In some embodiments, the polypeptide can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified. In some embodiments, the 2D crystalline material is chemically modified with inorganic nanoparticles. In some embodiments, the 2D crystalline material is modified with one or more organic functional groups. In some embodiments, the 2D crystalline material is modified for different modes of controllable self-assembly. In some embodiments, organic functional group is a fluorophore, metal chelating group or a host complex. In some embodiments, the 2D crystalline material can be genetically modified/fused with functional proteins and peptides. In some embodiments, the 2D crystalline material can be assembled by visible light and dissembled by UV light.

BRIEF DESCRIPTION OF THE DRAWINGS

FIG. 3 shows proteins as building blocks for functional nanomaterials.

FIG. 4 shows the advantages of fabricating 20 supramolecular protein assemblies.

FIG. 7 shows an outline of preparing disulfide-mediated assembly of 2D protein materials and the advantages.

As shown in FIG. 10B are expected 2D molecular arrangements of $^{C98}$RhuA, $^{H63/H98}$RhuA and $^{F88/C98}$RhuA lattices. In the top row showing the oxidation-reduction reaction, the corners are bound by disulfide bonds (curvy lines in between the square structures). The structure can be the lattice on the left or the lattice structure on the right which is to assume a checkered pattern in which the middle square structure in the top row is equivalent to the first and third square structure in the second row and the middle structure in the third row. As shown for the $^{H63/H98}$RhuA, the Self-assembly was initiated by addition of 4-40 molar equivalents of Zn2+ and Cu2+ (1-10 equiv. per bis-His motif), both of which can accommodate the desired four-coordinate geometries to link H63/H98RhuA building blocks at their corners. It is envisioned that the C4-symmetric $^{C98}$RhuA and H63/H98RhuA variants could yield square lattices with two distinct patterns in terms of the orientation of the building blocks with respect to the 2D plane. For the $^{H63/H98}$RhuA lattice, the structure can be the lattice on the left or the lattice structure on the right which is to assume a checkered pattern in which the middle square structure in the top row is equivalent to the first and third square structure in the second row and the middle structure in the third row. In the bottom row showing the reaction with the F88/C98RhuA, the square structure as shown has angled lines representing the cysteines.

TEM characterization of optimized 2D $^{C98}$RhuA crystals: 11D: 125 μM $^{C98}$RhuA was incubated in the presence of 10 mM βME at 4° C. in a standing solution for 3 days. 11E: 125 μM $^{C98}$RhuA was incubated in the presence of 10 mM βME at 4° C. with gentle shaking for 3 days, followed by 2 days at rest, during which a dense precipitate of crystals formed.

FIG. 12 shows: (12A) Reconstructed 2D images of seven distinct conformational states (I-VII) of 2D C98RhuA crystals. 12B, High-magnification views and derived structural models of conformations II, V and VII. Unit cells and hinge angles (α) between C98RhuA units are highlighted by the black square and the hinge angle shown, respectively. The four corners of the square in the figure (bottom panel) represent the top half of the structure shown in 10A (structure on the left), while the structure in the middle of the square in the second row of 12B is in a checkboard confirmation with the structures in the corner and is also represented by the bottom half of the structure shown in FIG. 10A (left structure). 12C, Population distributions of C98RhuA crystals in different conformational states during repeated resuspension/sedimentation cycles. n refers to the total number of individual lattices analyzed in each panel. 12D, Schematic representation of the rotating, rigid-square model that describes the 2D C98RhuA lattice dynamics (as in FIG. 10; the building blocks are numbered for clarity) As shown, numbers 9, 11, 23, 1, 13, 7, 3, 21, 5, 15, 19 and 17 are equivalent to one another. Numbers 24, 10, 12, 8, 2, 22, 0, 14, 6, 4, 20, 18 and 16 are equivalent to one another. Thus there is a check patterning. Δx and Δy denote changes in the transverse- and longitudinal-dimension lengths upon lattice opening and closing. 12E, Digital image-correlation analysis of reconstructed TEM images of C98RhuA crystals for determining auxetic behavior. Representative volume elements (RVEs) in the lattices of the two extreme states (I and VII) are indicated with squares, with the vertices of the RVEs numbered 1-4, and the vectors M, N (in state I) and m, n (in state VII) used to calculate local engineering strains are shown with the arrows. The edges of the lattice pores, used for determining the positions of the RVE vertices, are shown as lines that are tracing around the edges of the lattice pores in state I and VII. 12F, Calculated Poisson's ratios (v) of lattice conformational states with respect to state I. The error bars correspond to the uncertainties in pixel selection during digital image processing (see Methods for details). Additional structural characterization of 2D C98RhuA crystals is shown in 12G-12I. 12G, AFM; 12H, SEM; 12I, Cryo-TEM. The middle column in 12G shows the profiles along the arrows in the left column.

Figure 13:
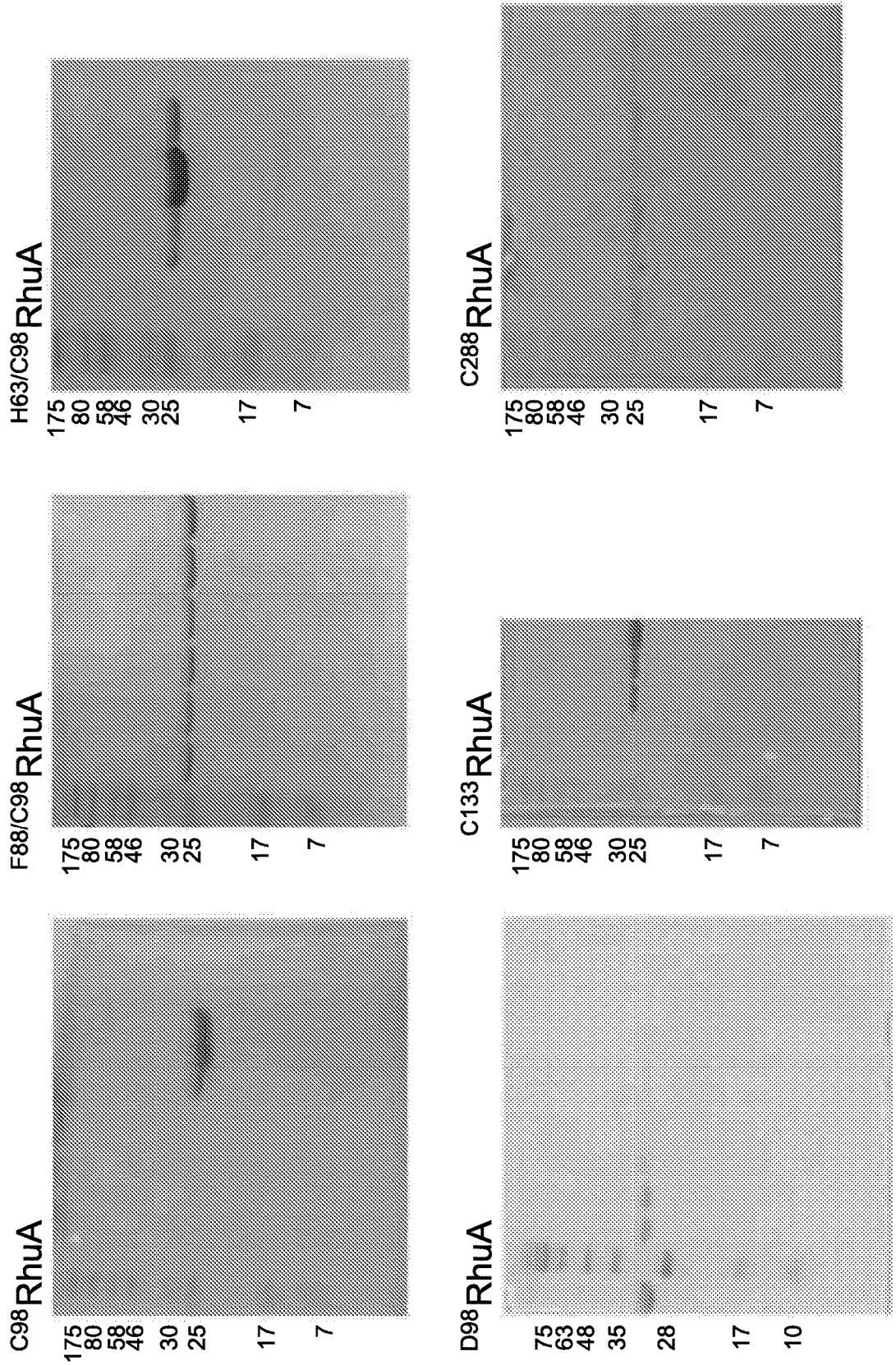

FIG. 13 shows the SDS-PAGE characterization of RhuA mutants.

Figure 14:
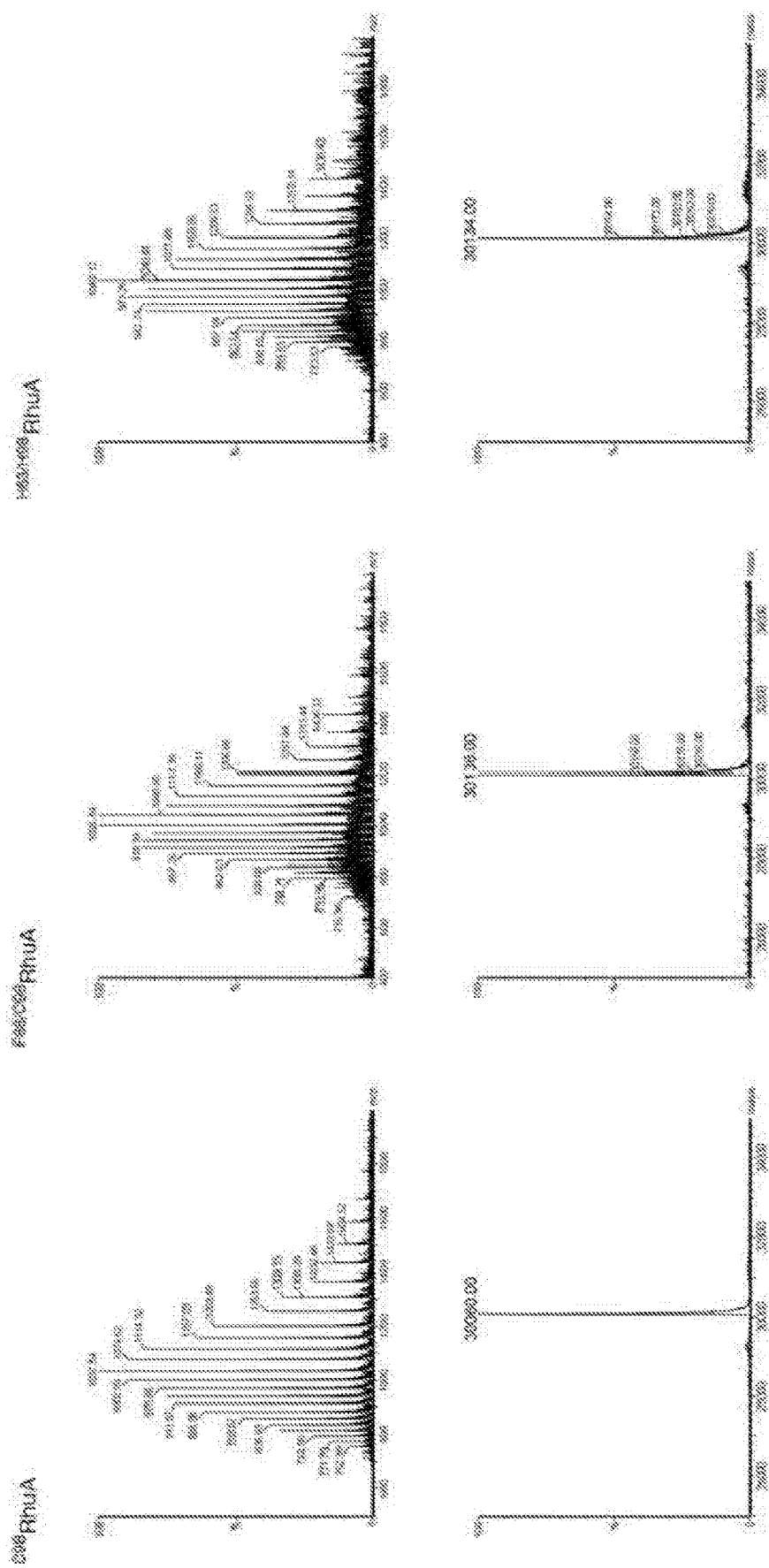

FIG. 14 shows the positive ESI-MS characterization of RhuA mutants. Top spectrum displays the raw data showing the cluster ions. The bottom spectrum is the deconvoluted spectrum after software transformation.

Figure 15:
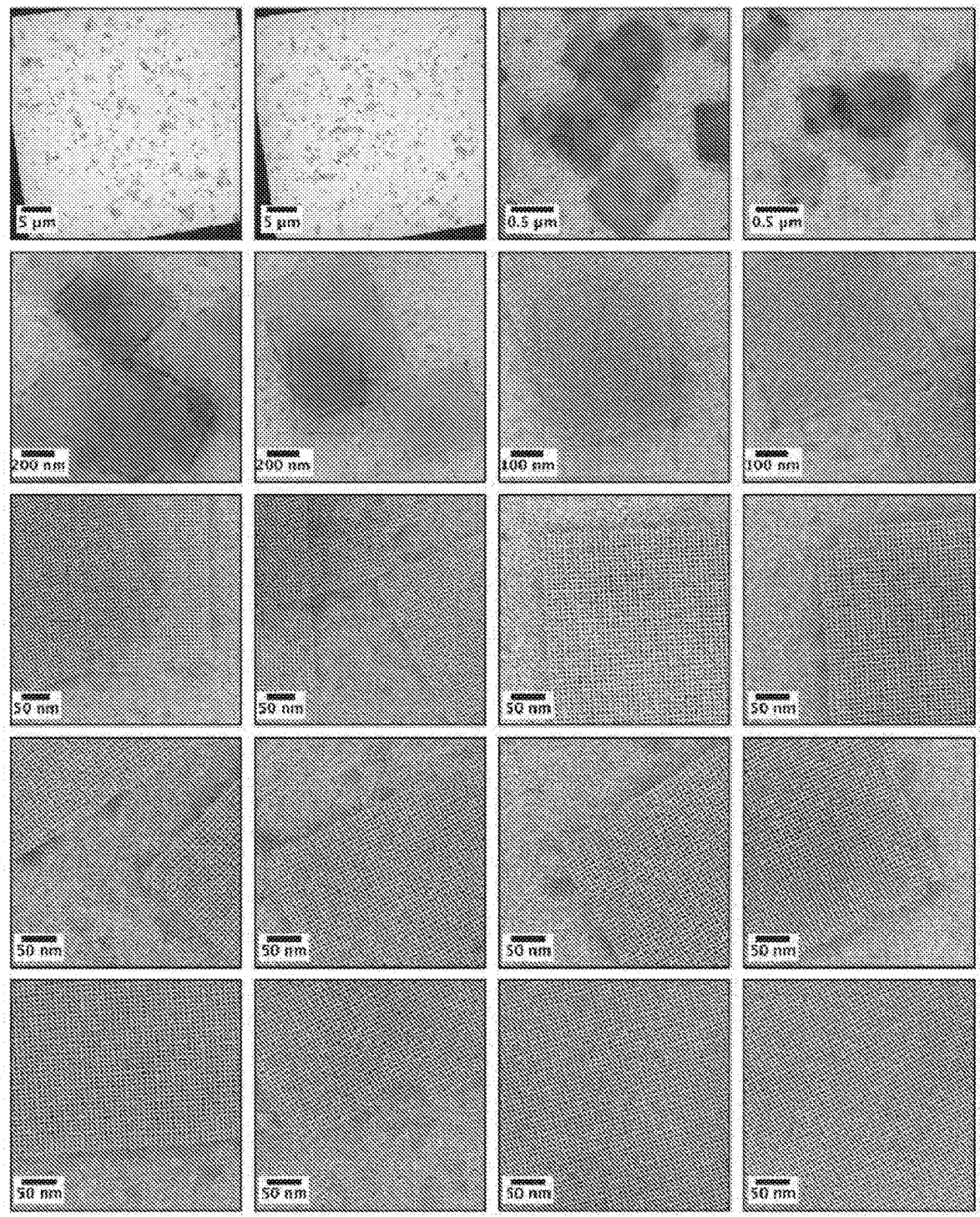

FIG. 15 shows ns-TEM images of 2D $^{C98}$RhuA crystals. 125 μM $^{C98}$RhuA was incubated in the presence of 10 mM βME at 4° C. in a standing solution for 3 days.

Figure 16:
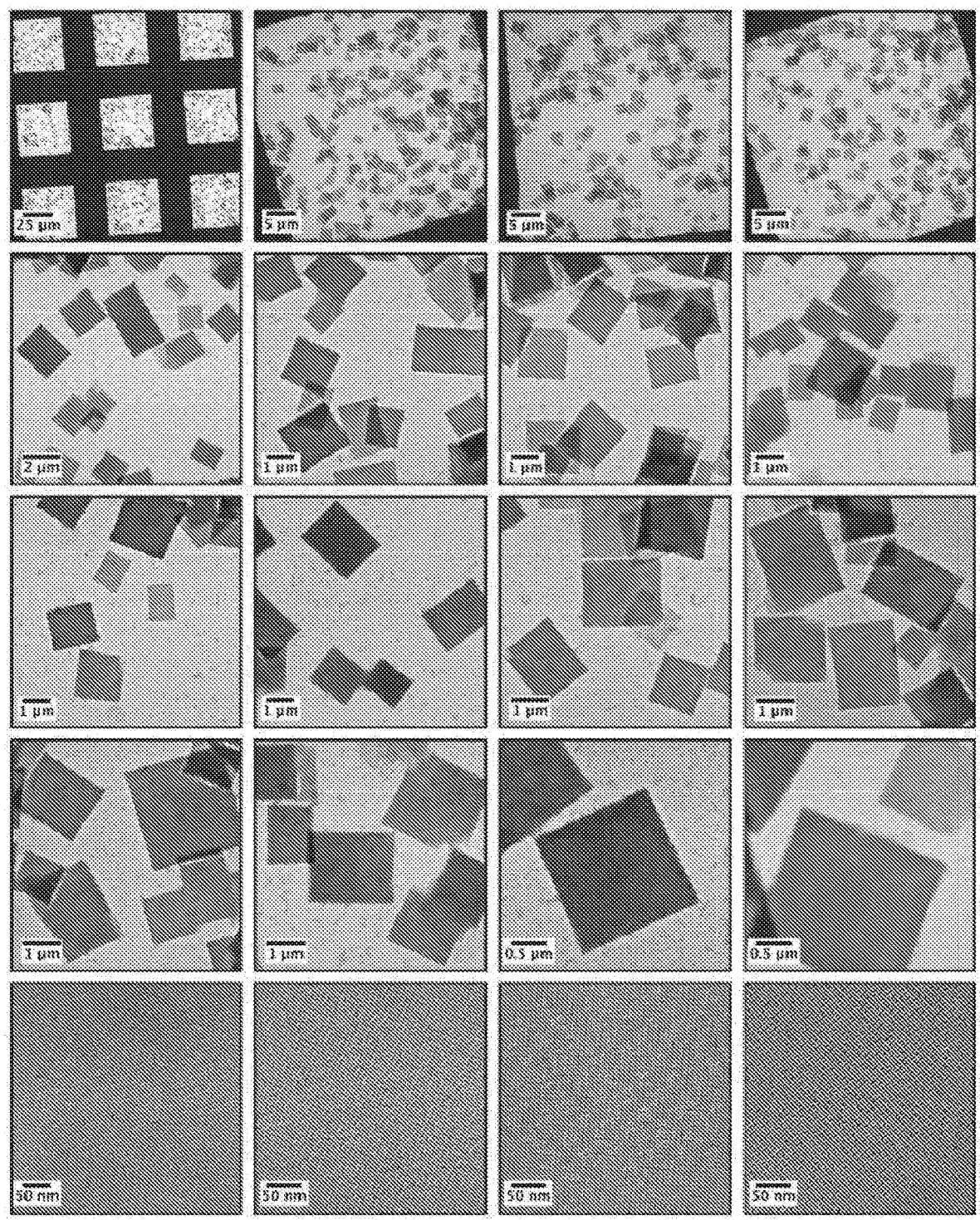

FIG. 16 shows ns-TEM images of 2D $^{C98}$RhuA crystals. 125 μM $^{C98}$RhuA was incubated in the presence of 10 mM βME at 4° C. with gentle shaking for 3 days, followed by 2 days at rest, during which a dense precipitate of crystals formed.

Figure 17A:
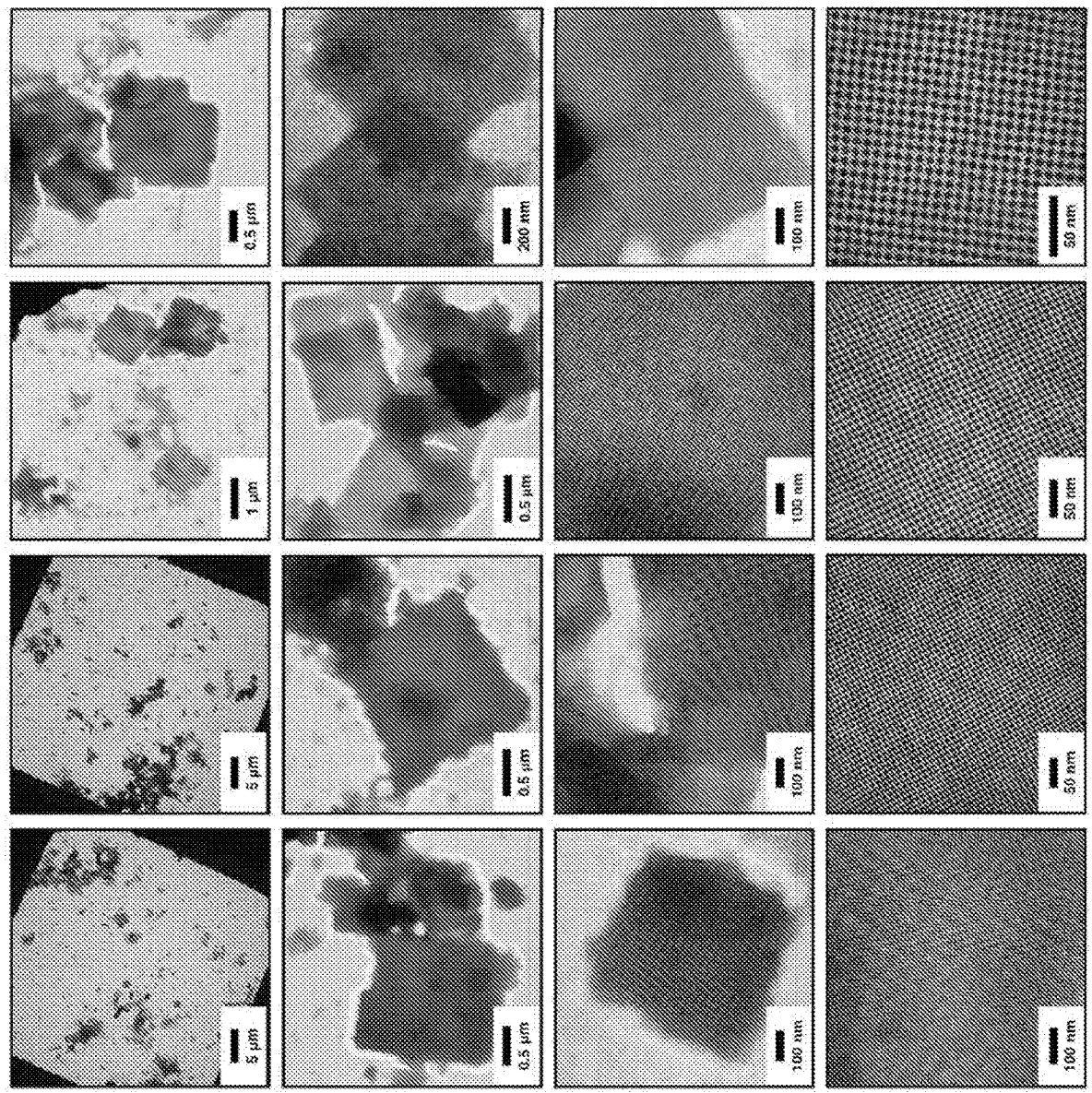
Figure 17B:
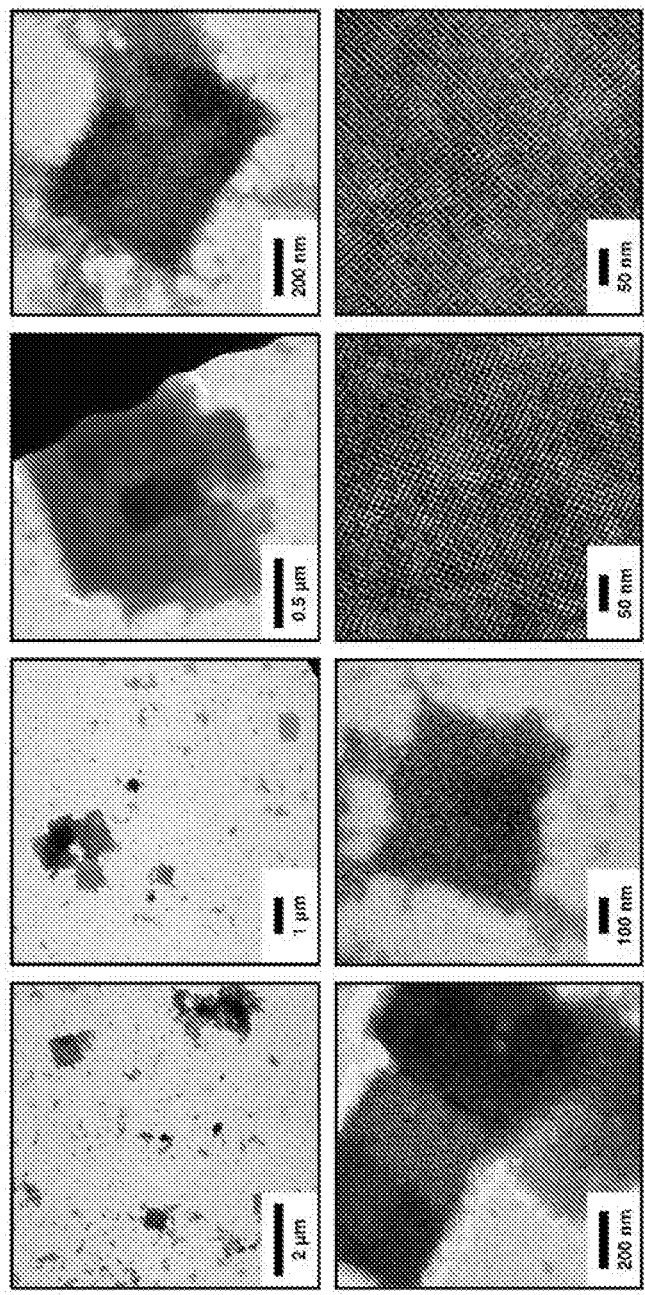

FIG. 17 shows ns-TEM images of 2D $^{H63/H98}$RhuA crystals. 25 μM $^{H63/H98}$RhuA was incubated with 200 μM ZnCl$_2$ (17A) or CuCl$_2$ (17B) in a 20 mM MOPS buffer solution (pH 7.0) at 4° C. for 1 day.

Figure 18A:
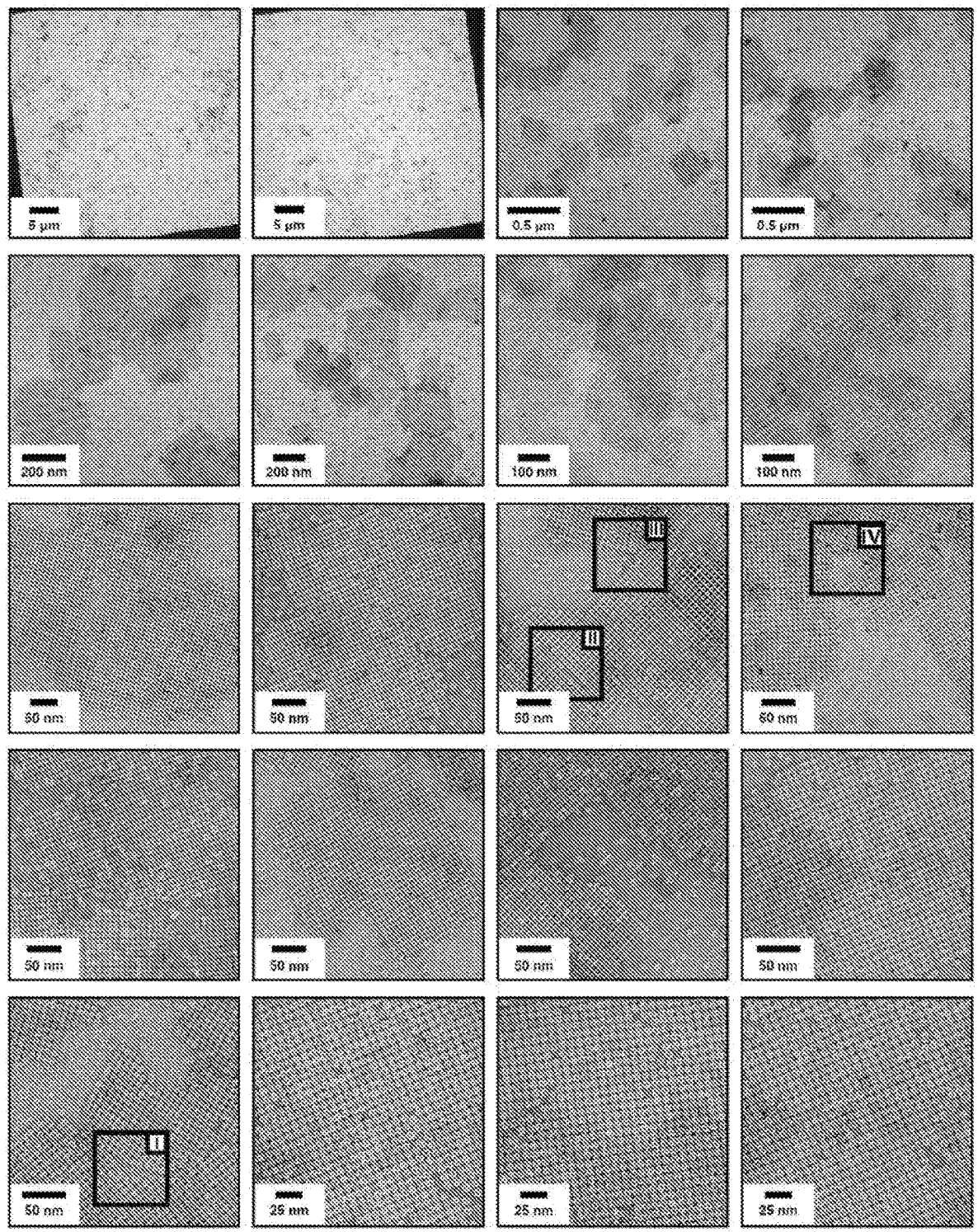

FIG. 18 shows: (18A) ns-TEM images for $^{F88/C98}$RhuA 2D crystals. 125 μM $^{F88/C98}$RhuA was incubated in the presence of 10 mM βME at 4° C. with gentle shaking for 2 days. (18B) Cartoon representations of various types of defects observed in $^{F88/C98}$RhuA crystals, corresponding to boxed areas (I-IV) in FIG. 18A.

Figure 19A:
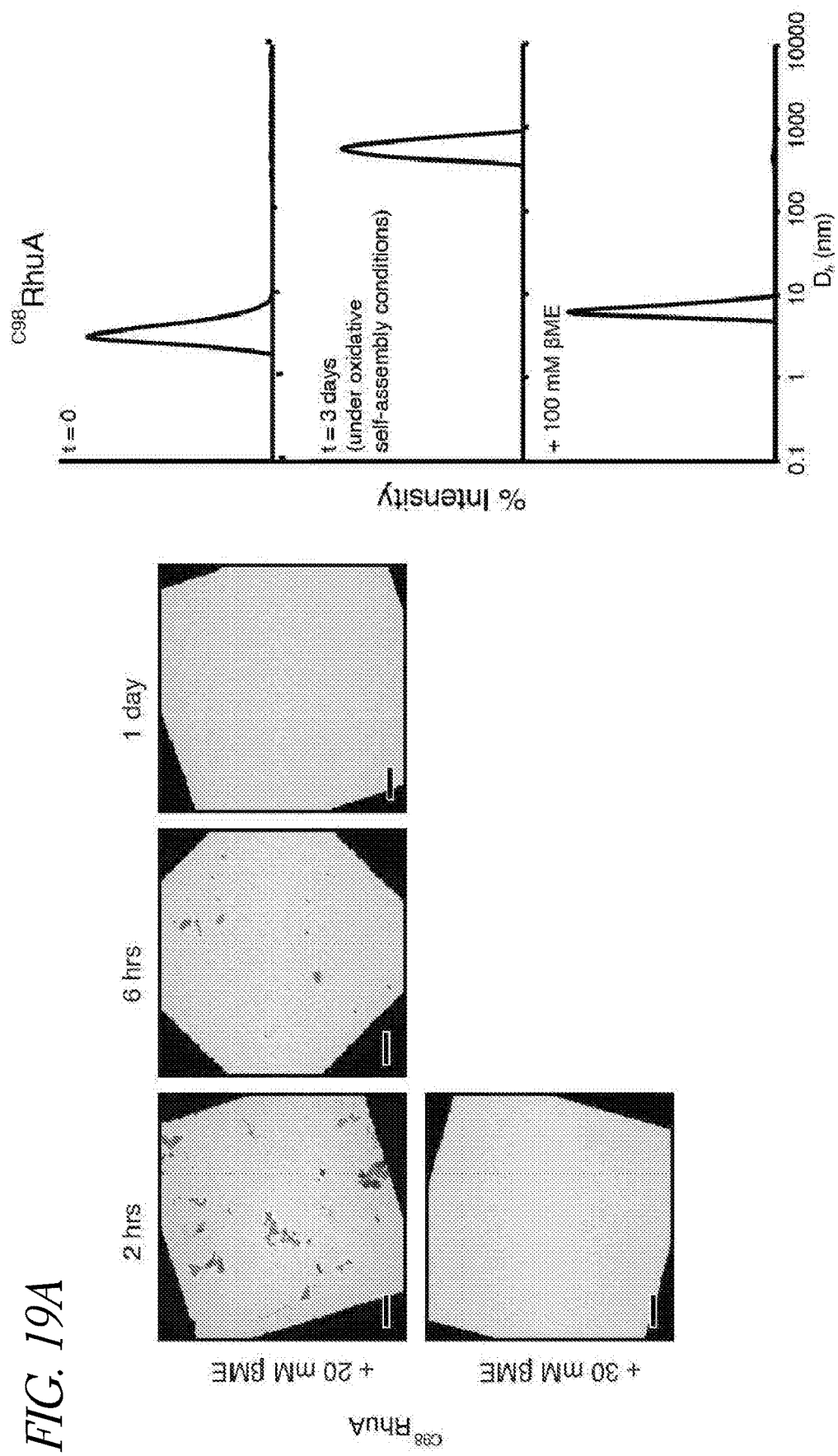
Figure 19B:
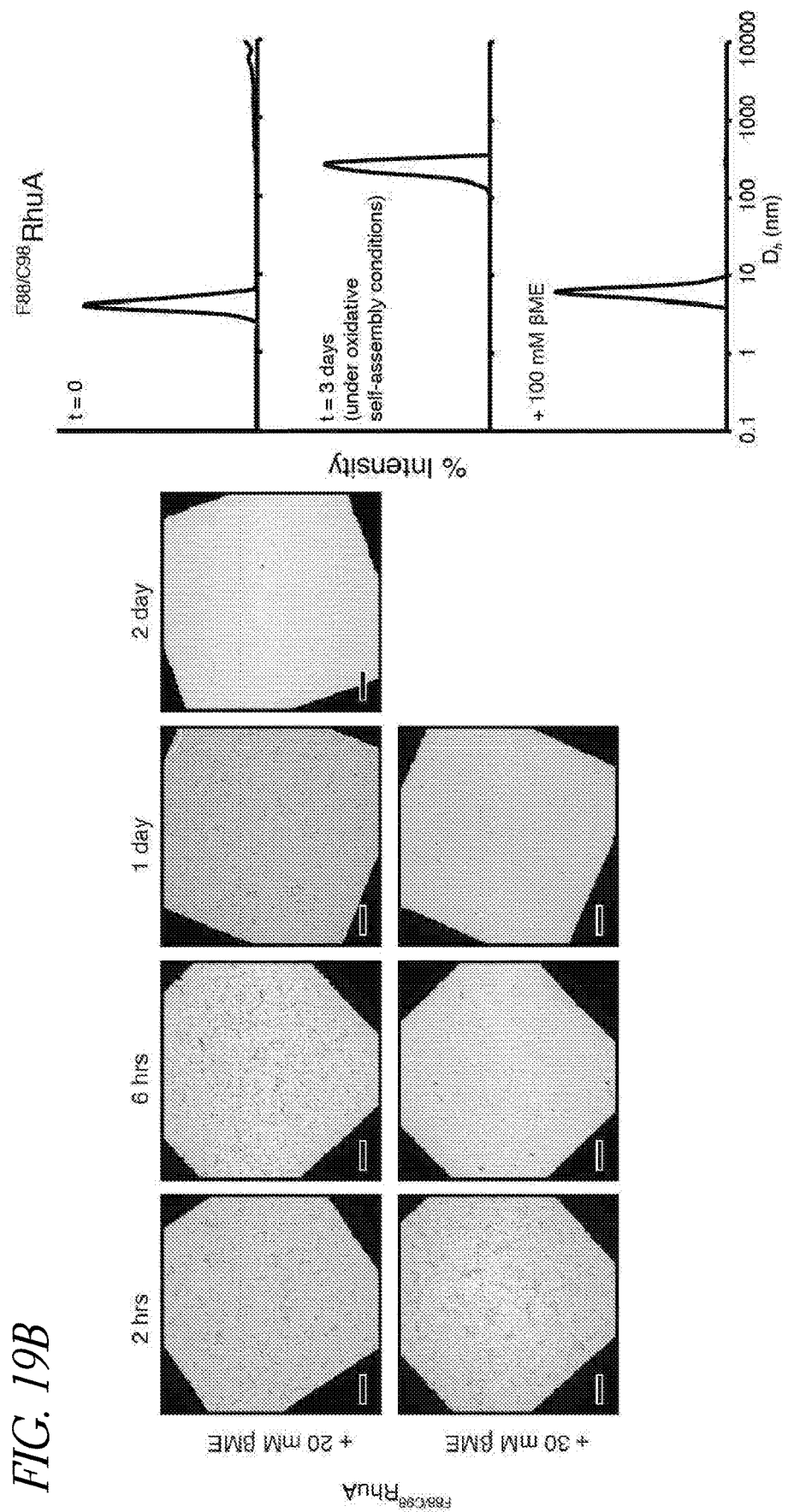
Figure 19C:
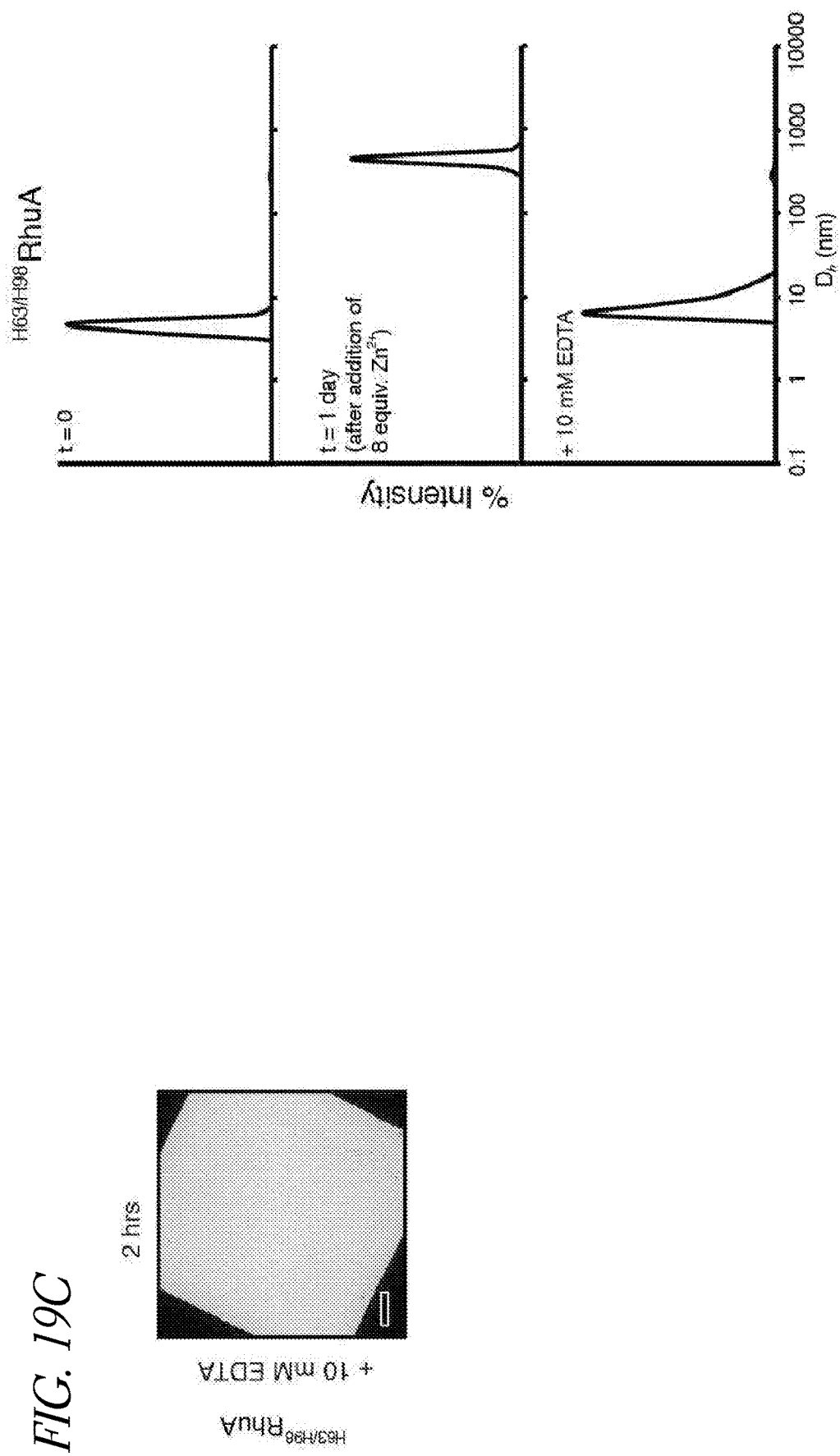

FIG. 19 shows the reversibility of oxidative or metal-mediated self-assembly of RhuA variants. 19A and 19B: C98RhuA (19a) and F88/C98RhuA (19B) crystals. Left panels, the crystals were incubated in the presence of 20 mM or 30 mM βME (as indicated) and imaged by TEM at the indicated times after addition of βME. Right panels, 125 μM C98RhuA (19A) or F88/C98RhuA (19B) were incubated under oxidative self-assembly conditions (in the presence of 10 mM βME at 4° C. with gentle shaking) and self-assembly was monitored by DLS at t=0 (top), t=3 days (center) and upon addition of 100 mM βME after self-assembly (bottom). Dh refers to the hydrodynamic diameter. 19C, Left panel, H63/H98RhuA crystals were incubated in the presence of 10 mM EDTA and imaged by TEM at 2 h after addition of EDTA. Right panels, 25 μM H63/H98RhuA was incubated under metal mediated self-assembly conditions (in the presence of 200 μM ZnCl2 at 4° C.) and self-assembly was monitored by DLS at t=0 (top), t=3 days (center) and upon addition of 10 mM EDTA (bottom). Scale bars are 5 μm in all panels.

Figure 20:
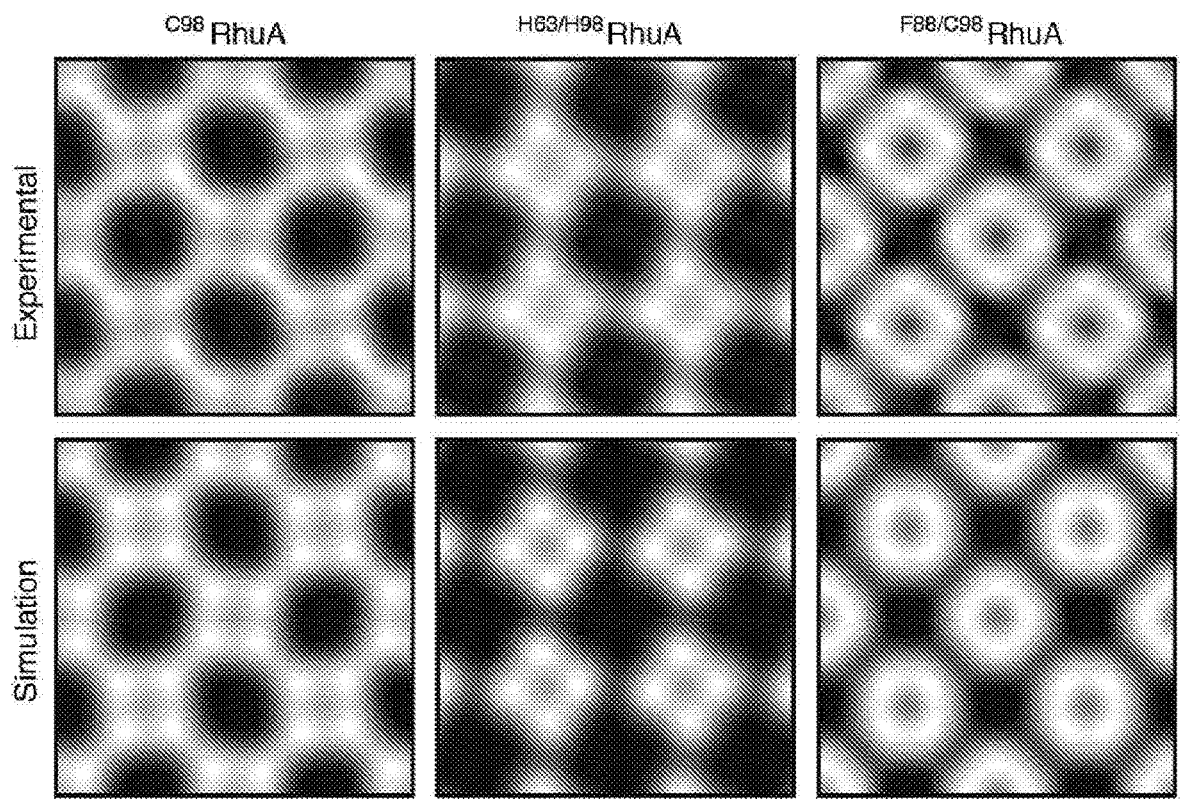

FIG. 20 shows the 2D TEM reconstruction and structural modelling of the 2D lattices of RhuA variants. Comparison of the observed (experimental) and simulated projection maps of the 2D lattices of RhuA variants.

Figure 21:
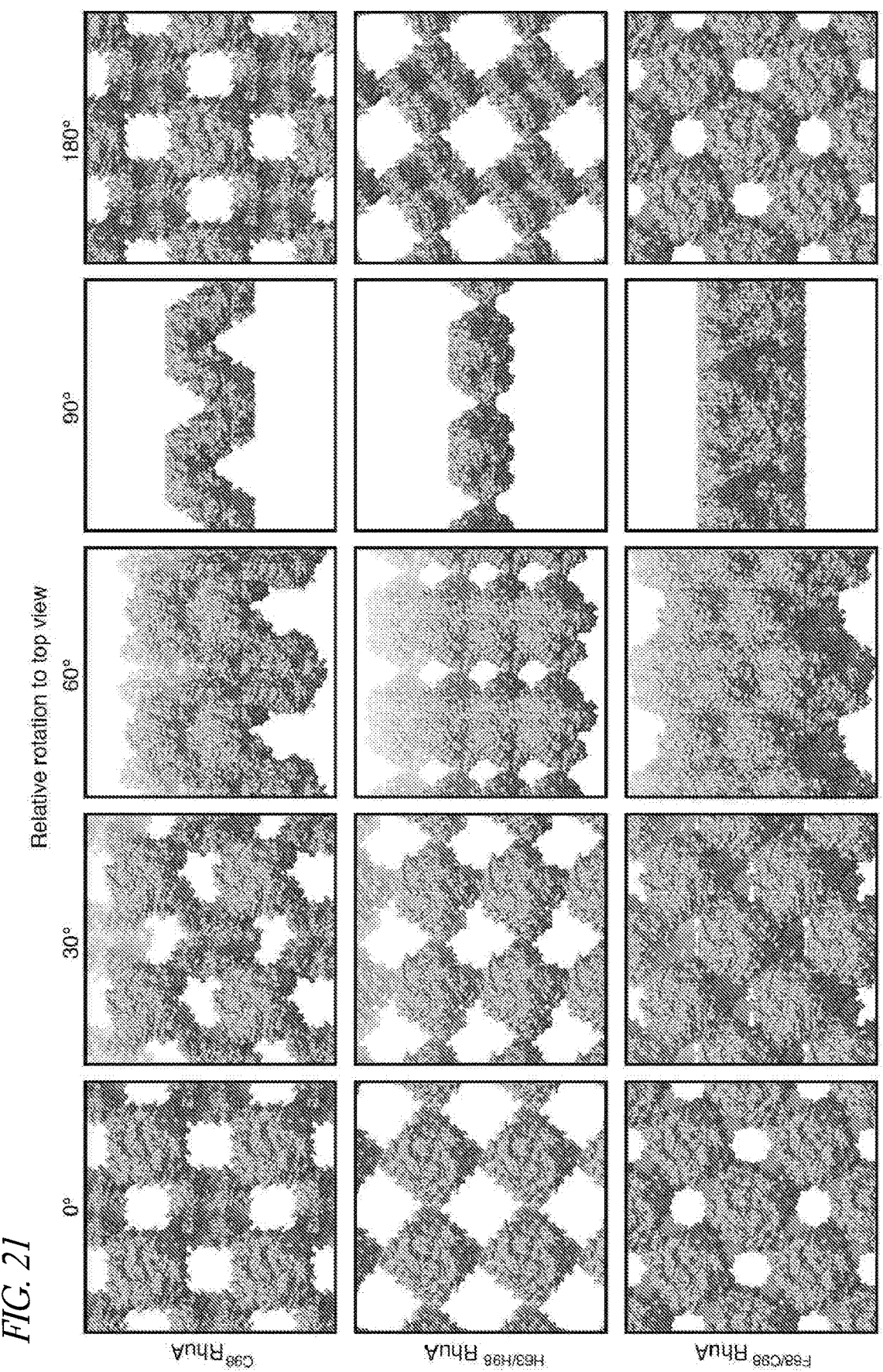

FIG. 21 shows molecular arrangements in $^{C98}$RhuA, $^{H63/H98}$RhuA and $^{F88/C98}$RhuA lattices viewed from different angles. As shown for C98-RhuA, the first and second panel corresponds to the panels on the left column of FIG. 10. The top and bottom of the protein structure shown in FIG. 10 that is separated by the dashed line is shown in the lattice structure of in the panels of the first row. In the first panel of the first row, the structures are arranged side by side but in contrasting orientations. In a repeated unit, the protein structure is arranged in a checkered pattern such that for each row, the protein are side by side, but alternating units are flipped such that in every other unit, the bottom portion of the protein as shown in FIG. 10 is right side up. In the first and second row, the proteins that make up the lattice structure are all in the same orientation in which the tops of the proteins as shown in FIG. 10 are right side up. However in the third row, the protein units of F88/C98 RhuA, are stacked as shown in FIG. 10, and these stacked units make up the lattices as shown in the third row.

Figure 22A:
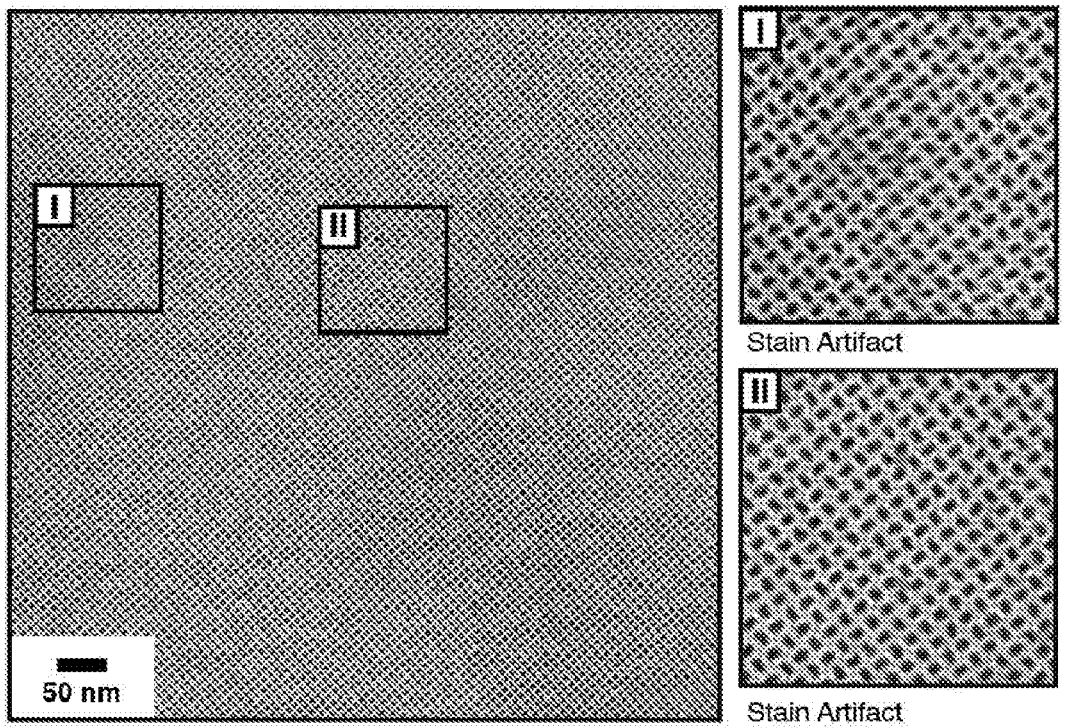
Figure 22B:
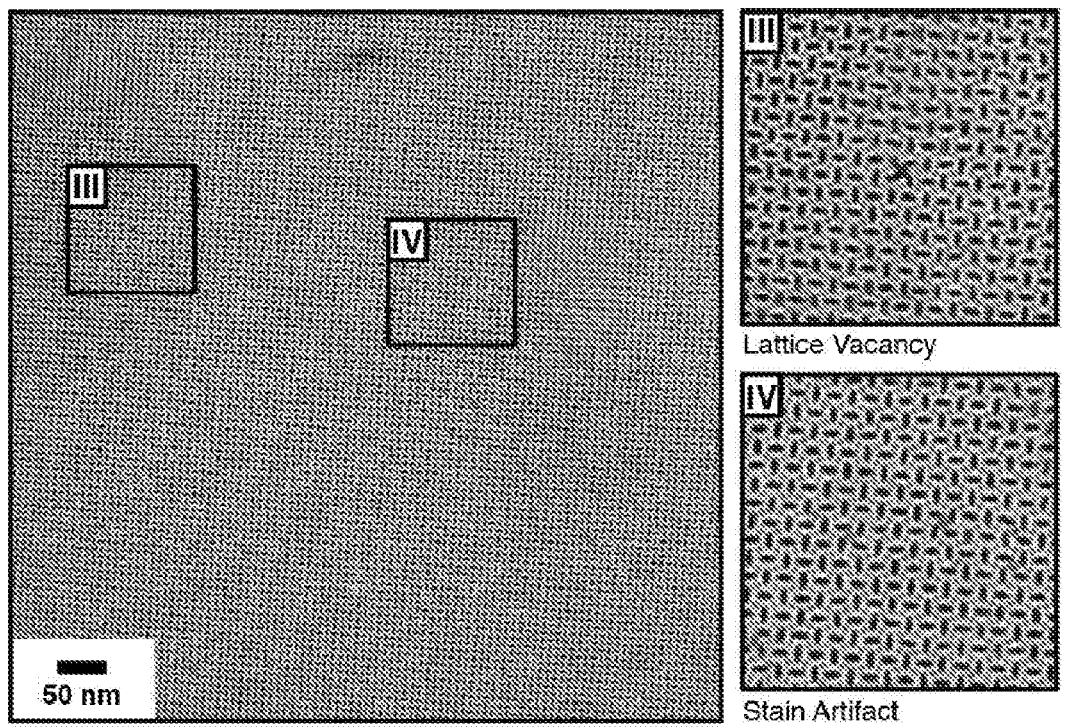

FIG. 22 shows representative images of 2D C98RhuA crystals containing no defects. Representative images 2D $^{C98}$RhuA crystals contain no defects (FIG. 22A) or one lattice vacancy (FIG. 22B). The stain artifacts images are shown to highlighted areas that may appear to contain lattice vacancies in low-magnification images but in actuality do not.

FIG. 23 shows conformational analysis of C98RhuA lattices. 23A, Photographs of sedimented and resuspended C98RhuA crystals (alternative views with different backgrounds are shown for clarity). 23B, Representative TEM images for different conformational states (I-VII) of the C98RhuA crystals shown in FIG. 12. Scale bars are 25 nm in all panels. 23C, Digital image processing of reconstructed images of each conformational state. Lines represent the border of the pores in the lattice structure which outline the pores, in which the pores represent the black circular or oval structures. Selected RVEs are shown with drawn in squares which enclose points 1, 2, 3 and 4, with the vertices of the RVEs numbered 1-4. Lines that show the circles are circumscribed to the square RhuA building block. Values of the scaling between these and the TEM images (with conformational state I as a reference) are shown below each image. 23D, Changes in the dimensions of a C98RhuA lattice of arbitrary size assuming a rotating-rigid-squares model.

FIG. 24 shows Rhu-C98 sheet on Grid followed by the addition of Maleimido-Au for two hours.

FIG. 25 shows another example of Rhu-C98 Rhu-C98 sheet on Grid followed by the addition of Maleimido-Au for two hours.

FIG. 26 shows Rhu-C98 sheet on Grid followed by the addition of Maleimido-Au for overnight experiment.

FIG. 27 shows Rhu-C98 sheet on Grid followed by the addition of Maleimido-Au for three hours.

FIG. 28 shows Rhu-C98 sheet stock sample with HauCl$_4$.

FIG. 29 shows Rhu-C98 (44,) added into 0.5 mM HauCl$_4$ in 5 mM NaPi pH 7.2 for 6 days then an addition of 5 mM βME for one day.

FIG. 30 shows Rhu-C98 (4 μL) added into 100 μL of Au(I) (HauCl$_4$ plus 2eq thiodiethanol) in 5 mM NaPi pH 7.2 for 4 days.

Figure 31:
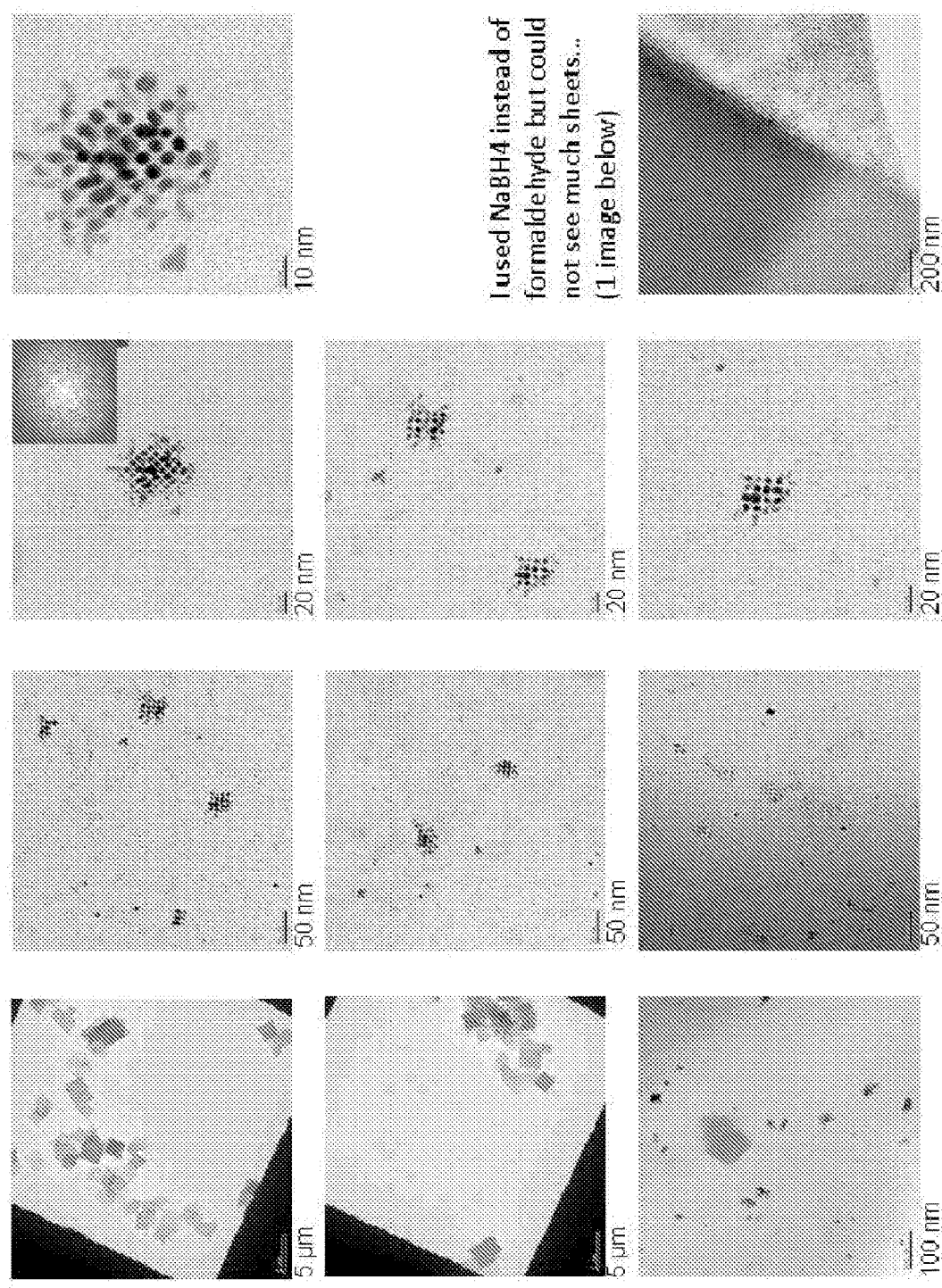

FIG. 31 shows Rhu-C98 on Grids followed by the addition of HauCl$_4$/K$_2$CO$_3$/NaBH$_4$ for one hour then in 10% formaldehyde for 2 hours.

FIG. 32 shows Rhu-C98 sheet/HauCl$_4$ on grids followed by HauCl$_4$/K$_2$CO$_3$/NaBH$_4$ in NaPi pH 7.2 for two hours.

FIG. 33 shows Rhu-C98 sheet/HauCl$_4$ on grids followed by HauCl$_4$/K$_2$CO$_3$/formaldehyde in NaPi pH 7.2 for two hours.

FIG. 34 shows Rhu-C98 sheet with addition of 200 μM Iodo-Fl.

FIG. 35 shows another example of Rhu-C98 sheet with addition of 200 μM Iodo-Fl.

FIG. 36 shows synthesis of Rhu-Cys-iPhen.

Figure 37:
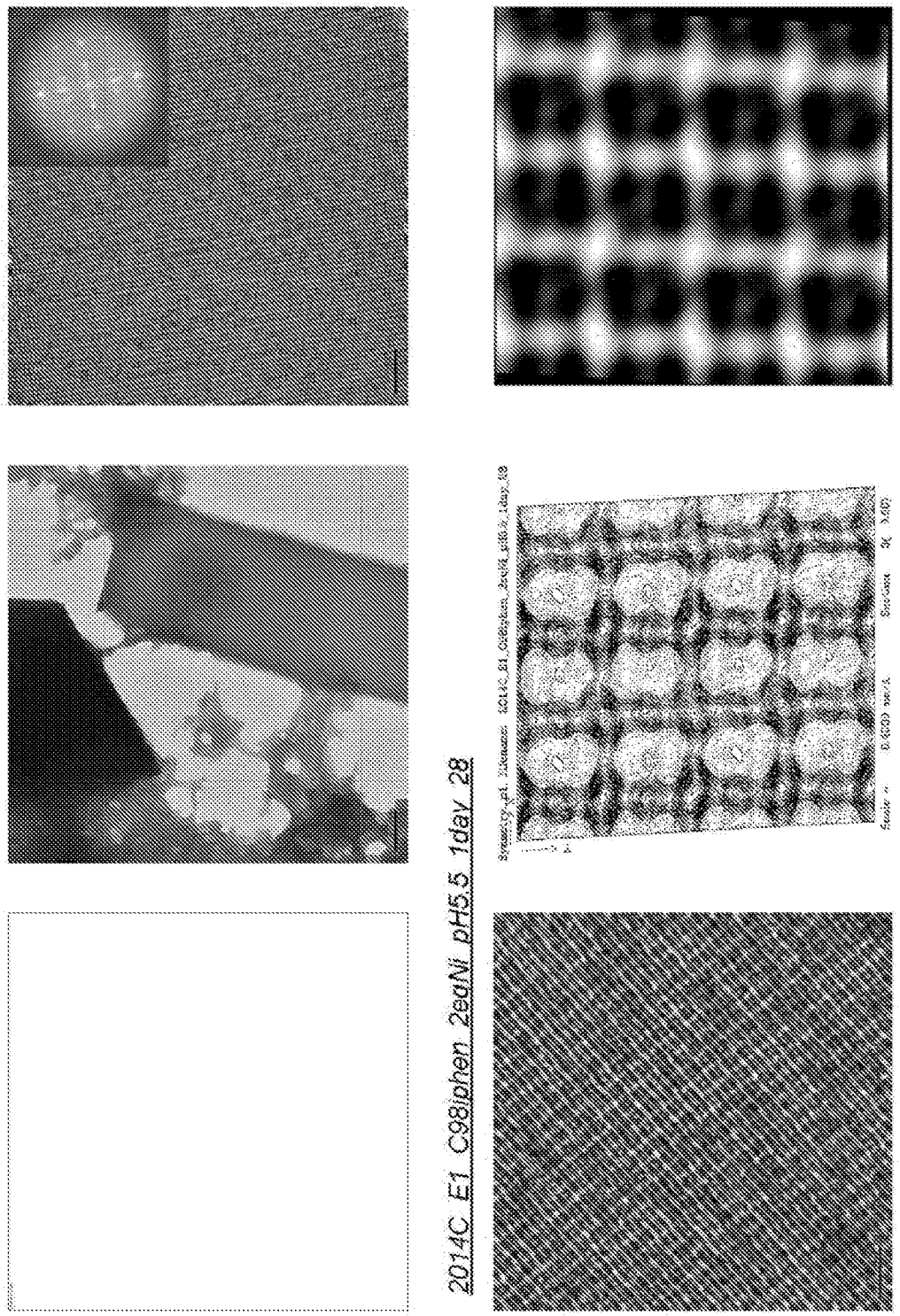

FIG. 37 shows Rhu-Cys-iPhen (100 μM) with 2eq NiCl$_2$ in 20 mM Mes at pH 5.5 after day 1.

Figure 38:
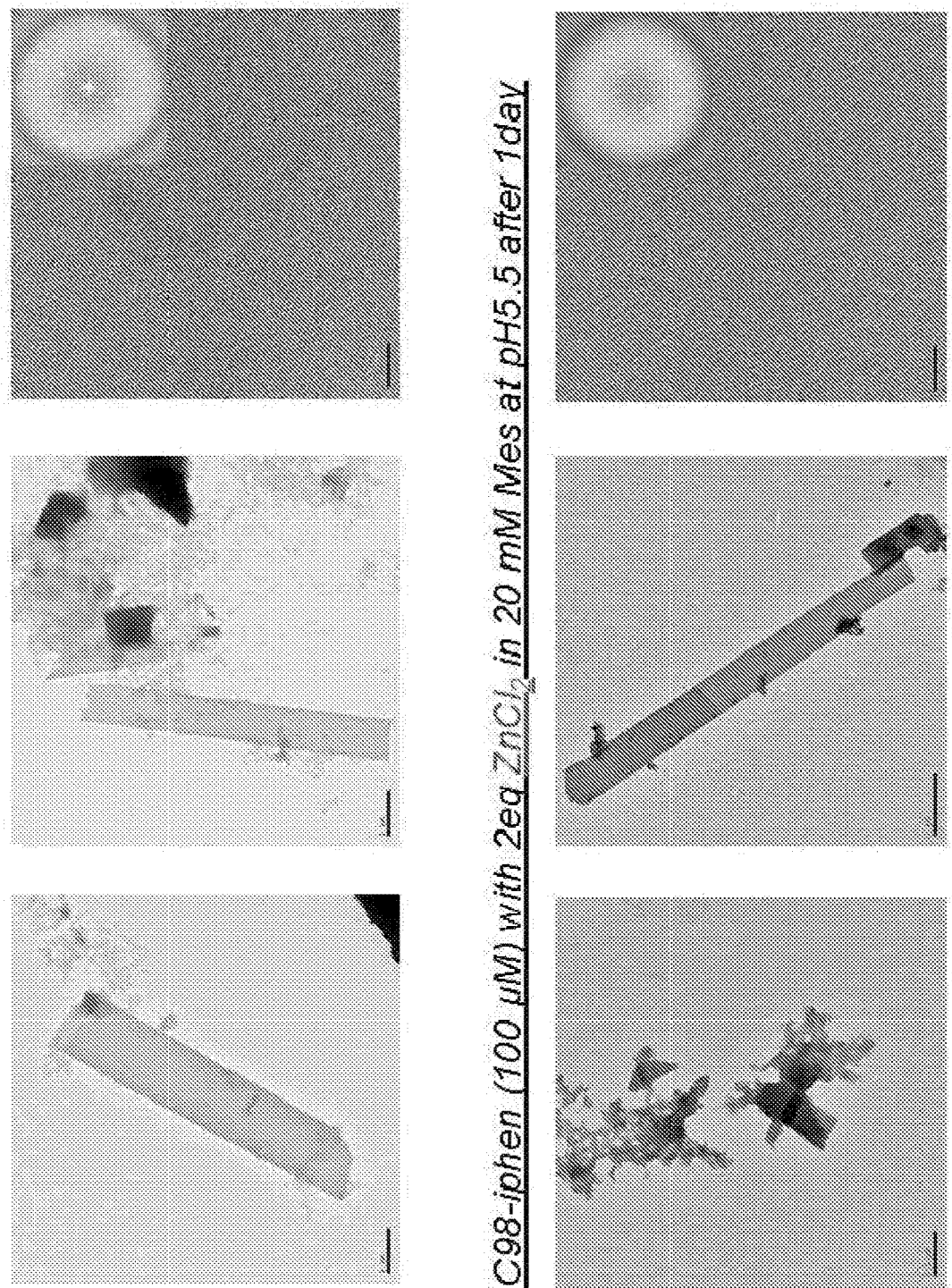

FIG. 38 shows Rhu-Cys-iPhen (100 μM) with 2eq CuCl$_2$ in 20 mM Mes at pH 5.5 after day 1 and Rhu-Cys-iPhen (100 μM) with 2eq ZnCl$_2$ in 20 mM Mes at pH 5.5 after day 1.

Figure 39:
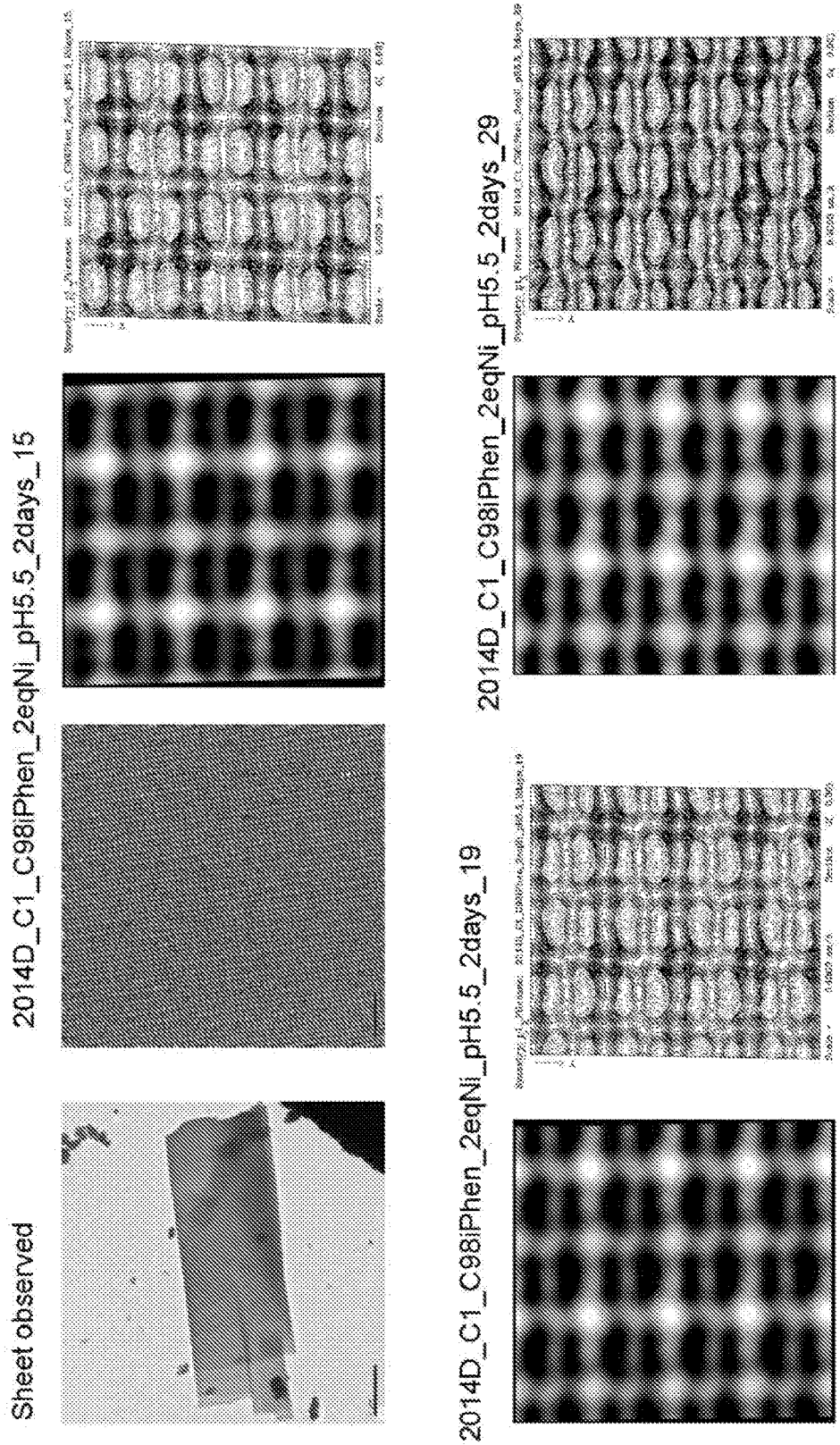

FIG. 39 shows CD-iPhen with 2eq Ni in at pH 5.5 after day 2.

FIG. 40 shows Rhu-Cys-iPhen (100 μM) with 2eq NiCl$_2$ in 20 mM Mes at pH 5.5 after day 12 and with the addition of 4 eq imidazole.

FIG. 41 shows Rhu-Cys-iPhen (100 μM) with 2eq NiCl$_2$ in 20 mM Mes at pH 5.5 after day 12 and with the addition of 2 eq zinc.

FIG. 42 shows photoswitchable protein assembly by Azo-CD.

FIG. 43 shows protein assembly by small molecules.

Figure 44:
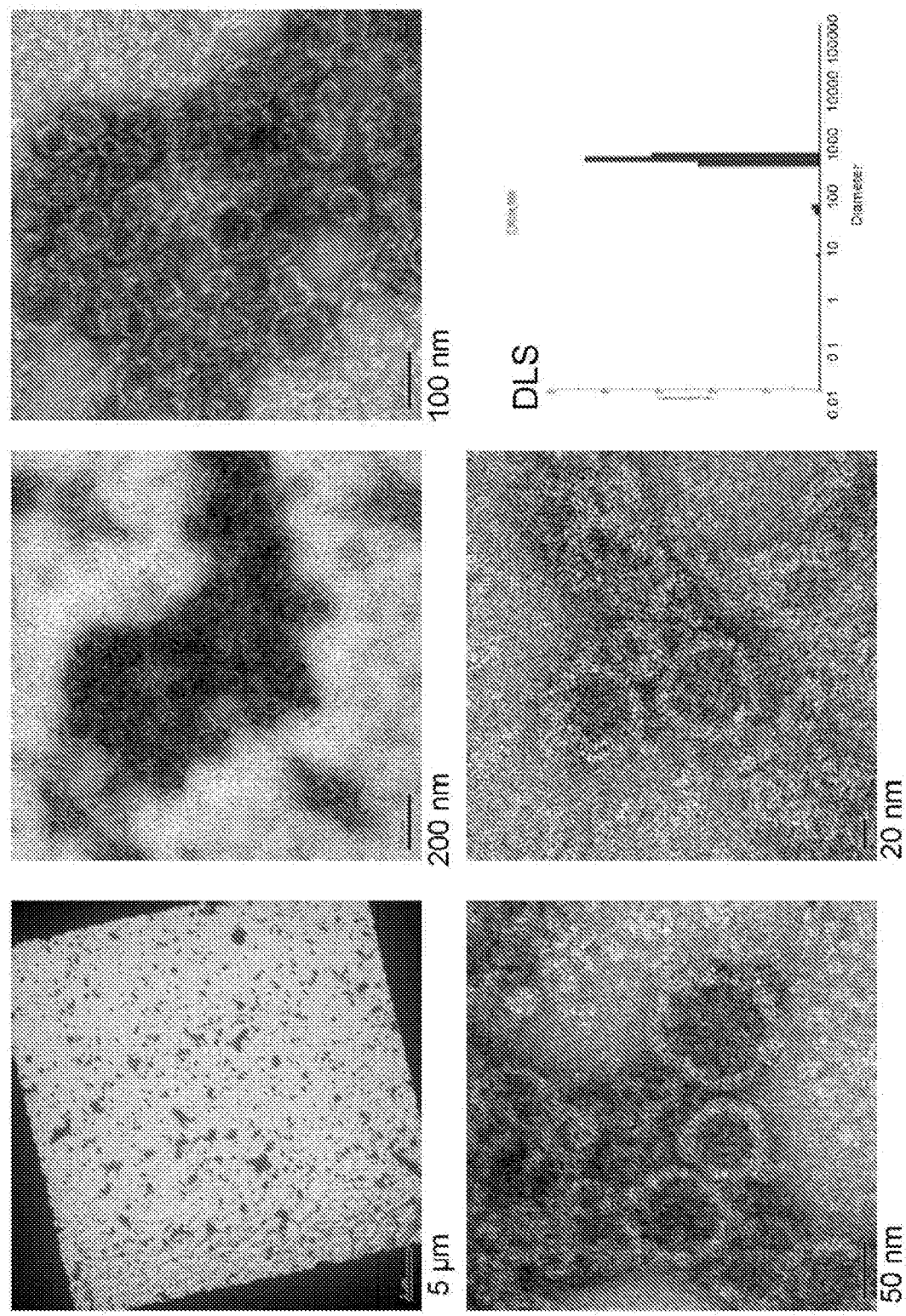

FIG. 44 shows protein assembly by small molecules, 1 mM Curcumin after one hour.

Figure 45:
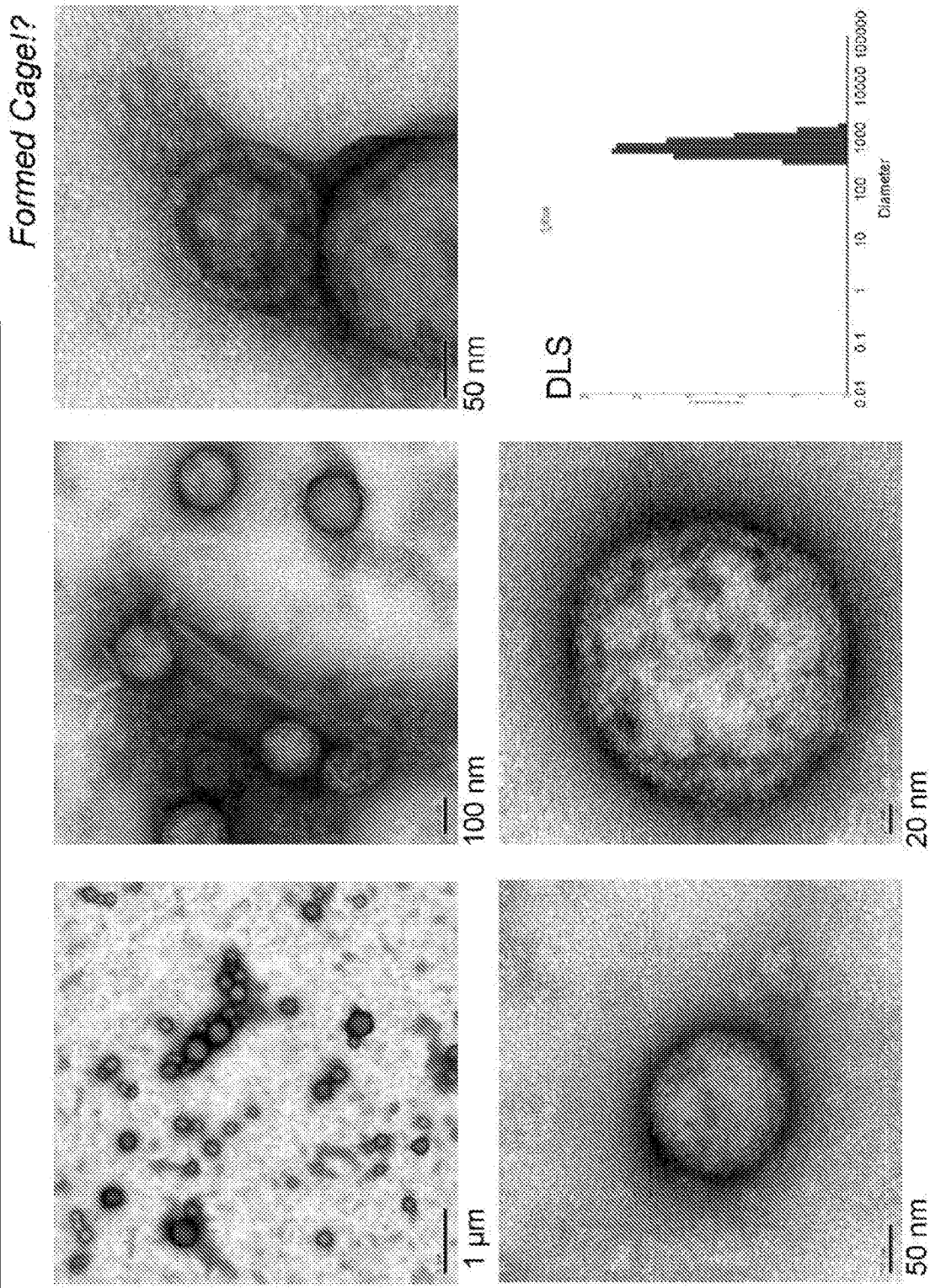

FIG. 45 shows protein assembly by small molecules, 5 mM Curcumin after one hour.

FIG. 46 shows protein assembly by small molecules, with Biz-azobenzene and then using Curcumin as a binding partner.

Figure 47:
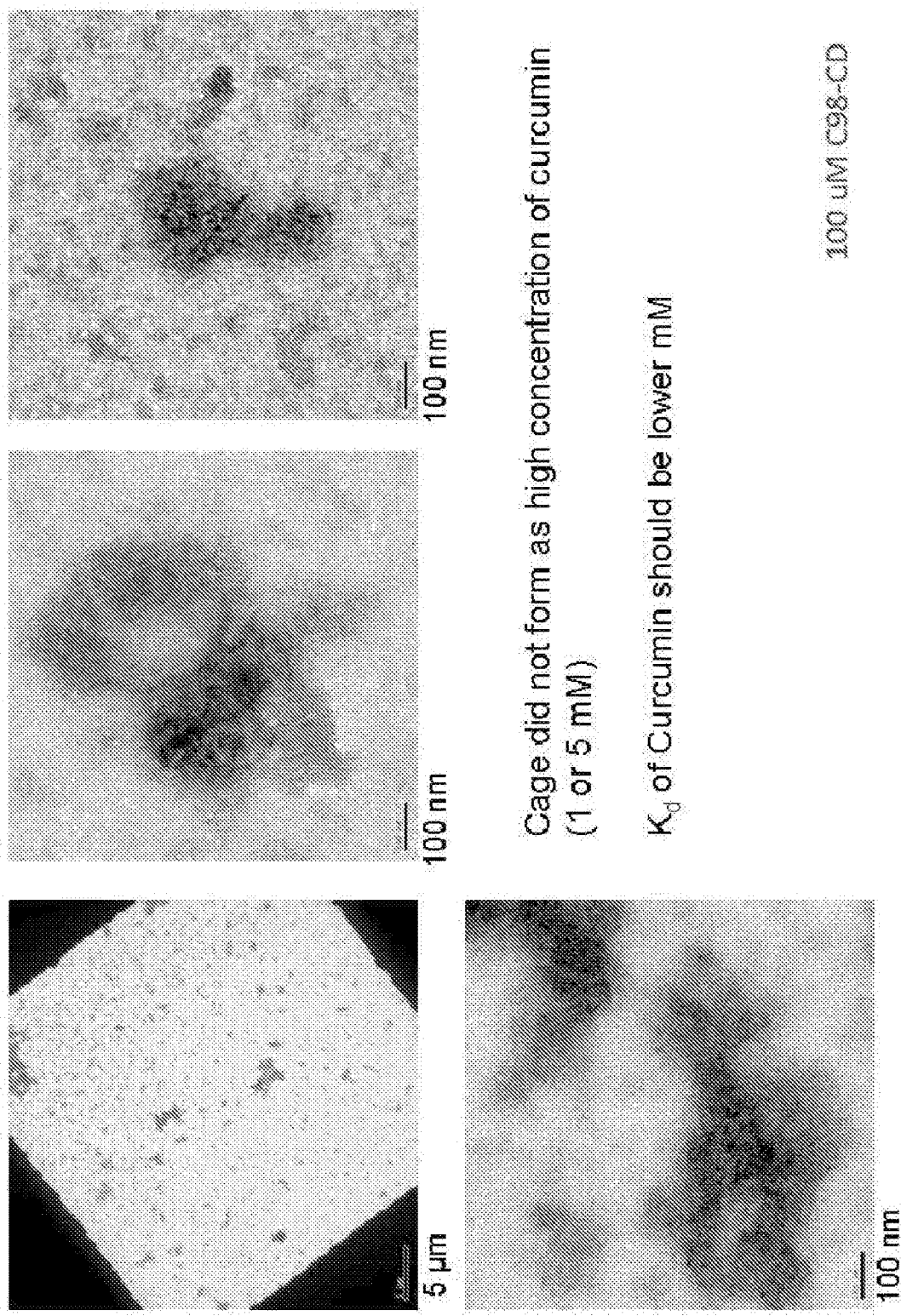

FIG. 47 shows protein assembly by small molecules, 100 μM Curcumin after one hour.

Figure 48:
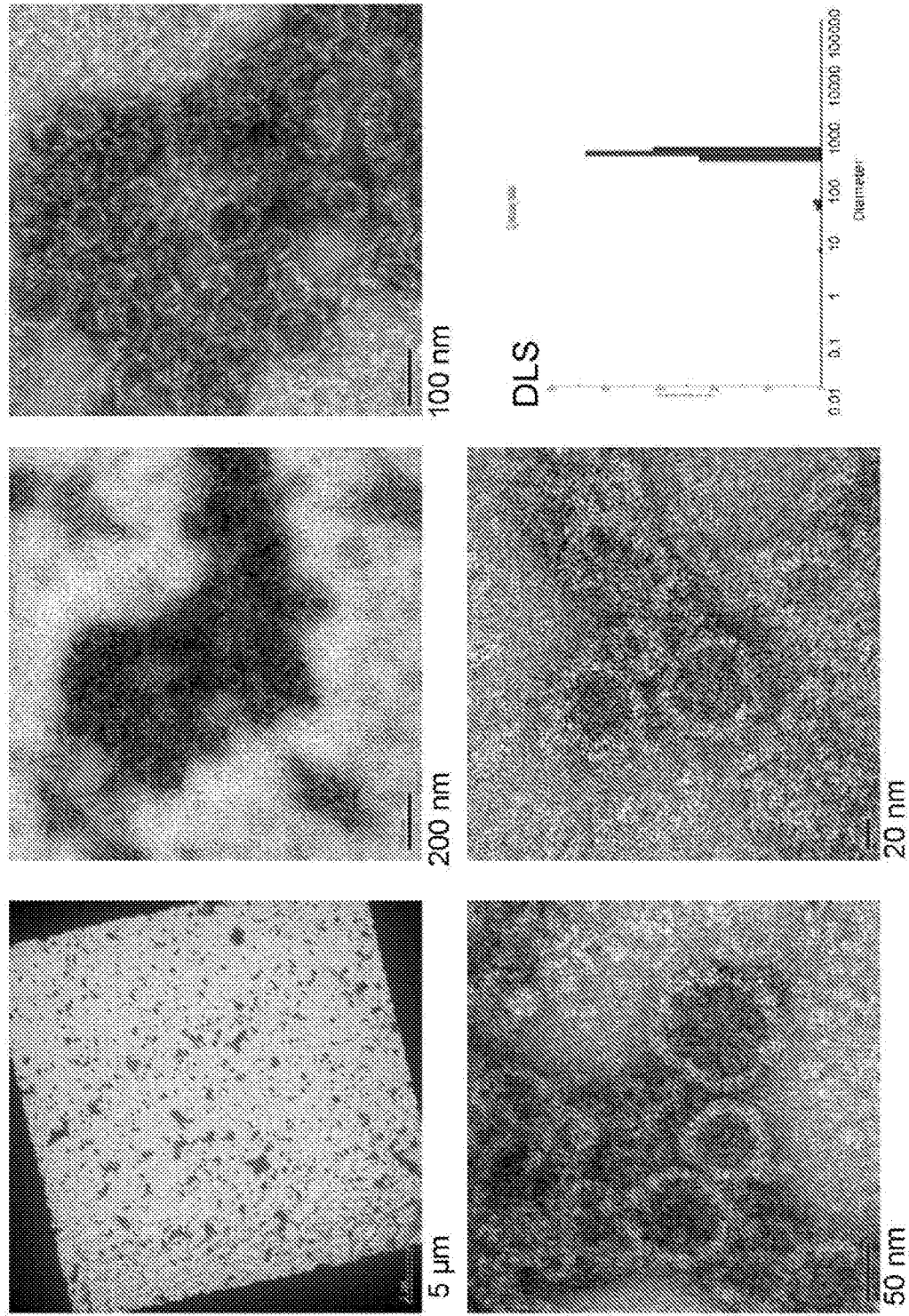

FIG. 48 shows another example of protein assembly by small molecules, 1 mM Curcumin after one hour.

Figure 49:
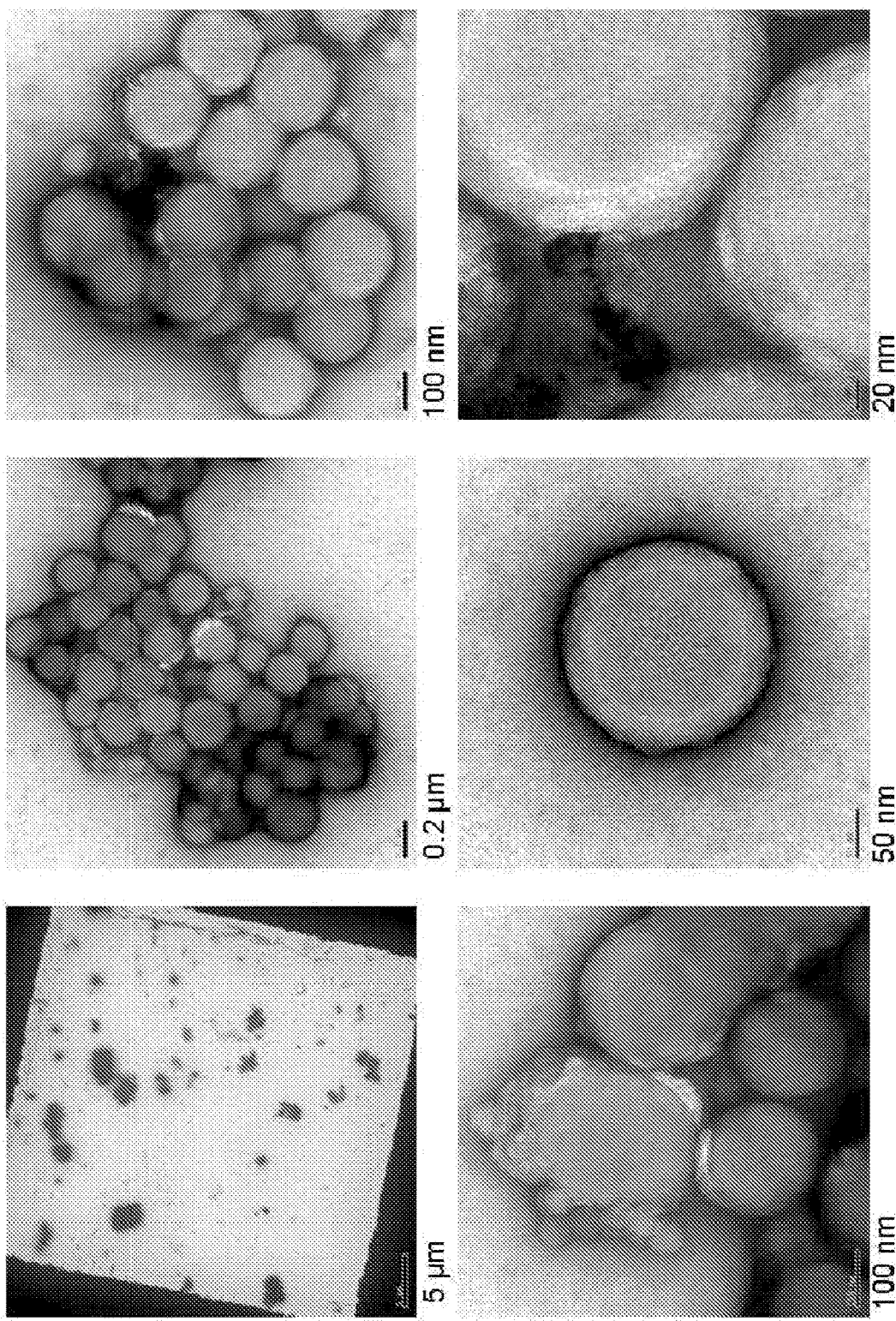

FIG. 49 shows another example of protein assembly by small molecules, 1 mM Curcumin after three days.

Figure 50:
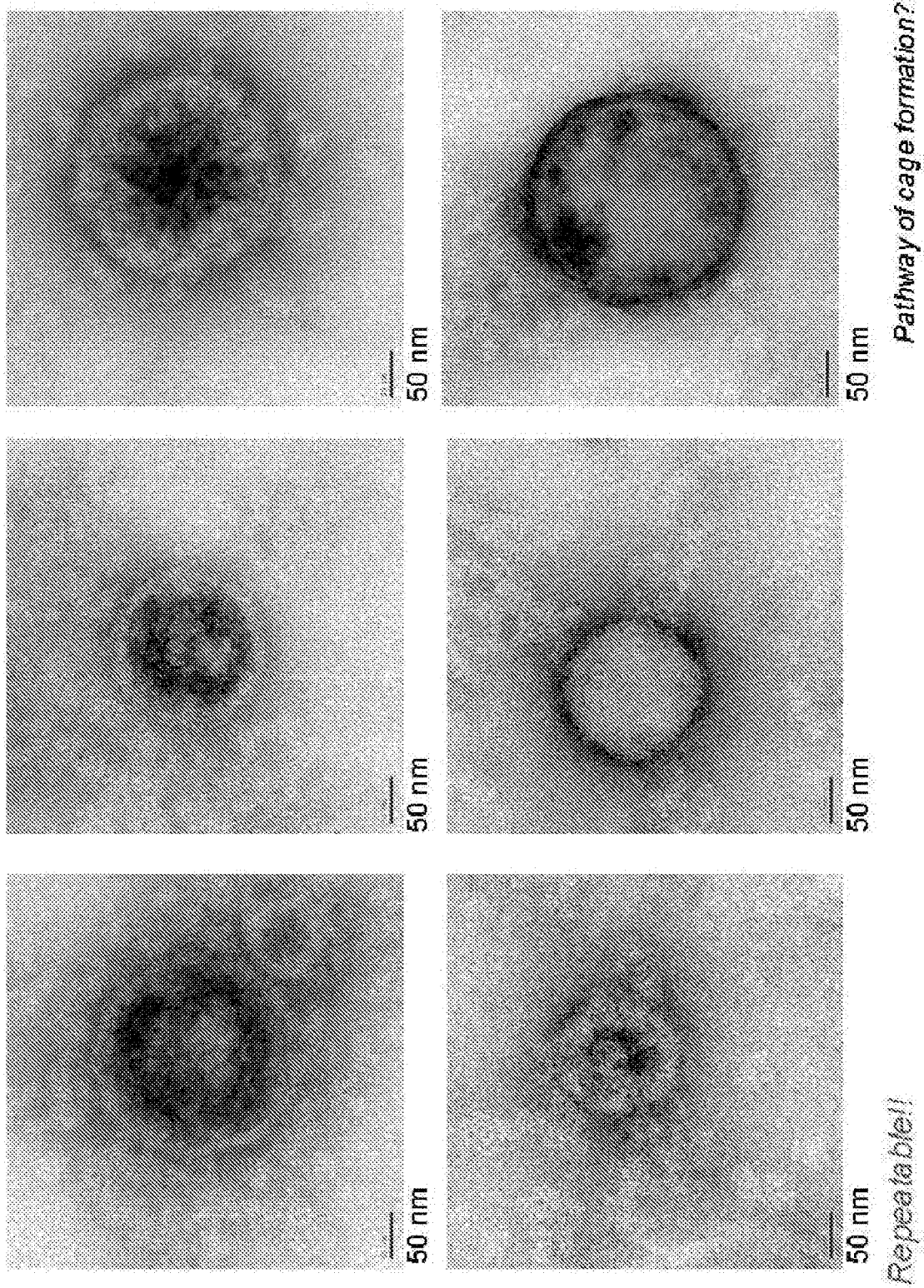

FIG. 50 shows another example of protein assembly by small molecules, 1 mM Curcumin after one hour. The results are repeatable.

Figure 51:
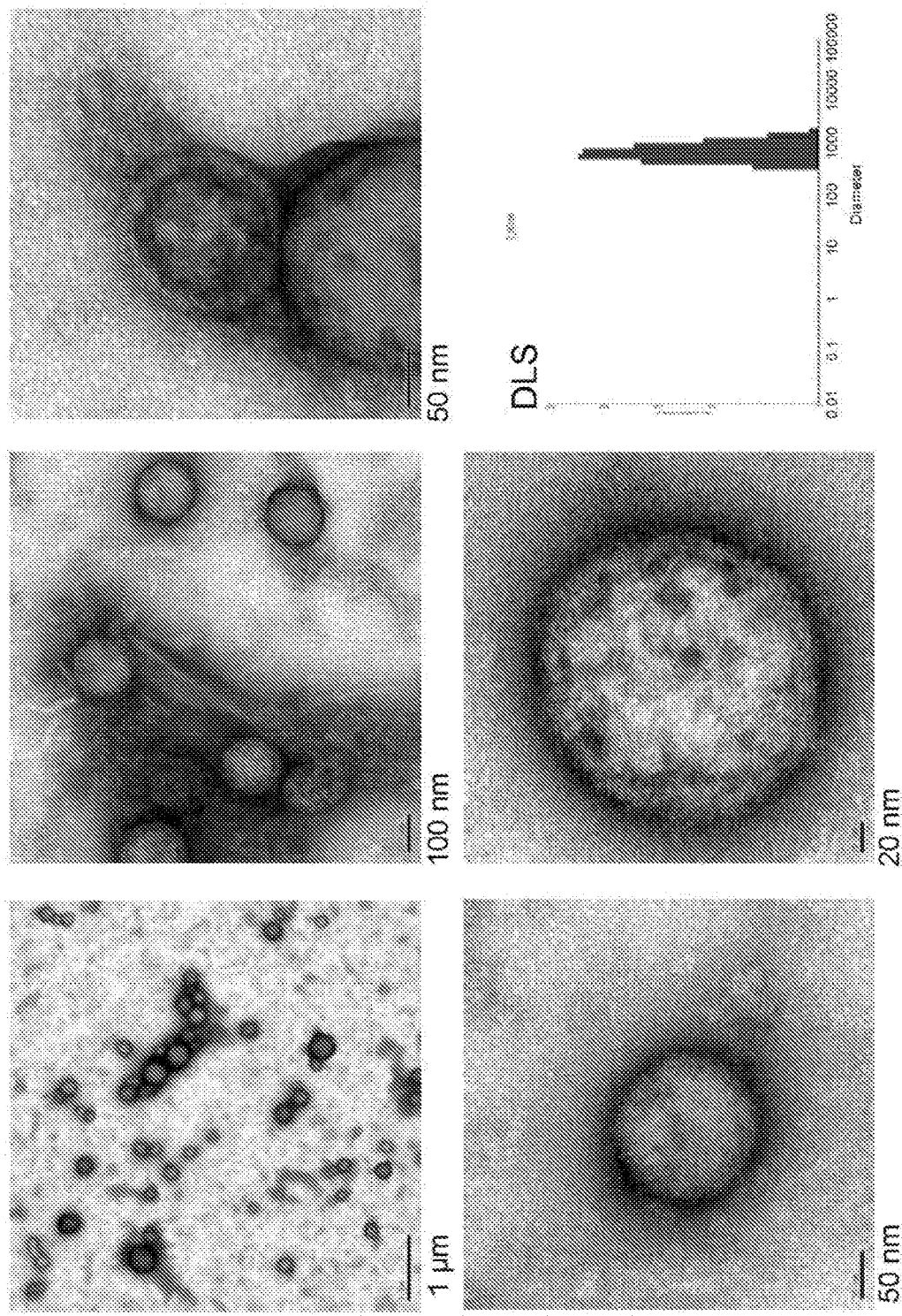

FIG. 51 shows another example of protein assembly by small molecules, 5 mM Curcumin after one hour.

Figure 52:
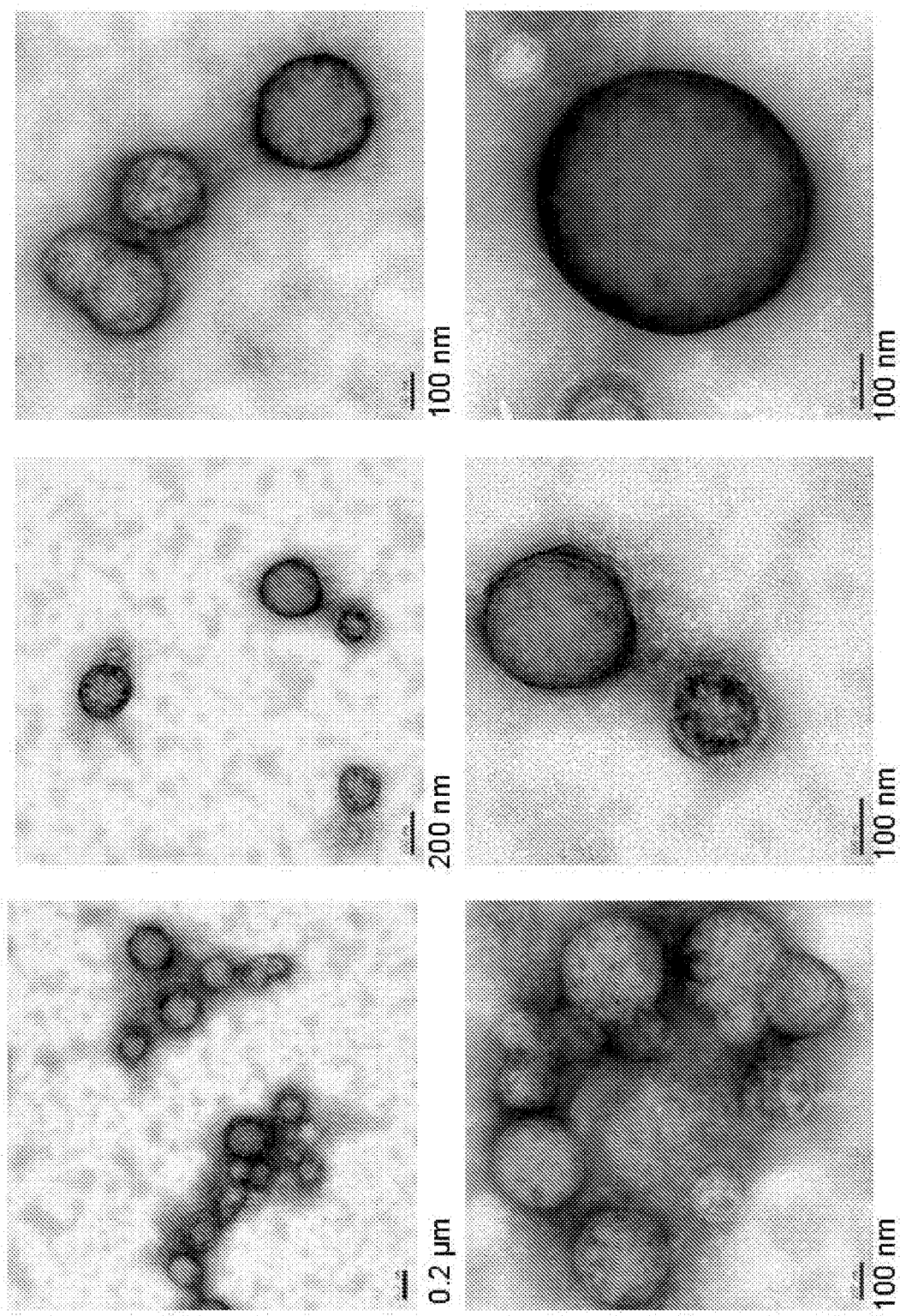

FIG. 52 shows another example of protein assembly by small molecules, 5 mM Curcumin after three days.

Figure 53:
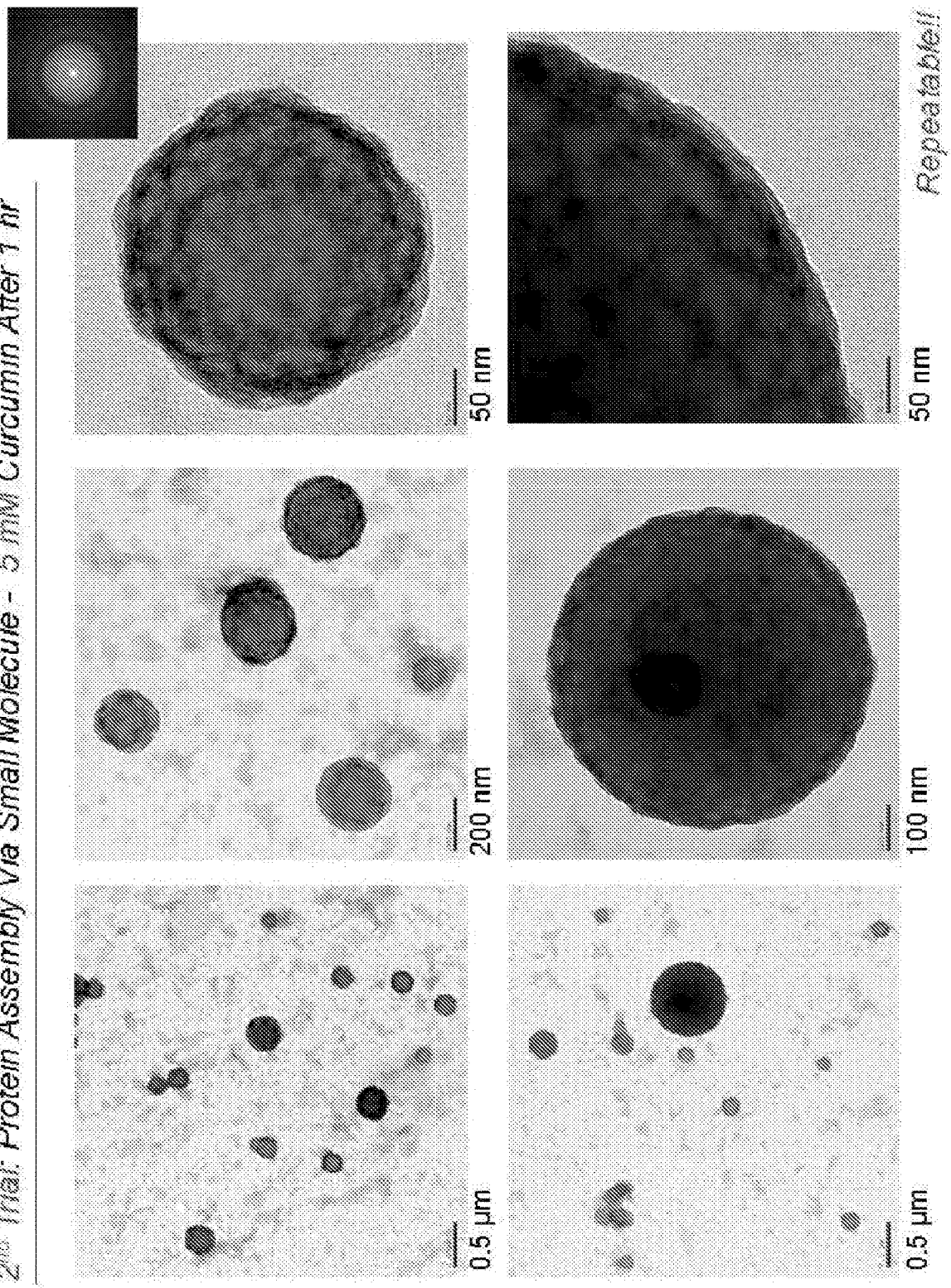

FIG. 53 shows another example of protein assembly by small molecules, 5 mM Curcumin after one hour.

Figure 54:
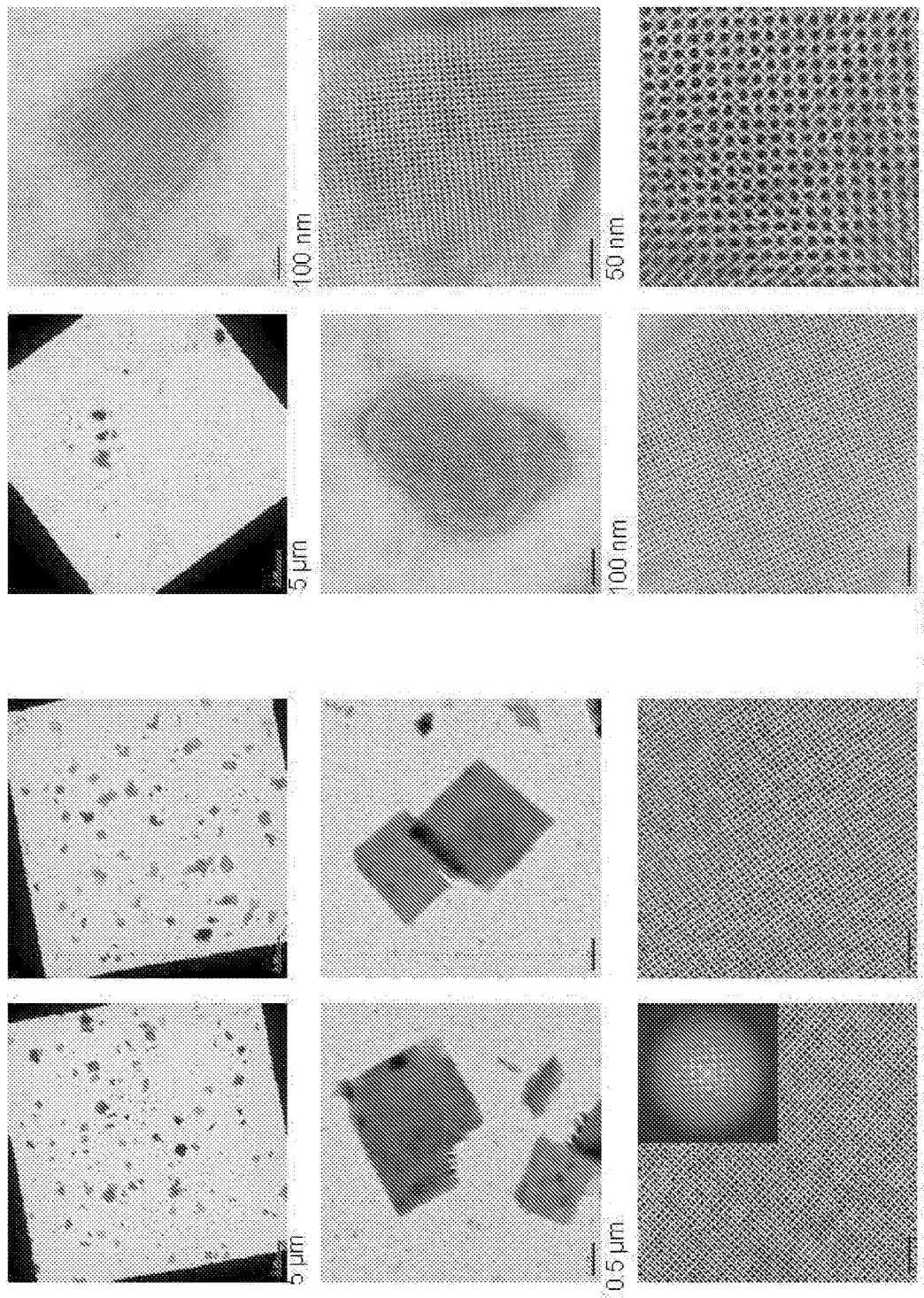

FIG. 54 shows crystals of C98C18 RhuA and 198C22 RhuA mutants.

Figure 55:
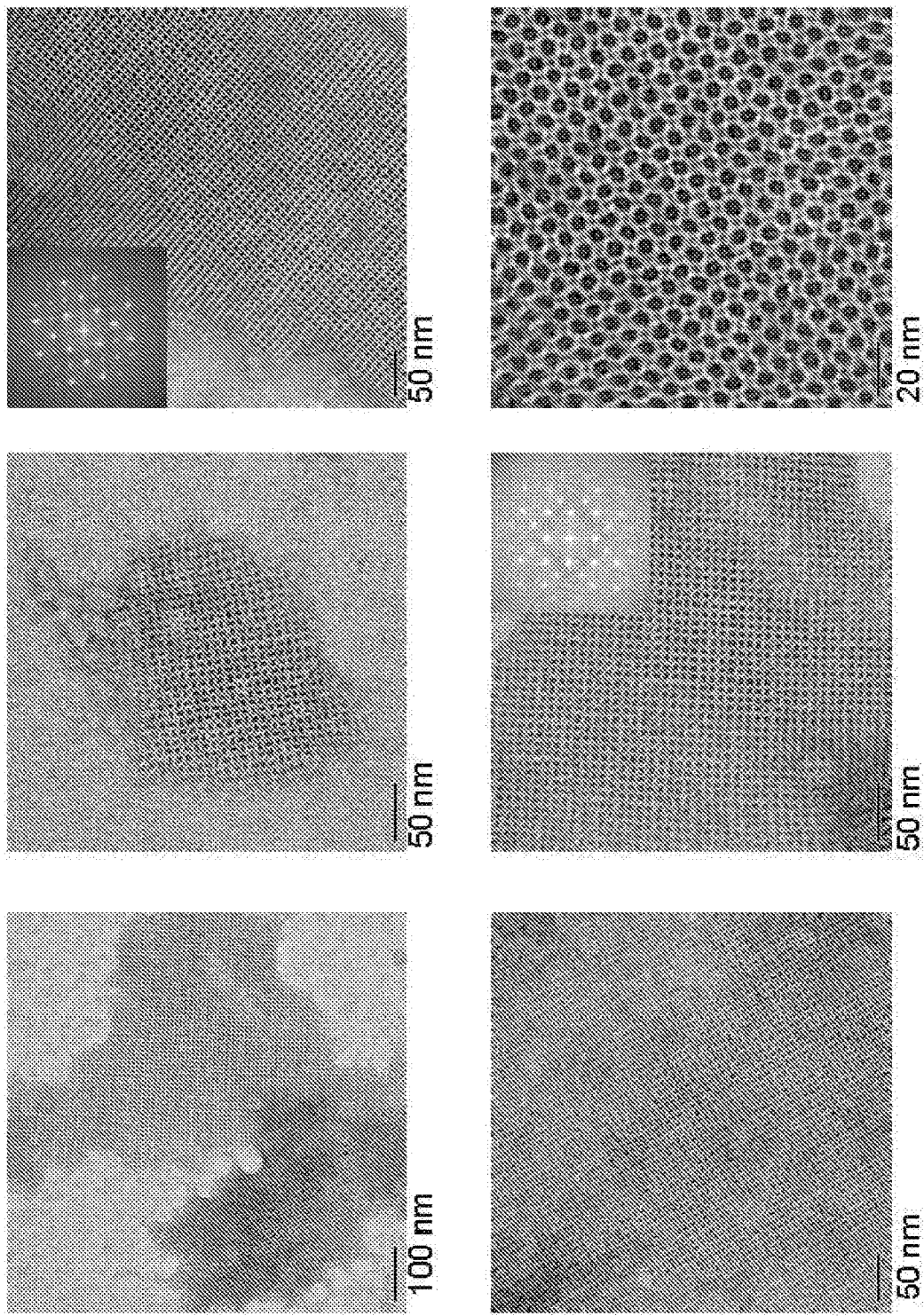

FIG. 55 shows crystals of C98-His tagged RhuA mutant (100 µM) in 20 mM MOPS at pH 7 in reduced conditions after 5 days.

Figure 56:
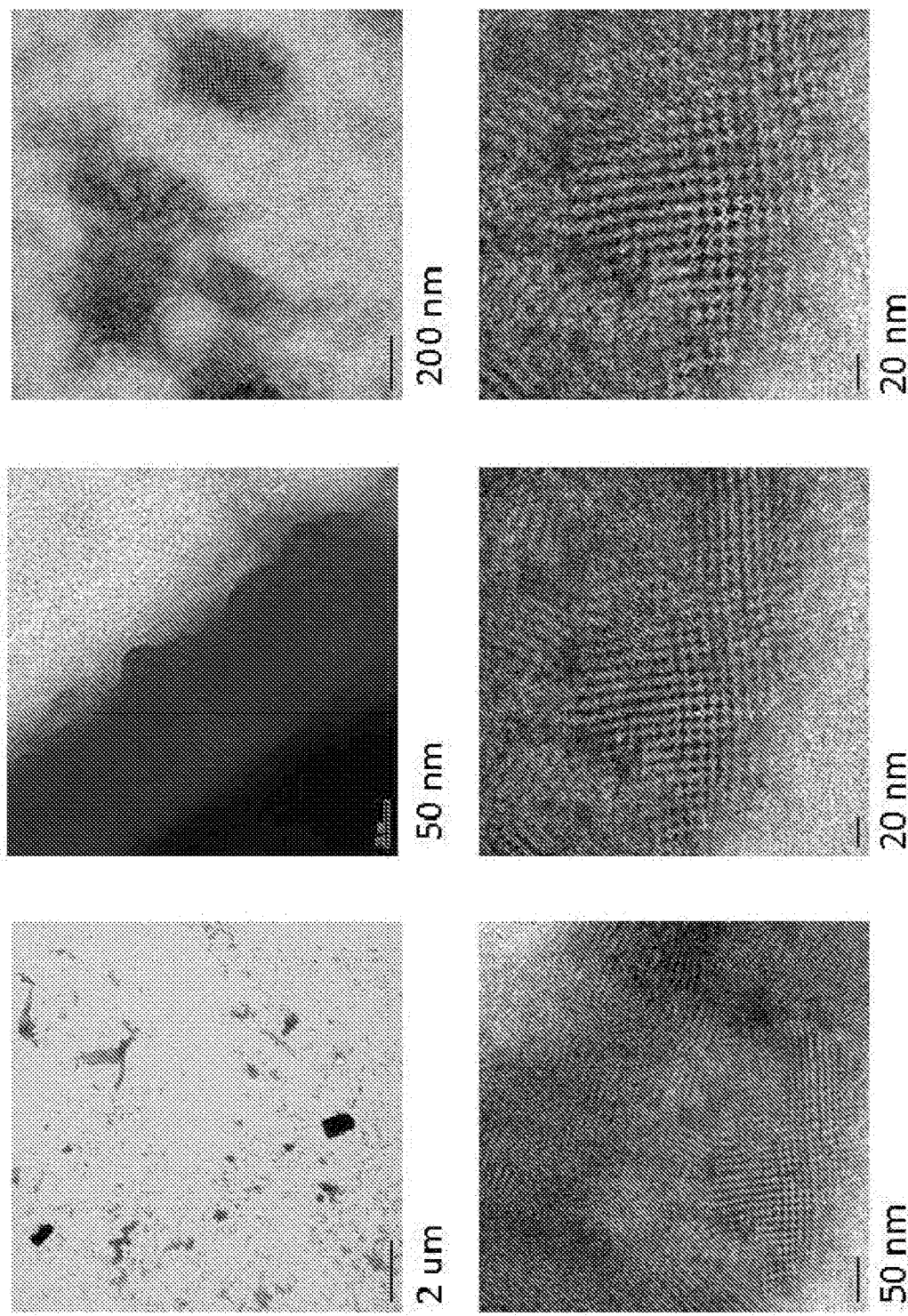

FIG. 56 shows crystals of C98-His tagged RhuA mutant (100 µM) in 20 mM MOPS at pH 7 in redoxed conditions after 1 day.

FIG. 57 shows assembly of C98-RhuA-Pd4 mutant (125 µM) under various conditions after 1 day with shaking conditions (20 mM Mes pH 5.5 10 mM βME, no ZnCl2; and 10 mM Tris pH 7.5, 10 mM βME, no ZnCl2).

FIG. 58 shows assembly of C98-RhuA-Pd4 mutant (125 µM) under various conditions after 1 day with shaking conditions (20 mM Tris pH 7.5 10 mM βME, 1 mM ZnCl2; 10 mM Tris pH 7.5, 5 mM βME, no ZnCl2; and 10 mM Tris pH 7.5, 10 mM βME, no ZnCl2).

FIG. 59 shows fusion protein 2D assemblies: RhuA-ACP

Figure 10A:
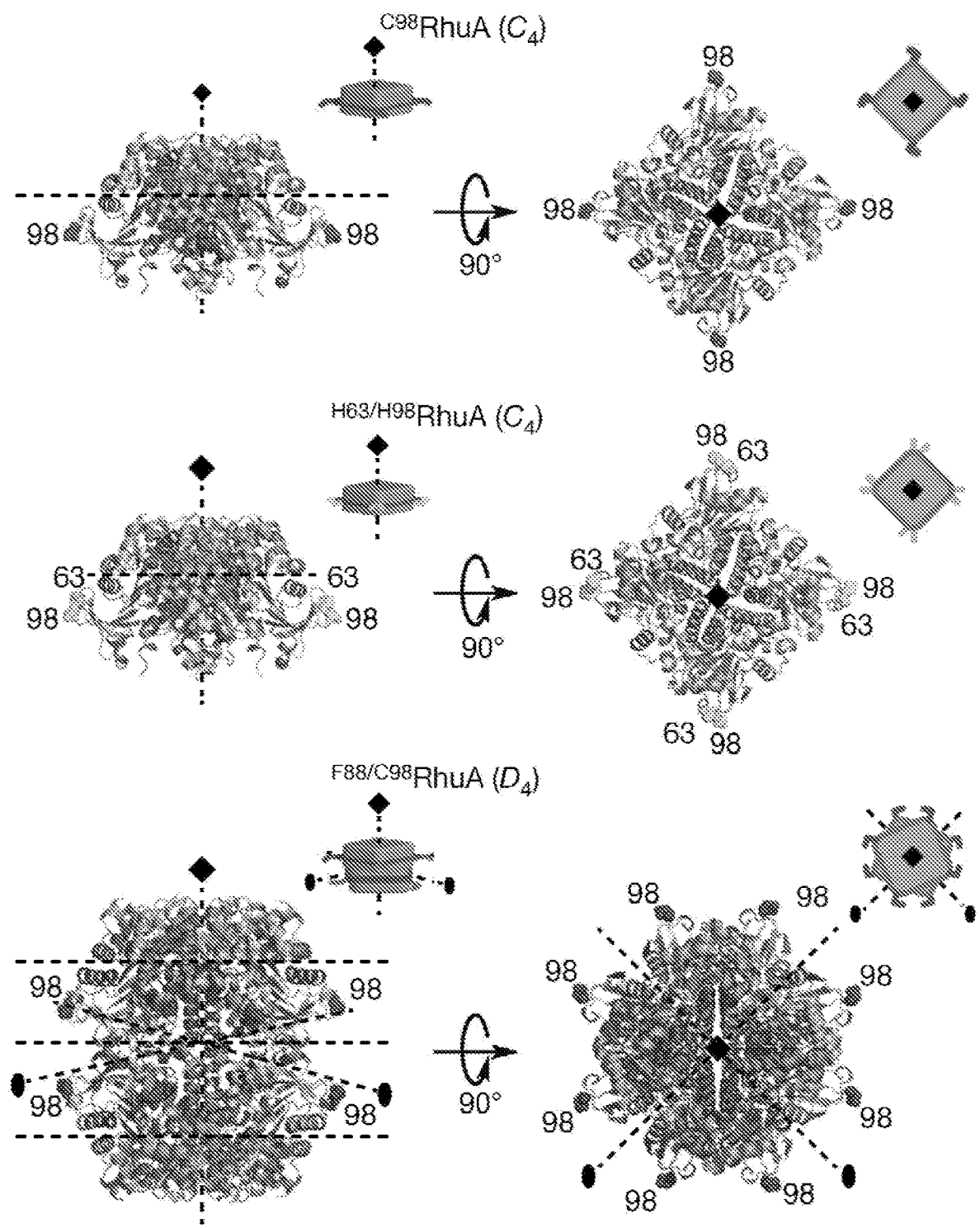
FIG. 10 shows RhuA constructs and their disulfide- and metal-mediated self-assembly modes. 10A) schematic representations of the C98RhuA, H63/H98RhuA and F88/C98RhuA structures. The top and bottom halves of RhuA have different relative molecular orientations as shown in 10A, in which a horizontal line splits the molecule in to the top portion and bottom portion. As shown for the F88/C98 RhuA protein, the top portion and bottom portion are equivalent to one another and the two portions in the middle are equivalent to one another.
FIG. 10B. Cys and His residues inserted into positions 98 and 63 are shown by the numbering on the FIGS. 98 and 63).
FIG. 10C shows 25 μM C98RhuA was incubated at 4° C. under air exposure for 1 day; the solution contained 20 mM Tris (pH 8) and no reductants or oxidants. 10D, 25 μM H63/H98RhuA was incubated in the presence of 1 mM ZnCl2 at 4° C. for 1 day; the solution contained 20 mM MOPS (pH 7).
Figure 10B:
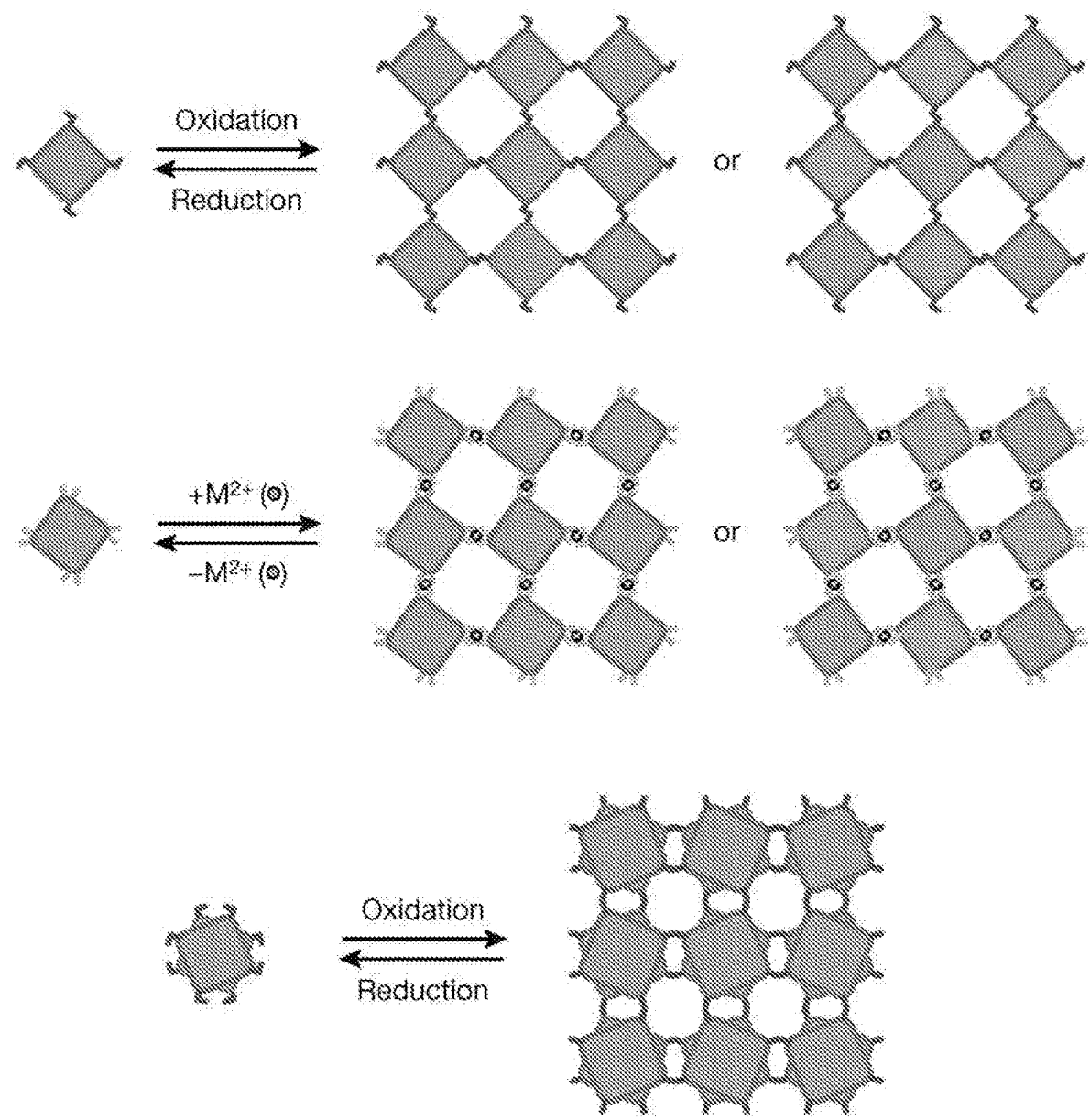
Figure 10C:
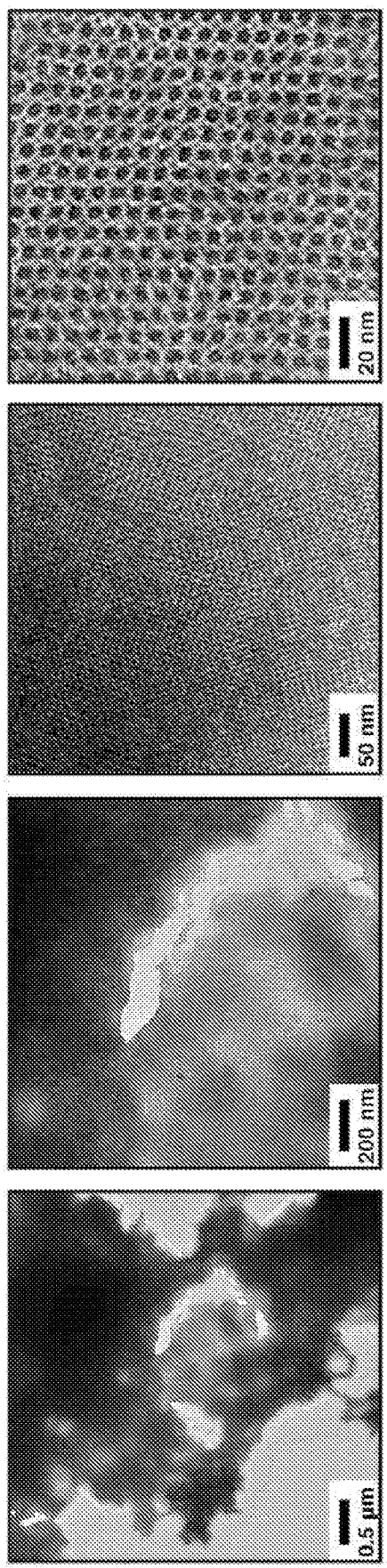
Figure 10D:
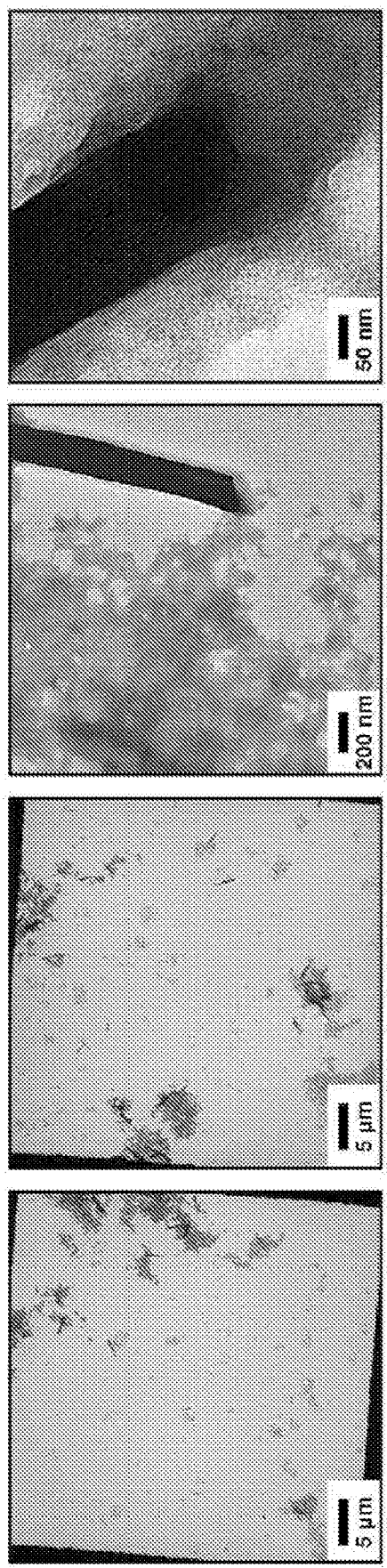
Figure 11D:
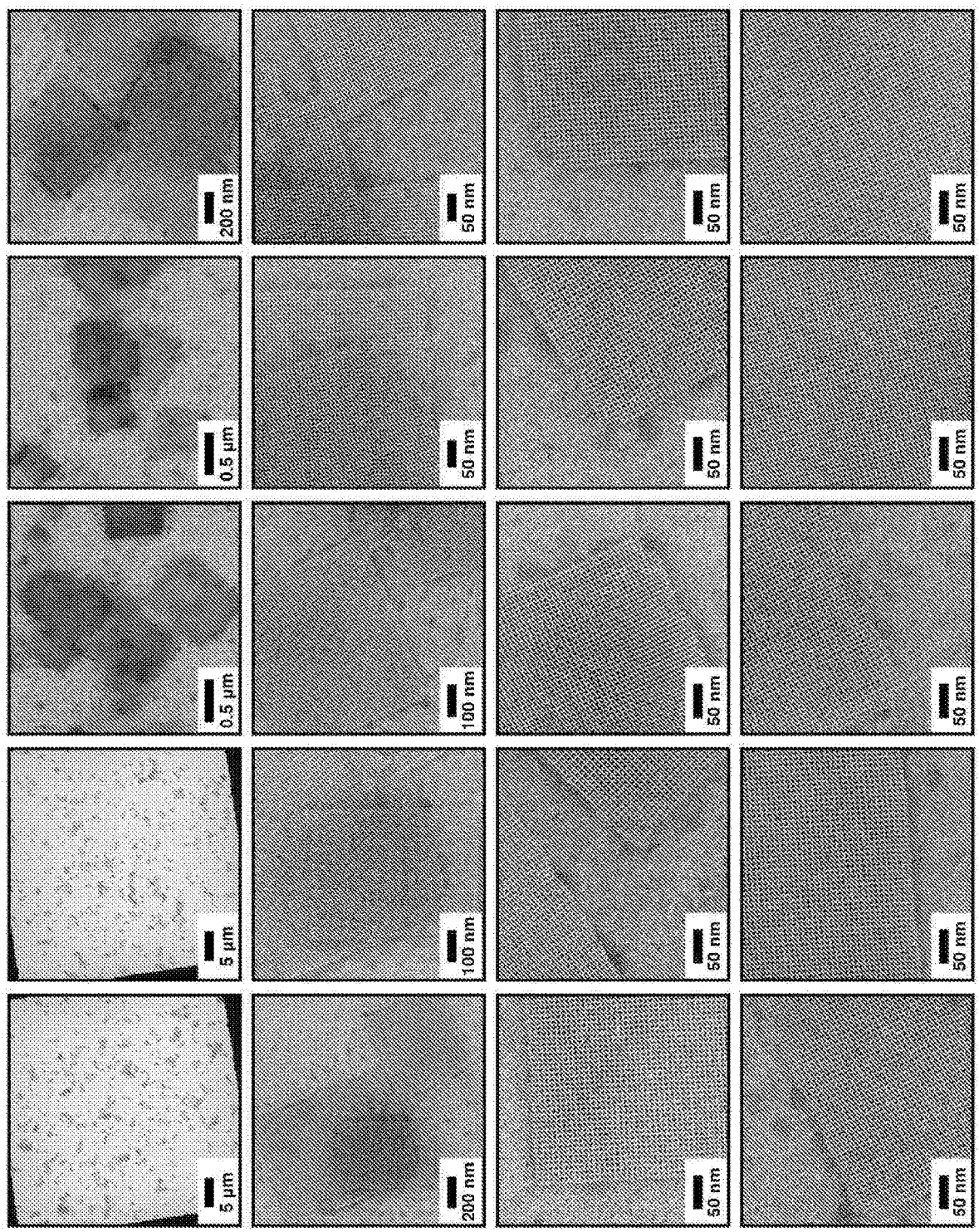
FIG. 11 shows ns-TEM characterization of the 2D crystals of $^{C98}$RhuA (11A), $^{H63/H98}$RhuA (Zn$^{2+}$ coordination) (11B) and $^{F88/C98}$RhuA (11C). (i) Low-magnification views, (ii) high-magnification views, (iii) Fourier transforms of ii, (iv) reconstructed 2D images, (v) structural models based on the 2D reconstructions. The high resolution limits in panels iii are ~14 Å. For a comparison of experimental and computed 2D reconstructions, see FIG. 20. Unit cells are shown as black squares (with corners placed at two-fold symmetry axes); unit cell constants (α=β, γ) are: $^{C98}$RhuA (114 Å, 90°); $^{H63/H98}$RhuA (91 Å, 90°); $^{F88/C98}$RhuA (115 Å, 90°).
Figure 11E:
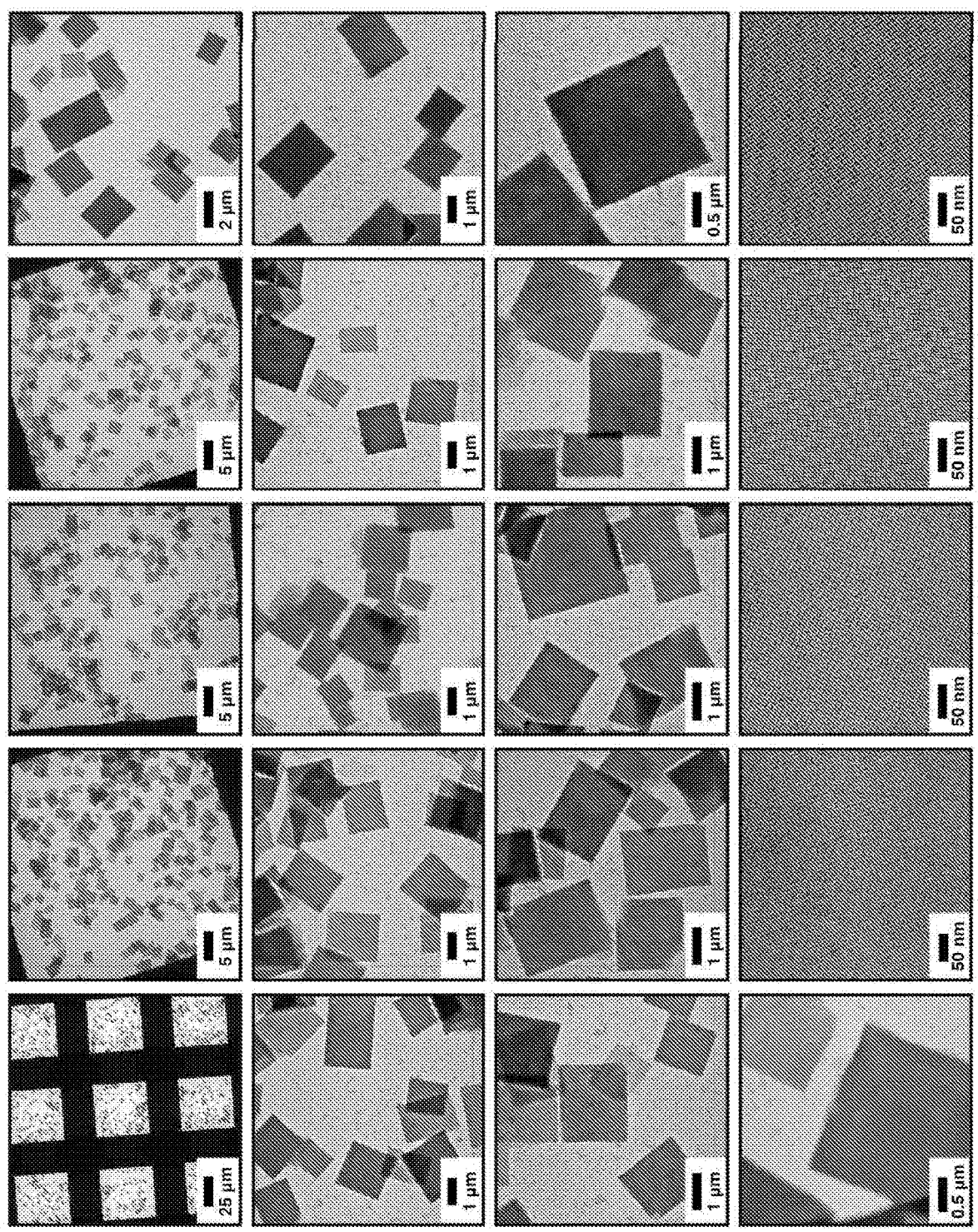

FIG. 60 shows the characterization of the self-assembly of D98RhuA, C133RhuA and C266RhuA variants by TEM and DLS. 60A, TEM (right panels) and DLS (left panels) characterization of D98RhuA self-assembly under oxidative or metal-mediated self-assembly conditions that were optimized for C98RhuA; FIGS. 11D and 11E and FIG. 17 for details. 60B: Possible mode of disulfide-mediated self-assembly of C133RhuA (top panels) and TEM characterization of the self-assembly products obtained under conditions that were optimized for C98RhuA (bottom panels). 60C, Possible mode of disulfide-mediated self-assembly of C266RhuA (top panels) and TEM characterization of the self-assembly products obtained under conditions that were optimized for C98RhuA (bottom panels). No crystalline assemblies were detected under these conditions for any of these three variants (or other conditions that were used for screening C98RhuA self-assembly). In the top panels of 60B and 60C as in FIG. 10.

FIG. 61 shows the crystallographic analysis of the 2D lattices of RhuA variants. 61A, (i) Representative Fourier transforms calculated from the full field of view of crystal images, displayed up to 10 Å. Reciprocal lattice axes are indicated with H and K. The reflections are consistent with the plane group symmetries estimated from the analysis of the phase residuals (Table 8). (ii) Integer quality (IQ) plots calculated from the spectra in column (i). The size of the boxes around the reflections reflects their IQ value, defined as the ratio of the reflectionpeak amplitude and the amplitude of the background signal around each peak[42]. The most significant reflections are labelled with their IQ values, 1-4. Rings are displayed at resolutions of 30 Å, 15 Å and 10 Å. (iii) Overlap of fast Fourier transform and IQ plots. 61B, Crystallographic data for the 2D lattices of RhuA variants. Reported are the numbers of TEM images used for the analysis of plane group symmetry. The numbers in parentheses are the number of images used for determining the statistics for the unit-cell dimensions of each lattice. The plane group symmetry was determined by consensus from all the available images. 61C, Electron diffraction patterns of C98RhuA and H63/H98RhuA lattices.

Figure 62A:
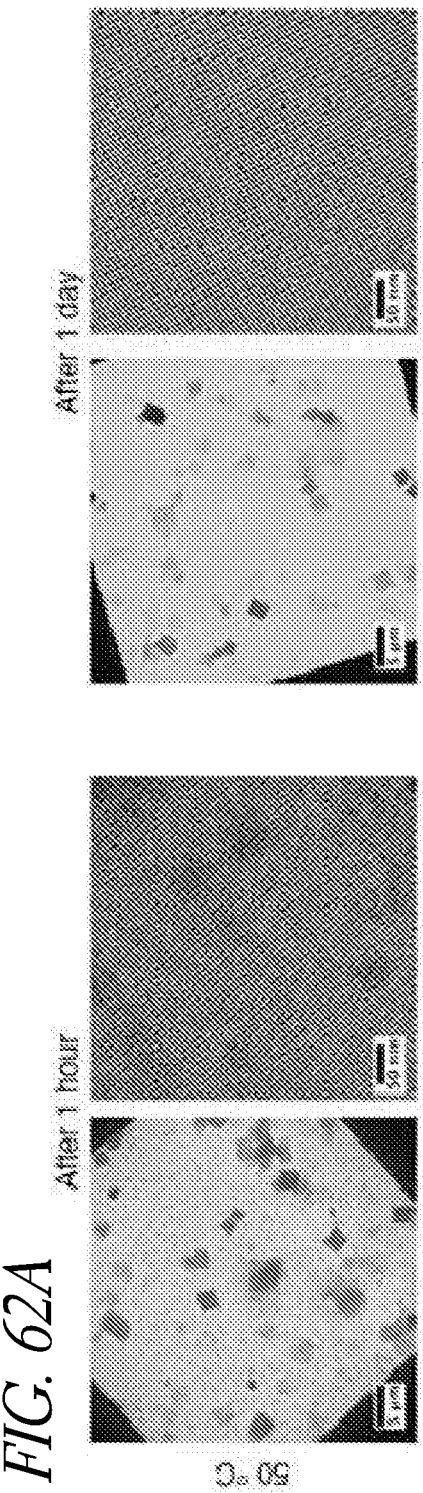
Figure 62B:
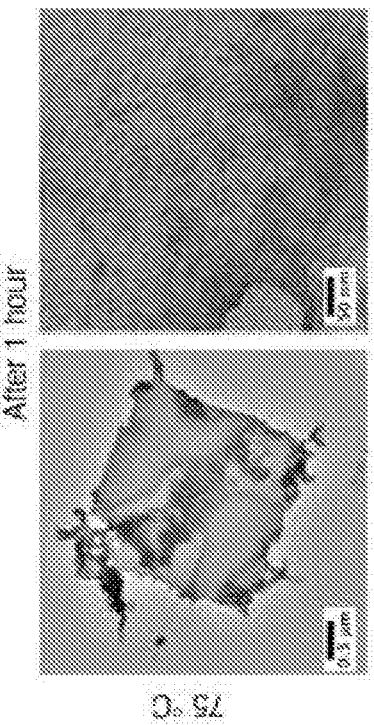

FIG. 62 (62A, 62B, 62C, 62D, 62E) shows the thermal and organic-solvent stability of $^{C98}$RhuA crystals. FIGS. 62A-E, $^{C98}$RhuA crystals were incubated at 50° C., 75° C., 50% DMF/H$_2$O and 100% DMF for indicated periods and characterized by TEM. The lattices were found to be stable at 50° C. for prolonged periods and retained their crystallinity, whereas at 75° C., both the lattice morphology and the crystallinity were lost due likely to the denaturation of $^{C98}$RhuA building blocks. Likewise, in 50 50% DMF/H$_2$O solutions, the lattices were indefinitely stable and crystalline, but appear to gradually lose both properties in 100% DMF. Interestingly, the lattice morphologies were retained, suggesting that the $^{C98}$RhuA building blocks likely denatured but still remained tightly associated with one another within the framework. 62E, The crystallinity of the samples in 100% DMF could not be recovered upon exchange into aqueous buffer, indicating that protein denaturation is irreversible.

Figure 63:
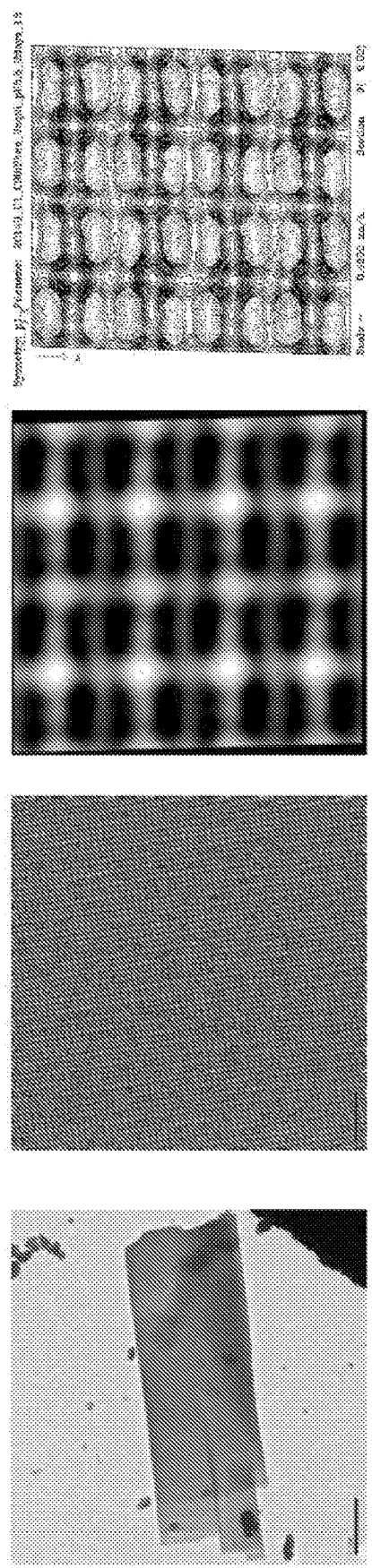

FIG. 63 shows the Metal directed self-assembly of $^{iPhen-C98}$RhuA (and $^{iPhen-C133}$RhuA) 2 eq of ZnCl$_2$, CuCl$_2$, or NiSO$_4$ was mixed with 100 µM $^{iPhenC98}$RhuA at pH 5.5 in 20 mM MES for 1 day (or as indicated) to assemble 2D crystals. Sample was deposited onto negatively glow-discharged carbon-coated Cu grids, washed with Milli-Q water at 4° C., and stained with 1% uranyl acetate at 4° C. $^{C133}$RhuA (control) was also tested in this experiment. Even though $^{C133}$RhuA could not form ordered array via disulfide bonds, $^{iPhen-C133}$RhuA (modification of cysteines) was able to form crystals via metal directed assembly due to additional space between protein-protein interactions.

FIG. 64 shows additional Cys residues onto $^{C98}$RhuA: $^{C18C98}$RhuA and $^{C22C98}$RhuA Several solution conditions were screened for optimizing the formation of 2D protein crystals of fusion proteins and best condition so far was indicated in the figure.

DEFINITIONS

Unless defined otherwise, all technical and scientific terms used herein have the same meaning as commonly understood by one of ordinary skill in the art to which the invention pertains.

"About" as used herein when referring to a measurable value is meant to encompass variations of ±20% or ±10%, more preferably ±5%, even more preferably ±1%, and still more preferably ±0.1% from the specified value.

As described herein, a linear chain of amino acid residues is called a "polypeptide." A protein contains at least one long polypeptide. Short polypeptides, can have less than 20-30 residues, although they can be considered to be proteins, they are commonly called peptides, or sometimes oligopeptides. The individual amino acid residues are bonded together by peptide bonds and adjacent amino acid residues. The sequence of amino acid residues in a protein is defined by the sequence of a gene, which is encoded in the genetic code. In general, the genetic code specifies 20 standard amino acids, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Shortly after or even during synthesis, the residues in a protein can also be chemically modified by posttranslational modification, which can alter the physical and chemical properties, folding, stability, activity, and ultimately, the function of the proteins. Sometimes proteins have nonpeptide groups attached, which can be called prosthetic groups or cofactors. Proteins can also work together to achieve a particular function, and they can often associate to form stable protein complexes.

"Proteins" as described herein, are large biomolecules, or macromolecules, that can consist of one or more long chains of amino acid residues. Proteins can perform a vast array of functions within living organisms, including catalyzing metabolic reactions, DNA replication, responding to stimuli, and transporting molecules from one location to another. Proteins differ from one another primarily in their sequence of amino acids, which is dictated by the nucleotide sequence of their genes, and which usually results in protein folding into a specific three-dimensional structure that determines its activity. As described herein "enzymes" are proteins that can accelerate, or catalyze, chemical reactions. The molecules at the beginning of the process are called substrates and the enzyme converts these into different molecules, called products. In some embodiments described herein, a stabilized polypeptide formulation comprising the 2D crystalline material of any one of the embodiments described herein is provided. In some embodiments, the stabilized polypeptide comprises an enzyme or protein.

"Disulfide bonds" can also be called an S—S bond, or disulfide bridge, and is a covalent bond derived from two thiol groups. In some embodiments described herein, cysteine residues can be positioned such that formation of disulfide bonds between two cysteine residues can occur.

"Protein crystallization," as described herein, is a process or method of forming a protein crystal. Protein crystals can been observed in nature, however the protein crystallization method can also be used for scientific or industrial purposes, such as, for example, study by X-ray crystallography. Proteins can be prompted to form crystals when the solution in which they are dissolved becomes supersaturated. Under these conditions, individual protein molecules can pack in a repeating array, held together by noncovalent interactions. These crystals can then be used in structural biology to study the molecular structure of the protein, or for various industrial or biotechnological purposes. Some embodiments described herein relate to a non-naturally occurring symmetrical polypeptide building block comprising a plurality of cysteine residues positioned such that formation of disulfide bonds between some or all of said plurality of cysteine residues facilitates formation of 2D crystals. In some embodiments described herein, a 2D crystalline material comprising a polypeptide building block of any one of the embodiments described herein is provided. The 2D crystalline material can reside on a lab-on-a-chip, a molecular membrane, a molecular template, stabilized polypeptide formulation, molecular scaffold, protective armor, smart textile, piezo electronic component, controlled drug release formulation or a run-flat tire.

Proteins are biological macromolecules and function in an aqueous environment. As such protein crystallization, for example, can be carried out in water. However, protein crystallization is challenging due to restrictions of the aqueous environment, difficulties in obtaining high-quality protein samples, as well as sensitivity of protein samples to temperature, pH, ionic strength, and other factors. Proteins can greatly in their physicochemical characteristics, and so crystallization of a particular protein is rarely predictable. Determination of appropriate crystallization conditions for a given protein often requires empirical testing of many conditions before a successful crystallization condition is found.

In crystallography, a crystallographic point group is a set of symmetry operations, like rotations or reflections that leave a central point fixed while moving other directions and faces of the crystal to the positions of features of the same kind. This symmetry can be described as $C_n$ (for cyclic) which indicates that the group has an n-fold rotation axis. $C_{nh}$ is $C_n$ with the addition of a mirror (reflection) plane perpendicular to the axis of rotation. $C_{nv}$ is Cn with the addition of n mirror planes parallel to the axis of rotation.

$S_{2n}$ (for Spiegel, German for mirror) denotes a group that contains only a 2n-fold rotation-reflection axis.

$D_n$ (for dihedral, or two-sided) indicates that the group has an n-fold rotation axis plus n twofold axes perpendicular to that axis. $D_{nh}$ has, in addition, a mirror plane perpendicular to the n-fold axis. Dnd has, in addition to the elements of $D_n$, mirror planes parallel to the n-fold axis.

The letter T (for tetrahedron) indicates that the group has the symmetry of a tetrahedron. $T_d$ includes improper rotation operations, T excludes improper rotation operations, and $T_h$ is T with the addition of an inversion.

The letter O (for octahedron) indicates that the group has the symmetry of an octahedron (or cube), with ($O_h$) or without (O) improper operations (those that change handedness). Due to the crystallographic restriction theorem, n=1, 2, 3, 4, or 6 in 2- or 3-dimensional space. In some embodiments described herein, a polypeptide is provided wherein the polypeptide has inherent C3, C4, C6, D3, D4 or D6 symmetry.

"Genetic engineering," as described herein, is the direct manipulation of an organism's genome using biotechnology. One skilled in the art would appreciate the variety of technologies that can be used to change the genetic makeup of nucleic acid in order to make mutations, insertions or deletions. Without being limiting, this can also include transfer of genes within and across species boundaries to produce improved or novel organisms. New DNA may be inserted in the host genome by first isolating and copying the genetic material of interest using molecular cloning methods to generate a DNA sequence, or by synthesizing the DNA, and then inserting this construct into the host organism. Genes can also be mutated at certain points in order to make introduction of polypeptide segments into a protein, create a deletion mutant or make protein mutants with point mutations, for example. In some embodiments described herein, the polypeptide described comprises at least one cysteine residue that has been introduced into said polypeptide building block through genetic engineering. In some embodiments, polypeptide is genetically engineered.

"Solid phase synthesis" as described herein refers to a method in which molecules are bound on a bead and synthesized step-by-step in a reactant solution. In this method, building blocks can be protected at all reactive functional groups. The two functional groups that are able to participate in the desired reaction between building blocks in the solution and on the bead can be controlled by the order of deprotection. This method can be used, for example, for the synthesis of peptides, deoxyribonucleic acid (DNA), and other molecules that need to be synthesized in a certain alignment. In some embodiments described herein, polypeptide is generated via solid phase synthesis.

"Chemical Modification," as described herein, refers to addition or removal, through chemical reaction, of any of a variety of macromolecules, without being limiting, this can include proteins, polypeptides and nucleic acids, and are known to those skilled in the art.

"Modification by enzymatic reaction," refers to modification of macromolecules, without being limiting, this can include proteins, polypeptides and nucleic acids, in which the macromolecule is modified in a reaction using an enzyme. As there are a variety of commercially available enzymes for modification, techniques for enzymatic modification can be appreciated by those skilled in the art.

"Peptide tags" as described herein, are known to those skilled in the art and can be used as an affinity tag or can be a small organic molecule, such as biotin or a short peptide sequence. Tags can be attached at the N-terminus, or C terminus, but in principle can be positioned anywhere in a molecule and can be separated from the molecule by a spacer. There are a variety of spacers of varying length and polarity. Additionally, peptide tags can be attached by a cleavable linker. In some embodiments, a polypeptide building block is provided, wherein the polypeptide building block comprises a peptide tag.

"Functional groups" as described herein are specific moieties within a molecule that are responsible for a chemical reaction or a characteristic of a molecule. Common functional groups can include but are not limited to alkyls, alkenyl, alkynyl, phenyls, haloalkanes, fluoroalkanes, chloroalkanes, bromoalkanes, iodoalkanes, alcohols (hydroxyl), ketones (cabonyls), aldehydes, Acyl halides, carbonates (carbonate ester), carboxylate, carboyxlic acids (carboxyl), esters, methoxy, hydroperoxide (hydroperoxy), peroxide (peroxy), ethers, hemiacetals, hemiketals, acetals, ketals, orthoester, heterocycles (methylenedioxy), orthocarbonate esters, amides (carboxyamides), primary amines, secondary amines, tertiary amines, quaternary amines, primary ketimines, secondary ketimines, primary aldimine, secondary almidine, imides, axides, azo compounds, cyanate, isocyanta, nitrate, nitriles, isonitriles, nitosooxy, nitro compounds, nitroso compounds, oxime, pyridines, sulfhydril, sulfides, disulfides, sulfinyls, sulfonyl, sulfino, sulfo, tiocyanate, isothiocyanate, carbonotyioyl, carbonothioyl, phosphine, phosphonic acids, phosphate, boronic acids, boronic esters borinic acids and borinic esters. In some embodiments, a polypeptide building block is provided, wherein the polypeptide building block comprises a functional group.

"Fluorophores" as described herein are fluorescent chemical compound that can re-emit light upon light excitation. Without being limiting, fluorophores can include, for example, Xanthene derivatives (fluorescein, rhodamine, Oregon green, eosin, and Texas red), Cyanine derivatives (cyanine, indocarbocyanine, oxacarbocyanine, thiacarbocyanine, and merocyanine), Squaraine derivatives and ring-substituted squaraines (Seta, SeTau, and Square dyes), Naphthalene derivatives (dansyl and prodan derivatives) Coumarin derivatives, oxadiazole derivatives (pyridyloxazole, nitrobenzoxadiazole and benzoxadiazole), Anthracene derivatives (anthraquinones, including DRAQ5, DRAQ7 and CyTRAK Orange), Pyrene derivatives (cascade blue), Oxazine derivatives (Nile red, Nile blue, cresyl violet, oxazine 170), Acridine derivatives (proflavin, acridine orange, acridine yellow), Arylmethine derivatives (auramine, crystal violet, malachite green, and Tetrapyrrole derivatives (porphin, phthalocyanine, bilirubin). In some embodiments, a polypeptide building block is provided, wherein the polypeptide building block comprises a fluorophore.

"Nanoparticles" as described herein, refers to particles between 1 and 100 nanometers in size. In nanotechnology, a particle is defined as a small object that behaves as a whole unit with respect to its transport and properties. In some embodiments, a polypeptide building block is provided, wherein the polypeptide building block comprises a nanoparticle.

As used herein, "nucleic acid" or "nucleic acid molecule" refers to polynucleotides or oligonucleotides such as deoxyribonucleic acid (DNA) or ribonucleic acid (RNA), oligonucleotides, fragments generated by the polymerase chain reaction (PCR), and fragments generated by any of ligation, scission, endonuclease action, exonuclease action, and by synthetic generation. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded."

"Rhamnulose-1-phosphate aldolase," or RhuA, is an enzyme belonging to the lyase family. In some embodiments described herein, a polypeptide building block is provided. In some embodiments, the polypeptide comprises the RhuA protein.

A "2D crystalline material" as described herein are atoms or molecules are arranged in a regular, periodic manner, in which they are in two dimensions. In some embodiments, the 2D crystalline material is auxetic.

"Auxetic" as described herein, refers to structures or materials that have a negative "Poisson's ratio." When a material that is auxetic is stretched, it becomes thicker perpendicular to the applied force. This occurs due to their particular internal structure and the way this deforms when the sample is uniaxially loaded. Auxetics can be single molecules, crystals, or a particular structure of macroscopic matter. Such materials and structures are expected to have mechanical properties such as high energy absorption and fracture resistance. In some embodiments described herein, a 2D crystalline material is provided, wherein the 2D crystalline material is auxetic.

A lab-on-a-chip (LOC), as described herein, can be a device that integrates one or several laboratory functions on a single chip of only millimeters to a few square centimeters to achieve automation and high-throughput screening, for example. Lab-on-a-chip are used for the handling of extremely small fluid volumes down to less than pico liters. Lab-on-a-chip devices are can also be a subset of Microelectro-mechanical systems (MEMS) devices, for example and can be indicated by "Micro Total Analysis Systems" (µTAS) as well. Lab-on-a-chip is closely related to, and overlaps with, microfluidics which describes primarily the physics, the manipulation and study of minute amounts of fluids. Lab-on-a-Chip can also indicate the scaling of single or multiple lab processes down to chip-format, whereas "µTAS" is dedicated to the integration of the total sequence of lab processes to perform chemical analysis.

"Molecular membrane" can refer to the two dimensional membrane comprising molecules with polar and nonpolar regions, such as for example, a lipid, polypeptides and/or proteins.

A "molecular template" as described herein, can comprise a molecule, such as, for example, DNA that serves as a pattern for the synthesis of a macromolecule. In some embodiments described herein, a molecular template is provided, wherein the molecular template comprises a 2D crystalline material of any one of the embodiments described herein.

"Protective armor" as described herein is refers to armor that can protect a body from high heat, cold temperature, strong force or impact. Without being limiting, protective armor can be a scuba suit, a lab coat, work boots material, motorcycle vest, motorcycle pants, motorcycle protective clothing, race protective gear, bullet proof vest, bulletproof gear, cryoprotecting gloves, cryoprotecting material and heat resistant clothing or gear.

"Smart textile" as described herein is a passive textile structure capable of responding to external stimulation i.e. from pressure, temperature, light, low voltage current etc. The definition generally means that SMART textiles is a form of textiles that utilizes materials which aids it purpose, and can 'sense' what is around it. For example, a textiles company explains it as: Smart materials respond to differences in temperature or light and change in some way. They are called smart because they sense conditions in their environment and respond to those conditions. Smart materials appear to 'think' and some have a 'memory' as they revert back to their original state. In some embodiments, a smart textile comprising any one of the 2D crystalline material of any one of the embodiments described herein is provided.

"Piezo electronic component" as described herein can be a material that can convert mechanical signals, such as force, pressure, strain or acceleration, into electrical voltage, or, vice versa, an electrical voltage into mechanical motion or oscillations. In some embodiments, a Piezoelectronic component comprising any one of the 2D crystalline material of any one of the embodiments described herein is provided.

"Adaptive membrane or sieve" as described herein, can be a filter made of the materials described herein for preventing the passage of certain molecules, particles or substances. In some embodiments, the adaptive membrane or sieve is a passive and kinetic system that allows expansion of geometry in response to heat, temperature and other changes in its environment. In some embodiments, an adaptive membrane or sieve comprising any one of the 2D crystalline material of any one of the embodiments described herein is provided.

A "controlled drug release formulation" as described herein, refers to a drug which can be gradually released at a constant set dosage for a specific amount of time. In some embodiments herein, the polypeptide building block is attached to a drug for delivery. In some embodiments herein the polypeptide building block attached to a drug for delivery A "run-flat tire" as described herein is pneumatic vehicle tire that is designed to resist the effects of deflation when punctured, and to enable the vehicle to continue to be driven at reduced speeds (under 55 mph (89 km/h)), and for limited distances (up to 10 mi (16 km), depending on the type of tire). In some embodiments described herein, a run-flat tire comprising the 2D crystalline material of any one of the embodiments described herein is provided. The run-flat tire can resist the effects of deflation when punctured. In some embodiments the tire can be used in a vehicle wherein the vehicle is driven at a speed of 30, 35, 40, 45, 50 or 55 mph or any speed in between any two aforementioned values, when the tire is punctured. In some embodiments, a run flat tire comprising any one of the 2D crystalline material of any one of the embodiments described herein is provided.

"Poisson's ratio" as described herein, is the coefficient of expansion on the transverse axial, and is the negative ratio of transverse to axial strain. When a material is compressed in one direction, it can tend to expand in the other two directions perpendicular to the direction of compression. This phenomenon is called the Poisson effect. Poisson's ratio, $\nu$ (nu) is a measure of this effect. The Poisson ratio is the fraction (or percent) of expansion divided by the fraction (or percent) of compression, for small values of these changes. The Poisson's ratio of a stable, isotropic, linear elastic material cannot be less than −1.0 or greater than 0.5 because of the requirement for Young's modulus, the shear modulus and bulk modulus to have positive values. In some embodiments described herein, the 2D crystalline material of any of the embodiments herein comprises a Poisson's ratio of −1.

DETAILED DESCRIPTION OF THE PREFERRED EMBODIMENT

Figure 1:
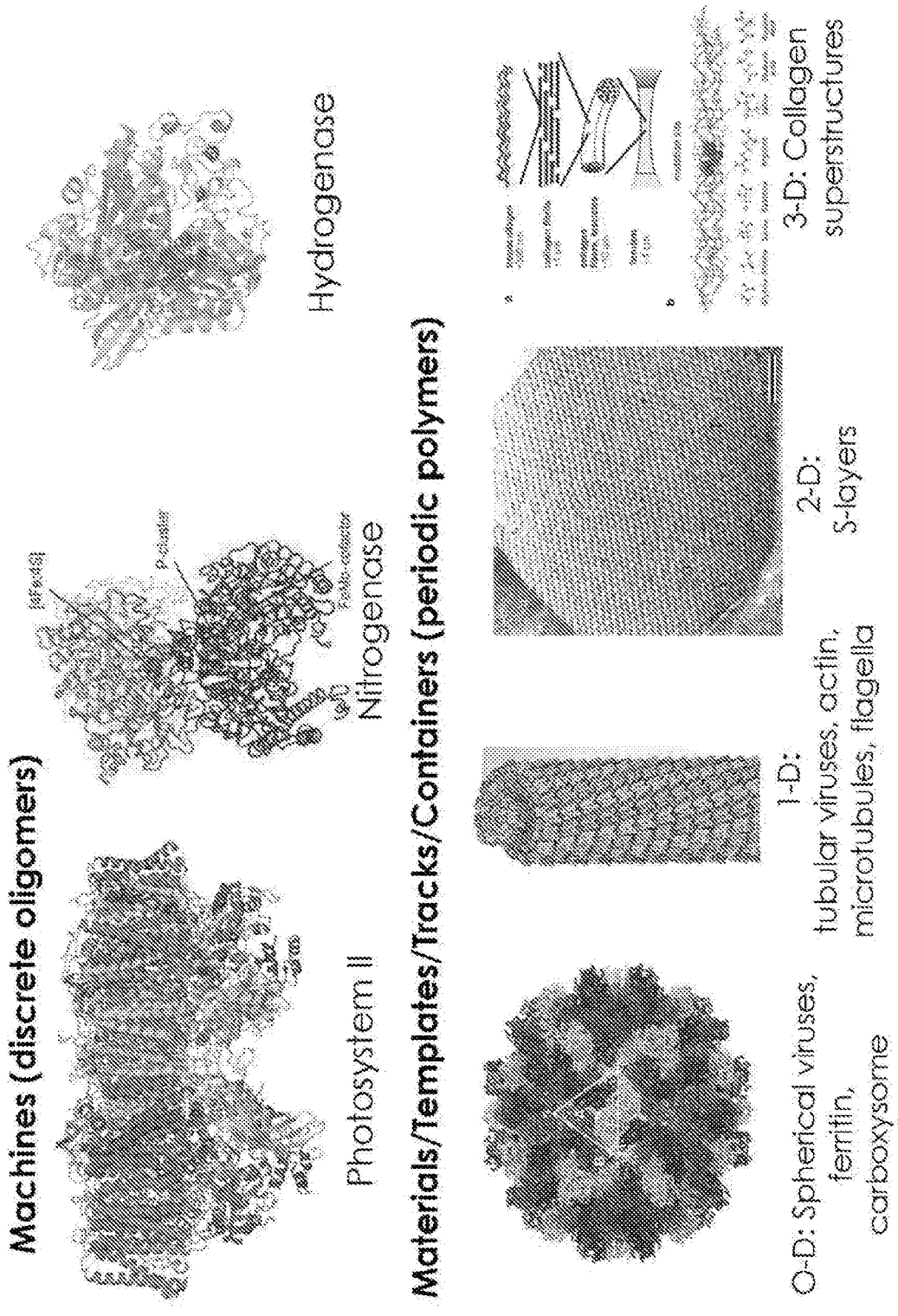
FIG. 1 shows that a majority of biological machines and materials are self assembled and have dynamic/responsive multiprotein architecture.

A majority of biological machines and materials are self-assembled, dynamic/responsive multiprotein architectures. For example, biological machines such as Photosystem II, nitrogenase and hydrogenase involve discrete oligomers (FIG. 1). Some systems involve periodic polymers. For example, spherical viruses, ferritin, and carboxysome are 0-D, tubular viruses, actin, microtubules, and flagella are 1-D, S-layers are 2D and collagen superstructures are 3-D.

Figure 2:
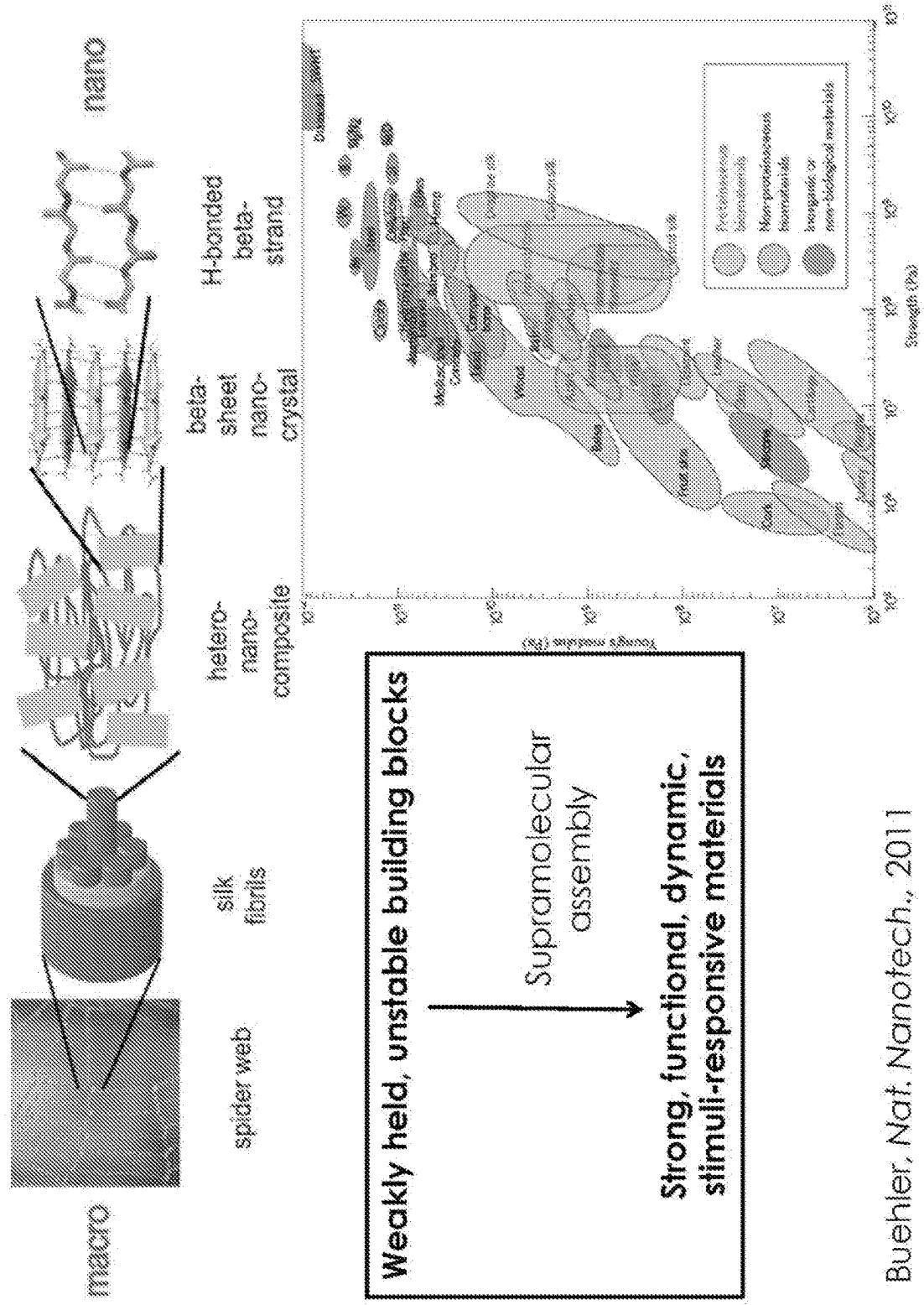
FIG. 2 shows hierarchically assembled protein materials.

Some protein materials are assembled hierarchically. For example, going from the macro scale to the nano scale, a spider web may comprise a silk fibril, which can further comprise a hetero-nano-composite, which can further comprise beta-sheet nano-crystal, which can also further comprise H-bonded beta-strands. Via supramolecular assembly, weakly held, unstable building blocks may give rise to strong, functional, dynamic, stimuli-responsive materials. (See FIG. 2).

2D crystalline materials exhibit unique mechanical and electronic attributes, possess high surface area-to-volume ratios, offer a uniform display of atomic/molecular entities as well as pores, and provide structural access to materials with all other dimensionalities: to 0- and 1D materials through folding and to 3D materials through stacking. These properties have rendered synthetic 2D materials immensely attractive in applications including electronics, sensing, coating, filtration and catalysis. Nevertheless, the rational design of self-assembling 2D crystals remains a considerable challenge and a very active area of development.

Currently, the fabrication of non-biological 2-D crystalline materials is not generalizable and scalable. Other protein design strategies require extensive computational work and protein engineering, have low success rates, contain large defects, are not single-layered, and often require the presence of lipids for supported assembly. Some embodiments of the 2D crystalline materials described herein are essentially defect-free and self-assemble in an unsupported fashion in solution. They also offer a better strategy because of their simplicity, low cost nature, effectiveness, and potential generalizability. These new 2D crystalline materials as described herein led to a surprising effect of providing a mechanism for making these 2D crystalline materials that had a higher success rate, no large defects and little to no need for the presence of lipids for supported assembly.

Proteins provide certain advantages as building blocks for functional nanomaterials. For example, they involve 20 distinct components (i.e., amino acids) which allow nearly infinite structural and functional diversity. They are inherently nanoscale. In addition, they are genetically encoded and are producible and evolvable in living systems. However, their utilization of 20 distinct components may render their structure, self-assembly and function difficult to program (See FIG. 3).

Fabrication of 2D supramolecular protein assemblies may provide one or more of the following advantageous features: 1) high surface area/volume ratio; 2) dense display of a diverse set of chemical functionalities in a highly ordered, yet dynamic fashion; 3) innately functional building blocks (e.g., functional enzymes); and 4) potential for smart materials, lab-on-a-chip technologies, heterogeneous catalyst platforms (FIG. 4). As described herein, some embodiments of the 2D crystalline structures are advantageous over previous crystalline materials as they are designed to have a high surface area/volume ratio. As such the 2D crystalline materials as described herein can be used for a variety of materials as well as functions.

Figure 5:
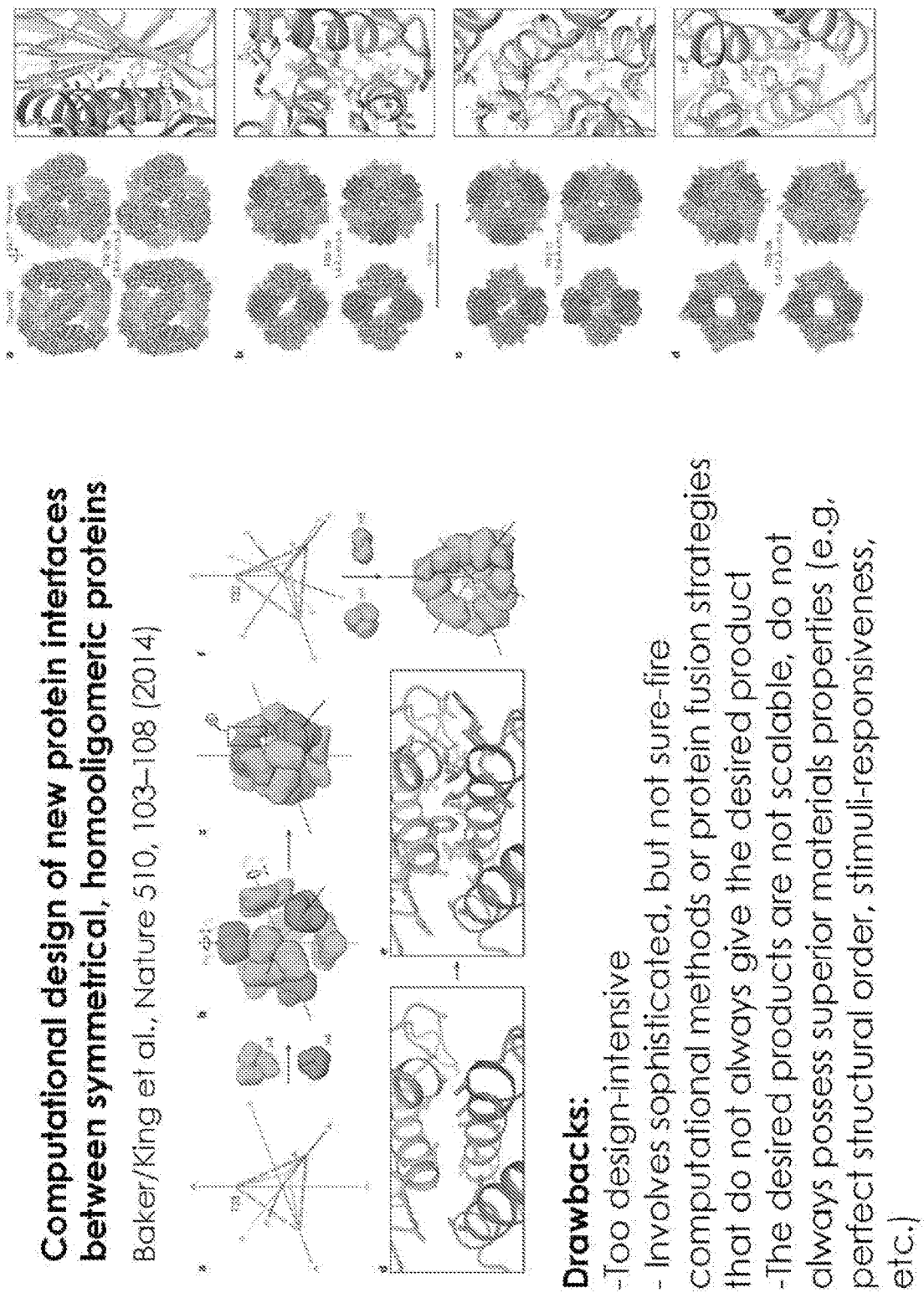
FIG. 5 shows the existing approaches for designed protein assembly.

However, some existing approaches for designed protein assembly may be too design-intensive and involve sophisticated, but not sure-fire computational methods or protein fusion strategies that do not always give the desired product, and the desired products are not scalable and do not always possess superior materials properties (e.g, perfect structural order, stimuli-responsiveness, etc.) (FIG. 5). (See, for example, Baker/King et al., Nature 510, 103-108 (2014)).

Figure 6:
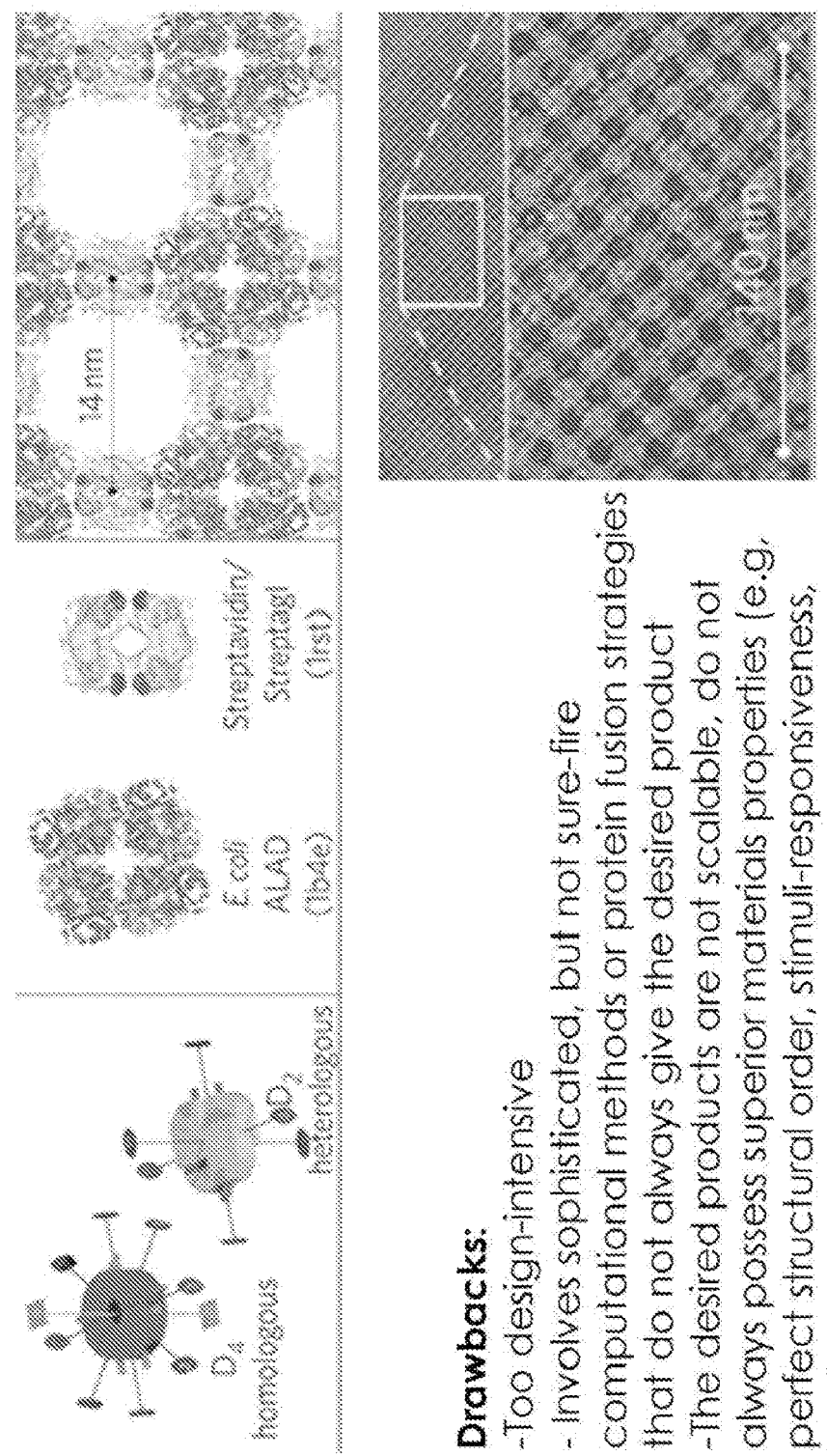
FIG. 6 shows the existing approaches for designed protein assembly, in particular covalent fusion of homooligomeric proteins or self-assembling protein monomers.

Other approaches are also too design-intensive, involve sophisticated and but not sure-fire computational methods or protein fusion strategies that do not always give the desired product and the desired products are not scalable, and do not always possess superior materials properties (e.g, perfect structural order, stimuli-responsiveness, etc.) (FIG. 6). (See, for example, Sinclair, Yeates etc. Nat. Nanotech. 6, 558-562 (2011)).

Other approaches have been described in Colson, J. W.; Dichtel, W. R. Rationally synthesized two-dimensional polymers. *Nat. Chem.* 2013, 5, 453-465" and Butler, S. Z.; Hollen, S. M.; Cao, L.; Cui, Y.; Gupta, J. A.; Gutiérrez, H. R.; Heinz, T. F.; Hong, S. S.; Huang, J.; Ismach, A. F.; Johnston-Halperin, E.; Kuno, M.; Plashnitsa, V. V.; Robinson, R. D.; Ruoff, R. S.; Salahuddin, S.; Shan, J.; Shi, L.; Spencer, M. G.; Terrones, M.; Windl, W.; Goldberger, J. E. Progress, Challenges, and Opportunities in Two-Dimensional Materials Beyond Graphene. *ACS Nano* 2013, 7, 2898-2926; Sinclair, J. C.; Davies, K. M.; Venien-Bryan, C.; Noble, M. E. M. Generation of protein lattices by fusing proteins with matching rotational symmetry. *Nat. Nanotechnol.* 2011, 6, 558-562; Lanci, C. J.; MacDermaid, C. M.; Kang, S.-g.; Acharya, R.; North, B.; Yang, X.; Qiu, X. J.; DeGrado, W. F.; Saven, J. G. Computational design of a protein crystal. *Proc. Natl. Acad. Sci. USA* 2012, 109, 7304-7309; King, N. P.; Sheffler, W.; Sawaya, M. R.; Vollmar, B. S.; Sumida, J. P.; Andro, I.; Gonen, T.; Yeates, T. O.; Baker, D. Computational Design of Self-Assembling Protein Nanomaterials with Atomic Level Accuracy. *Science* 2012, 336, 1171-1174; Lai, Y.-T.; Cascio, D.; Yeates, T. O. Structure of a 16-nm Cage Designed by Using Protein Oligomers. *Science* 2012, 336, 1129; Lebeau, L. et al., Two-dimensional crystallization of a membrane protein on a detergent-resistant lipid monolayer. (2001). *J Mol. Biol,* 306, 639-647; Uzgiris, E. & Kornberg, R. Two-dimensional crystallization technique for imaging macromolecules with application to antigen-antibody-complement complexes. (1983). *Nature,* 301, 125-129. (All incorporated by reference in their entireties herein).

Some embodiments provided herein relate to a highly efficient/expeditious design strategy for the fabrication of single layered, ultra-low defect 2D crystalline materials out of protein building blocks. Such 2D crystalline materials exhibit unique mechanical and electronic attributes, possess high surface area-to-volume ratios, offer a uniform display of atomic/molecular entities as well as pores, and provide structural access to materials with all other dimensionalities: to 0- and 1D materials through folding and to 3D materials through stacking.

In some embodiments, an inherently symmetrical or an artificially "symmetrized" protein is modified with Cys residues in appropriate locations. The selective and easily tunable nature of Cys-Cys disulfide bonding is then utilized to assemble these protein building blocks into crystalline, 2D materials that 1) exhibit very low frequency of defects, 2) exhibit coherent dynamicity (i.e., lattices that open up and close in a cooperative fashion without loss of crystallinity), 3) are scalable, and 4) are readily modified chemically or genetically. The 2D crystalline materials produced by the methods of the embodiments described herein, are coherently dynamic and show large flexibility.

In some embodiments, the 2D crystalline protein materials described herein may be used in applications including the following: 1) Fabrication of self-assembled, chemically dense, lab-on-a-chip platforms for sensing, diagnostics, vaccine development, and drug delivery; 2) Fabrication of molecular membranes for sieving and filtration; 3) Fabrication of molecular templates that provide 5-100 nm spatial resolution for patterning and deposition (which is a length scale that is hard to attain with diffraction-based methods); 4) Stabilization of enzymes and proteins of commercial value; and 5) Fabrication of crystalline molecular scaffolds for macromolecular structure determination by 2D crystallography and electron microscopy.

In some embodiments, an inherently symmetrical or an artificially "symmetrized" protein is very simply modified with Cys residues in appropriate locations. The selective and easily tunable nature of Cys-Cys disulfide bonding is then utilized to assemble these protein building blocks into crystalline, 2D materials that 1) exhibit very low frequency of defects; 2) exhibit coherent dynamicity (i.e., lattices that open up and close in a cooperative fashion without loss of crystallinity); 3) are scalable; and 4) are readily modified chemically or genetically.

Some embodiments of the methods and compositions described herein provide advantages over prior approaches due to their simplicity, low cost nature, effectiveness and potential generalizability. For example, some embodiments require a simple visual inspection of the protein building block that possesses the proper symmetry (C3, C4, C6, D3, D4 or D6), and incorporation of single Cys residues into appropriate positions for self-assembly. This contrasts with other protein design strategies that require extensive computational work and protein engineering, and have low success rates. It also contrasts with the fabrication of non-biological 2-D crystalline materials, which are not generalizable and scalable.

Some embodiments of the 2D crystalline materials described herein are essentially defect-free and self-assemble in an unsupported fashion in solution. These contrasts with other 2D protein crystalline materials previously designed or produced that contain large defects, are not single-layered and often require the presence of lipids for supported assembly. In some embodiments, the 2D crystalline materials described herein are coherently dynamic. Other previous examples of dynamic 2D materials (based on proteins or other building blocks) do not show large flexibility. As such, the methods of some of the embodiments described herein, produce 2D crystals that are surprisingly flexible and dynamic and do not require the presence of lipids for supported assembly.

In some embodiments described herein, a protein building block with inherent C3, C4, C6, D3, D4 or D6 symmetry is appropriately engineered to contain a single set of surface cysteine residues in the corner positions. The resulting variant may be incubated in solution under controllable oxidizing conditions (such as controlled atmosphere, a redox buffer consisting of reduced and oxidized glutathione, or a slowly degrading reducing agent like beta-mercaptoethanol) to self-assemble into suspended crystalline materials. The quality of the material may be readily validated by routine transmission electron microscopy or atomic force microscopy measurements. When/if desired, the protein building blocks may be genetically or chemically modified prior to self-assembly with functional groups and tags, including other proteins, peptide tags, fluorophores, nanoparticles.

The strategy described here can be readily implemented on other protein systems that possess the appropriate inherent symmetry.

As described herein, the 2D crystalline protein materials generated by the embodiments have diverse potential applications: 1) Fabrication of self-assembled, chemically dense, lab-on-a-chip platforms for sensing, diagnostics, vaccine development, drug delivery; 2) Fabrication of molecular membranes for sieving and filtration; 3) Fabrication of molecular templates that provide 5-100 nm spatial resolution for patterning and deposition (which is a length scale that is hard to attain with diffraction-based methods; 4) Stabilization of enzymes and proteins of commercial value; 5) Fabrication of crystalline molecular scaffolds for macromolecular structure determination by 2D crystallography and electron microscopy. In some embodiments, the 2D crystalline protein materials can be used in lab-on-a-chip platforms for sensing, diagnostics, vaccine development, drug delivery, fabrication of molecular membranes for sieving and filtration, fabrication of molecular templates that provide 5-100 nm spatial resolution for patterning and deposition (which is a length scale that is hard to attain with diffraction-based methods), stabilization of enzymes and proteins of commercial value and fabrication of crystalline molecular scaffolds for macromolecular structure determination by 2D crystallography and electron microscopy.

Some embodiments described herein involve disulfide-mediated assembly of 2D protein materials. Some embodiments bypass the need for time-/cost-intensive computational design or protein-fusion. For example, in some embodiments the only step is the engineering of cysteine residues at proper positions on a protein building block of choice. In some embodiments, the cysteine residues are in appropriate positions in a C3, C4 or C6-symmetric protein that is expressible in bacteria or other desired organism, cell, or system. In some embodiments, the experimental flow/feasibility testing is highly streamlined, involving protein expression/purification, testing of different oxidative conditions for self-assembly (such as air oxidation or redox buffer systems), and characterization by electron microscopy) (FIG. 7).

Figure 8:
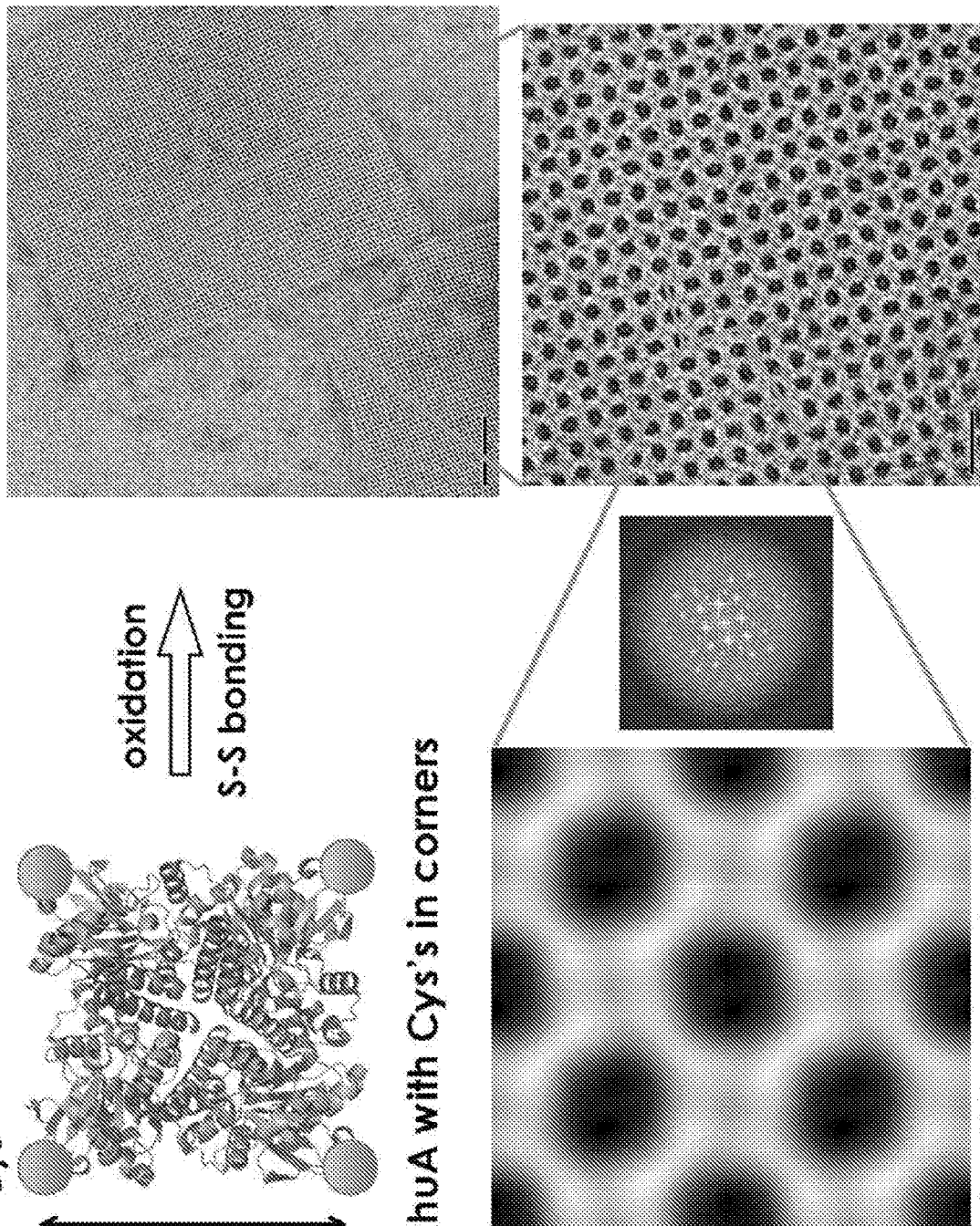
FIG. 8 shows the proof of principle of preparing the assembly of 2D protein materials.
Figure 9:
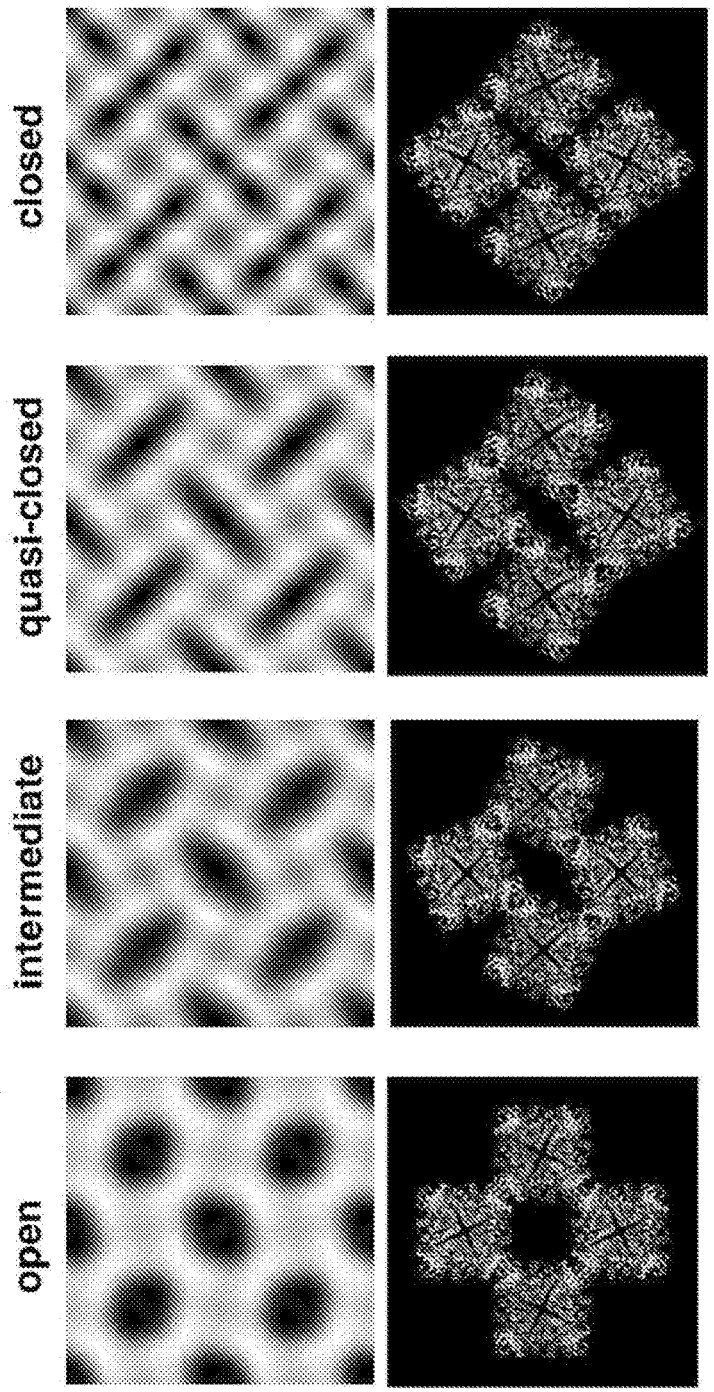
FIG. 9 shows disulfide-linker 20 C98-RhuA crystals.

In an exemplary embodiment, the RhuA protein was engineered to have cysteines at the corners of the protein. In particular, the wild type RhuA protein of SEQ ID NO: 1 (RCSB Protein Data Bank accession number 1OJR, the disclosure of which is incorporated herein by reference in its entirety) was modified to replace the Asp at position 98 with Cys and to replace the Cys at position 126 with a Ser (SEQ ID NO: 2). In addition, to replacing the Asp at position 98 with Cys and to replacing the Cys at position 126, the modified protein RhuA protein had the E192A mutation such that the modified RhuA protein had the sequence of SEQ ID NO: 3. Oxidation was performed via gradual degradation of the reducing agent β-mercaptoethanol (10 mM) at 4° C. under constant shaking to allow formation of disulfide bonds. This approach was simple to design, (only took 10 min to find proper locations for Cys incorporation) and readily tested. In particular, visual inspection of the RhuA crystal structure indicated four protrusions from the surface (since it is C4 symmetry protein, cysteines will be exact same location) which were identified as ideal locations for incorporating single cysteine residues (FIGS. 8-10).

In addition, it provided robust, reproducible self-assembly, crystalline order over large length-scales (up to several microns), and single-layered structures which were essentially defect-free and dynamic.

In some embodiments, new potential for smart/stimuli-responsive nano- and bio-materials or mechanical Nano devices are provided.

Additional embodiments are provided in the figures submitted herewith.

Fabrication of crystalline materials with distinct dimensionalities and tailorable structural, physical and chemical properties represents a major goal in fundamental and applied sciences. As reported herein, the bottom-up self-assembly of unsupported, two-dimensional protein lattices with precise spatial arrangements and patterns through a readily accessible design strategy, are provided. Three single- or double-point mutants of the soluble, C4 symmetric protein RhuA were designed to assemble via different modes of intermolecular interactions (single disulfide, double disulfide and metal coordination) into crystalline, two-dimensional arrays in a chemically tunable fashion. Owing to the flexibility of the single disulfide interactions, the lattices of one of the variants (C98RhuA) are essentially defect-free and undergo substantial but highly correlated changes in molecular arrangement and porosity, yielding a Poisson's ratio of −1, the lowest thermodynamically possible value for an isotropic material. In some embodiments described herein, the polypeptide building block can be designed to have one, two, three, four or more point mutations to allow assembly of intermolecular interactions into crystalline, two-dimensional arrays. In some embodiments, the sites for the point mutations that allow the protein-protein interactions are selected by structure prediction programs, which are known to those skilled in the art.

Some embodiments relate to a self-assembled, protein-based molecular material that is auxetic. In some embodiments, this material displays the thermodynamically lowest possible Poisson's ratio of −1 for an isotropic material. Some embodiments relate to a general method to fabricate such auxetic materials from protein building blocks. In some embodiments, the self-assembled, protein-based molecular material comprises 2D crystals of a protein termed C98-RhuA. The method to fabricate auxetic self-assembled protein-based molecular material, such as, for example, 2D C98-RhuA crystals, is highly expeditious and can be readily utilized with a wide variety of protein building blocks. In some embodiments of this methodology, an inherently symmetrical or an artificially "symmetrized" protein is very simply modified with cysteine (Cys) residues in appropriate, "corner" locations. In some embodiments, the inherently symmetrical or an artificially "symmetrized" protein is selected to have cysteine mutations that allow the proteins to self assemble, wherein the cysteine mutation sites selected by studying the predicted protein structures from protein structure prediction databases. Alternatively, if there is a wild-type cysteine, these can also be mutated into an amino acid whose functional group will not interfere with self-assembly. These Cys-containing protein building blocks self-assemble selectively through the formation of disulfide bonds between Cys side chains. The simultaneous flexibility and short linker-length of Cys-Cys disulfide bonding allows the formation of highly ordered (crystalline) lattices that undergo dramatic conformational changes in a coherent manner. The "rotary" motion of each protein building block results in auxetic behavior.

Poisson's ratio is a fundamental parameter that describes the response of a material to uniaxial strain. Most materials have positive Poisson's ratios, meaning that when they are stretched in one direction, they become thinner in the lateral direction (for example, a rubber band). Materials with negative Poisson's ratios (auxetic materials), on the other hand, display the counterintuitive behavior of lateral expansion upon transverse stretching. This property endows them with enhanced toughness, resistance to indentation, and shear stiffness, among many other advantageous. Though several auxetic materials have been identified or fabricated at the macroscopic level (most of them having Poisson's ratios between −0.3 and 0), in some embodiments the auxetic self-assembled, protein-based molecular material, such as for example, the 2D C98-RhuA crystals described herein, display the minimum allowed value of −1, which is not only significant because of its unprecedented magnitude, but also because it was achieved through bottom-up molecular design (which is extremely rare-if not unprecedented-among auxetic materials). As such the material processed by the methods described in some of the embodiments herein led to a material with surprising characteristics. In some embodiments the auxetic self-assembled, protein-based molecular material, such as for example, the C98-RhuA crystals, can be used as feedstocks for macroscopic auxetic and adaptive materials. This in turn permits tailoring of the macroscopic auxetic properties of resulting materials through molecular engineering. Several functionalized 2D crystalline protein arrays have been prepared using the procedures provided herein.

Due to their superior/advantageous physical properties (toughness, high resistance to indentation, high shear stiffness while being lightweight, adaptiveness), auxetic materials have numerous potential applications, including, for example, as structural and functional components of: 1) protective armors; 2) smart textiles; 3) piezo electronics; 4) adaptive membranes, sieves; 5) controlled drug release; 6) run-flat tires.

Some embodiments relate to a self-assembled, protein-based molecular material that is auxetic. In some embodiments, this material displays the thermodynamically lowest possible Poisson's ratio (−1; minus one) for an isotropic material. In some embodiments, the auxetic material comprises 2D crystals of a protein termed C98-RhuA. Other embodiments relate to a general method to fabricate such auxetic materials from protein building blocks.

Poisson's ratio is a fundamental parameter that describes the response of a material to uniaxial strain. Most materials have positive Poisson' ratios, meaning that when they are stretched in one direction, they become thinner in the lateral direction (for example, a rubber band). Materials with negative Poisson' ratios (auxetic materials), on the other hand, display the counterintuitive behavior of lateral expansion upon transverse stretching. This property endows them with enhanced toughness, resistance to indentation, and shear stiffness, among many other advantageous.

Though several auxetic materials have been identified or fabricated at the macroscopic level (most of them having Poisson's ratios between v=0.5 to −0.85), 2D C98-RhuA crystals that were disclosed here displays the minimum allowed value of −1, which is not only significant because of its unprecedented magnitude, but also because it was achieved through bottom-up molecular design (which is extremely rare-if not unprecedented-among auxetic materials). In some embodiments, the auxetic materials, such as, for example, the C98-RhuA crystals, can be used as feedstocks for macroscopic auxetic and adaptive materials. This in turn allows tailoring of the macroscopic auxetic properties of resulting materials through molecular engineering.

The method to fabricate auxetic self-assembled protein-based molecular material, such as, for example, 2D C98-RhuA crystals, is highly expeditious and can be readily utilized with a wide variety of protein building blocks. In some embodiments, an inherently symmetrical or an artificially "symmetrized" protein is very simply modified with cysteine (Cys) residues in appropriate, "corner" locations. These Cys-containing protein building blocks self-assemble selectively through the formation of disulfide bonds between Cys side chains. The simultaneous flexibility and short linker-length of Cys-Cys disulfide bonding allows the formation of highly ordered (crystalline) lattices that undergo dramatic conformational changes in a coherent manner. The "rotary" motion of each protein building block results in auxetic behavior.

Some embodiments relate to a designed/synthetic, molecular material that has a Poisson's ratio of −1 (minus one). Other embodiments relate to a designed biological material that has a negative Poisson's ratio. Some embodiments provide a general method to fabricate molecular auxetic materials.

Auxetic materials have been described recently in G. N. Greaves, A. Greer, R. Lakes, T. Rouxel, Nat. Mater. 10, 823 (2011) as well as existing patents but these predominantly involve macroscopic materials obtained through physical fabrication methods (and not by molecular self-assembly).

In some embodiments, a protein building block (such as, for example, RhuA) with inherent C3, C4, C6 symmetry is appropriately engineered to contain a single set of surface cysteine residues in the corner positions. The resulting variant is incubated in solution under controllable oxidizing conditions (such as, for example, controlled atmosphere, a redox buffer consisting of reduced and oxidized glutathione, or a slowly degrading reducing agent like beta-mercaptoethanol) to self-assemble into suspended crystalline materials. If desired, the quality of the material may readily be validated by routine transmission electron microscopy or atomic force microscopy measurements. In some embodiments, the resulting 2D crystalline materials show dynamic/adaptive/auxetic behavior.

Due to their superior/advantageous physical properties (toughness, high resistance to indentation, high shear stiffness while being lightweight, adaptiveness), auxetic materials have numerous potential applications, including, for example, as structural and functional components of 1) protective armors; 2) smart textiles; 3) piezo electronics; 4) adaptive membranes, sieves; 5) controlled drug release; 6) run-flat tires. In some embodiments described herein, the 2D crystalline material can be utilized in aerospace applications, materials in aircraft gas turbine engines, prosthetic materials, surgical implants, suture/muscle/ligament anchors, electrodes, piezoelectric sensors, filters and actuators.

A summary of some applications for these materials is provided on the internet at www.azom.com/article.aspx?ArticleID=168.

In some embodiments, coherently dynamic 2D protein crystals are obtained by design and exhibit the lowest possible Poisson's ratio for an isotropic material.

Two-dimensional (2D) crystalline materials possess unique structural, mechanical, and electronic properties (R. Mas-Balleste, C. Gomez-Navarro, J. Gomez-Herrero, F. Zamora, Nanoscale 3, 20 (2011); S. Z. Butler et al., ACS Nano 7, 2898 (2013)), which has rendered them highly attractive in applications including electronics, sensing, coating, filtration and catalysis (S. Z. Butler et al., ACS Nano 7, 2898 (2013); F. Schedin et al., Nat. Mater. 6, 652 (2007); A. K. Geim, K. S. Novoselov, Nat. Mater. 6, 183 (2007); C.-H. Lu, H.-H. Yang, C.-L. Zhu, X. Chen, G.-N. Chen, Angew. Chem. Int. Ed. Engl. 121, 4879 (2009); R. K. Joshi et al., Science 343, 752 (2014); M. A. Lukowski et al., J. Am. Chem. Soc. 135, 10274 (2013)). Although there have been considerable advances in the preparation of 2D materials that consist of one or few atomic/molecular layers (V. Nicolosi, M. Chhowalla, M. G. Kanatzidis, M. S. Strano, J. N. Coleman, Science 340, 1226419 (2013); D. Li, M. B. Muller, S. Gilje, R. B. Kaner, G. G. Wallace, Nat. Nano. 3, 101 (2008)), bottom-up design and assembly of 2D crystalline materials remains a considerable challenge and a highly active area of development (J. W. Colson et al., Science 332, 228 (2011); P. Kissel, D. J. Murray, W. J. Wulftange, V. J. Catalano, B. T. King, Nat. Chem. 6, 774 (2014); M. J. Kory et al., Nat. Chem. 6, 779 (2014)). Even more challenging is the design of dynamic 2D lattices that can undergo large-scale coherent motions in the 2D plane without loss of crystallinity. Dynamicity in porous 3D crystalline solids has been exploited for stimuli-responsive functions and adaptive behavior (S. Shimomura et al., Nat. Chem. 2, 633 (2010); J. Rabone et al., Science 329, 1053 (2010); C. Serre et al., Science 315, 1828 (2007)). As in the case of such 3D materials, integrating flexibility into crystalline 2D lattices would greatly broaden the functional scope of 2D materials.

Proteins are attractive building blocks for 2D materials because of their structural and chemical diversity, genetic tailorability and inherent functions. Prominent examples for natural, protein-based 2D materials are bacterial surface-layer (S-layer) proteins and purple-membrane bacteriorhodopsin assemblies, which form crystalline arrays in association with cell walls and membranes, respectively, and have been employed in diverse technological applications (F. Baneyx, J. F. Matthaei, Curr. Opin. Biotech. 28, 39 (2014); U. B. Sleytr, B. Schuster, E. M. Egelseer, D. Pum, FEMS Microbiol. Rev., (2014); N. Hampp, Chem. Rev. 100, 1755 (2000)). On the synthetic front, methods for 2D protein crystallization have been developed for the structural characterization of membrane proteins (A. Engel et al., J. Struct. Biol. 109, 219 (1992); H. Stahlberg et al., FEBS Lett. 504, 166 (2001)) or functional applications (P. O. Saboe et al., Adv. Mater. 26, 7064 (2014)), generally relying on the presence of lipid layers as supports. Recently, there has been progress in the rational, de novo design of 2- or 3D supramolecular protein arrays (J. C. Sinclair, K. M. Davies, C. Venien-Bryan, M. E. M. Noble, Nat. Nanotechnol. 6, 558 (2011); J. D. Brodin et al., Nat. Chem. 4, 375 (2012); N. P. King et al., Science 336, 1171 (2012); S. Gonen, F. DiMaio, T. Gonen, D. Baker, Science 348, 1365 (2015); C. J. Lanci et al., Proc. Natl. Acad. Sci. USA 109, 7304 (2012)), which has entailed the symmetric polymerization of protein building blocks through computationally designed protein-protein interactions or through genetic fusion of protein components. While elegant, these approaches are design-intensive, and the integration of dynamic/adaptive behavior has not been explored.

To address these issues, a simple chemical bonding strategy to control protein self-assembly was used. It was reasoned that both cysteine (Cys)-mediated disulfide bonds and metal coordination interactions between protein building blocks could produce crystalline and dynamic protein arrays with minimal design, because these bonds are: 1) strong but reversible (to minimize the surface area to be designed and ensure self-healing), 2) short yet sufficiently flexible (to simultaneously afford crystallinity and adaptiveness), and 3) chemically tunable (to exert external control over self-assembly and enable stimuli-responsiveness), and 4) easily designed and engineered. As such, the embodiments described herein, the 2D crystalline material comprise polypeptides, wherein the polypeptides can form bond that are: 1) strong but reversible (to minimize the surface area to be designed and ensure self-healing), 2) short yet sufficiently flexible (to simultaneously afford crystallinity and adaptiveness), and 3) chemically tunable (to exert external control over self-assembly and enable stimuli-responsiveness), and 4) easily designed and engineered.

The most straightforward route to obtaining 2D lattices is the tesselation of $C_3$, $C_4$ or $C_6$ symmetric building blocks through appropriately positioned $C_2$ symmetric linkages such as disulfide bonds or many metal coordination interactions. As a model building block, the L-rhamnulose-1-phosphate aldolase (RhuA) protein, was chosen, which is a stable, $C_4$ symmetric homotetramer (4×274 residues) that was previously used as a synthon for engineering supramolecular assemblies (P. Ringler, G. E. Schulz, Science 302, 106 (2003)). RhuA roughly resembles a four-legged stool with dimensions of 7×7×5 nm (FIG. 10A). A quick inspection of the RhuA structure indicated protrusions in the four corner positions that would be ideal locations to incorporate single cysteine or two histidine residues for disulfide-mediated or metal-directed self-assembly, respectively. Two variants, $^{C98}$RhuA (SEQ ID NO: 3) and $^{H63/H98}$RhuA (SEQ ID NO: 4), were generated with four conditionally self-associating corners for forming square lattices (FIGS. 10A and 10B, top and middle rows). The relative positions of residues 63 and 98 were deemed to be conducive to forming a bis-histidine metal coordination motif to afford a tetrahedral or square planar coordination geometry for metal-mediated RhuA pairing interactions. Additionally, it was noted that RhuA could be converted into a stable $D_4$ symmetric octamer through a single point mutation (A88F) (D. Grueninger et al., Science 319, 206 (2008)). Thus, a third variant, $^{F88/C98}$RhuA (SEQ ID NO: 5) was prepared, which presents eight symmetry-related cysteine residues at roughly 45° angles in a 2D projection (FIG. 10A, bottom row). It was envisioned that the $C_4$ symmetric $^{C98}$RhuA and $^{H63/H98}$RhuA variants could potentially yield different square lattices with two distinct patterns in terms of the up/down orientation of the building blocks with respect to the 2D plane (FIG. 10B, top and middle rows). On the other hand, the $D_4$ symmetry of $^{F88/C98}$RhuA would necessarily dictate a 2D lattice with equivalent faces (FIG. 10B, bottom row). These RhuA building blocks would also provide three distinct modes of inter-building-block interactions, whose effects on self-assembly were to be investigated, such as, for example, single disulfide, double disulfide and bis-His-anchored metal coordination.

For the oxidation-driven self-assembly of the Cys-bearing variants $^{C98}$RhuA and $^{F88/C98}$RhuA, various strategies were tested, including air oxidation, redox buffer systems containing reduced and oxidized glutathione (GSH and GSSG) or low concentrations of the reductant β-mercaptoethanol βME (≤10 mM), which slowly decomposes in aqueous solution and results in gradually more oxidizing conditions. For the metal-coordination driven self-assembly of $^{H63/H98}$RhuA, two different divalent metal ions ($Zn^{2+}$ and $Cu^{2+}$) that can accommodate the desired four-coordinate geometries and various buffering agents were screened, which can influence metal coordination by regulating both the solution pH and effective metal ion concentration. It was found that the self-assembly of all three variants was robust and occurred under a broad range of conditions (protein concentrations ranging from 25 to 175 μM, all methods of oxidation, metal identity, and 6<pH<8) at 4° C. The following solution conditions yielded 2D assemblies that were optimized in terms of size, crystallinity, yield and reproducibility: $^{C98}$RhuA and $^{F88/C98}$RhuA (≥125 μM protein, 10 mM βME, pH 7.5, 10 mM TRIS); $^{H63/H98}$RhuA (25 μM protein, 200 μM $ZnCl_2$, pH 7, 20 mM MOPS). Under these conditions, $^{C98}$RhuA reproducibly and in high yield assembled into straight-edged, single- or few-layered 2D crystals that grew to several μm's over several days (FIGS. 11A, 11D and 11E). Transmission electron microscopy (TEM) measurements revealed that the $^{C98}$RhuA crystals were highly ordered and possessed uniform, square shapes with molecularly sharp boundaries, which has not been previously observed in designed 2D protein crystals ((J. C. Sinclair, K. M. Davies, C. Venien-Bryan, M. E. M. Noble, *Nat. Nanotechnol.* 6, 558 (2011); J. D. Brodin et al., *Nat. Chem.* 4, 375 (2012); N. P. King et al., *Science* 336, 1171 (2012); S. Gonen, F. DiMaio, T. Gonen, D. Baker, *Science* 348, 1365 (2015))). In many instances, the growing lattice edges and the surface attachment points of individual $^{C98}$RhuA molecules could be clearly visualized (FIG. 15), suggesting that further growth of $^{C98}$RhuA crystals was limited by the depletion of $^{C98}$RhuA molecules from solution. 2D crystals of $^{H63/H98}$RhuA (FIGS. 11B and 17) and $^{F88/C98}$RhuA (FIGS. 11C and 18) were several hundred nm's to 1 μm in size, but typically displayed irregular morphologies. $^{H63/H98}$RhuA lattices were monocrystalline but tended to grow in 3D over time, whereas $^{F88/C98}$RhuA crystals consisted of aggregates of smaller, single-layered poly-crystalline domains. Self-assembly of all three variants was reversible upon addition of high concentrations of βME (>20 mM) or the metal chelator ethylene-diaminetetraacetic acid (EDTA, >10 mM) as judged by the disappearance of the cloudiness of the suspensions and by TEM measurements (FIG. 19).

The computed diffraction patterns from negative stain (ns) TEM images are consistent with $P42_12$ plane group symmetry for $^{C98}$RhuA and $^{F88/C98}$RhuA and P4 symmetry for $^{H63/H98}$RhuA crystals (FIGS. 11 and 20). There is excellent agreement between experimental 2D EM projection maps and those calculated from structural models (FIG. 20). The square shape of the RhuA building blocks combined with the small footprints of the disulfide- and metal-mediated interactions makes the molecular arrangements in the 2D reconstructions unambiguous (FIG. 11, columns iv and v) and confirms the expected protein-protein interaction geometries: corner-attached $^{C98}$RhuA and $^{H63/H98}$RhuA, and side-attached $^{F88/C98}$RhuA. There are small but clearly distinguishable differences between the relative orientations of RhuA tetramers in the $^{C98}$RhuA and $^{H63/H98}$RhuA lattices, owing to the geometric differences between disulfide- and metal-mediated linkages. As illustrated in FIG. 10B, the plane group symmetries suggest that $^{C98}$RhuA tetramers adopt a checkerboard pattern (alternating up and down; $P42_12$ symmetry) whereas $^{H63/H98}$RhuA tetramers self-assemble in the same orientation with respect to the 2D plane (P4 symmetry). Together with the fact that $^{F88/C98}$RhuA possesses two-fold symmetry parallel to the 2D plane, the three distinct 2D molecular patterns were obtained with minimal alteration of a single protein building block. Different views of the three lattices are shown in FIG. 21. It is noteworthy that $^{C98}$RhuA and $^{H63/H98}$RhuA molecules self-assemble in specific and distinct orientations in the 2D plane despite limited protein interaction surfaces. Although atomic resolution structures are necessary to determine how these orientational specificites arise, it was postulated that the energetic bias stemming from disulfide or metal coordination configurations and the surrounding protein-protein interactions must be sufficiently large to favor one orientation over others to yield long-range crystalline order.

Figure 18B:
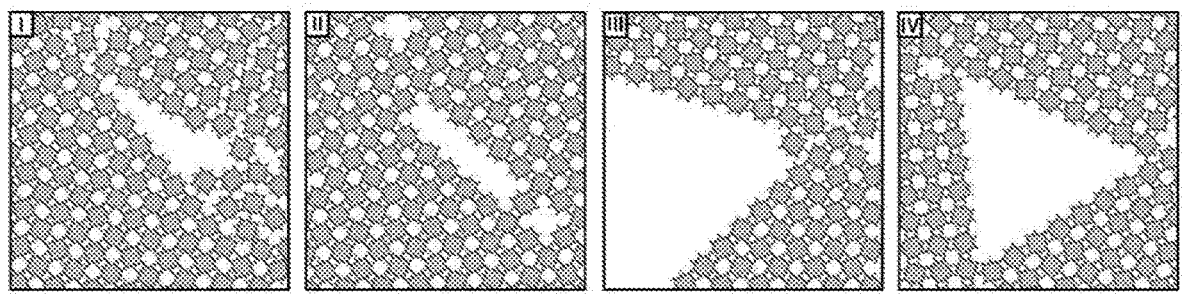

The superior quality and the larger sizes of $^{C98}$RhuA crystals compared to the $^{F88/C98}$RhuA and $^{H63/H98}$RhuA lattices can be readily explained by the bonding interactions that direct the self-assembly of the three variants. The $^{F88/C98}$RhuA building block presents a roughly circular distribution of eight cysteines (FIG. 10A, bottom row). This arrangement renders the desired double-disulfide-mediated, side-to-side self-assembly mode non-unique and permits alternate attachment geometries between $^{F88/C98}$RhuA molecules (FIG. 18). Moreover, the increased poly-Cys-valency of $^{F88/C98}$RhuA leads to considerably stronger, less reversible intermolecular interactions and therefore "stiffer" lattices: in fact, the dissolution of $^{F88/C98}$RhuA polycrystallites require significantly higher amounts of βME and longer incubation periods compared to the $^{C98}$RhuA lattice (FIG. 19). Consequently, $^{F88/C98}$RhuA crystals display frequently lattice vacancies as well as both high- (>30°) and low-angle (<10°) grain boundaries (FIG. 18B). $^{H63/H98}$RhuA crystals possess significantly fewer such defects owing to the reversibility and the orientational specificity of $Zn^{2+}$-coordination interactions. Yet, each $^{H63/H98}$RhuA building block also contains numerous surface residues that can weakly coordinate $Zn^{2+}$ ions, promoting crystal growth in the third dimension (FIG. 17A).

In contrast to $^{F88/C98}$RhuA and $^{H63/H98}$RhuA, the self-assembly of $^{C98}$RhuA is both chemically and orientationally specific. Moreover, the reversibility and inherent flexibility of single Cys-Cys linkages—containing five rotatable bonds—likely allows for the correction of any defects such as step or surface vacancies and grain boundaries, which would be difficult to accomplish in a rigid lattice composed of strongly interacting building blocks such as $^{F88/C98}$RhuA. Indeed, as TEM images of mono-layered $^{C98}$RhuA crystals indicate, the outcomes are a) macroscopic crystal morphologies that reflect the molecular symmetry of the building blocks, b) molecularly sharp crystal boundaries, and c) lattices with very low defect frequencies. In hundreds of monocrystalline $^{C98}$RhuA lattices with surface areas >1 μm$^2$ that were examined closely, a single lattice defect was not detected (vacancies or grain boundaries), despite the fact that these crystals grow in 3D space in an unsupported fashion. In a rare instance where a single lattice vacancy was found, the defect frequency still was one missing $^{C98}$RhuA molecule in a 2D grid of ~9000 molecules (~0.6 μm$^2$) (FIG. 22).

Figure 12A:
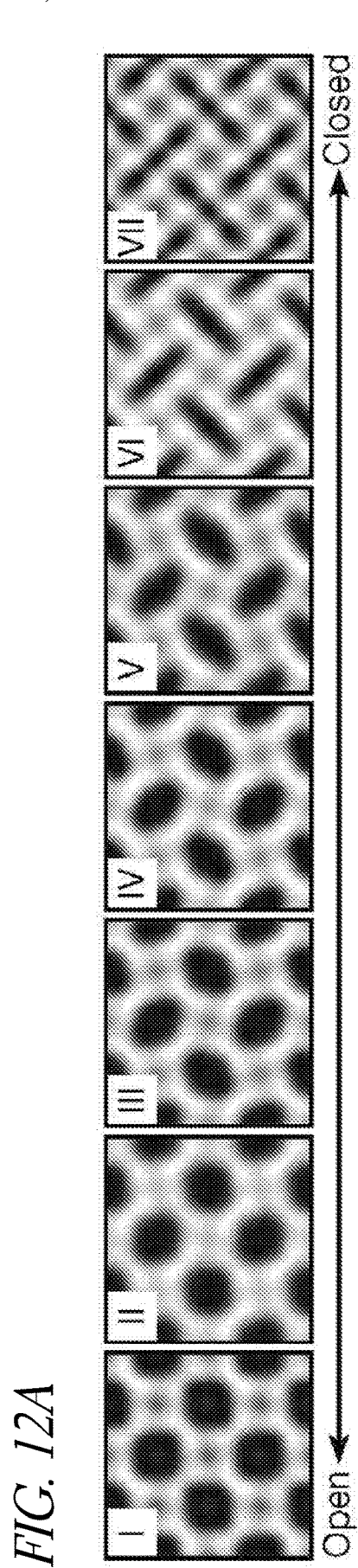
Figure 12B:
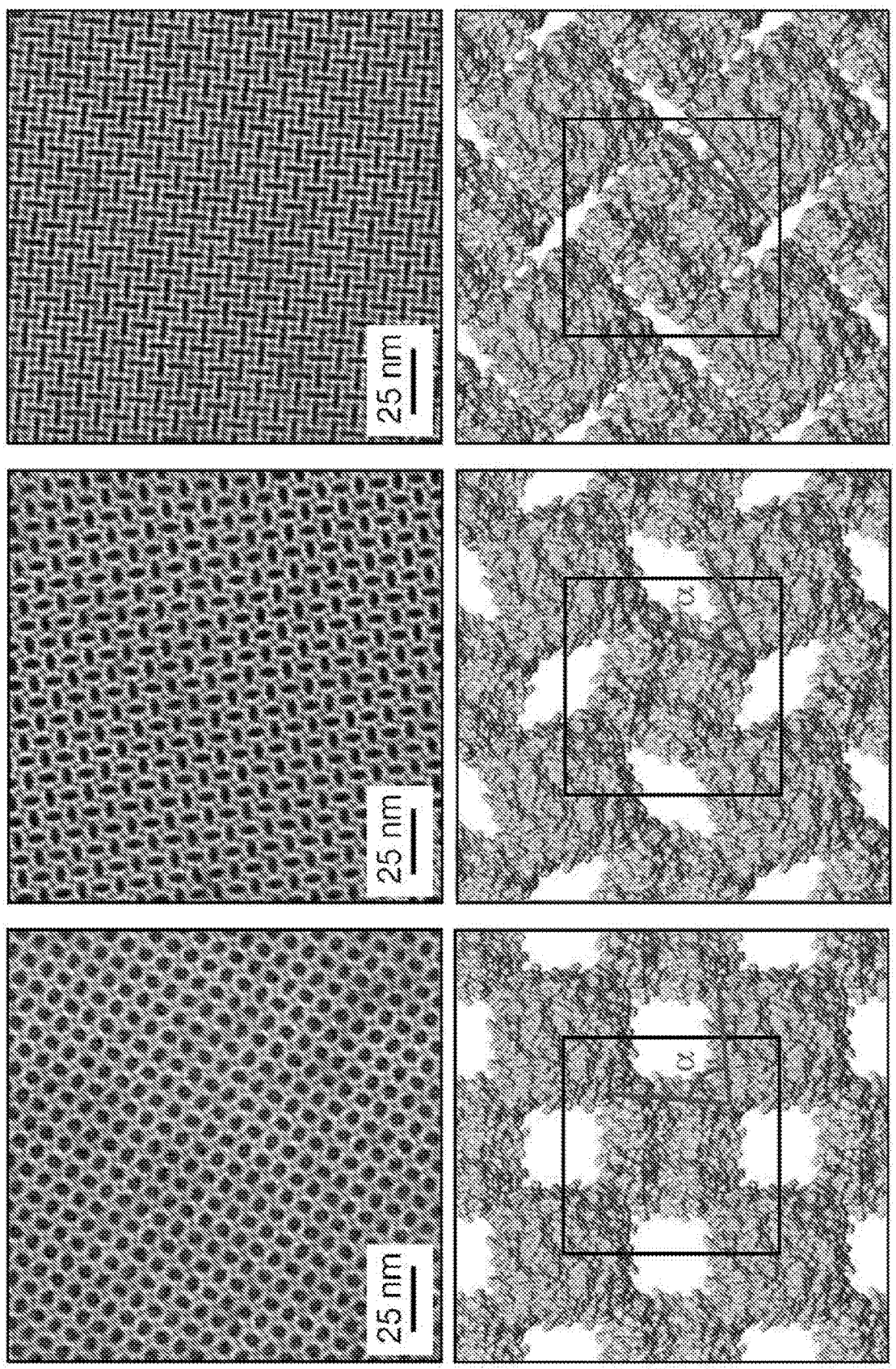

A perhaps more striking consequence of the flexibility of Cys-Cys linkages is the coherent dynamicity of the $^{C98}$RhuA crystals. While our initial preparations predominantly yielded open lattices with large pores (FIG. 11A), the sample suspensions developed over several days a sediment of $^{C98}$RhuA crystals, which featured a densely packed lattice arrangement. Upon resuspension of these sedimented crystals with gentle mechanical agitation and subsequent TEM analysis of the resulting samples, at least seven distinct types of 2D $^{C98}$RhuA crystals in different conformational states (I through VII) were captured (FIGS. 12A and 23). These conformational snapshots implicate a continuous motion of the lattice between fully open and fully closed states, afforded by a remarkable extent of hinging about the flexible Cys-Cys linkages. The transition from the open to the closed state is accompanied by the compression of the inter-$^{C98}$RhuA hinge angle (a) from >80° to 17°, the decrease of the pore size from ~4.4 nm to ~1.0 nm (for the passage of a spherical object), and an increase in the relative protein/hole surface density (per unit cell) of 170% (FIG. 12B and Table 1).

TABLE 1

Structural parameters for conformations II, V and VII of $^{C98}$RhuA crystals derived from images shown in FIG. 12.

| | Open (II) | Intermediate (V) | Closed (VII) |
|---|---|---|---|
| Unit cell (a = b, γ) | 114.4 Å, 90° | 110.0 Å, 90° | 107.8 Å, 90° |
| Intertetramer hinge angle, α | 79° | 49° | 17° |
| Protein surface area per unit cell, $A_{protein}$ | 84.9 nm$^2$ | 86.2 nm$^2$ | 88.0 nm$^2$ |
| Pore surface area per unit cell, $A_{pore}$ | 46.0 nm$^2$ | 34.7 nm$^2$ | 28.2 nm$^2$ |
| Relative protein/pore density, $A_{protein}/A_{pore}$ | 1.8 | 2.5 | 3.1 |

Figure 12C:
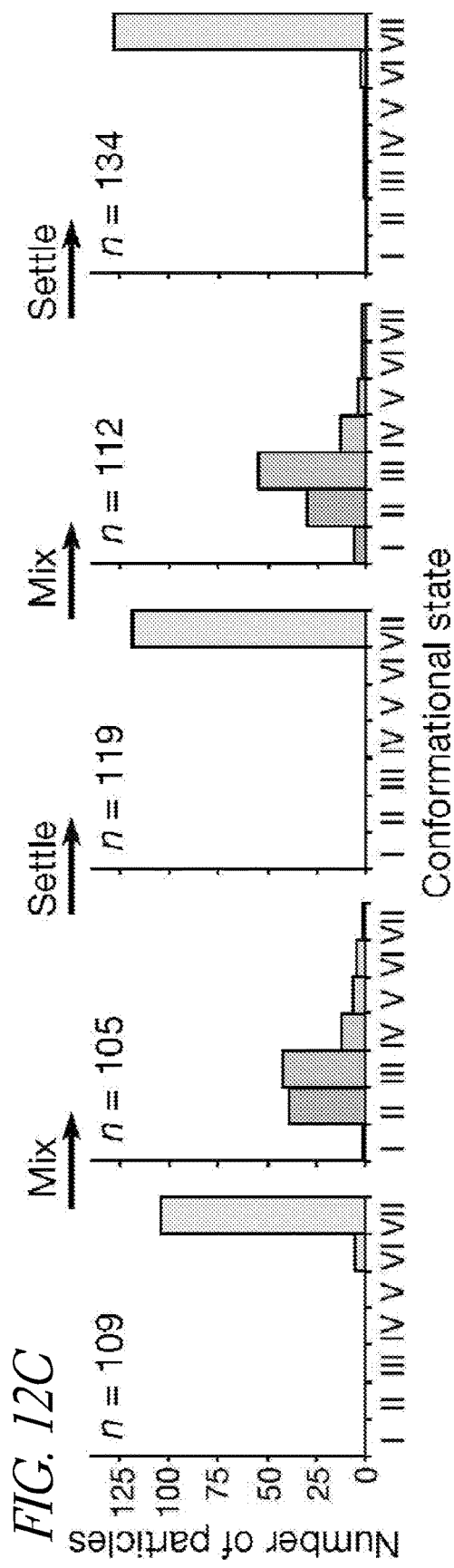
Figure 12D:
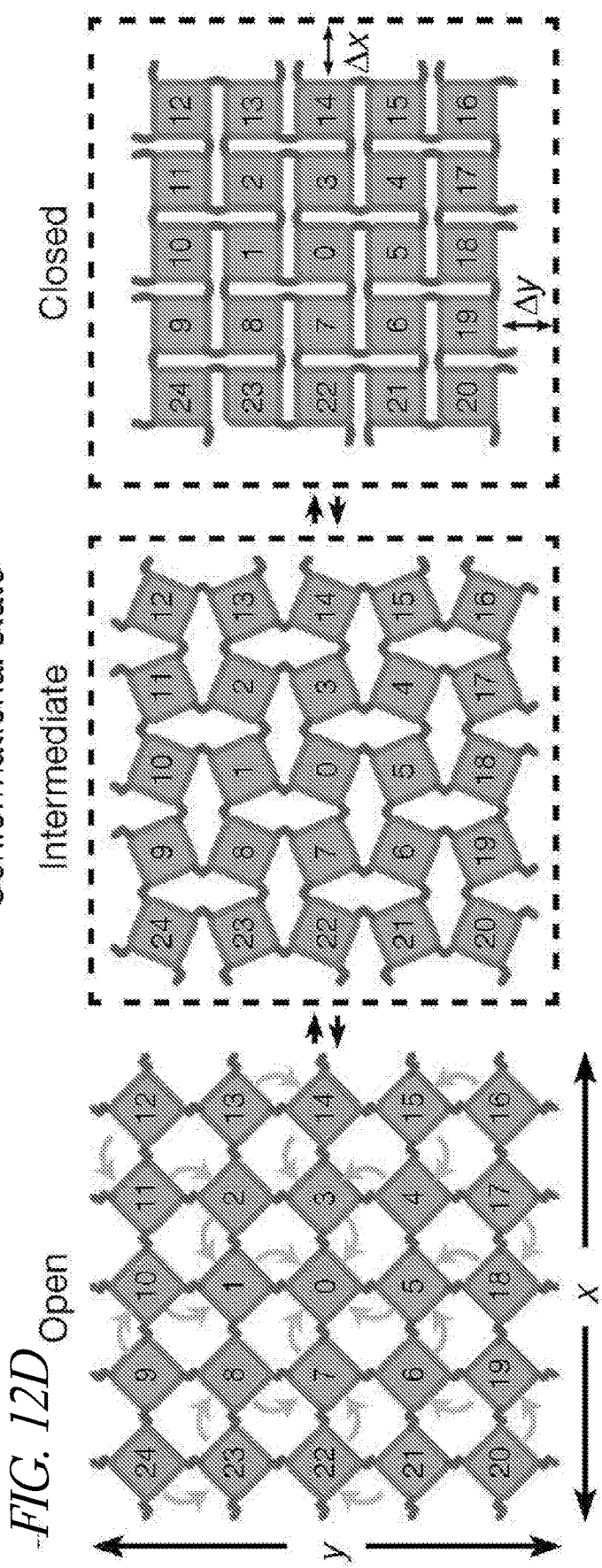

Conformational dynamics of $^{C98}$RhuA crystals are fully coherent: in each crystal examined, only one type of conformational state is observed throughout the lattice and the overall P4$_2$1$_2$ plane group symmetry is preserved (FIG. 12B). This observation implies that any mechanical deformation of a $^{C98}$RhuA crystal is rapidly and cooperatively propagated in the 2D lattice, enabled by both the flexibility and short linker-length of the Cys-Cys linkages: a longer, more flexible type of linkage would preclude coherent dynamics, whereas an inflexible linkage would lead to non-adaptive lattices. Conformational dynamics of the $^{C98}$RhuA crystals are reversible as indicated by the interconversion of the open and closed conformational states during repeated sedimentation/resuspension cycles (FIG. 12C). It was posited that the energetic activation barriers between different $^{C98}$RhuA lattice conformations (due to different Cys-Cys configurations and long-range protein-protein interactions) must be small enough to be overcome by mechanical agitation and internal protein dynamics.

Geometric considerations (FIG. 12D) indicate that $^{C98}$RhuA crystals are auxetic, with a Poisson's ratio of −1. Poisson's ratio (ν) is a scale-independent metric that describes the response of a material to strain; it is defined as the ratio between transverse ($e_x$) and longitudinal strains ($e_y$) under uniaxial loading (G. N. Greaves, A. Greer, R. Lakes, T. Rouxel, Nat. Mater. 10, 823 (2011)). $e_x$ and $e_y$ are, in turn, approximated by changes in material length in transverse (ΔX) and longitudinal (ΔY) directions (G. N. Greaves, A. Greer, R. Lakes, T. Rouxel, Nat. Mater. 10, 823 (2011)):

$$v = -\frac{e_y}{e_x} \approx -\frac{\Delta Y}{\Delta X}$$

where −1≤ν≤0.5 for an isotropic material. Most materials possess positive Poisson's ratios, i.e., they become thinner in the longitudinal direction when stretched transversely (G. N. Greaves, A. Greer, R. Lakes, T. Rouxel, Nat. Mater. 10, 823 (2011)). Materials with negative Poisson's ratios (i.e., auxetic materials), on the other hand, display the counterintuitive behavior of longitudinal expansion upon transverse stretching. Thus, auxetic materials can be expected to possess enhanced toughness, resistance to indentation, and shear stiffness, and have been proposed for use in body armors, smart textiles, actuated filtration and piezoelectric devices, among many others (G. N. Greaves, A. Greer, R. Lakes, T. Rouxel, Nat. Mater. 10, 823 (2011); K. E. Evans, A. Alderson, Adv. Mater. 12, 617 (2000); R. H. Baughman, Nature 425, 667 (2003)). Although natural and synthetic materials with negative Poisson's ratios exist, most fall in the range of −0.4<ν<0, with the lowest value reported of −0.7, observed in reentrant polyurethane foams (R. Lakes, Science 235, 1038 (1987)). It was postulated that for a 2D lattice of rotating rigid squares with flexible hinges, the Poisson's ratio should be negative at all rotation angles and equal to the lowest thermodynamically permissible value of −1 (J. Grima, A. Alderson, K. Evans, Phys. Stat. Sol. b 242, 561 (2005)). $^{C98}$RhuA lattices represent a true realization of this theoretical model at the molecular scale and represent— to our knowledge—the first synthetic or natural isotropic material with ν=−1. In the embodiments described herein, the 2D crystalline material comprises a Poisson's ratio of −1.

It was envisioned that upon hierarchical assembly through physical methods, molecular architectures like 2D $^{C98}$RhuA lattices can be used as feedstocks for adaptive and auxetic macroscopic materials. Of particular importance is the observation that compression and expansion of $^{C98}$RhuA-type, "rotary" lattices occur without the deformation of individual building blocks, thereby opening the way for incorporating their inherent molecular functions and properties into higher-order assemblies. Due to their chemical tunability, reproducible production and high structural quality, $^{C98}$RhuA lattices provide an ideal medium for studying molecular self-assembly, crystal nucleation and growth. The resulting understanding of structural/lattice dynamics at the nanoscale should greatly aid the fabrication of functional materials.

Example 1-Design of RhuA Variants and Site-Directed Mutagenesis

RhuA variants were designed as described above based on previously reported crystal structures (PDB ID: 1OJR for $^{C98}$RhuA and $^{H63/H98}$RhuA (P. Ringler, G. E. Schulz, Science 302, 106 (2003)) and PDB ID 2UYU for $^{F88/C98}$RhuA (D. Grueninger et al., Science 319, 206 (2008)). All RhuA variants also contain the mutations E192A and C126S as reported in (P. Ringler, G. E. Schulz, Science 302, 106 (2003)) and (D. Grueninger et al., Science 319, 206 (2008)). The gene for $^{C98}$RhuA, pre-inserted into the pJ414 expression vector optimized for expression in E. coli (Ampicillin resistant), was purchased from DNA2.0. $^{F88/C98}$RhuA and $^{H63/H98}$RhuA were prepared using QuikChange mutagenesis (Stratagene) with primers obtained from Integrated DNA Technologies (Table 2). The mutant plasmids were transformed into XL-1 Blue E. coli cells followed by purification using the QIAprep Spin Miniprep kit (Qiagen). The presence of the mutations was verified by sequencing (Retrogen).

$^{C98}$RhuA Sequence (SEQ ID NO: 3):
MQNITQSWFVQGMIKATTDAWLKGWDERNGGNLTLRLDDADIAPYHDNF HQQPRYIPLSQPMPLLANTPFIVTGSGKFFRNVQLDPAANLGIVKVDS<u>C</u>

GAGYHILWGLTNEAVPTSELPAHFLSHSERIKATNGKDRVIMHCHATNL

IALTYVLENDTAVFTRQLWEGSTECLVVFPDGVGILPWMVPGTDAIGQA

TAQEMQKHSLVLWPFHGVFGSGPTLDETFGLIDTAEKSAQVLVKVYSMG

GMKQTISREELIALGKRFGVTPLASALAL $^{H63/H98}$RhuA Sequence (SEQ ID NO: 4):
MQNITQSWFVQGMIKATTDAWLKGWDERNGGNLTLRLDDADIAPYHDNF HQQPRYIPLSQPM<u>H</u>LLANTPFIVTGSGKFFRNVQLDPAANLGIVKVDS<u>H</u>

GAGYHILWGLTNEAVPTSELPAHFLSHSERIKATNGKDRVIMHCHATNL

IALTYVLENDTAVFTRQLWEGSTECLVVFPDGVGILPWMVPGTDAIGQA

TAQEMQKHSLVLWPFHGVFGSGPTLDETFGLIDTAEKSAQVLVKVYSMG

GMKQTISREELIALGKRFGVTPLASALAL $^{F88/C98}$RhuA Sequence (SEQ ID NO: 5):
MQNITQSWFVQGMIKATTDAWLKGWDERNGGNLTLRLDDADIAPYHDNF HQQPRYIPLSQPMPLLANTPFIVTGSGKFFRNVQLDPA<u>F</u>NLGIVKVDS<u>C</u>

GAGYHILWGLTNEAVPTSELPAHFLSHSERIKATNGKDRVIMHCHATNL

IALTYVLENDTAVFTRQLWEGSTECLVVFPDGVGILPWMVPGTDAIGQA

TAQEMQKHSLVLWPFHGVFGSGPTLDETFGLIDTAEKSAQVLVKVYSMG

GMKQTISREELIALGKRFGVTPLASALAL

Example 2-Protein Expression and Purification

Bacterial expression of RhuA variants was performed according to previously published procedures with slight modifications (M. Kroemer, G. E. Schulz, Acta Cryst. D 58, 824 (2002)). Plasmids bearing the variants were transformed into BL21(DE3) E. coli cells, and the colonies were grown overnight at 37° C. on lysogeny broth (LB) agar plates (pH 7.4) containing 100 mg/L ampicillin. Starter cultures (5 mL with 100 mg/L ampicillin) from single colonies were grown for ~4-6 h at 37° C. (with shaking at 250 rpm) before inoculation into 1-L LB cultures containing 100 mg/L ampicillin. After the cells were grown to an optical density of ~0.8 at 600 nm, protein expression was induced with 1 mM isopropyl β-D-1-thiogalactopyranoside (IPTG, Gold Biotechnology) for 12-13 h (at 37° C. with shaking at 250 rpm). Cells were pelleted by centrifugation (5,000 rpm at 4° C. for 10 min), and resuspended in a buffer solution containing 10 mM Tris(hydroxymethyl)aminomethane hydrochloride (TRIS) (pH 7.5), 1 mM ZnCl$_2$, and 10 mM β-mercaptoethanol (βME). For $^{H63/H98}$RhuA preparations, ZnCl$_2$ was excluded from buffer solutions to avoid possible protein precipitation during purification. Cell lysis was performed by sonication for 15 min on ice. The lysis solution was centrifuged for 30 min at 12,000 rpm at 4° C. Polymin-P (Acros) was added to the supernatant at a final concentration of 0.15% (w/v) for nucleic acid precipitation and the resulting mixture was stirred for 30 min prior to centrifugation for 30 min at 12,000 rpm at 4° C. The supernatant was loaded onto a DEAE-Sepharose CL-6B (GE Healthcare) column and eluted using a gradient of 0-500 mM NaCl in Tris buffer at 4° C. Fractions containing RhuA which eluted at ~200 mM NaCl were added 1.7 M ammonium sulfate, and were centrifuged for 45 min at 12,000 rpm at 4° C. The precipitate was dissolved in a buffer solution containing 5 mM sodium phosphate (NaPi) (pH 7.2), 1 mM ZnCl$_2$, and 10 mM βME, and then dialyzed three times against 5 L of the same buffer solution. Further purification was done using either a High Q cartridge column (BioRad) (at pH 8.0) using a 0-500 mM NaCl gradient or a Mini CHT™ Type I hydroxyapatite column (BioRad) (at pH 7.2) using a 5-500 mM NaPi gradient on a DuoFlow fast protein chromatography workstation (Bio-Rad). Pure protein fractions eluted at 350 mM NaCl and 200 mM NaPi, respectively. These fractions were combined, dialyzed three times against a buffer solution of 10 mM TRIS (pH 7.5), 1 mM ZnCl$_2$, and 10 mM β-mercaptoethanol (βME), and concentrated in an Amicon stirred cell at 4° C. The protein was then flash frozen and kept at −80° C. until use. Protein purity was confirmed by SDS-PAGE (FIG. 13) and ESI-MS (FIG. 14 and Table 3), and stock concentrations (~100-175 μM for $^{C98}$RhuA and $^{F88/C98}$RhuA; 100 μM for $^{H63/H98}$RhuA) was determined as previously reported (H. Edelhoch, Biochemistry 6, 1948 (1967)).

Purification techniques can be performed using standard protein purification kits, columns, and methods and are known to those skilled in the art. In some embodiments described herein, the polypeptides or proteins purified for use in creating the 2D crystalline material is purified to a purity of 80%, 85%, 90%, 95% or 100% purity or any percent purity in between a range defined by any two aforementioned values.

Example 3-Preparation of 2D RhuA Crystals

All 2D RhuA crystals reported herein were obtained in an unsupported fashion in solutions. Several solution conditions were screened for optimizing the formation of 2D protein crystals of $^{C98}$RhuA, $^{F88/C98}$RhuA and $^{H63/H98}$RhuA variants. For all variants, these screening conditions included various pH's (6 to 8), starting protein concentrations (25 to 175 μM), buffer salt concentration and identity (5-20 mM bis-TRIS, CHES, MES, MOPS, NaPi, and TRIS), and temperature (4-37° C.). In some embodiments, the polypeptides are screened for formation of 2D crystals in buffers that comprise a pH of 5, 5.5, 6, 6.5, 7, 7.5, 8 or 8.5 or any pH in between a range defined by any two aforementioned values. For the disulfide-mediated self-assembly of $^{C98}$RhuA and $^{F88/C98}$RhuA, various oxidizing conditions were additionally screened (1-2 mM total GSH/GSSG at ratios varying from 1:19 to 19:1, or 5-10 mM βME, which slowly decomposed in aqueous solution in the presence of metal ions). For the metal-mediated assembly of $^{H63/H98}$RhuA, 4-20 molar equivalents (over protein concentration) of ZnCl$_2$ and CuCl$_2$ were screened. As stated, in some of the embodiments herein, the best conditions were: $^{C98}$RhuA and $^{F88/C98}$RhuA (≥125 μM protein, 10 mM βME, pH 7.5, 10 mM TRIS); $^{H63/H98}$RhuA (25 μM protein, 200 mM ZnCl$_2$, pH 7, 20 mM MOPS) at 4° C. In general, the formation of crystals was either immediate (upon metal addition for $^{H63/H98}$RhuA) or lasted overnight to several days (for $^{C98}$RhuA and $^{F88/C98}$RhuA). Crystal formation resulted in increasing cloudiness of the self-assembly solutions. The growth of $^{C98}$RhuA crystals could be accelerated by gentle shaking (compare FIGS. 15 and 16). In some embodiments of the methods of forming the 2D crystalline material, the crystal formation is accelerated by gentle shaking.

Example 4-TEM Measurements and Image Processing

For TEM sample preparation, 3-3.5 µL aliquots of crystal suspensions were applied onto a negatively glow-discharged carbon-coated Cu grids (Ted Pella, Inc), washed with Milli-Q water, and stained with 1% uranyl acetate at 4° C. Sample screening was preformed in an FEI Sphera transmission electron microscope equipped with a $LaB_6$ electron gun at 200 keV and imaged on Gatan $2K^2$ CCD.

Selected micrographs were each processed separately using the 2dx software package (B. Gipson, X. Zeng, Z. Y. Zhang, H. Stahlberg, *J. Struct. Biol.* 157, 64 (2007)) to determine 2D plane group lattice symmetry of each crystal, to calculate their unit cell dimensions and to generate a projection density map of each crystal. The estimated resolution limit of each image (between 15 and 30 Å) was assessed by visual inspection of its computed Fourier transform.

Example 5-Structural Modeling and Simulations

Projected electron density maps were used as a reference in the visualization software UCSF Chimera (E. F. Pettersen et al., *J. Comput. Chem.* 25, 1605 (2004)) to determine the orientation of the RhuA molecules in each crystal. The atomic coordinates were extracted from the PDB entries 1OJR ($C_4$-symmetric tetramer for $^{C98}$RhuA and $^{H63/H98}$RhuA) and 2UYU ($D_4$-symmetric octamer for $^{F88/C98}$RhuA) and placed manually to fit the position of one subunit in the observed projected density map. The orientation of the molecule was refined in an iterative manner by comparing the experimental density with the density simulated from a model of the unit cell, obtained as explained below.

Simulated projected electron density maps were computed using Bsoft (lsbr.niams.nih.gov/bsoft) (J. B. Heymann, *J. Struct. Biol.* 133, 156 (2001)) and EMAN2 (blake.bcm.edu/emanwiki/EMAN2) (G. Tang et al., *J. Struct. Biol.* 157, 38 (2007)). Starting from the estimated position and orientation of a single subunit, multiple copies of the model were generated to cover one unit cell (bmoledit in Bsoft) and converted to electron density (e2pdb2mrc.py in EMAN2) with a resolution limit of 30 Å. Finally, the density volume was projected along the vertical direction (bproject in Bsoft) to generate a 2D density map comparable to the experimental map.

Example 6—Classification of the Conformational States of 2D $^{C98}$RhuA Crystals TEM micrographs of $^{C98}$RhuA crystals were analyzed computationally to categorize different conformational states of the 2D lattice. Essentially, for each raw image it was determined a roundness index number derived from the shape of the pores in the lattice, and used this value to classify the images. The analysis was performed using an ad hoc algorithm coded as a macro in Fiji (fiji.sc/Fiji) (J. Schindelin et al., *Nat. Meth.* 9, 676 (2012)) and ImageJ (imagej.nih.gov/ij/) (C. A. Schneider, W. S. Rasband, K. W. Eliceiri, *Nat. Methods* 9, 671 (2012)). Each image was initially processed by applying a 3×3 mean filter applied three times, and then it was converted to a binary image after automatic thresholding to segment out the pores. The mask was then filtered using the opening morphological operator to smooth the shape of the pores and to remove small outliers. Pores that were distorted from potential bending of the crystal in some regions of the field of view were discarded using their size for screening. For images acquired at a nominal magnification of ×50,000 and ×68,000 (calibrated pixel size=2.033 Å and 1.646 Å, respectively), only pores with areas that covered 500-1200 pixels were kept. The remaining pores were modeled as ellipses and their roundness index was determined as the ratio between the lengths of the major and the minor elliptical axes. A single index value was assigned to each micrograph as the average from all the segmented pores. The images were assigned to one of the seven identified states using the following criterion: State I: >0.85; State II: >0.75-0.85; State III: >0.65-0.75; State IV: >0.55-0.65; State V: >0.35-0.45; State VI: > 0.35-0.45; State VII<0.35.

TABLE 2

List of primers used in constructing site-directed mutants of RhuA using C98RhuA as a base.

| Variant | Mutation | Primer Sequence |
|---|---|---|
| $^{F88/C98}$RhuA | A88F | 5'-CGCAATGTCCAGTTGGACCCAGCGTTTAACCTGGGCATTGTTAAGGTGG-3' (SEQ ID NO: 6)<br>5'-CCACCTTAACAATGCCCAGGTTAAACGCTGGGTCCAACTGGACATTGCG-3' (SEQ ID NO: 7) |
| $^{H63/H98}$RhuA | P63H | 5'-CGCTGAGCCAGCCGATGCATCTGTTGGCGAATACCC-3' (SEQ ID NO: 8) |
| | C98H | 5'-GGGTATTCGCCAACAGATGCATCGGCTGGCTCAGCG-3' (SEQ ID NO: 9)<br>5'-GGGCATTGTTAAGGTGGATAGCCATGGTGCAGGTTACCACATCC-3' (SEQ ID NO: 10)<br>5'-GGATGTGGTAACCTGCACCATGGCTATCCACCTTAACAATGCCC-3' (SEQ ID NO: 11) |

TABLE 3

Positive ESI-MS characterization of RhuA mutants.
For the actual mass spectra, refer to FIG. 14.

| Variant | Calculated Mass (Da) | Observed Mass (Da) |
|---|---|---|
| $^{C98}$RhuA | 30059.5 | 30060.0 |
| $^{F88/C98}$RhuA | 30135.6 | 30136.0 |
| $^{H63/H98}$RhuA | 30133.5 | 30134.0 |

Two-dimensional (2D) crystalline materials possess unique structural, mechanical, and electronic properties (Mas-Balleste, R., Gomez-Navarro, C., Gomez-Herrero, J. & Zamora, F. 2D materials: to graphene and beyond. *Nanoscale* 3, 20-30, (2011); Butler, S. Z. et al. Progress, challenges, and opportunities in two-dimensional materials beyond graphene. *ACS Nano* 7, 2898-2926, (2013)), which have rendered them highly attractive in many applications (Schedin, F. et al. Detection of individual gas molecules adsorbed on graphene. *Nat. Mater.* 6, 652-655, (2007); Lu, C.-H., Yang, H.-H., Zhu, C.-L., Chen, X. & Chen, G.-N. A Graphene Platform for Sensing Biomolecules. *Angew. Chem. Int. Ed. Engl.* 121, 4879-4881, (2009); Joshi, R. K. et al. Precise and Ultrafast Molecular Sieving Through Graphene Oxide Membranes. *Science* 343, 752-754, (2014)). Although there have been advances in preparing 2D materials that consist of one or few atomic/molecular layers (Nicolosi, V., Chhowalla, M., Kanatzidis, M. G., Strano, M. S. & Coleman, J. N. Liquid exfoliation of layered materials. *Science* 340, 1226419, (2013); Li, D., Muller, M. B., Gilje, S., Kaner, R. B. & Wallace, G. G. Processable aqueous dispersions of graphene nanosheets. *Nat. Nano.* 3, 101-105, (2008)), bottom-up assembly of 2D crystalline materials remains a considerable challenge and an active area of development (Colson, J. W. et al. Oriented 2D covalent organic framework thin films on single-layer graphene. *Science* 332, 228-231, (2011; Kissel, P., Murray, D. J., Wulftange, W. J., Catalano, V. J. & King, B. T. A nanoporous two-dimensional polymer by single-crystal-to-single-crystal photopolymerization. *Nat. Chem.* 6, 774-778, (2014); Kory, M. J. et al. Gram-scale synthesis of two-dimensional polymer crystals and their structure analysis by X-ray diffraction. *Nat. Chem.* 6, 779-784, (2014)). Even more challenging is the design of dynamic 2D lattices that can undergo large-scale motions without loss of crystallinity. Dynamicity in porous 3D crystalline solids has been exploited for stimuli-responsive functions and adaptive behavior (Shimomura, S. et al. Selective sorption of oxygen and nitric oxide by an electron-donating flexible porous coordination polymer. *Nat. Chem.* 2, 633-637, (2010); Rabone, J. et al. An adaptable peptide-based porous material. *Science* 329, 1053-1057, (2010); Serre, C. et al. Role of solvent-host interactions that lead to very large swelling of hybrid frameworks. *Science* 315, 1828-1831, (2007)). As in the case of such 3D materials, integrating flexibility/adaptiveness into crystalline 2D lattices would greatly broaden the functional scope of 2D materials. As described herein is the self-assembly of unsupported, 2D protein lattices with precise spatial arrangements and patterns through a readily accessible design strategy. Three single- or double-point mutants of the $C_4$ symmetric protein RhuA were designed to assemble via different modes of intermolecular interactions (single disulfide, double disulfide and metal coordination) into crystalline 2D arrays. Owing to the flexibility of the single disulfide interactions, the lattices of one of the variants ($^{C98}$RhuA) are essentially defect-free and undergo substantial but fully correlated changes in molecular arrangement, giving coherently dynamic 2D molecular lattices. Notably, $^{C98}$RhuA lattices possess a Poisson's ratio of −1, the lowest thermodynamically possible value for an isotropic material. In some of the embodiments described herein, the 2D crystalline material comprises a Poisson's ratio of −1.

Proteins are attractive building blocks for 2D materials because of their structural/chemical diversity and inherent functions. Examples for natural, protein-based 2D materials can include, but are not limited to bacterial S-layer proteins and purple-membrane assemblies, which form crystalline arrays in association with cell walls and membranes, respectively, and have been employed in diverse technological applications (Sleytr, U. B., Schuster, B., Egelseer, E. M. & Pum, D. S-layers: principles and applications. *FEMS Microbiol. Rev.* 38, 823-864, (2014), Hampp, N. Bacteriorhodopsin as a photochromic retinal protein for optical memories. *Chem. Rev.* 100, 1755-1776, (2000)). On the synthetic front, methods for 2D protein crystallization have been developed for the structural characterization of membrane proteins (Engel, A. et al. Assembly of 2-D membrane protein crystals: dynamics, crystal order, and fidelity of structure analysis by electron microscopy. *J. Struct. Biol.* 109, 219-234, (1992); Stahlberg, H. et al. Two-dimensional crystals: a powerful approach to assess structure, function and dynamics of membrane proteins. *FEBS Lett.* 504, 166-172, (2001)) or functional applications (Saboe, P. O. et al. Two-Dimensional Protein Crystals for Solar Energy Conversion. *Adv. Mater.* 26, 7064-7069, (2014)), generally relying on lipid layers as supports. Recently, 2D or 3D supramolecular protein arrays have been designed through the symmetric polymerization of protein building blocks via computationally designed protein-protein interactions or fusion of protein components (Sinclair, J. C., Davies, K. M., Venien-Bryan, C. & Noble, M. E. M. Generation of protein lattices by fusing proteins with matching rotational symmetry. *Nat. Nanotechnol.* 6, 558-562, (2011); Brodin, J. D. et al. Metal-directed, chemically tunable assembly of one-, two- and three-dimensional crystalline protein arrays. *Nat. Chem.* 4, 375-382, (2012); Gonen, S., DiMaio, F., Gonen, T. & Baker, D. Design of ordered two-dimensional arrays mediated by noncovalent protein-protein interfaces. *Science* 348, 1365-1368, (2015); Lanci, C. J. et al. Computational design of a protein crystal. *Proc. Natl. Acad. Sci. USA* 109, 7304-7309, (2012)). While elegant, these approaches are engineering-intensive and highly dependent on the accuracy of the design, and the integration of dynamic/adaptive behavior has not been explored.

In order to address these issues, described herein is a developed simple chemical bonding strategy to control protein self-assembly. It was reasoned that both cysteine (Cys)-mediated disulfide bonds and metal coordination interactions between protein building blocks can produce crystalline and dynamic arrays with minimal design, because these bonds are: 1) strong but reversible (to minimize the surface area to be designed and ensure self-healing), 2) short yet sufficiently flexible (to simultaneously afford crystallinity and adaptiveness), and 3) chemically tunable (to exert external control over self-assembly and enable stimuli-responsiveness), and 4) easily designed and engineered. In some embodiments described herein, cysteine (Cys)-mediated disulfide bonds and metal coordination interactions between protein building blocks can produce crystalline and dynamic arrays with minimal design. In some embodiments, the cysteine bonds are strong but flexible. In some embodiments, the cysteine bonds and metal coordination interactions are strong but flexible. In some embodiments, the bonds are short yet sufficiently flexible. In some embodiments, the bonds are chemically tunable. In some embodiments, the bonds are easily designed and engineered.

The most straightforward route to obtaining 2D lattices is the tesselation of $C_3$, $C_4$ or $C_6$ symmetric building blocks through appropriately positioned $C_2$ symmetric linkages such as disulfide bonds or many metal coordination interactions. As such, as described in several embodiments herein, 2D lattices were produced by the methods herein to have $C_3$, $C_4$ or $C_6$ symmetric building blocks through appropriately positioned $C_2$ symmetric linkages such as disulfide bonds or many metal coordination interactions. As a model building block, L-rhamnulose-1-phosphate aldolase (RhuA), and a $C_4$ symmetric homotetramer (dimensions: 7×7×5 nm) that was previously used as a synthon for supramolecular assemblies, were chosen (Ringler, P. & Schulz, G. E. Self-assembly of proteins into designed networks. *Science* 302, 106-109, (2003)) (FIG. 10A). An inspection of RhuA indicated protrusions in the four corner positions as ideal locations to incorporate single Cys or two histidine (His) residues for disulfide- or metal-directed self-assembly, respectively. As described in some embodiments described herein, two variants were generated, $^{C98}$RhuA and $^{H63/H98}$RhuA, with four conditionally self-associating corners for forming square lattices (FIG. 10A, 10B, top and middle rows). The relative positions of residues 63 and 98 were deemed to be conducive to forming a bis-His metal coordination motif to afford a tetrahedral or square planar coordination geometry for metal-mediated RhuA pairing interactions. Additionally, it was noted that RhuA could be converted into a stable $D_4$ symmetric octamer through a single point mutation (A88F) (Grueninger, D. et al. Designed protein-protein association. *Science* 319, 206-209, (2008)). Thus, a third variant, $^{F88/C98}$RhuA, was prepared, which presents eight symmetry-related cysteines at roughly 45° angles in a 2D projection (FIG. 10A, bottom row). It was envisioned that the $C_4$ symmetric $^{C98}$RhuA and $^{H63/H98}$RhuA variants could yield square lattices with two distinct patterns in terms of the orientation of the building blocks with respect to the 2D plane (FIG. 10B). On the other hand, the $D_4$ symmetry of $^{F88/C98}$RhuA would dictate a 2D lattice with equivalent faces (FIG. 10B). These RhuA building blocks would also provide three distinct modes of inter-building-block interactions, whose effects on self-assembly were to be investigated, such as single disulfide, double disulfide and bis-His-anchored metal coordination.

For the oxidative self-assembly of $^{C98}$RhuA and $^{F88/C98}$RhuA, various strategies were tested including air oxidation, redox buffer systems containing reduced and oxidized glutathione (GSH and GSSG) or low concentrations (≤10 mM) of the reductant β-mercaptoethanol (βME), which slowly decomposes in aqueous solution and results in gradually more oxidizing conditions. In these experiments, solutions of purified $^{C98}$RhuA and $^{F88/C98}$RhuA were first rapidly exchanged via repeated centrifugal filtration into solutions that varied in terms of their pH (6 to 8.5), buffering species (sodium phosphate, CHES, MES, MOPS, TRIS; at 5 to 20 mM), different compositions of the redox buffering system (1:19 or 19:1 GSH:GSSG; at 1 mM total concentration) or different concentrations of βME (0-10 mM). After adjustment to the desired final protein concentration (25-175 μM), these solutions were monitored for the formation of self-assembled structures by visual inspection for emergence of cloudiness and by transmission electron microscopy (TEM). Likewise, for metal-directed assembly, purified $^{H63/H98}$RhuA was exchanged into solutions with varying pH's and buffer ions (to modulate metal binding kinetics and thermodynamics), with the exception that these solutions did not contain any reductants. Self-assembly was initiated by addition of 4-40 molar equivalents of $Zn^{2+}$ and $Cu^{2+}$ (1-10 equiv. per bis-His motif), both of which can accommodate the desired four-coordinate geometries to link $^{H63/H98}$RhuA building blocks at their corners.

It was found that the assembly of all variants into 2D arrays was robust and occurred under a wide range of conditions. As expected, crystalline self-assembly was favored by conditions that promoted slow, controlled oxidation or slow metal-binding kinetics. For example, uncontrolled air oxidation of $^{C98}$RhuA solutions or addition of large molar excess of $Zn^{2+}$ and $Cu^{2+}$ to $^{H63/H98}$RhuA samples resulted largely in amorphous aggregates in addition to some crystalline domains (FIGS. 10C and 10D). The following solution conditions yielded 2D assemblies that were optimized in terms of size, crystallinity, and yield: $^{C98}$RhuA and $^{F88/C98}$RhuA (≥125 μM protein, 10 mM βME, pH 7.5, 10 mM TRIS); $^{H63/H98}$RhuA (25 μM protein, 200 μM $ZnCl_2$, pH 7, 20 mM MOPS). Under these conditions, $^{C98}$RhuA reproducibly assembled into straight-edged, single- or few-layered 2D crystals that grew to several μm's over several days (FIG. 11A). Negative-stain and cryo-TEM, scanning electron microscopy (SEM) and atomic force microscopy (AFM) measurements revealed that the $^{C98}$RhuA crystals were highly ordered and possessed uniform square/rectangular shapes with molecularly sharp boundaries (FIGS. 11A, 11D, 11E 12G, 12H and 12I); these features have not been previously observed in designed 2D protein crystals (Sinclair, J. C., Davies, K. M., Venien-Bryan, C. & Noble, M. E. M. Generation of protein lattices by fusing proteins with matching rotational symmetry. *Nat. Nanotechnol.* 6, 558-562, (2011); Gonen, S., DiMaio, F., Gonen, T. & Baker, D. Design of ordered two-dimensional arrays mediated by noncovalent protein-protein interfaces. *Science* 348, 1365-1368, (2015)). 2D crystals of $^{H63/H98}$RhuA (FIGS. 11B and 17) and $^{F88/C98}$RhuA (FIGS. 11C and 18) were several hundred nm's to 1 μm in size, but typically displayed irregular morphologies. $^{H63/H98}$RhuA lattices were monocrystalline, but tended to grow in 3D over time, whereas $^{F88/C98}$RhuA crystals consisted of poly-crystalline domains.

Figure 60A:
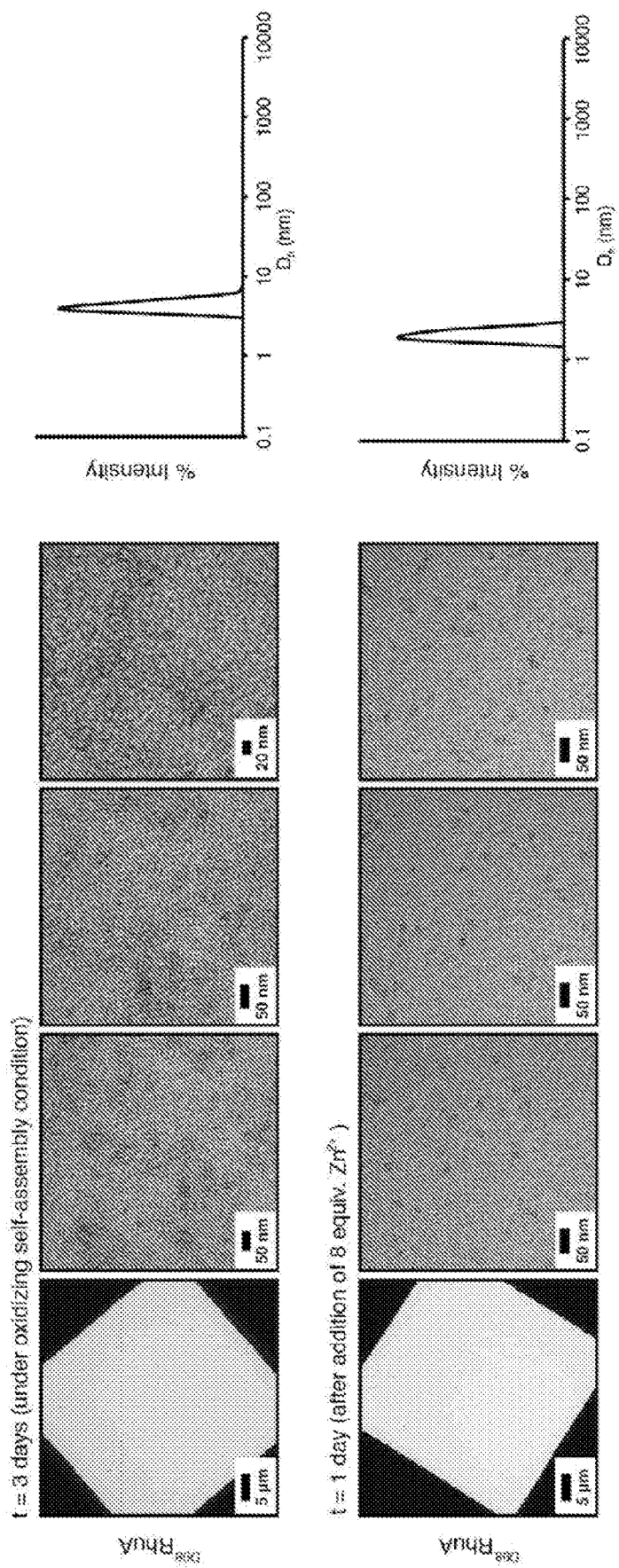
Figure 60B:
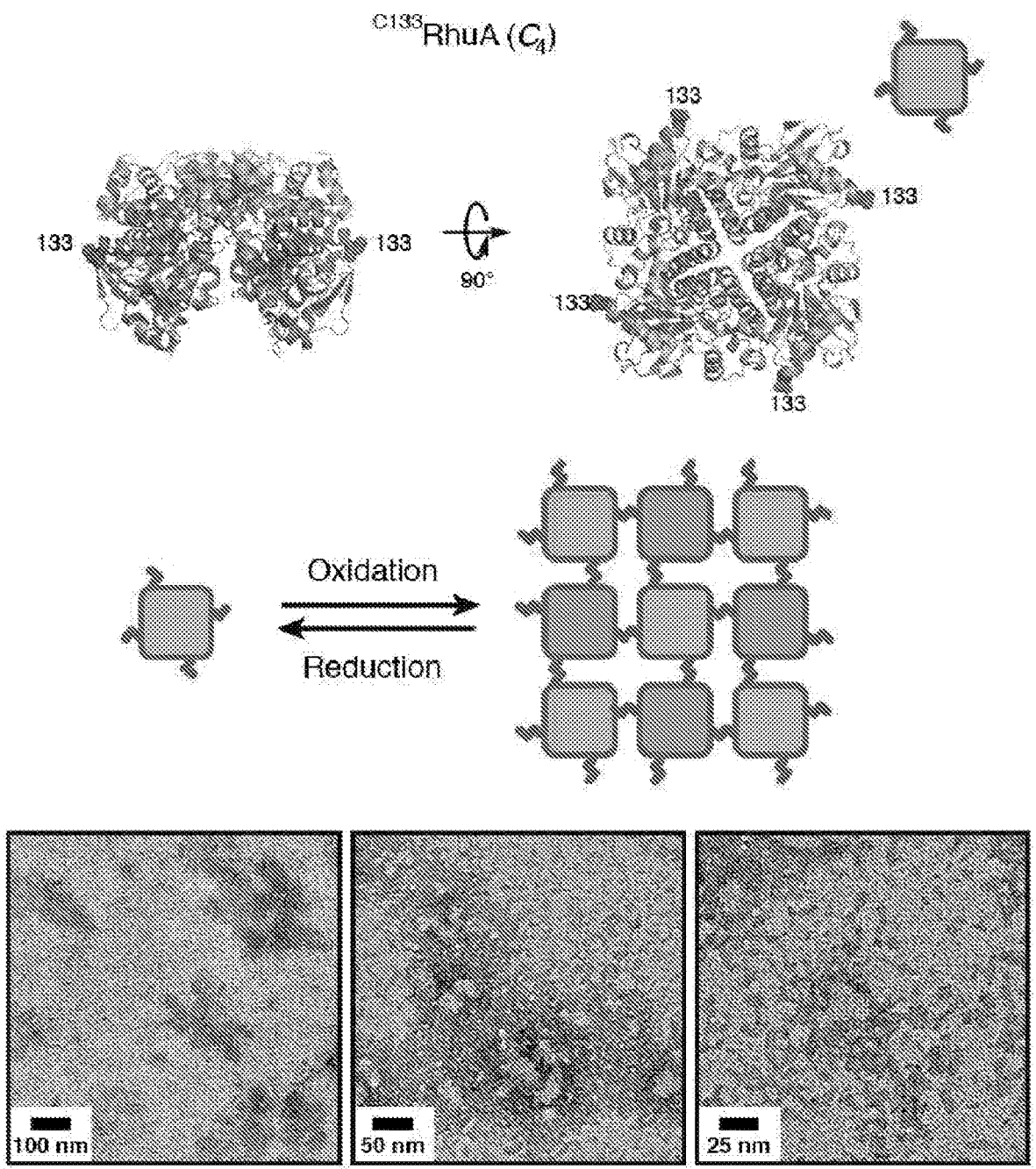
Figure 60C:
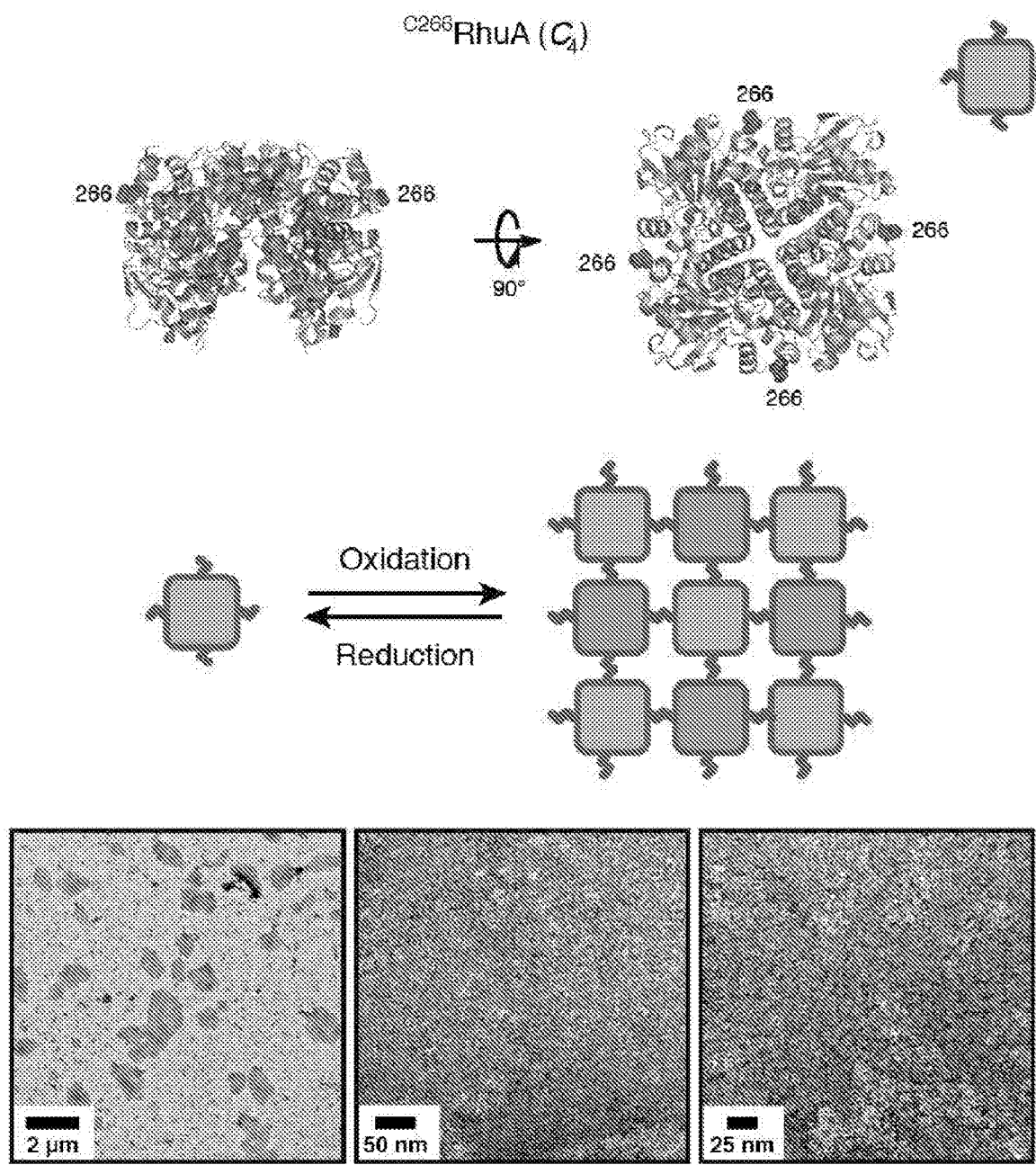

As monitored by TEM and dynamic light scattering (DLS), self-assembly of all variants was reversible, either upon addition of high concentrations of βME (>10 mM) in the case of $^{C98}$RhuA and $^{F88/C98}$RhuA crystals or ethylenediaminetetraacetic acid (EDTA, >10 mM) in the case of $^{H63/H98}$RhuA (FIG. 19). The variant $^{D98}$RhuA, which bears the native D98 residue and is devoid of corner Cys's or the bis-His motifs, was not competent to self-assemble upon oxidation or metal addition (FIG. 60A). These observations confirm the proposed modes of disulfide- or metal-mediated self-assembly. Two additional variants ($^{C133}$RhuA and $^{C266}$RhuA) were prepared with surface cysteines located on the sides of the tetramers (FIGS. 60B and 60C). Theoretically, these variants could be envisioned to self-associate into close-packed 2D square lattices through disulfide linkages. Instead, they both formed non-crystalline aggregates upon oxidation, which was ascribed to the steric crowding around the C133 and C266 positions that precludes the orientation of RhuA molecules for planar self-assembly. These experiments suggest that the placement of Cys residues at sterically isolated, corner locations is preferable for the formation of 2D crystalline arrays.

Figure 61A:
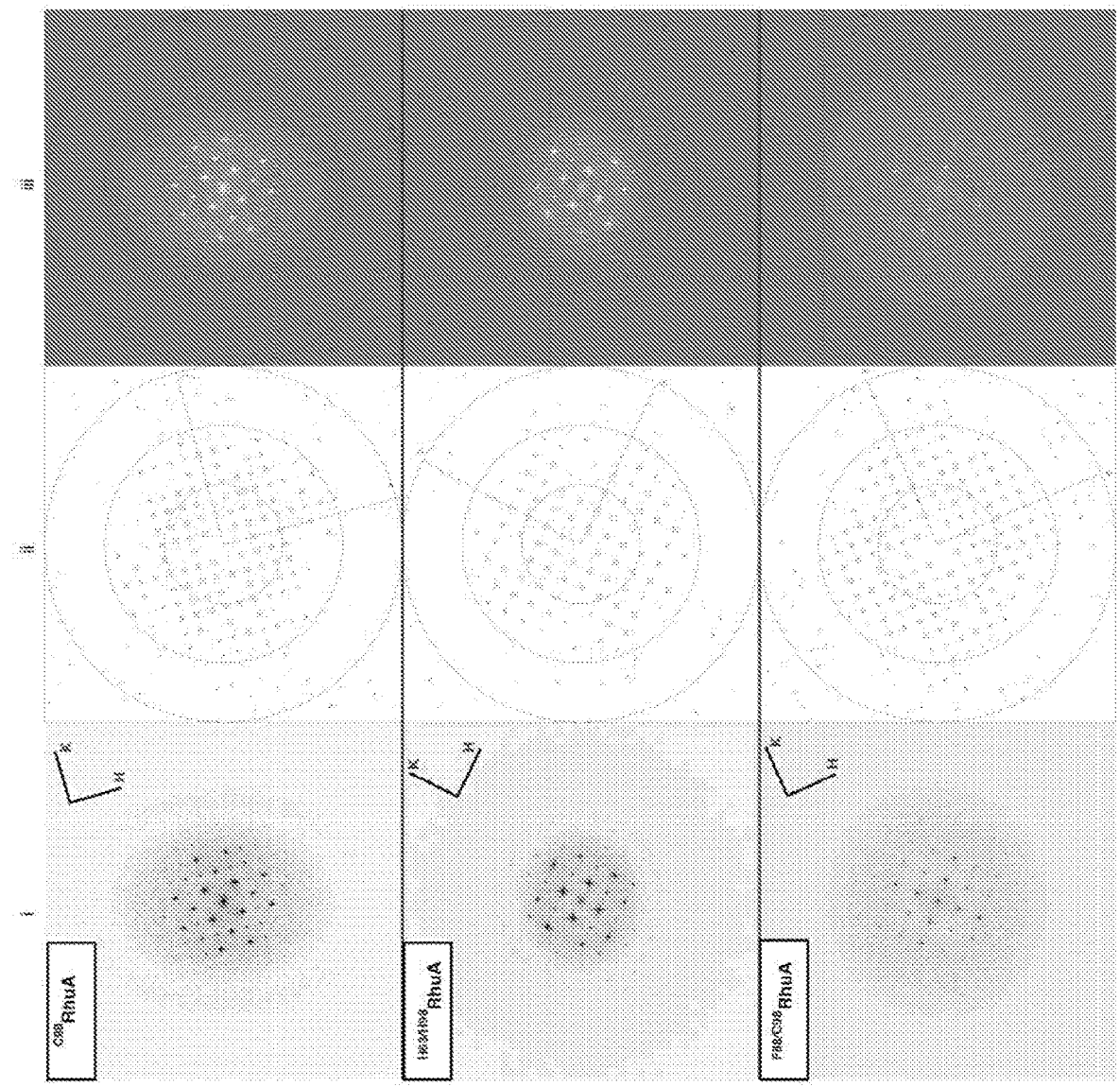
Figures 61B, 61C:
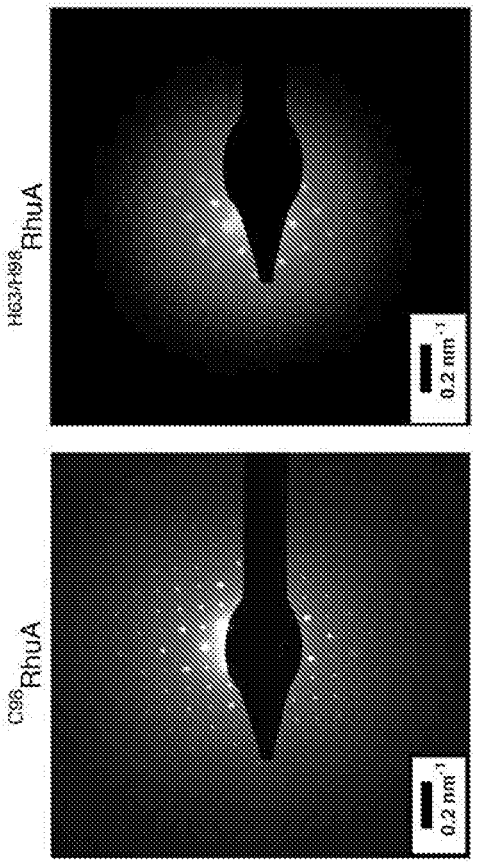

Exhaustive TEM analyses involving many crystals of each variant indicated $p42_12$ plane group symmetry for $^{C98}$RhuA and $^{F88/C98}$RhuA, and p4 symmetry for $^{H63/H98}$RhuA crystals (FIG. 11, FIGS. 61A, 61B, and Table 8). These assignments were corroborated by electron diffraction (ED) data for $^{C98}$RhuA and $^{H63/H98}$RhuA crystals (FIG. 61C). Experimental 2D EM projection maps agree very well with those calculated from structural models (FIG. 20A) and confirm the expected protein-protein interaction geometries: corner-attached $^{C98}$RhuA and $^{H63/H98}$RhuA, and side-attached $^{F88/C98}$RhuA (FIG. 11, columns iv and v). Plane group symmetries suggest that $^{C98}$RhuA tetramers adopt a checkerboard pattern ($p42_12$ symmetry) whereas $^{H63/H98}$RhuA tetramers self-assemble in the same orientation with respect to the 2D plane (p4 symmetry). Together with the fact that $^{F88/C98}$RhuA possesses two-fold symmetry parallel to the 2D plane, thus three distinct 2D molecular patterns with minimal alteration of a single protein building block were obtained (FIG. 20B). It is noteworthy that $^{C98}$RhuA and $^{H63/H98}$RhuA molecules self-assemble in distinct orientations in the 2D plane, suggesting that the energetic bias stemming from disulfide or metal bonding configurations and surrounding protein-protein interactions must be sufficiently large to favor one orientation over others to yield long-range order.

Superior quality and larger sizes of $^{C98}$RhuA crystals compared to $^{F88/C98}$RhuA and $^{H63/H98}$RhuA lattices are readily explained by interactions that direct the self-assembly of the variants. $^{F88/C98}$RhuA presents a roughly circular distribution of eight cysteines (FIG. 10A, bottom row). This arrangement renders the desired double-disulfide-mediated, side-to-side self-assembly mode non-unique and permits alternate attachment geometries between $^{F88/C98}$RhuA molecules (FIG. 18). Moreover, the increased Cys-valency of $^{F88/C98}$RhuA leads to considerably stronger interactions and therefore "stiffer" lattices: in fact, the dissolution of $^{F88/C98}$RhuA polycrystallites requires significantly higher amounts of βME and longer incubation periods compared to $^{C98}$RhuA lattices (FIG. 19). Consequently, $^{F88/C98}$RhuA lattices display vacancies as well as both high- (>30°) and low-angle (<10°) grain boundaries (FIG. 18). $^{H63/H98}$RhuA crystals possess fewer such defects owing to the reversibility of $Zn^{2+}$-coordination interactions. Yet, each $^{H63/H98}$RhuA building block also contains numerous surface residues that can weakly coordinate $Zn^{2+}$ ions, promoting crystal growth in the third dimension (FIG. 17A).

In contrast to $^{F88/C98}$RhuA and $^{H63/H98}$RhuA, self-assembly of $^{C98}$RhuA is both chemically and orientationally specific. Moreover, the reversibility and inherent flexibility of single Cys-Cys linkages—containing five rotatable bonds—likely allows for the correction of any defects such as vacancies and grain boundaries, which would be difficult to accomplish in a rigid lattice composed of strongly interacting building blocks such as $^{F88/C98}$RhuA. Indeed, as TEM images of mono-layered $^{C98}$RhuA crystals illustrate, the outcomes are a) macroscopic crystal morphologies that reflect the molecular symmetry of the building blocks, b) molecularly sharp crystal boundaries, and c) lattices with extremely low defect frequencies. In hundreds of monocrystalline $^{C98}$RhuA lattices with surface areas >1 μm² that were examined closely, a lattice defect was rarely found, despite the fact that these crystals grow in 3D space in an unsupported fashion. Even in a rare instance such as that shown in FIG. 20C, the defect frequency still was one missing $^{C98}$RhuA molecule within a lattice grid of ~9000 molecules (~0.6 μm²).

A more striking consequence of the disulfide bond flexibility is the coherent dynamicity of $^{C98}$RhuA crystals. While the initial sample preparations of $^{C98}$RhuA crystals predominantly yielded open lattices with large pores (FIG. 11A), it was noticed that these crystal suspensions developed a dense sediment over a period of 1-3 days at 4° C. (FIG. 21A). TEM analysis of these sedimented crystals indicated a close-packed lattice arrangement (FIGS. 12A and 12B, right panels). Upon resuspension of the sedimented crystals by repeated gentle mixing with a pipette and subsequent TEM imaging of the resulting samples, a total of at least seven types of 2D $^{C98}$RhuA crystals in distinct conformational states were captured (I through VII) (FIGS. 12A and 21B). These conformational states were categorized by computational image analysis according to the roundness indices of the lattice pores, ranging from ≥0.85 for State I to ≤0.35 for State VII (see Methods). As evidenced by the retention of $p42_12$ symmetry and nearly equal unit cell dimensions, these seven conformational states are clearly interconnected and implicate a continuous lattice motion between fully open and fully closed states. These large amplitude motions of the $^{C98}$RhuA lattices are afforded by a remarkable extent of hinging about the flexible disulfide linkages and their placement at corner locations of RhuA molecules. The transition from the open to the closed state is accompanied by the compression of the inter-$^{C98}$RhuA hinge angle (α) from >80° to 17°, decrease of the pore size from ~4.4 nm to ~1.0 nm (for the passage of a spherical object), and increase in the relative protein/hole surface density of 170% (FIG. 12B, Table 4).

TABLE 4

Structural parameters for conformations II, V and VII of C98RhuA crystals derived from images shown in FIG. 12(A-F).

| | State II | State V | State VII |
|---|---|---|---|
| Unit cell (a = b, γ) | 114.4 Å, 90° | 110 Å, 90° | 107.8 Å, 90° |
| Plane-group symmetry | $p42_12$ | $p42_12$ | $p42_12$ |
| Intertetramer hinge angle, α | 79° | 49° | 17° |
| Protein surface area per unit cell, $A_{protein}$ | 82.7 nm² | 86.2 nm² | 88.0 nm² |
| Pore surface area per unit cell, $A_{pore}$ | 44.7 nm² | 34.7 nm² | 28.2 nm² |
| Relative protein/pore density, $A_{protein}/A_{pore}$ | 1.9 | 2.5 | 3.1 |

Conformational dynamics of $^{C98}$RhuA crystals are fully coherent: in each crystal examined, only one type of conformational state (I-VII) was observed throughout the lattice (FIG. 12B). This observation implies that any mechanical deformation of a $^{C98}$RhuA crystal is cooperatively propagated along the 2D plane, enabled by both the flexibility and short linker-length of single disulfide linkages: longer, more flexible linkages would preclude coherent dynamics, whereas inflexible linkages would lead to non-adaptive lattices. Indeed, $^{F88/C98}$RhuA and $^{H63/H98}$RhuA lattices do not display any apparent dynamic behavior because their double-disulfide- or metal-mediated modes of assembly do not allow rotation of the neighboring protein molecules with respect to one another.

To establish that the conformational dynamics of $^{C98}$RhuA crystals are reversible, the $^{C98}$RhuA crystals were subjected to repeated sedimentation/resuspension cycles within the solutions in which they self-assembled at 4° C. In each cycle, TEM images of >100 individual crystals from the same container were obtained, collected either a) from the sediments that formed overnight, or b) from the suspensions immediately after mixing the sediments by repeated pipetting. As shown in FIG. 12C, the conversion between the closed states (VI and VII) and open/intermediate states (I-V) is completely reversible and absolute. Sedimented samples do not contain any open/intermediate states and resuspended samples do not contain any closed states, providing unambiguous evidence that $^{C98}$RhuA lattices are reversibly dynamic. Based on the observed distribution profiles, the opening of the lattices by mechanical agitation and their distribution among conformational states I-V appear to be immediate (at least within the ~5-min time scale of TEM sample preparation), whereas their full closure takes several hours. It was posited that the energetic barriers between different $^{C98}$RhuA lattice conformations (due to different disulfide bond configurations and long-range protein-protein interactions) must be small enough to be overcome by mechanical agitation and internal protein dynamics. The fully closed conformation (state VII) appears to be a kinetically stable conformation that accumulates over time in unagitated solutions at 4° C. This kinetic stability may be ascribed to the dense protein packing interactions in state VII and the resulting restriction of the dynamics of both the lattice and the individual building blocks.

Figure 12F:
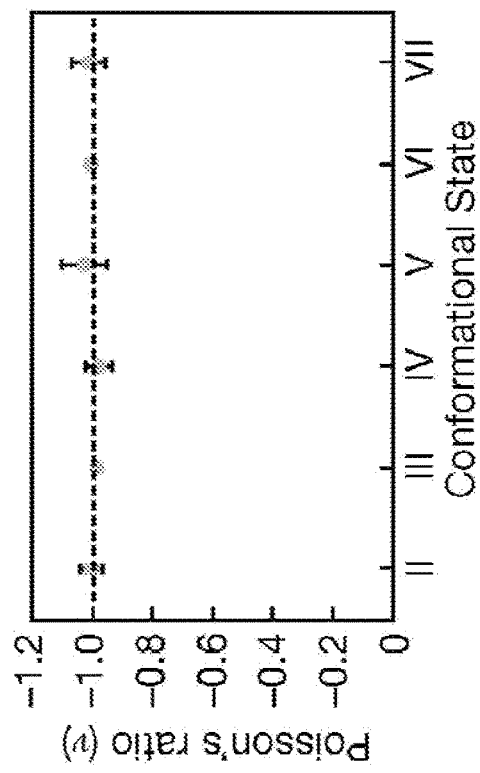
Figure 12E:
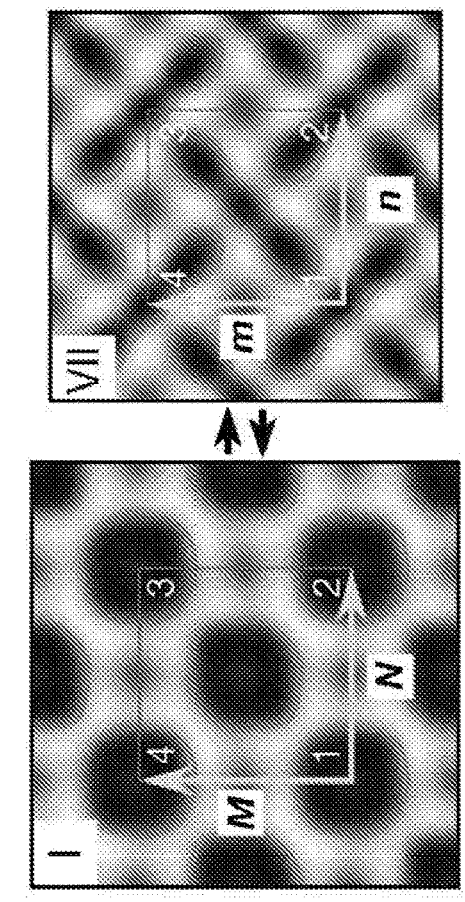
Figure 12G:
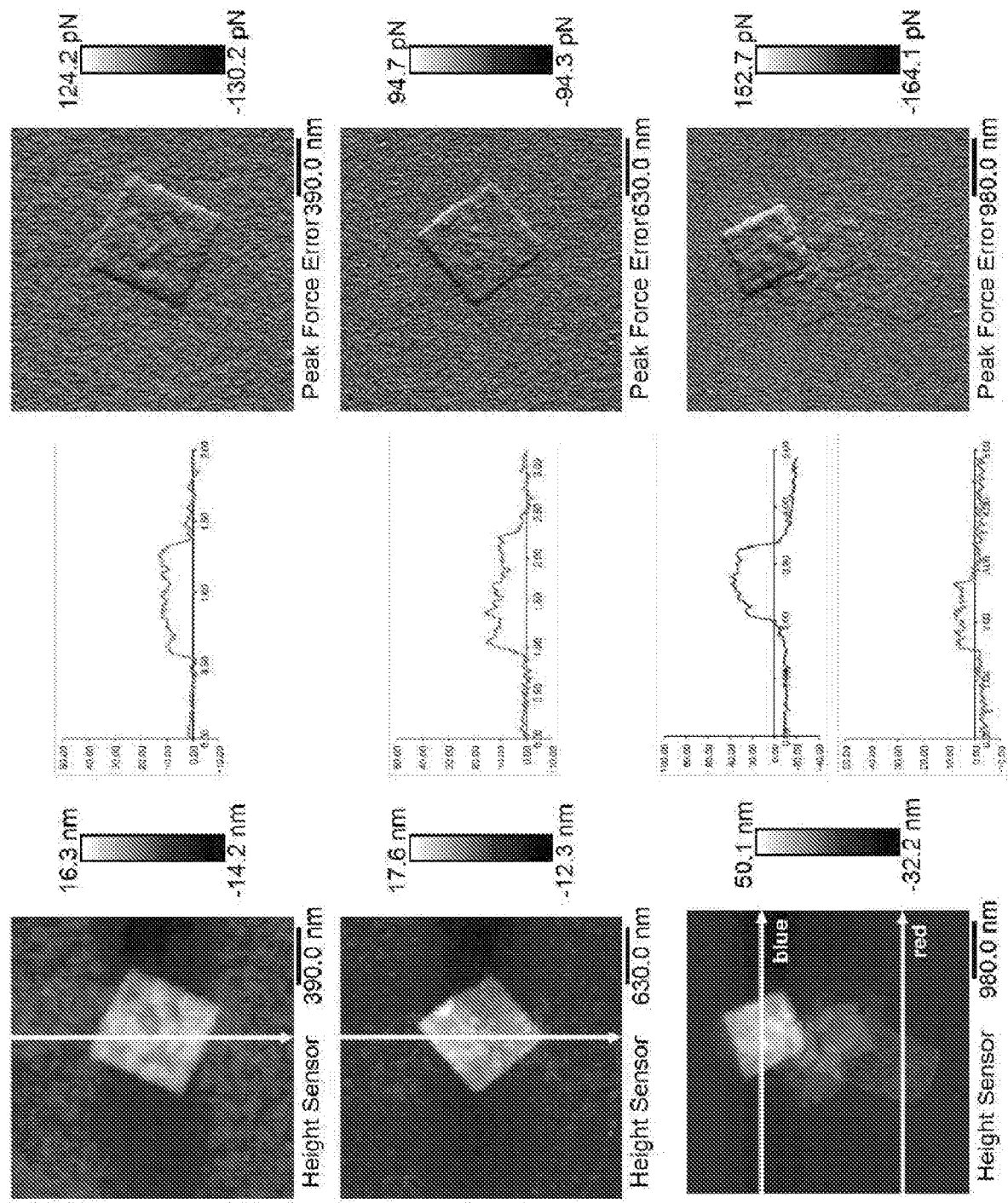
Figure 12H:
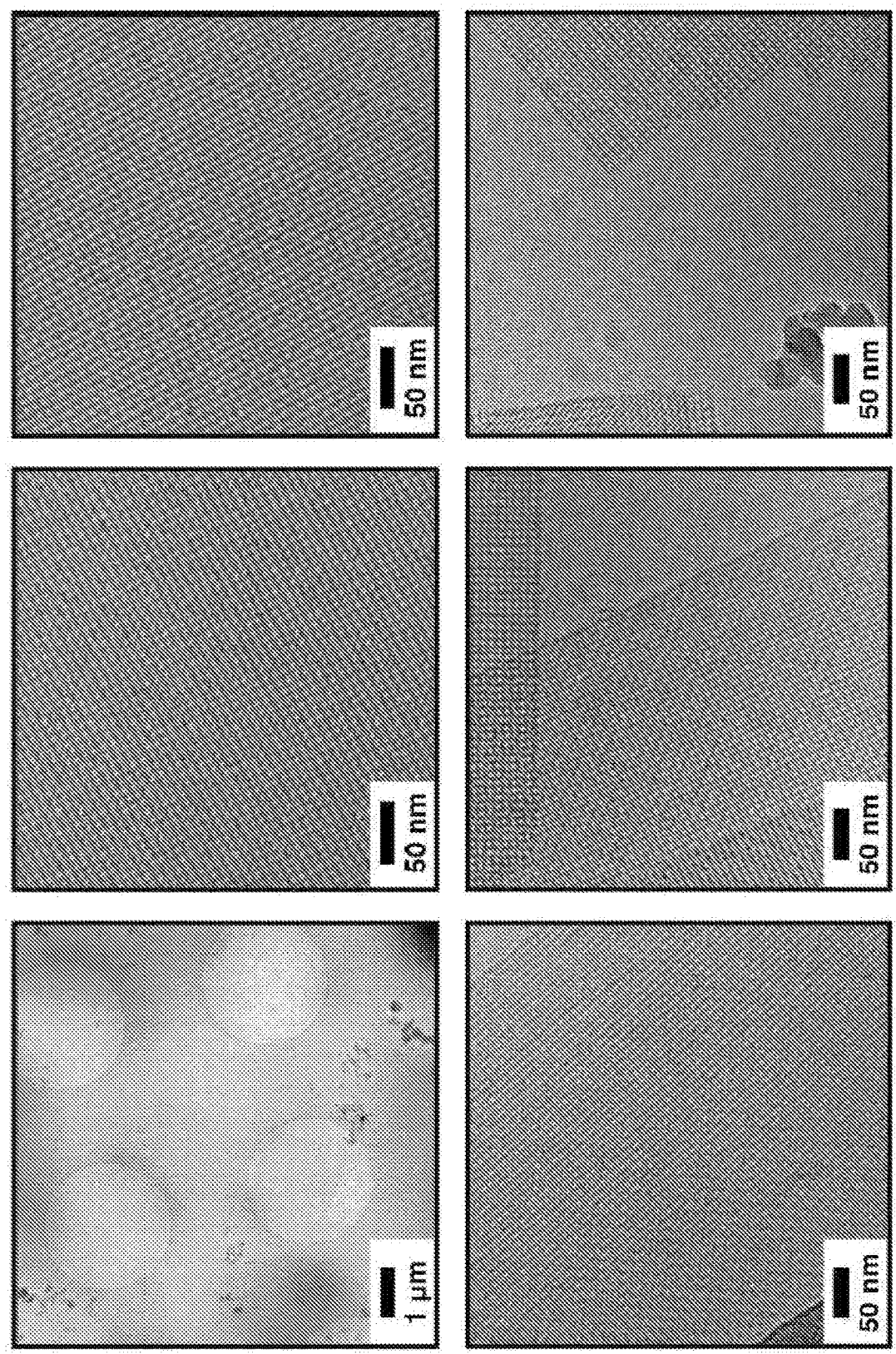
Figure 12I:
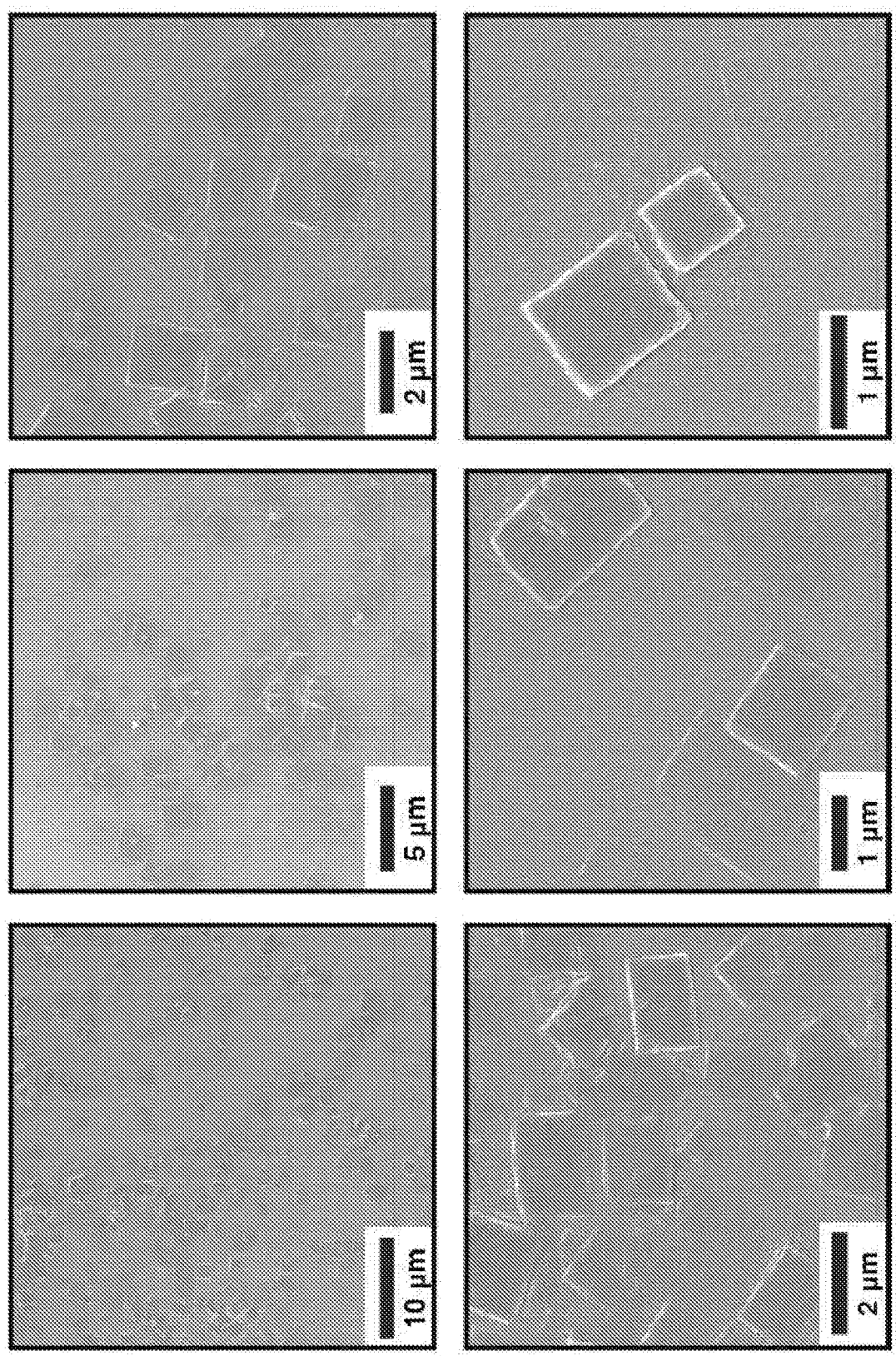
Figure 23A:
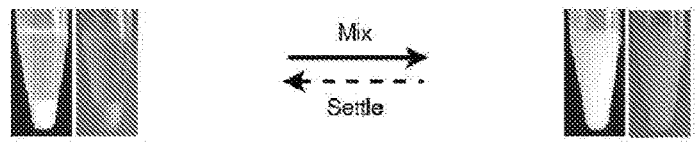
Figure 23C:
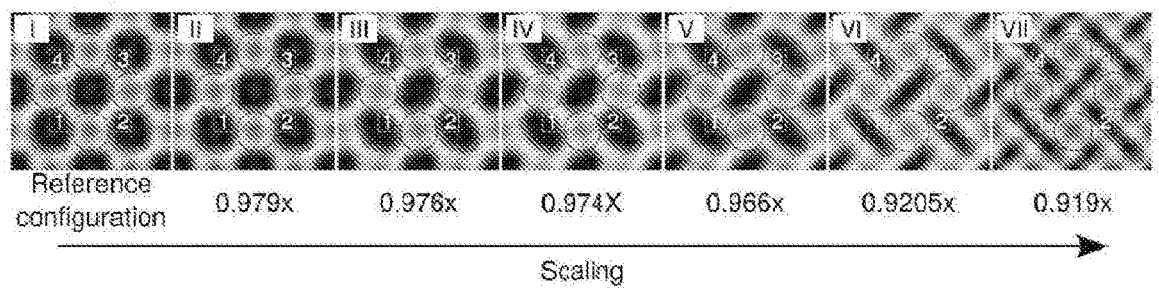
Figure 23D:
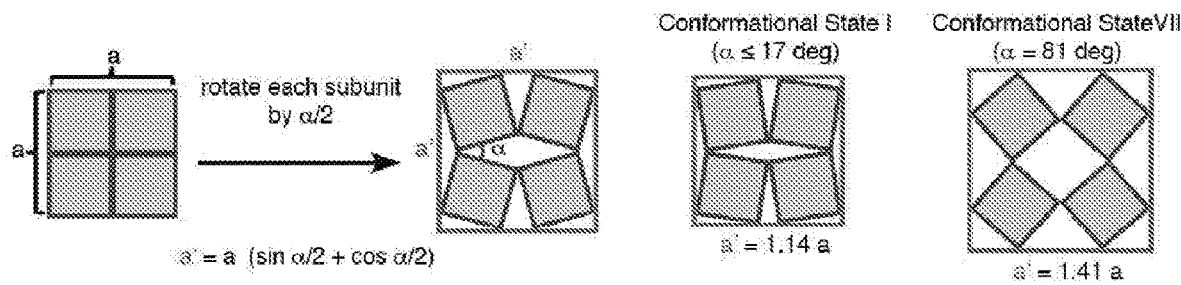
Figure 23B:
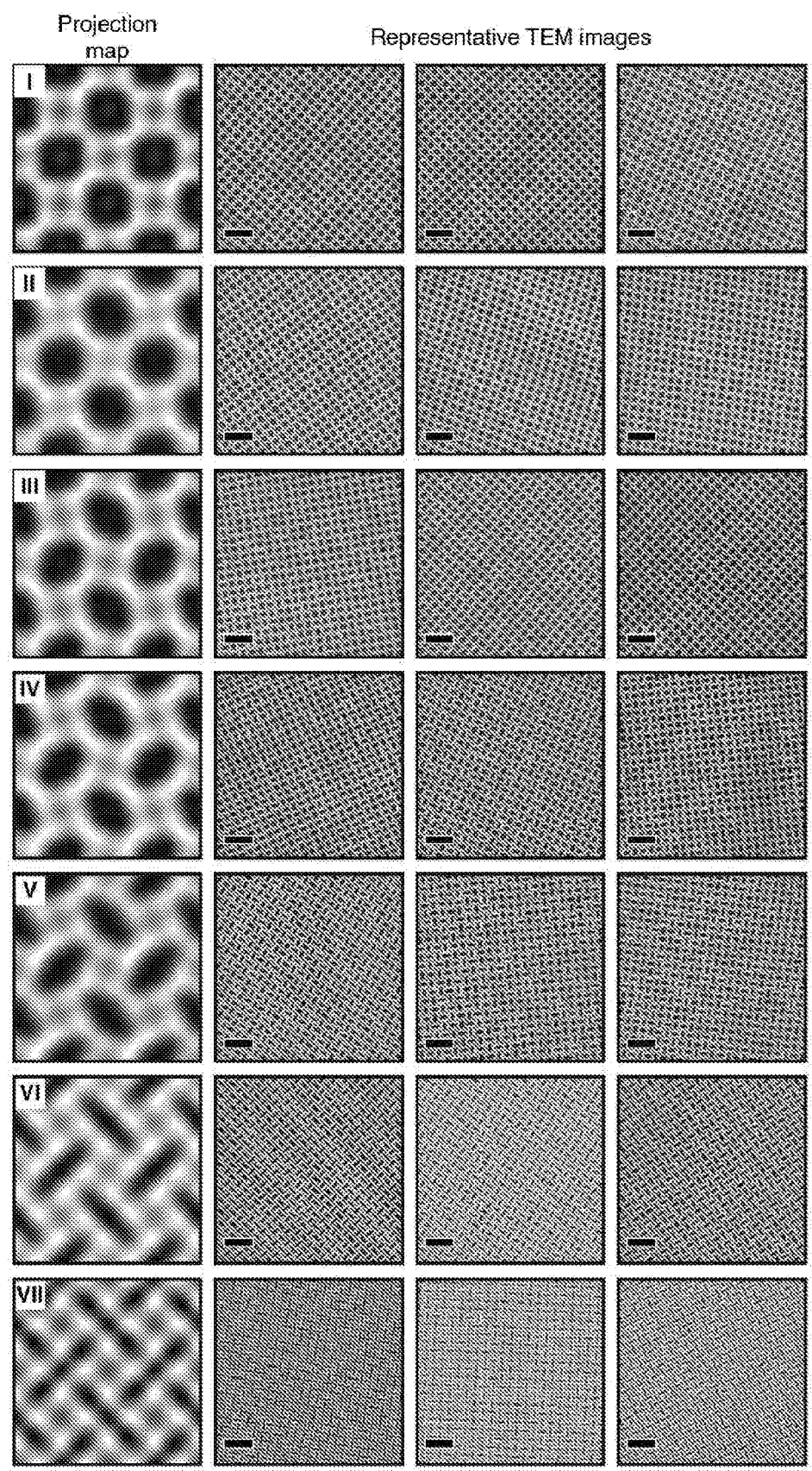

Geometric considerations based on the retention of $p42_12$ symmetry (FIGS. 12B, 12D) as well as a strain analysis of the seven conformational states by digital image correlation (FIGS. 12E and 23C) indicate that $^{C98}$RhuA crystals are auxetic and possess a Poisson's ratio of −1.00±0.01 (FIG. 12F). Poisson's ratio (v) is a scale-independent metric that describes the response of a material to strain; it is defined as the ratio between transverse ($e_x$) and longitudinal strains ($e_y$) under uniaxial loading (Greaves, G. N., Greer, A., Lakes, R. & Rouxel, T. Poisson's ratio and modern materials. *Nat. Mater.* 10, 823-837, (2011)). $e_x$ and $e_y$ are, in turn, approximated by changes in material length in transverse (ΔX) and longitudinal (ΔY) directions (FIG. 12D) (Greaves, G. N., Greer, A., Lakes, R. & Rouxel, T. Poisson's ratio and modern materials. *Nat. Mater.* 10, 823-837, (2011)):

$$v = -\frac{e_y}{e_x} \approx -\frac{\Delta Y}{\Delta X}$$

where −1≤v≤0.5 for an isotropic 3D material and −1≤v≤1 for an isotropic 2D material (Grima, J., Alderson, A. & Evans, K. Auxetic behaviour from rotating rigid units. *Phys. Stat. Sol. b* 242, 561-575, (2005)). Most materials possess positive v's, i.e., they become thinner in the longitudinal direction when stretched transversely (Greaves, G. N., Greer, A., Lakes, R. & Rouxel, T. Poisson's ratio and modern materials. *Nat. Mater.* 10, 823-837, (2011)). Materials with negative v's (i.e., auxetic materials), in contrast, display the counterintuitive behavior of longitudinal expansion upon transverse stretching. Thus, auxetic materials can be expected to possess enhanced toughness, resistance to indentation and shear stiffness as well as favorable damping and acoustic response, and have been proposed for use in protective armors, smart textiles, actuated filtration, piezoelectric and biomedical devices (Greaves, G. N., Greer, A., Lakes, R. & Rouxel, T. Poisson's ratio and modern materials. *Nat. Mater.* 10, 823-837, (2011); Evans, K. E. & Alderson, A. Auxetic materials: functional materials and structures from lateral thinking! *Adv. Mater.* 12, 617-628, (2000); Baughman, R. H. Auxetic materials: Avoiding the shrink. *Nature* 425, 667-667, (2003); Scarpa, F., Ciffo, L. & Yates, J. Dynamic properties of high structural integrity auxetic open cell foam. *Smart Mat. Struct.* 13, 49, (2004)). Although materials with negative v's exist, most fall in the range of −0.4<v<0, with lowest reported values of −0.7 to −0.8 observed in reentrant foams (Lakes, R. Foam structures with a negative Poisson's ratio. *Science* 235, 1038-1040, (1987); Choi, J. B. & Lakes, R. S. Non-linear properties of metallic cellular materials with a negative Poisson's ratio. *J. Mater. Sci.* 27, 5375-5381, (1992)). Grima et al. postulated that for a 2D lattice of rotating rigid squares with flexible hinges, v should be equal to the lowest thermodynamically permissible value of −1 at all rotation angles (Grima, J., Alderson, A. & Evans, K. Auxetic behaviour from rotating rigid units. *Phys. Stat. Sol. b* 242, 561-575, (2005)). $^{C98}$RhuA lattices represent a true realization of this theoretical model and represent the first isotropic material with v=−1 designed and constructed at the molecular scale. Assuming Grima's model, it was calculated that $^{C98}$RhuA crystals should shrink or expand simultaneously in x and y dimensions by at least 24% during the conversion between fully open (state I) and fully closed states (state VII) (FIG. 23D).

It was envisioned that upon hierarchical assembly through physical methods or incorporation into polymeric materials through chemical strategies, molecular architectures like 2D $^{C98}$RhuA lattices may be used as feedstocks for adaptive and auxetic macroscopic materials. In general, in some embodiments described herein, this study underscores the utility of dynamic covalent bonds in the construction of highly ordered yet adaptive protein materials. Specifically, due to their high structural quality and chemically tunable assembly under ambient conditions, $^{C98}$RhuA crystals provide a unique medium for studying molecular self-assembly and crystallization as well as for investigating the energy landscape of lattice dynamics. The resulting understanding of structural dynamics at the nanoscale should greatly aid the fabrication of functional materials.

More Alternatives
Methods

Example 7: Design of RhuA Variants and Site-Directed Mutagenesis

RhuA variants were designed as described in some of the embodiments herein, and were based on previously reported crystal structures (PDB ID: 1GT7[23] for $^{C98}$RhuA, $^{H63/H98}$RhuA, $^{D98}$RhuA, $^{C133}$RhuA, and $^{C266}$RhuA and PDB ID: 2UYU (Grueninger, D. et al. Designed protein-protein association. *Science* 319, 206-209, (2008)) for $^{F88/C98}$RhuA. All RhuA variants also contain the mutations E192A and C126S as previously reported (Ringler, P. & Schulz, G. E. Self-assembly of proteins into designed networks. *Science* 302, 106-109, (2003); Grueninger, D. et al. Designed protein-protein association. *Science* 319, 206-209, (2008)). The gene for $^{C98}$RhuA, pre-inserted into the pJ414 expression vector optimized for expression in *E. coli*, was purchased from DNA2.0. $^{F88/C98}$RhuA, $^{H63/H98}$RhuA, $^{D98}$RhuA, $^{C133}$RhuA, and $^{C266}$RhuA were prepared using QuikChange mutagenesis (Stratagene) with primers obtained from Integrated DNA Technologies (Table 5). The mutant plasmids were transformed into XL-1 Blue *E. coli* cells followed by purification using the QIAprep Spin Miniprep kit (Qiagen). The presence of the mutations was verified by sequencing (Retrogen). Amino acid sequences of RhuA variants are shown in Table 6.

TABLE 5

List of primers used in constructing site-directed mutants of RhuA using $^{C98}$RhuA as a base.

| Variant | Mutation | Primer Sequence |
|---|---|---|
| $^{F88/C98}$RhuA | A88F | 5'-CGCAATGTCCAGTTGGACCCAG CGTTTAACCTGGGCATTGTTAAGGT GG-3' (SEQ ID NO: 6) <br> 5'-CCACCTTAACAATGCCCAGGTT AAACGCTGGGTCCAACTGGACATTG CG-3' (SEQ ID NO: 7) |
| $^{H63/H98}$RhuA | P63H | 5'-CGCTGAGCCAGCCGATGCATCT GTTGGCGAATACCC-3' (SEQ ID NO: 8) |
|  | C98H | 5'-GGGTATTCGCCAACAGATGCAT CGGCTGGCTCAGCG-3' (SEQ ID NO: 9) <br> 5'-GGGCATTGTTAAGGTGGATAGC CATGGTGCAGGTTACCACATCC-3' (SEQ ID NO: 10) <br> 5'-GGATGTGGTAACCTGCACCATG GCTATCCACCTTAACAATGCCC-3' (SEQ ID NO: 11) |
| $^{D98}$RhuA | C98D | 5'-GCATTGTTAAGGTGGATAGCGA CGGTGCAGGTTACCACATCC-3' (SEQ ID NO: 13) <br> 5'-GGATGTGGTAACCTGCACCGTC GCTATCCACCTTAACAATGC-3' (SEQ ID NO: 14) |

TABLE 5-continued

List of primers used in constructing site-directed mutants of RhuA using $^{C98}$RhuA as a base.

| Variant | Mutation | Primer Sequence |
| --- | --- | --- |
| $^{C133}$RhuA | N133C | 5'-GCGAGCGTATCAAGGCGACCTG CGGCAAAGACCGCG-3' (SEQ ID NO: 15) 5'-CGCGGTCTTTGCCGCAGGTCGC CTTGATACGCTCGC-3' (SEQ ID NO: 16) |
| $^{C266}$RhuA | T266C | 5'-GGTAAGCGTTTTGGTGTCTGTC CGCTGGCGTCCGCGCTGG-3' (SEQ ID NO: 17) 5'-CCAGCGCGGACGCCAGCGGACA GACACCAAAACGCTTACC-3' (SEQ ID NO: 18) |

TABLE 6

Amino acid sequences of RhuA variants.

| Variant | Amino Acid Sequence |
| --- | --- |
| $^{C98}$RhuA | MQNITQSWFVQGMIKATTDAWLKGWDERNGGNLTLRLDDADIAPYHDNFHQQPRYIPLSQ PMPLLANTPFIVTGSGKFFRNVQLDPAANLGIVKVDSCGAGYHILWGLTNEAVPTSELPA HFLSHSERIKATNGKDRVIMHCHATNLIALTYVLENDTAVFIRQLWEGSTECLVVFPDGV GILPWMVPGTDAIGQATAQEMQKHSLVLWPFHGVFGSGPTLDETFGLIDTAEKSAQVLVK VYSMGGMKQTISREELIALGKRFGVTPLASALAL (SEQ ID NO: 3) |
| $^{H63/H98}$RhuA | MQNITQSWFVQGMIKATTDAWLKGWDERNGGNLTLRLDDADIAPYHDNFHQQPRYIPLSQ PMHLLANTPFIVTGSGKFFRNVQLDPAANLGIVKVDSHGAGYHILWGLINEAVPTSELPA HFLSHSERIKATNGKDRVIMHCHATNLIALTYVLENDTAVFTRQLWEGSTECLVVFPDGV GILPWMVPGTDAIGQATAQEMQKHSLVLWPFHGVFGSGPTLDETFGLIDTAEKSAQVLVK VYSMGGMKQTISREELIALGKRFGVTPLASALAL (SEQ ID NO: 4) |
| $^{F88/C98}$RhuA | MQNITQSWFVQGMIKATTDAWLKGWDERNGGNLTLRLDDADIAPYHDNFHQQPRYIPLSQ PMPLLANTPFIVTGSGKFFRNVQLDPAFNLGIVKVDSCGAGYHILWGLTNEAVPTSELPA HFLSHSERIKATNGKDRVIMHCHATNLIALTYVLENDTAVFTRQLWEGSTECLVVFPDGV GILPWMVPGTDAIGQATAQEMQKHSLVLWPFHGVFGSGPTLDETFGLIDTAEKSAQVLVK VYSMGGMKQTISREELIALGKRFGVTPLASALAL (SEQ ID NO: 5) |
| $^{D98}$RhuA | MQNITQSWFVQGMIKATTDAWLKGWDERNGGNLTLRLDDADIAPYHDNFHQQPRYIPLSQ PMPLLANTPFIVTGSGKFFRNVQLDPAANLGIVKVDSDGAGYHILWGLTNEAVPTSELPA HFLSHSERIKATNGKDRVIMHCHATNLIALTYVLENDTAVFTRQLWEGSTECLVVFPDGV GILPWMVPGTDAIGQATAQEMQKHSLVLWPFHGVFGSGPTLDETFGLIDTAEKSAQVLVK VYSMGGMKQTISREELIALGKRFGVTPLASALAL (SEQ ID NO: 19) |
| $^{C133}$RhuA | MQNITQSWFVQGMIKATTDAWLKGWDERNGGNLTLRLDDADIAPYHDNFHQQPRYIPLSQ PMPLLANTPFIVTGSGKFFRNVQLDPAANLGIVKVDSDGAGYHILWGLTNEAVPTSELPA HFLSHSERIKATCGKDRVIMHCHATNLIALTYVLENDTAVFTRQLWEGSTECLVVFPDGV GILPWMVPGTDAIGQATAQEMQKHSLVLWPFHGVFGSGPTLDETFGLIDTAEKSAQVLVK VYSMGGMKQTISREELIALGKRFGVTPLASALAL (SEQ ID NO: 20) |
| $^{C266}$RhuA | MQNITQSWFVQGMIKATTDAWLKGWDERNGGNLTLRLDDADIAPYHDNFHQQPRYIPLSQ PMPLLANTPFIVTGSGKFFRNVQLDPAANLGIVKVDSDGAGYHILWGLTNEAVPTSELPA HFLSHSERIKATNGKDRVIMHCHATNLIALTYVLENDTAVFIRQLWEGSTECLVVFPDGV GILPWMVPGTDAIGQATAQEMQKHSLVLWPFHGVFGSGPTLDETFGLIDTAEKSAQVLVK VYSMGGMKQTISREELIALGKRFGVCPLASALAL (SEQ ID NO: 21) |

Point mutation positions are underlined.

Example 8 Protein Expression and Purification

Bacterial expression of RhuA variants was performed according to previously published procedures with slight modifications (Kroemer, M. & Schulz, G. E. The structure of L-rhamnulose-1-phosphate aldolase (class II) solved by low-resolution SIR phasing and 20-fold NCS averaging. *Acta Cryst. D.* 58, 824-832, (2002)). Plasmids bearing the variants were transformed into BL21(DE3) *E. coli* cells, and the colonies were grown overnight at 37° C. on lysogeny broth (LB) agar plates (pH 7.4) containing 100 mg/L ampicillin. Starter cultures (5 mL with 100 mg/L ampicillin) from single colonies were grown for ~4-6 h at 37° C. (with shaking at 250 rpm) before inoculation into 1-L LB cultures containing 100 mg/L ampicillin. After the cells were grown to an optical density of ~0.8 at 600 nm, protein expression was induced with 1 mM isopropyl β-D-1-thiogalactopyranoside (IPTG, Gold Biotechnology) for 12-13 h (at 37° C. with shaking at 250 rpm). Cells were pelleted by centrifugation (5,000 rpm at 4° C. for 10 min), and resuspended in a buffer solution containing 10 mM Tris(hydroxymethyl) aminomethane hydrochloride (TRIS) (pH 7.5), 1 mM $ZnCl_2$, and 10 mM β-mercaptoethanol (βME). For $^{H63/H98}$RhuA preparations, $ZnCl_2$ was excluded from buffer solutions to avoid possible protein precipitation during purification. Cell lysis was performed by sonication for 15 min on ice. The lysis solution was centrifuged for 30 min at 12,000 rpm at 4° C. Polymin-P (Acros) was added to the supernatant at a final concentration of 0.15% (w/v) for nucleic acid precipitation and the resulting mixture was stirred for 30 min prior to centrifugation for 30 min at 12,000 rpm at 4° C. The supernatant was loaded onto a DEAE-Sepharose CL-6B (GE Healthcare) column and eluted using a gradient of 0-500 mM NaCl in Tris buffer at 4° C. Fractions containing RhuA which eluted at ~200 mM NaCl were added 1.7 M ammonium sulfate, and were centrifuged for 45 min at 12,000 rpm at 4° C. The precipitate was dissolved in a buffer solution containing 5 mM sodium phosphate (NaPi) (pH 7.2), 1 mM $ZnCl_2$, and 10 mM βME, and then dialyzed three times against 5 L of the same buffer solution. Further purification was done using either a High Q cartridge column (BioRad)

(at pH 8.0) using a 0-500 mM NaCl gradient or a Mini CHT Type I hydroxyapatite column (BioRad) (at pH 7.2) using a 5-500 mM NaPi gradient on a DuoFlow fast protein chromatography workstation (Bio-Rad). Pure protein fractions eluted at 350 mM NaCl and 200 mM NaPi, respectively. These fractions were combined, dialyzed three times against a buffer solution of 10 mM TRIS (pH 7.5), 1 mM $ZnCl_2$, and 10 mM β-mercaptoethanol (βME), and concentrated in an Amicon stirred cell at 4° C. The protein was then flash frozen and kept at −80° C. until use. Protein purity was confirmed by SDS PAGE (FIG. 13) and ESI-MS (FIG. 14 and Table 7), and stock concentrations were determined as previously reported (Edelhoch, H. Spectroscopic determination of tryptophan and tyrosine in proteins. *Biochemistry* 6, 1948-1954, (1967)).

TABLE 7

Molecular masses of RhuA mutants. For the actual mass spectra, refer to FIG. 14.

| Variant | Calculated Mass (Da) | Observed Mass (Da) |
|---|---|---|
| $^{C98}$RhuA | 30059.5 | 30060.0 |
| $^{F88/C98}$RhuA | 30135.6 | 30136.0 |
| $^{H63/H98}$RhuA | 30133.5 | 30134.0 |
| $^{D98}$RhuA | 30071.4 | 30075.0 |
| $^{C133}$RhuA | 30060.4 | 30061.0 |
| $^{C266}$RhuA | 30073.4 | 30073.0 |

TABLE 8

Symmetry analysis for the 2D lattices of RhuA variants. Internal phase residuals for all possible non-hexagonal plane groups. Residuals were determined from the power spectra shown in FIG. 23A using the program ALLSPACE, as described in Methods. Reflections up to 11 Å and with IQ less than 6 were included in the calculations.

| 2D plane group | Phase Residual[a] (°) | Number of comparisons | Target Residual[b] (°) |
|---|---|---|---|
| a, $^{C98}$RhuA | | | |
| p1 | 22.4[c] | 126 | |
| p2 | 29.6* | 63 | 32.5 |
| p12_b | 74.6 | 45 | 23.1 |
| p12_a | 73.8 | 45 | 23.1 |
| p12$_1$_b | 18.1* | 45 | 23.1 |
| p12$_1$_a | 12.8* | 45 | 23.1 |
| c12_b | 74.6 | 45 | 23.1 |
| c12_a | 73.8 | 45 | 23.1 |
| p222 | 56.1 | 153 | 26.6 |
| p222$_1$_b | 54.2 | 153 | 26.6 |
| p222$_1$_a | 56.6 | 153 | 26.6 |
| p22$_1$2$_1$ | 21.6* | 153 | 26.6 |
| c222 | 56.1 | 153 | 26.6 |
| p4 | 26.7* | 155 | 26.5 |
| p422 | 52.6 | 333 | 24.3 |
| p42$_1$2 | 24.4* | 333 | 24.3 |
| b, $^{H63/H98}$RhuA | | | |
| p1 | 21.8[c] | 96 | |
| p2 | 29.4* | 48 | 31.6 |
| p12_b | 44.7 | 28 | 23.2 |
| p12_a | 46.0 | 31 | 24.0 |
| p12$_1$_b | 73.0 | 28 | 23.2 |
| p12$_1$_a | 79.5 | 31 | 24.0 |
| c12_b | 44.7 | 28 | 23.2 |
| c12_a | 46.0 | 31 | 24.0 |
| p222 | 38.5 | 107 | 26.2 |
| p222$_1$_b | 64.7 | 107 | 26.2 |
| p222$_1$_a | 70.9 | 107 | 26.2 |
| p22$_1$2$_1$ | 62.6 | 107 | 26.2 |
| c222 | 38.5 | 107 | 26.2 |
| p4 | 23.1* | 112 | 26.0 |
| p422 | 31.9[§] | 231 | 23.8 |

TABLE 8-continued

Symmetry analysis for the 2D lattices of RhuA variants. Internal phase residuals for all possible non-hexagonal plane groups. Residuals were determined from the power spectra shown in FIG. 23A using the program ALLSPACE, as described in Methods. Reflections up to 11 Å and with IQ less than 6 were included in the calculations.

| 2D plane group | Phase Residual[a] (°) | Number of comparisons | Target Residual[b] (°) |
|---|---|---|---|
| p42$_1$2 | 62.1 | 231 | 23.8 |
| c, $^{F88/C98}$RhuA | | | |
| p1 | 26.8[c] | 160 | |
| p2 | 26.4* | 80 | 39.3 |
| p12_b | 71.2 | 54 | 27.7 |
| p12_a | 70.4 | 56 | 28.1 |
| p12$_1$_b | 14.1* | 54 | 27.7 |
| p12$_1$_a | 13.1* | 56 | 28.1 |
| c12_b | 71.2 | 54 | 27.7 |
| c12_a | 70.4 | 56 | 28.1 |
| p222 | 52.1 | 190 | 32.1 |
| p222$_1$_b | 56.9 | 190 | 32.1 |
| p222$_1$_a | 58.3 | 190 | 32.1 |
| p22$_1$2$_1$ | 19.3* | 190 | 32.1 |
| c222 | 52.1 | 190 | 32.1 |
| p4 | 17.3* | 204 | 31.7 |
| p422 | 45.7 | 431 | 29.1 |
| p42$_1$2 | 16.0* | 431 | 29.1 |

[a]Phase residual versus other spots (90° = random).
[b]Expected residual based on the quality of the reflections involved in the calculation.
[c]Theoretical, based on the quality of the reflections observed
*acceptable (better than target or within 1°)
[†] to be considered (within 5° from target)
[§]possibility (within 10° from target)

Example 9: Preparation of 2D RhuA Crystals

All 2D RhuA crystals reported herein were obtained in an unsupported fashion in solutions. As described in the in several embodiments herein, several solution conditions were screened for optimizing the formation of 2D protein crystals of $^{C98}$RhuA, $^{F88/C98}$RhuA and $^{H63/H98}$RhuA variants. For all variants, these screening conditions included various pH's (6 to 8), starting protein concentrations (25 to 175 μM), buffer salt concentration and identity (5-20 mM bis-TRIS, CHES, MES, MOPS, NaPi, and TRIS), and temperature (4-37° C.). For the disulfide-mediated self-assembly of $^{C98}$RhuA and $^{F88/C98}$RhuA, various oxidizing conditions (1-2 mM total GSH/GSSG at ratios varying from 1:19 to 19:1, or 5-10 mM βME, which slowly decomposed in aqueous solution in the presence of metal ions) were additionally screened. For the metal-mediated assembly of $^{H63/H98}$RhuA, 4-20 molar equivalents (over tetrameric protein concentration) of $ZnCl_2$ and $CuCl_2$ were screened. As stated previously, the best conditions were: $^{C98}$RhuA and $^{F88/C98}$RhuA (≥125 μM protein, 10 mM βME, pH 7.5, 10 mM TRIS); $^{H63/H98}$RhuA (25 μM protein, 200 μM $ZnCl_2$, pH 7, 20 mM MOPS) at 4° C. In general, the formation of crystals was either immediate (upon metal addition for $^{H63/H98}$RhuA) or lasted overnight to several days (for $^{C98}$RhuA and $^{F88/C98}$RhuA). Crystal formation resulted in increasing cloudiness of the self-assembly solutions. The growth of $^{C98}$RhuA crystals could be accelerated by gentle shaking (Figures=11A, 11B). In additional experiments, the thermo- and chemo-stability of $^{C98}$RhuA crystals as shown in FIG. 62 were tested.

Example 10: Electron Microscopy

For negative-stain TEM sample preparation, 3-3.5 μL aliquots of crystal suspensions were applied onto negatively glow-discharged carbon-coated Cu grids (Ted Pella, Inc.), washed with Milli-Q water, and stained with 1% uranyl acetate at 4° C. For cryo-EM sample preparation, 3-3.5 µl aliquots of 25 $^{C98}$RhuA sample (diluted sample) were deposited onto negatively glow-discharged Quantifoil grids, and then plunged into liquid ethane after blotting. The sample was then stored under liquid nitrogen until analysis. Sample screening was performed in an FEI Sphera transmission electron microscope equipped with a LaB6 electron gun at 200 keV and imaged on Gatan $2K^2$ CCD. A complete electron crystallographic analysis was done on 43, 50 and 33 micrographs for $^{C98}$RhuA, $^{H63/H98}$RhuA and $^{F88/C98}$RhuA respectively, which were selected by visual assessment. Micrographs were each processed separately using the 2dx software[33], which implements a semi-automatic processing pipeline mostly based on programs from the MRC suite (Crowther, R., Henderson, R. & Smith, J. MRC image processing programs. *J. Struct. Biol.* 116, 9-16, (1996)). The program allows one to determine the 2D plane group lattice symmetry of each crystal, to calculate its unit cell dimensions and to generate a projection density map. The processing involves estimation of the Contrast Transfer Function (CTF) by CTFFIND3 (Mindell, J. A. & Grigorieff, N. Accurate determination of local defocus and specimen tilt in electron microscopy. *J. Struct. Biol.* 142, 334-347, (2003)), spot-list determination, automatic lattice determination, crystal masking, unbending and generation of projection map after CTF correction. Within this program, the symmetry plane group is determined using ALLSPACE (Valpuesta, J. M. a., Carrascosa, J. L. & Henderson, R. Analysis of electron microscope images and electron diffraction patterns of thin crystals of Ø29 connectors in ice. *J. Mol. Biol.* 240, 281-287, (1994)) by comparing the internal phase residual for each symmetry to its expected value. Lattice unit cell dimensions were determined on a subset of images, screened by the quality of the reflections, of 12, 44 and 13 for $^{C98}$RhuA, $^{H63/H98}$RhuA and $^{F88/C98}$RhuA, respectively. The estimated resolution limit of each image (between 15 and 30 Å) was assessed both by visual inspection of its computed Fourier transform and by comparison with simulated images filtered at different levels of resolution.

Example 11: AFM Measurements

For AFM sample preparation, 2 µL of crystal suspensions were applied on freshly cleaved mica, washed with deionized water and dried. AFM images were collected using a Dimension Icon microscope (Bruker, USA) using Scan Asyst peak force tapping (in air) mode at a resolution of 512 lines per image and a scan rate of 0.3-0.5 Hz. AFM images obtained were processed using Nanoscope Analysis (Bruker, USA).

Example 12: SEM Measurements

For SEM sample preparation, 2 µL of crystal suspensions were applied onto $SiO_2$ substrates. Sample was sputter-coated with iridium oxide before analysis to reduce charging effects. SEM micrographs were collected on an FEIXL 30UHR scanning electron microscope operated at 5 keV.

Example 13: DLS Measurements

DLS experiments were performed using Wyatt DynaPro NanoStar instrument. The experiment runs were performed to collect 10 acquisitions with 657 nm excitation at a power setting of 100%. Measurements were plotted using a Rayleigh sphere model. Peak radius cutoffs were fixed according to default settings (0.5-10000 nm).

Example 14: Structural Modelling and Simulations

Projected electron density maps were used as a reference in the visualization software UCSF Chimera (Pettersen, E. F. et al. UCSF Chimera—a visualization system for exploratory research and analysis. *J. Comput. Chem.* 25, 1605-1612, (2004)) to determine the orientation of the RhuA molecules in each crystal. The atomic coordinates were extracted from the PDB entries 1GT7 ($C_4$-symmetric tetramer for $^{C98}$RhuA and $^{H63/H98}$RhuA) and 2UYU ($D_4$-symmetric octamer for $^{F88/C98}$RhuA) and placed manually to fit the position of one subunit in the observed projected density map. The orientation of the molecule was refined in an iterative manner by comparing the experimental density with the density simulated from a model of the unit cell, obtained as explained below. Simulated projected electron density maps were computed using Bsoft (lsbr.niams.nih.gov/bsoft) (Heymann, J. B. Bsoft: image and molecular processing in electron microscopy. *J. Struct. Biol.* 133, 156-169, (2001)) and EMAN2 (blake.bcm.edu/emanwiki/EMAN2) (Tang, G. et al. EMAN2: an extensible image processing suite for electron microscopy. *J. Struct. Biol.* 157, 38-46, (2007)). Software for calculating projected electron density maps are readily available and are known to those skilled in the art. Starting from the estimated position and orientation of a single subunit, multiple copies of the model were generated to cover one unit cell (bmoledit in Bsoft) and converted to electron density (e2pdb2mrc.py in EMAN2) with a resolution limit of 30 Å. Finally, the density volume was projected along the vertical direction (bproject in Bsoft) to generate a 2D density map comparable to the experimental map.

Example 15: Classification of the Conformational States of 2D $^{C98}$RhuA Crystals TEM micrographs of $^{C98}$RhuA crystals were analyzed computationally to categorize different conformational states of the 2D lattice. Essentially, for each raw image a roundness index number derived from the shape of the pores in the lattice was determined, and used this value to classify the images. The analysis was performed on 982 images using an ad hoc algorithm coded as a macro in Fiji (fiji.sc/Fiji) (Schindelin, J. et al. Fiji: an open-source platform for biological-image analysis. *Nat. Meth.* 9, 676-682, (2012)) and ImageJ (imagej.nih.gov/ij) (Schneider, C. A., Rasband, W. S. & Eliceiri, K. W. NIH Image to ImageJ: 25 years of image analysis. *Nat. Methods* 9, 671-675, (2012)). Each image was initially processed by applying a 3×3 mean filter applied three times and then converted to a binary image after automatic thresholding to segment out the pores. The mask was then filtered using the opening morphological operator to smooth the shape of the pores and to remove small outliers. Pores that were distorted from potential bending of the crystal in some regions of the field of view were discarded using their size for screening. For images acquired at nominal magnifications of ×50,000 and ×68,000 (calibrated pixel size=2.033 Å and 1.646 Å, respectively), only pores with areas that covered 500-1200 pixels were kept. The remaining pores were modeled as ellipses and their roundness index was determined as the ratio between the lengths of the major and the minor elliptical axes. A single index value was assigned to each micrograph as the average from all the segmented pores. The images were assigned to one of the seven identified states using the following criterion: State I: >0.85; State II: >0.75-0.85; State III: >0.65-0.75; State IV: >0.55-0.65; State V: >0.35-0.45; State VI: >0.35-0.45; State VII<0.35.

Example 16: Generation of Video Simulating the Lattice Motions

A video (Supplementary Video 1) to illustrate the dynamics of 2D $^{C98}$RhuA crystals was generated starting from the TEM snapshots of the seven conformational states (I-VII) (FIG. 12A). All projected density images were rescaled to include the same field of view (bint and bimg from Bsoft). Twenty four intermediate image frames were created between each pair in the sequence by pseudo-morphing, using the program convert from the software suite ImageMagick®. Finally, the video was generated with ffmpeg (www.ffmpeg.org) by combining the images as frames.

Example 17: Digital Image Correlation for Poisson's Value Determination

Using Matlab, digital image processing of the reconstructed 2D TEM images of dynamic $^{C98}$RhuA crystals for evaluating Poisson's ratios was performed. As a first step, histogram normalization was performed taking as a reference the image of conformational state I in order to normalize the intensity of the images (FIG. 23C). This normalization guarantees that the thresholds used for pixel selection have the same meaning through all the images. After normalizing, the representative volume element (RVE) in each one of the images was selected. The RVE considered has a rectangular section whose vertices correspond to the centroid of the lattice pores (shown as the squares with the vertices labeled 1, 2, 3 and 4 in FIG. 23C and rectangles with the vertices 1, 2, 3 and 4 and in FIG. 12E). To find the position of the centroids, the edges of the pores using the Sobel edge detection method was determined. The edges of the pores are shown as circles in FIG. 23C and FIG. 12E. Then, centroid calculation was performed by taking the mean of the coordinates in x and y for each pixel in the border. After the selection of the RVE, the size of the RhuA building blocks was measured on each image by defining the circle that is circumscribed to each square (shown as blue circles in FIG. 23C). Since the square shape of the RhuA building blocks can be assumed to remain rigid in each conformational state, it was determined that the images were at slightly different scales; thus, appropriate magnification factors were calculated taking as a reference the image corresponding to conformational state I. The applied scaling factors are shown in FIG. 23C. The position of the vertices of the RVE on each conformational state was then calculated and was then proceeded with the calculation of the Poisson's ratio. For each RVE, local values of engineering strains $e_x$ and $e_y$ can be calculated from the vectors M, N and m, n that span the RVE on its reference (state I) and deformed configurations (states II-VII), respectively (see FIG. 12E):

$$M = \begin{bmatrix} M_x \\ M_y \end{bmatrix}, \quad N = \begin{bmatrix} N_x \\ N_y \end{bmatrix} \text{ and } m = \begin{bmatrix} m_x \\ m_y \end{bmatrix}, \quad n = \begin{bmatrix} n_x \\ n_y \end{bmatrix}$$

and considering that the deformed and undeformed configurations can be related through the deformation gradient F:

$$\begin{bmatrix} m_x \\ m_y \end{bmatrix} = \begin{bmatrix} 1+e_x & e_{xy} \\ e_{yx} & 1+e_y \end{bmatrix} \begin{bmatrix} M_x \\ M_y \end{bmatrix} \text{ and } \begin{bmatrix} n_x \\ n_y \end{bmatrix} = \begin{bmatrix} 1+e_x & e_{xy} \\ e_{yx} & 1+e_y \end{bmatrix} \begin{bmatrix} N_x \\ N_y \end{bmatrix}$$

where $$F = \begin{bmatrix} 1+e_x & e_{xy} \\ e_{yx} & 1+e_y \end{bmatrix}$$

Then, homogenized values of the engineering strains for the RVE can be calculated as:

$$\begin{bmatrix} 1+e_x & e_{xy} \\ e_{yx} & 1+e_y \end{bmatrix} = \begin{bmatrix} n_x & m_x \\ n_y & m_y \end{bmatrix} \begin{bmatrix} N_x & M_x \\ N_y & M_y \end{bmatrix}^{-1}$$

Finally, the Poisson's ratio is calculated as:

$$\nu = -\frac{e_y}{e_x}$$

Example 18

Development of templating and growth of functionalities on $^{C98}$RhuA crystals:C98 with meleimido Au. Monomaleimino Nanogold® at 6 nmol was used for staining instead of UA. (See FIG. 24-33). The covalent modification of the RhuA lattices is carried out via the reaction of peripheral cysteines with monomaleimido nanogold or iodoacetamidofluorescein. The nucleation/growth of gold nanoparticle was also tested on $^{C98}$RhuA crystals using Gold(III) chloride trihydrate (HAuCl$_4$) under various reducing reagents.

As shown in FIG. 26 is a $^{C98}$RhuA crystal with monomaleimido nanogold. For making the crystal, 3-3.5 µL aliquots of crystal suspensions were applied onto negatively glow-discharged carbon-coated Cu grids, washed with Milli-Q water, and treated with 5 µL of 6 nmol Monomaleimido Nanogold (Nanoprobes, Inc) for 3 hours or overnight at 4° C. As shown in FIG. 27, $^{C98}$RhuA crystals were treated with iodoacetamidofluorescein. 4 µL aliquots of crystal suspensions were mixed into 200 µM iodoacetamidofluorescein for 1 day, and sample was deposited onto negatively glow-discharged carbon-coated Cu grids, washed with Milli-Q water, and stained with 1% uranyl acetate at 4° C. Sample was also tested by confocal microscopy to determine the addition of iodoacetamidofluorescein.

As shown in FIG. 28, are $^{C98}$RhuA crystals with HAuCl$_4$ 4 µL aliquots of crystal suspensions were mixed into 0.5 mM HAuCl$_4$ with various reducing reagents in 5 mM NaPi pH 7.2 for indicated time, and sample was deposited onto negatively glow-discharged carbon-coated Cu grids, washed with Milli-Q water at 4° C.

Example 19

The results for making the C98-CD with HAuCl4 is shown in FIGS. 28-34. For making the crystalline structures, 4 µL aliquots of crystal suspensions were mixed into 0.5 mM HAuCl$_4$ with various reducing reagents in 5 mM NaPi pH 7.2 for indicated time, and sample was deposited onto negatively glow-discharged carbon-coated Cu grids, washed with Milli-Q water at 4° C.

As shown in FIG. 28, 4 uL sheet was added into 0.5 mM HAuCl$_4$ for 1 day. As shown in FIG. 29, RhuA-C98 (4 uL) added into 0.5 mM HAuCl$_4$ in 5 mM NaPi pH 7.2 6 days then added 5 mM bME for 1 day. As shown in FIG. 30, RhuA-C98 (4 uL) added into 100 μL of Au(I) (HAuCl$_4$+2 eq thiodiethanol) in 5 mM NaPi pH 7.2 for 4 days and then the crystals were examined. As shown in FIG. 31, RhuA-C98 sheet/HAuCl$_4$ on grids followed by HAuCl$_4$/K$_2$CO$_3$/NaBH$_4$ for 1 hr then in 10% formaldehyde for 2 hours. As shown in FIG. 32, RhuA-C98 sheet/HAuCl4 on grids followed by HAuCl4/K2CO3/NaBH4 in NaPi pH 7.2 for 2 hours. As shown in FIG. 33, RhuA-C98 sheet/HAuCl4 on grids followed by HAuCl4/K2CO3/Formaldehyde in NaPi pH 7.2 for 2 hours.

Example 20: Investigation of New Connectivity's Via Covalent Modification of $^{C98}$RhuA In order to broaden the connectivity of lattices, the covalent modifications of cysteine on $^{C98}$RhuA were carried out, and their self-assemblies were tested via addition of Metals, Small Molecule, or Counter Partner.

Example 21: Addition of Functional Groups onto $^{c98}$RhuA 500 uM $^{C98}$RhuA was reduced with 18 eq TCEP for a hour followed by reaction with 20 eq of N-(1,10-Phenanthrolin-5-yl)iodoacetamide, dmco(cycloakyne)maleimide, or 4-phenylazomaleinanil in 10 mM Tris pH 7.5 with 5 DMF. Sample was dialyzed against 10 mM Tris (with 5 DMF if necessary) pH 7.5. $^{dmco(cycloakyne)maleimidoC98}$RhuA was then reacted with 20 eq of mono-6-Azido-6-deoxy-beta-cyclodextrin followed by dialysis.

Example 22: Metal Directed Self-Assembly of $^{iPhen\text{-}C98}$RhuA (and $^{iPhen\text{-}C133}$RhuA)

2 eq of ZnCl$_2$, CuCl$_2$, or NiSO$_4$ was mixed with 100 μM $^{iPhenC98}$RhuA at pH 5.5 in 20 mM MES for 1 day (or as indicated) to assemble 2D crystals. Sample was deposited onto negatively glow-discharged carbon-coated Cu grids, washed with Milli-Q water at 4° C., and stained with 1% uranyl acetate at 4° C.

$^{C133}$RhuA (control) was also tested in this experiment. Even though $^{C133}$RhuA could not form ordered array via disulfide bonds, $^{iPhen\text{-}C133}$RhuA (modification of cysteines) was able to form crystals via metal directed assembly due to additional space between protein-protein interactions. (See FIGS. 63, 38 and 41)

Example 23

Small molecule (curcumin) directed self-assembly of $^{CD\text{-}C98}$RhuA. 100 uM $^{CD\text{-}C98}$RhuA was incubated with 1 mM or 5 mM curcumin (stock in DMF) in 10 mM TRIS pH 7.5 with 5 DMF at 4° C. for indicated time. Sample was deposited onto negatively glow-discharged carbon-coated Cu grids, washed with Milli-Q water at 4° C., and stained with 1% uranyl acetate at 4° C. (See FIGS. 43, 44, 49, 51 and 52)

Example 24: Self-Assembly of $^{CD\text{-}C98}$RhuA and $^{Azo\text{-}C98}$RhuA

100 μM of $^{CD\text{-}C98}$RhuA and $^{Azo\text{-}C98}$RhuA was mixed for 1 day at 4° C. Sample was deposited onto negatively glow-discharged carbon-coated Cu grids, washed with Milli-Q water at 4° C., and stained with 1% uranyl acetate at 4° C. (FIGS. 42, 55, 58 and 59)

Example 25

The 2D protein lattices can be modified with inorganic compounds as shown in FIGS. 24-26. As shown, 2D crystalline material comprising a polypeptide building block of any one of the alternatives described herein is provided. The polypeptide building block can comprise the non-naturally occurring symmetrical polypeptide building block described herein. The non-naturally occurring symmetrical polypeptide building block can comprise a plurality of cysteine residues positioned such that formation of disulfide bonds between some or all of said plurality of cysteine residues facilitates formation of 2D crystals. polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In some embodiments, said polypeptide is generated via solid phase synthesis. In some embodiments, said polypeptide is genetically engineered. In some embodiments, said polypeptide further comprises an additional modification, wherein said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said polypeptide comprises the RhuA protein. In some embodiments, the polypeptide building block can be chemically modified with inorganic nanoparticles. In some embodiments, the polypeptide building block can be modified with organic functional groups (fluorophores, metal chelating groups or host complexes) for different modes of controllable self-assembly. In some embodiments, the polypeptide building block can be genetically modified/fused with functional proteins and peptides. In some embodiments, said 2D crystalline material is auxetic. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified with inorganic nanoparticles. In some embodiments, the 2D crystalline material can be modified with organic functional groups (fluorophores, metal chelating groups or host complexes) for different modes of controllable self-assembly. In some embodiments, the 2D crystalline material can be genetically modified/fused with functional proteins and peptides. The 2D crystalline material can be modified with maleimido AU and with the addition of HAuCl$_4$. The 2D crystalline material can also be fused to a protein.

Example 26: 2D Protein Lattices can be Used as Templates for Inorganic Nanoparticle Growth C98-CD with HAuCl$_4$. As shown in FIGS. 28-33, the 2D crystalline structures as described herein, can be used as templates for inorganic nanoparticle growth such as nanotubes for example. These can be shown in which the crystals have grown in 0.5 mM Au(I) to 0.125 mM Au(I).

Example 27: 2D Crystalline Structures can be Modified with Functional Groups. (FIGS. 34-53)

As shown, 2D crystalline material comprising a polypeptide building block of any one of the alternatives described herein is provided. The polypeptide building block can comprise the non-naturally occurring symmetrical polypeptide building block described herein. The non-naturally occurring symmetrical polypeptide building block can comprise a plurality of cysteine residues positioned such that formation of disulfide bonds between some or all of said plurality of cysteine residues facilitates formation of 2D crystals. polypeptide building block comprises a symmetrical polypeptide comprising a single set of surface cysteine residues in the corner positions. In some embodiments, said polypeptide has inherent C3, C4, C6, D3, D4 or D6 symmetry. In some embodiments, at least one of said cysteine residues has been introduced into said polypeptide building block through genetic engineering. In embodiments, said polypeptide is generated via solid phase synthesis. In some embodiments, said polypeptide is genetically engineered. In some embodiments, said polypeptide further comprises an additional modification, wherein said additional modification is selected from the group consisting of a chemical modification, a modification made via an enzymatic reaction, and a modification made via genetic engineering. In some embodiments, said additional modification is selected from the group consisting of functional groups, tags, other polypeptides, peptide tags, detectable labels, fluorophores, and nanoparticles. In some embodiments, said polypeptide comprises the RhuA protein. In some embodiments, the polypeptide building block can be chemically modified with inorganic nanoparticles. In some embodiments, the polypeptide building block can be modified with organic functional groups (fluorophores, metal chelating groups or host complexes) for different modes of controllable self-assembly. In some embodiments, the polypeptide building block can be genetically modified/fused with functional proteins and peptides. In some embodiments, said 2D crystalline material is auxetic. In some embodiments, wherein the 2D crystalline material can be assembled by visible light and dissembled by UV light. In some embodiments, the 2D crystalline material comprises a Poisson's ratio of at least −1. In some embodiments, the 2D crystalline material comprises a Poisson's ratio of −1. In some embodiments, the 2D crystalline material can be chemically modified with inorganic nanoparticles. In some embodiments, the 2D crystalline material can be modified with organic functional groups (fluorophores, metal chelating groups or host complexes) for different modes of controllable self-assembly. In some embodiments, the 2D crystalline material can be genetically modified/fused with functional proteins and peptides. The 2D crystalline material can be modified with maleimido AU and with the addition of $HAuCl_4$. The 2D crystalline material can also be fused to a protein. In the alternatives shown in FIGS. 34-53, the 2D crystalline materials can be modified by the addition of Iodo-Fl. Additionally there was covalent modification of the 2D crystalline materials with metal chelators and cyclodextrin.

As shown in FIG. 36, RhuA-Cys-iphen was synthesized. The Cys of RhuA-C133 and RhuA-C266 are conjugated with iPhen as of RhuA-C98. In the presence of CuCl2, there is the formation of a crystalline structure (FIG. 38). This is also seen in the presence of nickel and zinc as shown in FIGS. 39 and 41. Crystals were also formed in the presence of imidazole (FIG. 40).

Protein assembly was also shown to be photoswitchable as seen in FIG. 42.

Furthermore, the 2D crystalline materials can be further modified in some embodiments by Bis-azobenzene and curcumin (See FIG. 43-53).

Example 28: Genetic Fusions

As described herein, the 2D crystalline structures or materials of any one of the embodiments described herein can be further modified by a point mutation of an extra cysteine, covalent modification of the lattices (metal chealtors, cyclodextran), as well as any genetic fusions. This can include a His tag, a Pd4Tag or manufacturing of a ACP fusion protein for use (FIGS. 54-59).

As shown in FIG. 54, concentrated samples of C98C18 RhuA mutants (100 uM) were treated with iodo Fl for modification.

As shown in FIGS. 55-56, the RhuA-C98-HisTag (100 µM) was treated in 20 mM MOPS at pH 7 in Redox Condition after 1 Day and observed for crystalline materials.

Assembly of $^{C98}$RhuA-Pd4 (125 µM) under various conditions (after 1 day w/shake) was also examined (FIG. 57).

Assembly of $^{C98}$RhuA-Pd4 (125 µM) under various conditions (after 1 day w/shake) was also examined in the presence of beta mercaptoethanol and zinc chloride. (FIG. 58)

As shown in FIG. 59, Fusion Protein 2D Assemblies of RhuA-ACP was studied under various conditions. In some embodiments described herein, polypeptide can be genetically engineered to present a fusion peptide for lattice assembly.

Example 29: Addition of Functionalities onto $^{C98}$RhuA Via Genetic Fusions

To investigate the functionalities on $^{C98}$RhuA crystals, genetically added HisTag, Pd4, or acyl carrier protein (ACP) at C-terminus of $^{C98}$RhuA, and their self-assemblies via disulfide formation were tested accordingly. In addition, additional cysteine (C18 or C22) inside of cavity at $^{C98}$RhuA for chemical handle was also tested, not for self-assembly. The gene for $^{C98}$RhuA-HisTag, $^{C98}$RhuA-Pd4, and $^{C98}$RhuA-ACP based on $^{C98}$RhuA were pre-inserted into the pJ414 expression vector optimized for expression in E. coli, was purchased from DNA2.0. Protein expression and purification was followed as of $^{C98}$RhuA.

Right after C98RhuA sequence, below sequence was added:

$^{C98}$RhuA-HisTag:

(SEQ ID NO: 22)
GSGSGHHHHHH
(Linker-HisTag) (FIG. 55)

$^{C98}$RhuA-Pd4:

(SEQ ID NO: 23)
GSGSGTSNAVHPTLRHL
(Linker-Pd4 peptide) (FIG. 58)

$^{C98}$RhuA-ACP:

(SEQ ID NO: 24)
GSGSGSTIEERVKKIIGEQLGVKQEEVTNNASFVEDLGADSLDTVELV
MALEEEFDTEIPDEEAEKITTVQAAIDYINGHQA
(Linker-ACP protein) (FIG. 59)

Additional Cys onto $^{C98}$RhuA: $^{C18C98}$RhuA and $^{C22C98}$RhuA (FIG. 64)

Several solution conditions were screened for optimizing the formation of 2D protein crystals of fusion proteins and best condition so far was indicated in figures.

The disclosures of all references listed herein and each of the following references are incorporated herein by reference in their entireties:

REFERENCES

U.S. Pat. No. 9,030,079
U.S. Publication No. 2011/0059291
U.S. Publication No. 2011/0156314
U.S. Publication No. 2015/0075033
WO 2010/070505 A2
Baker/King et al., Nature 2014, 510:103-108.
Baneyx, F. & Matthaei, J. F. Curr. Opin. Biotech. 2014, 28:39.
Baughman, R. H. Auxetic materials: Avoiding the shrink. Nature 2003, 425:667-667.
Brodin, J. D. et al. Metal-directed, chemically tunable assembly of one-, two- and three-dimensional crystalline protein arrays. Nat. Chem. 2012, 4:375-382.
Buehler, Nat. Nanotech., 2011
Butler, S. Z.; Hollen, S. M.; Cao, L.; Cui, Y.; Gupta, J. A.; Gutiérrez, H. R.; Heinz, T. F.; Hong, S. S.; Huang, J.; Ismach, A. F.; Johnston-Halperin, E.; Kuno, M.; Plashnitsa, V. V.; Robinson, R. D.; Ruoff, R. S.; Salahuddin, S.; Shan, J.; Shi, L.; Spencer, M. G.; Terrones, M.; Windl, W.; & Goldberger, J. E. Progress, Challenges, and Opportunities in Two-Dimensional Materials Beyond Graphene. ACS Nano 2013, 7:2898-2926.
Choi, J. B. & Lakes, R. S. Non-linear properties of metallic cellular materials with a negative Poisson's ratio. J. Mater. Sci. 1992, 27:5375-5381.
Colson, J. W. et al. Oriented 2D covalent organic framework thin films on single-layer graphene. Science 2011, 332: 228-231.
Colson, J. W.; Dichtel, W. R. Rationally synthesized two-dimensional polymers. Nat. Chem. 2013, 5:453-465.
Crowther, R., Henderson, R. & Smith, J. MRC image processing programs. J. Struct. Biol. 1996, 116:9-16.
Edelhoch, H. Spectroscopic determination of tryptophan and tyrosine in proteins. Biochemistry 1967, 6:1948-1954.
Engel, A. et al. Assembly of 2-D membrane protein crystals: dynamics, crystal order, and fidelity of structure analysis by electron microscopy. J. Struct. Biol. 1992, 109:219-234.
Evans, K. E. & Alderson, A. Auxetic materials: functional materials and structures from lateral thinking! Adv. Mater. 2000, 12:617-628.
Geim, A. K., & Novoselov, K. S., Nat. Mater. 2007, 6:183.
Gipson, B., Zeng, X., Zhang, Z. Y., & Stahlberg, H., J. Struct. Biol. 2007, 157:64.
Gonen, S., DiMaio, F., Gonen, T. & Baker, D. Design of ordered two-dimensional arrays mediated by noncovalent protein-protein interfaces. Science 2015, 348:1365-1368.
Greaves, G. N., Greer, A., Lakes, R. & Rouxel, T. Poisson's ratio and modern materials. Nat. Mater. 2011, 10:823-837.
Grima, J., Alderson, A. & Evans, K. Auxetic behaviour from rotating rigid units. Phys. Stat. Sol. b 2005, 242:561-575.
Grueninger, D. et al. Designed protein-protein association. Science 2008, 319:206-209.
Hampp, N. Bacteriorhodopsin as a photochromic retinal protein for optical memories. Chem. Rev. 2000, 100: 1755-1776.
Heymann, J. B. Bsoft: image and molecular processing in electron microscopy. J. Struct. Biol. 2001, 133:156-169.
Joshi, R. K. et al. Precise and Ultrafast Molecular Sieving Through Graphene Oxide Membranes. Science 2014, 343:752-754.
King, N. P.; Sheffler, W.; Sawaya, M. R.; Vollmar, B. S.; Sumida, J. P.; Andro, I.; Gonen, T.; Yeates, T. O.; Baker, D. Computational Design of Self-Assembling Protein Nanomaterials with Atomic Level Accuracy. Science 2012, 336:1171-1174.
Kissel, P., Murray, D. J., Wulftange, W. J., Catalano, V. J. & King, B. T. A nanoporous two-dimensional polymer by single-crystal-to-single-crystal photopolymerization. Nat. Chem. 2014, 6:774-778.
Kory, M. J. et al. Gram-scale synthesis of two-dimensional polymer crystals and their structure analysis by X-ray diffraction. Nat. Chem. 2014, 6:779-784.
Kroemer, M. & Schulz, G. E. The structure of L-rhamnulose-1-phosphate aldolase (class II) solved by low-resolution SIR phasing and 20-fold NCS averaging. Acta Cryst. D. 2002, 58:824-832.
Kroemer, Biochemistry, Vol. 42 (2003), pp. 10560-10568, Structure and Catalytic Mechanism of L-Rhamnulose-1-phosphate Aldolase.
Lai, Y.-T.; Cascio, D.; Yeates, T. O. Structure of a 16-nm Cage Designed by Using Protein Oligomers. Science 2012, 336:1129.
Lakes, R. Foam structures with a negative Poisson's ratio. Science 1987, 235:1038-1040.
Lanci, C. J.; MacDermaid, C. M.; Kang, S.-g.; Acharya, R.; North, B.; Yang, X.; Qiu, X. J.; DeGrado, W. F.; Saven, J. G. Computational design of a protein crystal. Proc. Natl. Acad. Sci. USA 2012, 109:7304-7309.
Lebeau, L. et al., Two-dimensional crystallization of a membrane protein on a detergent-resistant lipid monolayer. J. Mol. Biol, 2001, 306:639-647.
Li, D., Muller, M. B., Gilje, S., Kaner, R. B. & Wallace, G. G. Processable aqueous dispersions of graphene nanosheets. Nat. Nano. 2008, 3:101-105.
Lu, C.-H., Yang, H.-H., Zhu, C.-L., Chen, X. & Chen, G.-N. A Graphene Platform for Sensing Biomolecules. Angew. Chem. Int. Ed. Engl. 2009, 121:4879-4881.
Lukowski. M. A. et al., J. Am. Chem. Soc. 2013, 135:10274.
Mas-Balleste, R., Gomez-Navarro, C., Gomez-Herrero, J. & Zamora, F. 2D materials: to graphene and beyond. Nanoscale 2011, 3:20-30.
Mindell, J. A. & Grigorieff, N. Accurate determination of local defocus and specimen tilt in electron microscopy. J. Struct. Biol. 2003, 142:334-347.
Nicolosi, V., Chhowalla, M., Kanatzidis, M. G., Strano, M. S. & Coleman, J. N. Liquid exfoliation of layered materials. Science 2013, 340:1226419.
Pettersen, E. F. et al. UCSF Chimera—a visualization system for exploratory research and analysis. J. Comput. Chem. 2004, 25:1605-1612.
Rabone, J. et al. An adaptable peptide-based porous material. Science 2010, 329:1053-1057.
Ringler, P. & Schulz, G. E. Self-assembly of proteins into designed networks. Science 2003, 302:106-109.
Saboe, P. O. et al. Two-Dimensional Protein Crystals for Solar Energy Conversion. Adv. Mater. 2014, 26:7064-7069.
Scarpa, F., Ciffo, L. & Yates, J. Dynamic properties of high structural integrity auxetic open cell foam. Smart Mat. Struct. 2004, 13:49.
Schedin, F. et al. Detection of individual gas molecules adsorbed on graphene. Nat. Mater. 2007, 6:652-655.

Schindelin, J. et al. Fiji: an open-source platform for biological-image analysis. Nat. Meth. 2012, 9:676-682.

Schneider, C. A., Rasband, W. S. & Eliceiri, K. W. NIH Image to ImageJ: 25 years of image analysis. Nat. Methods 2012, 9:671-675.

Serre, C. et al. Role of solvent-host interactions that lead to very large swelling of hybrid frameworks. Science 2007, 315:1828-1831.

Shimomura, S. et al. Selective sorption of oxygen and nitric oxide by an electron-donating flexible porous coordination polymer. Nat. Chem. 2010, 2:633-637.

Sinclair, J. C.; Davies, K. M.; Venien-Bryan, C.; Noble, M. E. M. Generation of protein lattices by fusing proteins with matching rotational symmetry. Nat. Nanotechnol. 2011, 6:558-562.

Sleytr, U. B., Schuster, B., Egelseer, E. M. & Pum, D. S-layers: principles and applications. FEMS Microbiol. Rev. 2014, 38:823-864.

Stahlberg, H. et al. Two-dimensional crystals: a powerful approach to assess structure, function and dynamics of membrane proteins. FEBS Lett. 2001, 504:166-172.

Suzuki, et al. Self-assembly of coherently dynamic, auxetic, two-dimensional protein crystals. Nature, 2016, 533:369-385.

Tang, G. et al. EMAN2: an extensible image processing suite for electron microscopy. J. Struct. Biol. 2007, 157:38-46.

Valpuesta, J. M. a., Carrascosa, J. L. & Henderson, R. Analysis of electron microscope images and electron diffraction patterns of thin crystals of 029 connectors in ice. J. Mol. Biol. 1994, 240:281-287.

Uzgiris, E. & Kornberg, R. Two-dimensional crystallization technique for imaging macromolecules with application to antigen-antibody-complement complexes. Nature 1983, 301:125-129.

Yeates, T. O. Nanobiotechnology: Protein arrays made to order. Nat. Nanotechnol. 2011, 6:541-542.

---

What is claimed is:

1. A non-naturally occurring symmetrical polypeptide building block comprising two or more RhuA proteins, wherein each subunit of the RhuA protein comprises a cysteine residue at position 98, and wherein the RhuA proteins of the polypeptide building block are coupled by formation of disulfide-bonds between some or all of said plurality of cysteine residues of different RhuA proteins to facilitate formation of 2D crystals.

2. The polypeptide building block of claim 1, wherein at least one of said cysteine residues has been introduced into said polypeptide building block through genetic engineering.

3. The polypeptide building block of claim 1, wherein said polypeptide building block is generated via solid phase synthesis.

4. The polypeptide building block claim 1, further comprising an additional polypeptide modification selected from the group consisting of functional groups, tags, other polypeptides, peptide tags, detectable labels, fluorophores, and nanoparticles.

5. The polypeptide building block of claim 4, wherein the peptide tag comprises a His tag comprising a sequence set forth in SEQ ID NO: 22.

6. The polypeptide building block of claim 4, wherein the peptide tag comprises a Pd4 peptide comprising a sequence set forth in SEQ ID NO: 23.

7. The polypeptide building block of claim 4, wherein the peptide tag comprises a ACP protein comprising a sequence set forth in SEQ ID NO: 24.

8. The polypeptide building block of claim 1, wherein the polypeptide building block is chemically modified with inorganic nanoparticles or one or more organic functional groups including a fluorophore, a metal chelating group or a host complex.

9. A 2D crystalline material comprising two or more RhuA proteins, wherein each subunit of each RhuA protein comprises a cysteine residue at position 98, wherein disulfide bonds are formed between some or all of said cysteine residues.

10. The 2D crystalline material of claim 9, wherein said 2D crystalline material is auxetic.

11. The 2D crystalline material of claim 9, wherein the 2D crystalline material comprises a Poisson's ratio of at least −1.

12. The 2D crystalline material of claim 9, wherein the 2D crystalline material is chemically modified with inorganic nanoparticles or one or more organic functional groups including a fluorophore, a metal chelating group or a host complex.

13. The 2D crystalline material of claim 9, wherein the 2D crystalline material can be genetically modified/fused with functional proteins and peptides.

14. The 2D crystalline material of claim 9, wherein the 2D crystalline material is free of defects.

15. The 2D crystalline material of claim 9, wherein the 2D crystalline material allows dynamic interconversion between an open conformational state and a closed conformational state.

\* \* \* \* \*